(12) United States Patent
Belema et al.

(10) Patent No.: US 8,377,980 B2
(45) Date of Patent: Feb. 19, 2013

(54) HEPATITIS C VIRUS INHIBITORS

(75) Inventors: Makonen Belema, North Haven, CT (US); Jeffrey Lee Romine, Meriden, CT (US); Van N. Nguyen, Meriden, CT (US); Gan Wang, Wallingford, CT (US); Omar D. Lopez, Wallingford, CT (US); Denis R. St. Laurent, Newington, CT (US); Qi Chen, Stamford, CT (US); John A. Bender, Middletown, CT (US); Zhong Yang, Southington, CT (US); Piyasena Hewawasam, Middletown, CT (US); Ningning Xu, Wallingford, CT (US); Nicholas A. Meanwell, East Hampton, CT (US); John A. Easter, East Hampton, CT (US); Bao-Ning Su, Kendall Park, NJ (US); Michael J. Smith, Somerset, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 12/957,512

(22) Filed: Dec. 1, 2010

(65) Prior Publication Data

US 2011/0286961 A1 Nov. 24, 2011

Related U.S. Application Data

(60) Provisional application No. 61/286,942, filed on Dec. 16, 2009.

(51) Int. Cl.
*A61K 31/4178* (2006.01)
*C07D 233/64* (2006.01)

(52) U.S. Cl. .................................. 514/397; 548/313.1
(58) Field of Classification Search ............... 548/313.1; 514/397
See application file for complete search history.

(56) References Cited

U.S. PATENT DOCUMENTS

| 5,654,451 | A | 8/1997 | Kari |
| 7,894,996 | B2 | 2/2011 | Rice et al. |
| 2010/0158862 | A1 | 6/2010 | Kim et al. |
| 2011/0092415 | A1 | 4/2011 | DeGoey et al. |

FOREIGN PATENT DOCUMENTS

| WO | WO 94/15909 | 7/1994 |
| WO | WO 2004/005264 | 1/2004 |
| WO | WO 2006/022442 | 3/2006 |
| WO | WO 2006/093867 | 9/2006 |
| WO | WO 2006/133326 | 12/2006 |
| WO | WO 2007/031791 | 3/2007 |
| WO | WO 2007/058384 | 5/2007 |
| WO | WO 2007/076034 | 7/2007 |
| WO | WO 2007/077186 | 7/2007 |
| WO | WO 2007/081517 | 7/2007 |
| WO | WO 2007/138242 | 12/2007 |
| WO | WO 2008/014430 | 1/2008 |
| WO | WO 2008/021927 | 2/2008 |
| WO | WO 2008/021928 | 2/2008 |
| WO | WO 2008/021936 | 2/2008 |
| WO | WO 2008/070447 | 6/2008 |
| WO | WO 2008/133753 | 11/2008 |
| WO | WO 2009/020825 | 2/2009 |
| WO | WO 2009/020828 | 2/2009 |
| WO | WO 2009/102318 | 8/2009 |
| WO | WO 2009/102325 | 8/2009 |
| WO | WO 2009/102568 | 8/2009 |
| WO | WO 2009/102633 | 8/2009 |
| WO | WO 2009/102694 | 8/2009 |
| WO | WO 2010/017401 | 2/2010 |
| WO | WO 2010/039793 | 4/2010 |
| WO | WO 2010/062821 | 6/2010 |
| WO | WO 2010/065668 | 6/2010 |
| WO | WO 2010/065674 | 6/2010 |
| WO | WO 2010/065681 | 6/2010 |
| WO | WO 2010/075376 | 7/2010 |
| WO | WO 2010/091413 | 8/2010 |
| WO | WO 2010/094977 | 8/2010 |
| WO | WO 2010/096302 | 8/2010 |
| WO | WO 2010/096462 | 8/2010 |
| WO | WO 2010/096462 A1 * | 8/2010 |
| WO | WO 2010/096777 | 8/2010 |
| WO | WO 2010/099527 | 9/2010 |
| WO | WO 2010/111534 | 9/2010 |
| WO | WO 2010/111673 | 9/2010 |
| WO | WO 2010/117635 | 10/2010 |
| WO | WO 2010/117704 | 10/2010 |
| WO | WO 2010/117977 | 10/2010 |
| WO | WO 2010/120621 | 10/2010 |
| WO | WO 2010/120935 | 10/2010 |
| WO | WO 2010/122162 | 10/2010 |
| WO | WO 2010/132538 | 11/2010 |
| WO | WO 2010/132601 | 11/2010 |
| WO | WO 2010/138368 | 12/2010 |

(Continued)

OTHER PUBLICATIONS

Claims of co-pending U.S. Appl. No. 11/835,462, commonly assigned to Bristol-Myers Squibb Co., filed Aug. 8, 2007.*
U.S. Appl. No. 12/846,152, filed Jul. 29, 2010, Romine.
U.S. Appl. No. 12/889,705, filed Sep. 24, 2010, Belema et al.
U.S. Appl. No. 13/195,317, filed Aug. 1, 2011, Gao et al.
U.S. Appl. No. 13/198,529, filed Aug. 4, 2011, Belema et al.
Fridell, R.A. et al., "Resistance Analysis of the Hepatitis C Virus NS5A Inhibitor BMS-790052 in an In Vitro Replicon System", Antimicrobial Agents and Chemotherapy, vol. 54, No. 9, pp. 3641-3650 (2010).
Gao, M. et al., "Chemical genetics strategy identifies an HCV NS5A inhibitor with a potent clinical effect", Nature, vol. 465, pp. 96-100 (2010).

(Continued)

*Primary Examiner* — Kamal Saeed
*Assistant Examiner* — Janet L Coppins
(74) *Attorney, Agent, or Firm* — Pamela A. Mingo

(57) ABSTRACT

The present disclosure relates to compounds, compositions and methods for the treatment of Hepatitis C virus (HCV) infection. Also disclosed are pharmaceutical compositions containing such compounds and methods for using these compounds in the treatment of HCV infection.

16 Claims, No Drawings

FOREIGN PATENT DOCUMENTS

| | | |
|---|---|---|
| WO | WO 2010/138488 | 12/2010 |
| WO | WO 2010/138790 | 12/2010 |
| WO | WO 2010/138791 | 12/2010 |
| WO | WO 2010/144646 | 12/2010 |
| WO | WO 2010/148006 | 12/2010 |
| WO | WO 2011/004276 | 1/2011 |
| WO | WO 2011/009084 | 1/2011 |
| WO | WO 2011/015657 | 2/2011 |
| WO | WO 2011/015658 | 2/2011 |
| WO | WO 2011/026920 | 3/2011 |
| WO | WO 2011/028596 | 3/2011 |
| WO | WO 2011/031904 | 3/2011 |
| WO | WO 2011/031934 | 3/2011 |
| WO | WO 2011/046811 | 4/2011 |
| WO | WO 2011/050146 | 4/2011 |
| WO | WO 2011/054834 | 5/2011 |
| WO | WO 2011/059850 | 5/2011 |
| WO | WO 2011/059887 | 5/2011 |
| WO | WO 2011/060000 | 5/2011 |
| WO | WO 2011/066241 | 6/2011 |
| WO | WO 2011/068941 | 6/2011 |
| WO | WO 2011/075607 | 6/2011 |
| WO | WO 2011/075615 | 6/2011 |
| WO | WO 2011/079327 | 6/2011 |
| WO | WO 2011/081918 | 7/2011 |
| WO | WO 2011/082077 | 7/2011 |
| WO | WO 2011/087740 | 7/2011 |
| WO | WO 2011/091417 | 7/2011 |
| WO | WO 2011/091446 | 7/2011 |
| WO | WO 2011/091532 | 8/2011 |

OTHER PUBLICATIONS

Lemm, J.A. et al., "Identification of Hepatitis C Virus NS5A Inhibitors", Journal of Virology, vol. 84, No. 1, pp. 482-491 (2010).
Romine, J.L. et al., "Inhibitors of HCV NS5A: Form Iminothiazolidinones to Symmetrical Stilbenes", ACS Medicinal Chemistry Letters, vol. 2, pp. 224-229 (2011).

* cited by examiner

HEPATITIS C VIRUS INHIBITORS

CROSS-REFERENCE TO RELATED APPLICATIONS

This application claims the benefit of U.S. Provisional Application Ser. No. 61/286,942 filed Dec. 16, 2009.

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

The current standard of care for HCV, which employs a combination of pegylated-interferon and ribavirin, has a non-optimal success rate in achieving sustained viral response and causes numerous side effects. Thus, there is a clear and long-felt need to develop effective therapies to address this unmet medical need.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS5B (also referred to herein as HCV polymerase) is a RNA-dependent RNA polymerase that is involved in the replication of HCV with other HCV proteins, including NS5A, in a replicase complex.

Compounds useful for treating HCV-infected patients are desired which selectively inhibit HCV viral replication. In particular, compounds which are effective to inhibit the function of the NS5A protein are desired. The HCV NS5A protein is described, for example, in the following references: Tan, S. L. et al., *Virology*, 284:1-12 (2001); Park, K.-J. et al., *J. Biol. Chem.*, 30711-30718 (2003); Tellinghuisen, T. L. et al., *Nature*, 435:374 (2005); Love, R. A. et al., *J. Virol.*, 83:4395 (2009); Appel, N. et al., *J. Biol. Chem.*, 281:9833 (2006); Huang, L., *J. Biol. Chem.*, 280:36417 (2005); Rice, C. et al., WO 2006/093867.

In one aspect the present disclosure provides a compound of Formula (I)

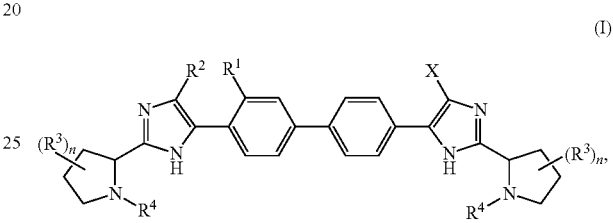

(I)

or a pharmaceutically acceptable salt thereof, wherein:
n is 0, 1, or 2;
X is selected from hydrogen, alkenyl, cyano, cycloalkyl, (cycloalkyl)alkyl, halo, and heterocyclyl;
$R^1$ is selected from hydrogen and halo;
$R^2$ is selected from hydrogen, alkenyl, cyano, cycloalkyl, (cycloalkyl)alkyl, halo, and heterocyclyl; or
$R^1$ and $R^2$, together with the carbon atoms to which they are attached, form a six-membered aromatic ring optionally substituted with one halo group;
provided that at least one of X and $R^2$ is selected from alkenyl, cyano, cycloalkyl, (cycloalkyl)alkyl, halo, and heterocyclyl;
each $R^3$ is alkyl, wherein the alkyl can optionally form a fused three- or four-membered ring with an adjacent carbon atom or a spirocyclic three- or four-membered ring with the carbon atom to which it is attached; wherein the fused and spirocyclic rings are optionally substituted with one or two alkyl groups;
each $R^4$ is independently selected from hydrogen and —C(O)$R^5$; and
each $R^5$ is independently selected from alkoxy, alkyl, arylalkoxy, arylalkyl, cycloalkyl, heterocyclyl, heterocyclylalkyl, (NR$^c$R$^d$)alkenyl, and (NR$^c$R$^d$)alkyl.

In a first embodiment of the first aspect the present disclosure provides a compound of Formula (I), or a pharmaceutically acceptable salt thereof, wherein each $R^5$ is independently selected from alkoxy, heterocyclyl, and (NR$^c$R$^d$)alkyl.

In a second embodiment of the first aspect the present disclosure provides a compound of Formula (I), or a pharmaceutically acceptable salt thereof, wherein X is halo. In a third embodiment of the first aspect $R^2$ is halo.

In a fourth embodiment of the first aspect the present disclosure provides a compound of Formula (I), or a pharmaceutically acceptable salt thereof, wherein $R^1$ and $R^2$, together with the carbon atoms to which they are attached, form a six-membered aromatic ring optionally substituted with one halo group.

In a fifth embodiment of the first aspect the present disclosure provides a compound of Formula (I), or a pharmaceutically acceptable salt thereof, wherein X is hydrogen.

In a second aspect the present disclosure provides a composition comprising a compound of Formula (I), or a pharmaceutically acceptable salt thereof, and a pharmaceutically acceptable carrier. In a first embodiment of the second aspect the composition further comprises at least one additional compound having anti-HCV activity. In a second embodiment of the second aspect at least one of the additional compounds is an interferon or a ribavirin. In a third embodiment of the second aspect the interferon is selected from interferon alpha 2B, pegylated interferon alpha, consensus interferon, interferon alpha 2A, and lymphoblastoid interferon tau.

In a fourth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of Formula (I), or a pharmaceutically acceptable salt thereof. In a first embodiment of the third aspect the method further comprises administering at least one additional compound having anti-HCV activity prior to, after or simultaneously with the compound of Formula (I), or a pharmaceutically acceptable salt thereof. In a second embodiment of the third aspect at least one of the additional compounds is an interferon or a ribavirin. In a third embodiment of the third aspect the interferon is selected from interferon alpha 2B, pegylated interferon alpha, consensus interferon, interferon alpha 2A, and lymphoblastoid interferon tau.

In a fourth embodiment of the third aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the third aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when $R^1$ and $R^2$ both contain an $R^4$ group, the two $R^4$ groups may be the same or different.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term "aryl".

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to six carbon atoms. In the compounds of the present disclosure, when $R^3$ is alkyl, the alkyl can optionally form a fused three- or four-membered ring with an adjacent carbon atom to provide the structure shown below:

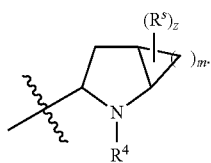

wherein m is selected from 1 and 2, wherein z is 0, 1, or 2, and wherein $R^s$ is alkyl; or wherein the alkyl can optionally form a spirocyclic three- or four-membered ring with the carbon atom to which it is attached to provide the structure shown below:

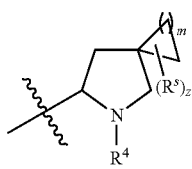

wherein m is selected from 1 and 2; wherein z is 0, 1, or 2, and wherein $R^s$ is alkyl.

The term "alkylcarbonyl," as used herein, refers to an alkyl group attached to the parent molecular moiety through a carbonyl group.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkenyl, alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^xR^y$, ($NR^xR^y$) alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, hydroxy, and nitro.

The term "arylalkoxy," as used herein, refers to an aryl group attached to the parent molecular moiety through an alkoxy group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —$NR^cR^d$, wherein the heterocyclyl is further optionally substituted with one or two substituents independently selected from alkoxy, alkyl, unsubstituted aryl, unsubstituted arylalkyl, unsubstituted arylalkoxycarbonyl, halo, haloalkoxy, haloalkyl, hydroxy, —$NR^xR^y$, and oxo.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxycarbonyl," as used herein, refers to an aryloxy group attached to the parent molecular moiety through a carbonyl group.

The term "arylsulfonyl," as used herein, refers to an aryl group attached to the parent molecular moiety through a sulfonyl group.

The term "carbonyl," as used herein, refers to —C(O)—.

The term "carboxy," as used herein, refers to —$CO_2H$.

The term "cyano," as used herein, refers to —CN.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclobutyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —$NR^xR^y$, wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "cycloalkylsulfonyl," as used herein, refers to a cycloalkyl group attached to the parent molecular moiety through a sulfonyl group.

The term "formyl," as used herein, refers to —CHO.

The term "halo," as used herein, refers to Cl, Br, F, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oct-2-yl, 2,5-diazabicyclo[2.2.1]heptan-2-yl, and 2-azabicyclo[2.2.2]oct-3-yl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isoquinolinyl, isothiazolyl, isoxazolyl, morpholinyl, oxazolyl, oxetanyl, piperazinyl, piperidinyl, pyrazolyl, pyridinyl, pyrrolidinyl, pyrrolopyridinyl, pyrrolyl, quinolinyl, tetrahydrofuranyl, tetrahydropyranyl, thiazolyl, thienyl, and thiomorpholinyl. The heterocyclyl groups of the present disclosure are optionally substituted with one, two, three, four, or five substituents independently selected from alkenyl, alkoxy, alkoxyalkyl, alkoxycarbonyl, alkyl, alkylcarbonyl, aryl, arylalkoxycarbonyl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^x$R$^y$, (NR$^x$R$^y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —NR$^c$R$^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^x$R$^y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —NO$_2$.

The term "—NR$^c$R$^d$," as used herein, refers to two groups, R$^c$ and R$^d$, which are attached to the parent molecular moiety through a nitrogen atom. R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkyloxy, cycloalkyloxycarbonyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^x$R$^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "(NR$^c$R$^d$)alkenyl," as used herein, refers to

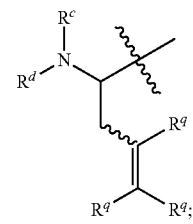

wherein R$^c$ and R$^d$ are as defined herein and each R$^q$ is independently hydrogen or C$_{1-3}$ alkyl.

The term "(NR$^c$R$^d$)alkyl," as used herein, refers to an alkyl group substituted with one, two, or three —NR$^c$R$^d$ groups. The alkyl part of the (NR$^c$R$^d$)alkyl is further optionally substituted with one or two additional groups selected from alkoxy, alkoxyalkylcarbonyl, alkoxycarbonyl, alkylsulfanyl, arylalkoxycarbonyl, carboxy, cycloalkyl, heterocyclyl, heterocyclylcarbonyl, hydroxy, and (NR$^e$R$^f$)carbonyl; wherein the heterocyclyl is further optionally substituted with one, two, three, four, or five substituents independently selected from alkoxy, alkyl, cyano, halo, haloalkoxy, haloalkyl, and nitro.

The term "—NR$^e$R$^f$," as used herein, refers to two groups, R$^e$ and R$^f$, which are attached to the parent molecular moiety through a nitrogen atom. R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^x$R$^y$)alkyl, and (NR$^x$R$^y$)carbonyl.

The term "(NR$^e$R$^f$)alkyl," as used herein, refers to an alkyl group substituted with one, two, or three —NR$^e$R$^f$ groups.

The term "(NR$^e$R$^f$)alkylcarbonyl," as used herein, refers to an (NR$^e$R$^f$)alkyl group attached to the parent molecular moiety through a carbonyl group.

The term "(NR$^e$R$^f$)carbonyl," as used herein, refers to an —NR$^e$R$^f$ group attached to the parent molecular moiety through a carbonyl group.

The term "(NR$^e$R$^f$)sulfonyl," as used herein, refers to an —NR$^e$R$^f$ group attached to the parent molecular moiety through a sulfonyl group.

The term "—NR$^x$R$^y$," as used herein, refers to two groups, R$^x$ and R$^y$, which are attached to the parent molecular moiety through a nitrogen atom. R$^x$ and R$^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{x'}$R$^{y'}$)carbonyl, wherein R$^{x'}$ and R$^{y'}$ are independently selected from hydrogen and alkyl.

The term "(NR$^x$R$^y$)alkyl," as used herein, refers to an alkyl group substituted with one, two, or three —NR$^x$R$^y$ groups.

The term "(NR$^x$R$^y$)carbonyl," as used herein, refers to an —NR$^x$R$^y$ group attached to the parent molecular moiety through a carbonyl group.

The term "—NR$^x$R$^y$," as used herein, refers to two groups, R$^x$ and R$^y$, which are attached to the parent molecular moiety through a nitrogen atom. R$^x$ and R$^y$ are independently selected from hydrogen and alkyl.

The term "(NR$^{x'}$R$^{y'}$)carbonyl," as used herein, refers to an —NR$^{x'}$R$^{y'}$ group attached to the parent molecular moiety through a carbonyl group.

The term "oxo," as used herein, refers to =O.

The term "sulfonyl," as used herein, refers to —SO$_2$—.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The compounds of the present disclosure also exist as tautomers; therefore the present disclosure also encompasses all tautomeric forms.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford anti-virally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6):318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology*, 38:1282 (2003); *Biochem. Biophys. Res. Commun.*, 313:42 (2004); *J. Gastroenterol.*, 38:567 (2003)).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin inhibitors | Novartis |
| Debio-025 | | | Debiopharm |
| Zadaxin | | Immunomodulator | SciClone |
| Suvus | | Methylene blue | Bioenvision |
| Actilon (CPG10101) | | TLR9 agonist | Coley |

TABLE 1-continued

| Brand Name | Physiological Class | Type of Inhibitor or Target | Source Company |
|---|---|---|---|
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA/ Elan Pharmaceuticals Inc., New York, NY |
| Summetrel | Antiviral | Antiviral | Endo Pharmaceuticals Holdings Inc., Chadds Ford, PA |
| GS-9132 (ACH-806) | Antiviral | HCV inhibitor | Achillion/Gilead |
| Pyrazolopyrimidine compounds and salts From WO 2005/047288 26 May 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B replicase inhibitor | Wyeth/Viropharma |
| NM-283 | Antiviral | NS5B replicase inhibitor | Idenix/Novartis |
| GL-59728 | Antiviral | NS5B replicase inhibitor | Gene Labs/Novartis |
| GL-60667 | Antiviral | NS5B replicase inhibitor | Gene Labs/Novartis |
| 2'C MeA | Antiviral | NS5B replicase inhibitor | Gilead |
| PSI 6130 | Antiviral | NS5B replicase inhibitor | Roche |
| R1626 | Antiviral | NS5B replicase inhibitor | Roche |
| 2'C Methyl adenosine | Antiviral | NS5B replicase inhibitor | Merck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |
| Ribavirin | Antiviral | Ribavirin | Schering-Plough Corporation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH 503034 | Antiviral | Serine protease inhibitor | Schering-Plough |
| Zadazim | Immune modulator | Immune modulator | SciClone Pharmaceuticals Inc., San Mateo, CA |
| Ceplene | Immunomodulator | Immune modulator | Maxim Pharmaceuticals Inc., San Diego, CA |
| CELLCEPT ® | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon - α | Interferon | Albumin IFN-α2b | Human Genome Sciences Inc., Rockville, MD |

TABLE 1-continued

| Brand Name | Physiological Class | Type of Inhibitor or Target | Source Company |
|---|---|---|---|
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| REBIF ® | Interferon | IFN-β1a | Serono, Geneva, Switzerland |
| Roferon A | Interferon | IFN-α2a | F. Hoffmann-La Roche LTD., Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | Antifibrotic | Indevus Pharmaceuticals Inc., Lexington, MA |
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering-Plough |
| TMS-435 | Antiviral | Serine protease inhibitor | Tibotec BVBA, Mechelen, Belgium |
| BI-201335 | Antiviral | Serine protease inhibitor | Boehringer Ingelheim Pharma KG, Ingelheim, Germany |
| MK-7009 | Antiviral | Serine protease inhibitor | Merck |
| PF-00868554 | Antiviral | Replicase inhibitor | Pfizer |
| ANA598 | Antiviral | Non-Nucleoside NS5B polymerase inhibitor | Anadys Pharmaceuticals, Inc., San Diego, CA, USA |
| IDX375 | Antiviral | Non-Nucleoside replicase inhibitor | Idenix Pharmaceuticals, Cambridge, MA, USA |

TABLE 1-continued

| Brand Name | Physiological Class | Type of Inhibitor or Target | Source Company |
|---|---|---|---|
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |
| VCH-759 | Antiviral | NS5B polymerase inhibitor | Vir °Chem Pharma |
| VCH-916 | Antiviral | NS5B polymerase inhibitor | Vir °Chem Pharma |
| GS-9190 | Antiviral | NS5B polymerase inhibitor | Gilead |
| Peg-interferon lamda | Antiviral | Interferon | ZymoGenetics/ Bristol-Myers Squibb |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative examples which follow, are well-known to those skilled in the art. Some of the abbreviations used are as follows: ca. for about; min or mins for minutes; h or hr or hrs for hours; rt or RT for room temperature or retention time (context will dictate); $R_t$ for retention time; TFA for trifluoroacetic acid; DMSO for dimethylsulfoxide; Me for methyl; THF for tetrahydrofuran; t-Bu or t-Bu for tert-butyl; EDCI for 1-(3-dimethylaminopropyl)-3-ethylcarbodiimide hydrochloride; DMAP for 4-dimethylaminopyridine; DBU for 1,8-diazabicycloundec-7-ene; Ph for phenyl; DEA for diethylamine; Et for ethyl; DMF for N,N-dimethylformamide; OAc for acetate; HMDS for hexamethyldisilane; pTsOH for para-toluenesulfonic acid; iPr$_2$EtN, DIEA, or DIPEA for diisopropylethylamine; EtOAc or EtOAc or EA for ethyl acetate; Et$_3$SiH for triethylsilane; MeOH for methanol; TMSCHN$_2$ for trimethylsilyldiazomethane; H-D-Ser-OBzl.HCl for D-serine benzyl ester hydrochloride; EtOH for ethanol; Me$_2$S for dimethylsulfide; TEA or Et$_3$N for triethylamine; LiHMDS for lithium hexamethyldisilazide; DIBAL for diisobutylaluminum hydride; TBDMS-Cl for tert-butyldimethylsilyl chloride; i-PrOH for isopropanol; Boc, boc, or BOC for tert-butoxycarbonyl; Cbz-Cl for benzyl chloroformate; Bn for benzyl; DEAD for diethylazodicarboxylate; mCPBA for meta-chloroperoxybenzoic acid; DCM for dichloromethane; TMSCN for trimethylsilyl cyanide; ACN or MECN for acetonitrile; dpppe for 1,5-bis(diphenylphosphino)pentane; TMEDA for tetramethylethylenediamine; DMA for N,N-dimethylacetamide; MeOD for CD$_3$OD; Hex for hexanes; NaOEt for sodium ethoxide; MTBE for methyl tert butyl ether; NCS for N-chlorosuccinimide; Et$_2$O for diethyl ether; DME for 1,2-dimethoxyethane; and EEDQ for N-ethoxycarbonyl-2-ethoxy-1,2-dihydroquinoline.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Starting materials can be obtained from commercial sources or prepared by well-established literature methods known to those of ordinary skill in the art.

Synthesis of Common Caps

Compound Analysis Conditions

Purity assessment and low resolution mass analysis were conducted on a Shimadzu LC system coupled with Waters MICROMASS® ZQ MS system. It should be noted that retention times may vary slightly between machines. Additional LC conditions applicable to the current section, unless noted otherwise.

Cond.-MS-W1
Column=XTERRA® 3.0×50 mm S7
Start % B=0
Final % B=100
Gradient time=2 min
Stop time=3 min
Flow Rate=5 mL/min
Wavelength=220 nm
Solvent A=0.1% TFA in 10% methanol/90% H$_2$O
Solvent B=0.1% TFA in 90% methanol/10% H$_2$O
Cond.-MS-W2
Column=XTERRA® 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% H$_2$O
Solvent B=0.1% TFA in 90% methanol/10% H$_2$O
Cond.-MS-W5
Column=XTERRA® 3.0×50 mm S7
Start % B=0
Final % B=30

Gradient time=2 min
Stop time=3 min
Flow Rate=5 mL/min
Wavelength=220 nm
Solvent A=0.1% TFA in 10% methanol/90% H₂O
Solvent B=0.1% TFA in 90% methanol/10% H₂O
Cond.-D1
Column=XTERRA® C18 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% H₂O
Solvent B=0.1% TFA in 90% methanol/10% H₂O
Cond.-D2
Column=PHENOMENEX® Luna 4.6×50 mm S10
Start % B=0
Final % B=100
Gradient time=3 min
Stop time=4 min
Flow Rate=4 mL/min
Wavelength=220 nm
Solvent A=0.1% TFA in 10% methanol/90% H₂O
Solvent B=0.1% TFA in 90% methanol/10% H₂O
Cond.-M3
Column=XTERRA® C18 3.0×50 mm S7
Start % B=0
Final % B=40
Gradient time=2 min
Stop time=3 min
Flow Rate=5 mL/min
Wavelength=220 nm
Solvent A=0.1% TFA in 10% methanol/90% H₂O
Solvent B=0.1% TFA in 90% methanol/10% H₂O
Condition I
Column=PHENOMENEX® Luna 3.0×50 mm S10
Start % B=0
Final % B=100
Gradient time=2 min
Stop time=3 min
Flow Rate=4 mL/min
Wavelength=220 nm
Solvent A=0.1% TFA in 10% methanol/90% H₂O
Solvent B=0.1% TFA in 90% methanol/10% H₂O
Condition II
Column=PHENOMENEX® Luna 4.6×50 mm S10
Start % B=0
Final % B=100
Gradient time=2 min
Stop time=3 min
Flow Rate=5 mL/min
Wavelength=220 nm
Solvent A=0.1% TFA in 10% methanol/90% H₂O
Solvent B=0.1% TFA in 90% methanol/10% H₂O
Condition III
Column=XTERRA® C18 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% H₂O
Solvent B=0.1% TFA in 90% methanol/10% H₂O

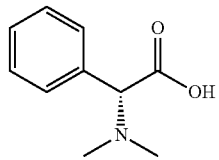

(R)-2-(Dimethylamino)-2-phenylacetic acid

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to H₂ (60 psi) for 3 hours. The reaction mixture was filtered through diatomaceous earth (CELITE®), and the filtrate was concentrated in vacuo. The resulting crude material was recrystallized from isopropanol to provide the HCl salt of Cap-1 as a white needle (4.0 g). Optical rotation: −117.1° [c=9.95 mg/mL in H₂O; λ=589 nm]. ¹H NMR (DMSO-$d_6$, δ=2.5 ppm, 500 MHz): δ 7.43-7.34 (m, 5H), 4.14 (s, 1H), 2.43 (s, 6H); LC (Condition I): RT=0.25; LC-MS: Anal. Calcd. for [M+H]⁺ $C_{10}H_{14}NO_2$ 180.10. found 180.17; HRMS: Anal. Calcd. for [M+H]⁺ $C_{10}H_{14}NO_2$ 180.1025. found 180.1017.

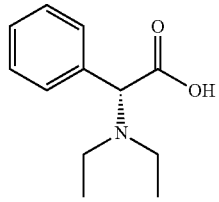

(R)-2-(Diethylamino)-2-phenylacetic acid

NaBH₃CN (6.22 g, 94 mmol) was added in portions over a few minutes to a cooled (ice/water) mixture of (R)-2-Phenylglycine (6.02 g, 39.8 mmol) and methanol (100 mL), and stirred for 5 minutes. Acetaldehyde (10 mL) was added dropwise over 10 minutes and stirring was continued at the same cooled temperature for 45 minutes and at ambient temperature for ~6.5 hours. The reaction mixture was cooled back with ice-water bath, treated with water (3 mL) and then quenched with a dropwise addition of concentrated HCl over ~45 minutes until the pH of the mixture was ~1.5-2.0. The cooling bath was removed and the stirring was continued while adding concentrated HCl in order to maintain the pH of the mixture around 1.5-2.0. The reaction mixture was stirred overnight, filtered to remove the white suspension, and the filtrate was concentrated in vacuo. The crude material was recrystallized from ethanol to afford the HCl salt of Cap-2 as a shining white solid in two crops (crop-1: 4.16 g; crop-2: 2.19 g). ¹H NMR (DMSO-$d_6$, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: $[\alpha]^{25}$-102.21° (c=0.357, H₂O); crop-2: $[\alpha]^{25}$−99.7° (c=0.357, H₂O). LC (Condition I): RT=0.43 min; LC-MS: Anal. Calcd. for [M+H]⁺ $C_{12}H_{18}NO_2$: 208.13. found 208.26.

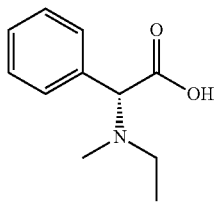

Cap-3

Acetaldehyde (5.0 mL, 89.1 mmol) and a suspension of 10% Pd/C (720 mg) in methanol/H$_2$O (4 mL/1 mL) was sequentially added to a cooled (~15° C.) mixture of (R)-2-phenylglycine (3.096 g, 20.48 mmol), 1N HCl (30 mL) and methanol (40 mL). The cooling bath was removed and the reaction mixture was stirred under a balloon of H$_2$ for 17 hours. An additional acetaldehyde (10 mL, 178.2 mmol) was added and stirring continued under H$_2$ atmosphere for 24 hours [Note: the supply of H$_2$ was replenished as needed throughout the reaction]. The reaction mixture was filtered through diatomaceous earth (CELITE®), and the filtrate was concentrated in vacuo. The resulting crude material was recrystallized from isopropanol to provide the HCl salt of (R)-2-(ethylamino)-2-phenylacetic acid as a shining white solid (2.846 g). $^1$H NMR (DMSO-d$_6$, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Condition I): RT=0.39 min; >95% homogeneity index; LC-MS: Anal. Calcd. for [M+H]$^+$ C$_{10}$H$_{14}$NO$_2$: 180.10. found 180.18.

A suspension of 10% Pd/C (536 mg) in methanol/H$_2$O (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL). The reaction mixture was stirred under a balloon of H$_2$ for ~72 hours, where the H$_2$ supply was replenished as needed. The reaction mixture was filtered through diatomaceous earth (CELITE®) and the filtrate was concentrated in vacuo. The resulting crude material was recrystallized from isopropanol (50 mL) to provide the HCl salt of Cap-3 as a white solid (985 mg). $^1$H NMR (DMSO-d$_6$, δ=2.5 ppm, 400 MHz): δ 10.48 (br s, 1H), 7.59-7.51 (m, 5H), 5.26 (s, 1H), 3.08 (app br s, 2H), 2.65 (br s, 3H), 1.24 (br m, 3H). LC (Condition I): RT=0.39 min; >95% homogeneity index; LC-MS: Anal. Calcd. for [M+H]$^+$ C$_{11}$H$_{16}$NO$_2$: 194.12. found 194.18; HRMS: Anal. Calcd. for [M+H]$^+$ C$_{11}$H$_{16}$NO$_2$: 194.1180. found 194.1181.

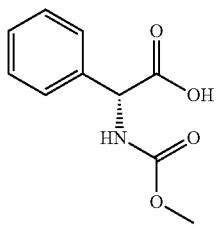

Cap-4

(R)-2-(Methoxycarbonylamino)-2-phenylacetic acid

ClCO$_2$Me (3.2 mL, 41.4 mmol) was added dropwise to a cooled (ice/water) THF (410 mL) semi-solution of (R)-tert-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated NaHCO$_3$ solution (30 mL), dried (MgSO$_4$), filtered, and concentrated in vacuo. The resultant colorless oil was triturated from hexanes, filtered and washed with hexanes (100 mL) to provide (R)-tert-butyl 2-(methoxycarbonylamino)-2-phenylacetate as a white solid (7.7 g). $^1$H NMR (DMSO-d$_6$, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Condition I): RT=1.53 min; ~90% homogeneity index; LC-MS: Anal. Calcd. for [M+Na]$^+$ C$_{14}$H$_{19}$NNaO$_4$: 288.12. found 288.15.

TFA (16 mL) was added dropwise to a cooled (ice/water) CH$_2$Cl$_2$ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: −176.9° [c=3.7 mg/mL in H$_2$O; λ=589 nm]. $^1$H NMR (DMSO-d$_6$, δ=2.5 ppm, 400 MHz): δ 12.84 (br s, 1H), 7.96 (d, J=8.3, 1H), 7.41-7.29 (m, 5H), 5.14 (d, J=8.3, 1H), 3.55 (s, 3H). LC (Condition I): RT=1.01 min; >95% homogeneity index; LC-MS: Anal. Calcd. for [M+H]$^+$ C$_{10}$H$_{12}$NO$_4$ 210.08. found 210.17; HRMS: Anal. Calcd. for [M+H]$^+$ C$_{10}$H$_{12}$NO$_4$ 210.0766. found 210.0756.

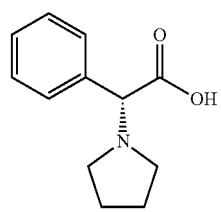

Cap-5

A mixture of (R)-2-phenylglycine (1.0 g, 6.62 mmol), 1,4-dibromobutane (1.57 g, 7.27 mmol) and Na$_2$CO$_3$ (2.10 g, 19.8 mmol) in ethanol (40 mL) was heated at 100° C. for 21 hours. The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). $^1$H NMR (DMSO-d$_6$, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H); RT=0.30 minutes (Condition I); >98% homogeneity index; LC-MS: Anal. Calcd. for [M+H]$^+$ C$_{12}$H$_{16}$NO$_2$: 206.12. found 206.25.

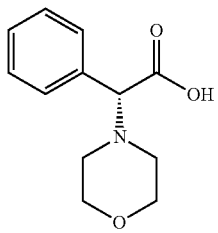

Cap-6

The TFA salt of Cap-6 was synthesized from (R)-2-phenylglycine and 1-bromo-2-(2-bromoethoxy)ethane by using the method of preparation of Cap-5. $^1$H NMR (DMSO-d$_6$, δ=2.5, 500 MHz) δ 12.20 (br s, 1H), 7.50 (m, 5H), 4.92 (s, 1H), 3.78 (app br s, 4H), 3.08 (app br s, 2H), 2.81 (app br s, 2H); RT=0.32 minutes (Condition I); >98%; LC-MS: Anal. Calcd. for [M+H]$^+$ C$_{12}$H$_{16}$NO$_3$: 222.11. found 222.20; HRMS: Anal. Calcd. for [M+H]$^+$ C$_{12}$H$_{16}$NO$_3$: 222.1130. found 222.1121.

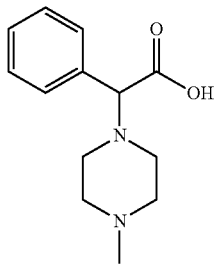

Cap-7

Cap-7a: enantiomer-1
Cap-7b: enantiomer-2

A CH$_2$Cl$_2$ (200 mL) solution of p-toluenesulfonyl chloride (8.65 g, 45.4 mmol) was added dropwise to a cooled (~5° C.) CH$_2$Cl$_2$ (200 mL) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried (MgSO$_4$), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. $^1$H NMR (DMSO-d$_6$, δ=2.5, 500 MHz) δ 7.78 (d, J=8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Condition III); >90% homogeneity index; LC-MS: Anal. Calcd. for [M+H]$^+$ C$_{22}$H$_{20}$NaO$_5$S: 419.09. found 419.04.

A THF (75 mL) solution of benzyl 2-phenyl-2-(tosyloxy)acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried (MgSO$_4$), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (CHIRALCEL® OD-H) indicated that the sample is a mixture of stereoisomers in a 38.2 to 58.7 ratio. The separation of the stereoisomers were effected as follow: the product was dissolved in 120 mL of ethanol/heptane (1:1) and injected (5 mL/injection) on chiral HPLC column (Chiracel OJ, 5 cm ID×50 cm L, 20 μm) eluting with 85:15 Heptane/ethanol at 75 mL/min, and monitored at 220 nm. Stereoisomer-1 (1.474 g) and stereoisomer-2 (2.2149 g) were retrieved as viscous oil. $^1$H NMR (CDCl$_3$, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Condition III); >98% homogeneity index; LC-MS: Anal. Calcd. for [M+H]$^+$ C$_{20}$H$_{25}$N$_2$O$_2$: 325.19. found 325.20.

A methanol (10 mL) solution of either stereoisomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 minutes. Immediately after the completion of the reaction, the catalyst was filtered through diatomaceous earth (CELITE®) and the filtrate was concentrated in vacuo to provide Cap-7, contaminated with phenylacetic acid as a tan foam (867.6 mg; mass is above the theoretical yield). The product was used for the next step without further purification. $^1$H NMR (DMSO-d$_6$, δ=2.5, 500 MHz) δ 7.44-7.37 (m, 2H), 7.37-7.24 (m, 3H), 3.92 (s, 1H), 2.63-2.48 (app. br s, 2H), 2.48-2.32 (m, 6H), 2.19 (s, 3H); RT=0.31 (Condition II); >90% homogeneity index; LC-MS: Anal. Calcd. for [M+H]$^+$ C$_{13}$H$_{19}$N$_2$O$_2$: 235.14. found 235.15; HRMS: Anal. Calcd. for [M+H]$^+$ C$_{13}$H$_{16}$N$_2$O$_2$: 235.1447. found 235.1440.

The synthesis of Cap-8 and Cap-9 was conducted according to the synthesis of Cap-7 by using appropriate amines for the SN$_2$ displacement step (i.e., 4-hydroxypiperidine for Cap-8 and (S)-3-fluoropyrrolidine for Cap-9) and modified conditions for the separation of the respective stereoisomeric intermediates, as described below.

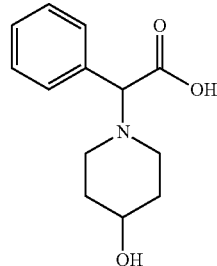

Cap-8

8a: enantiomer-1
8b: enantiomer-2

The stereoisomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 μm) eluting with 80:20 heptane/ethanol at 10 mL/min, monitored at 220 nm, to provide 186.3 mg of stereoisomer-1 and 209.1 mg of stereoisomer-2 as light-yellow viscous oils. These benzyl ester was hydrogenolysed according to the preparation of Cap-7 to provide Cap-8: ¹H NMR (DMSO-d$_6$, δ=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 2H), 1.70 (m, 2H), 1.42 (m, 2H). RT=0.28 (Condition II); >98% homogeneity index; LC-MS: Anal. Calcd. for [M+H]⁺ C$_{13}$H$_{18}$NO$_3$: 236.13. found 236.07; HRMS: Calcd. for [M+H]⁺ C$_{13}$H$_{18}$NO$_3$: 236.1287. found 236.1283.

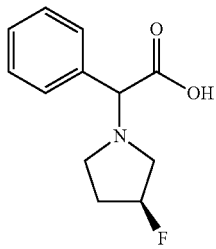

Cap-9

9a: diastereomer-1
9b: diastereomer-2

The diastereomeric separation of the intermediate benzyl 2-((S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 μm) eluting with 95% CO$_2$/5% methanol with 0.1% TFA, at 10 bar pressure, 70 mL/min flow rate, and a temperature of 35° C. The HPLC elute for the respective stereoisomers was concentrated, and the residue was dissolved in CH$_2$Cl$_2$ (20 mL) and washed with an aqueous medium (10 mL water+1 mL saturated NaHCO$_3$ solution). The organic phase was dried (MgSO$_4$), filtered, and concentrated in vacuo to provide 92.5 mg of fraction-1 and 59.6 mg of fraction-2. These benzyl esters were hydrogenolysed according to the preparation of Cap-7 to prepare Cap-9a and Cap-9b. Cap-9a (diastereomer-1; the sample is a TFA salt as a result of purification on a reverse phase HPLC using H$_2$O/methanol/TFA solvent): ¹H NMR (DMSO-d$_6$, δ=2.5, 400 MHz) 7.55-7.48 (m, 5H), 5.38 (d of m, J=53.7, 1H), 5.09 (br s, 1H), 3.84-2.82 (br m, 4H), 2.31-2.09 (m, 2H). RT=0.42 (Condition I); >95% homogeneity index; LC-MS: Anal. Calcd. for [M+H]⁺ C$_{12}$H$_{15}$FNO$_2$: 224.11. found 224.14; Cap-9b (diastereomer-2): ¹H NMR (DMSO-d$_6$, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Condition I); LC-MS: Anal. Calcd. for [M+H]⁺ C$_{12}$H$_{15}$FNO$_2$: 224.11. found 224.14.

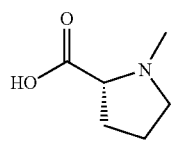

Cap-10

To a solution of D-proline (2.0 g, 17 mmol) and formaldehyde (2.0 mL of 37% wt. in H$_2$O) in methanol (15 mL) was added a suspension of 10% Pd/C (500 mg) in methanol (5 mL). The mixture was stirred under a balloon of hydrogen for 23 hours. The reaction mixture was filtered through diatomaceous earth (CELITE®) and concentrated in vacuo to provide Cap-10 as an off-white solid (2.15 g). ¹H NMR (DMSO-d$_6$, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Condition II); >98% homogeneity index; LC-MS: Anal. Calcd. for [M+H]⁺ C$_6$H$_{12}$NO$_2$: 130.09. found 129.96.

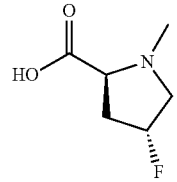

Cap-11

A mixture of (2S,4R)-4-fluoropyrrolidine-2-carboxylic acid (0.50 g, 3.8 mmol), formaldehyde (0.5 mL of 37% wt. in H$_2$O), 12 N HCl (0.25 mL) and 10% Pd/C (50 mg) in methanol (20 mL) was stirred under a balloon of hydrogen for 19 hours. The reaction mixture was filtered through diatomaceous earth (CELITE®) and the filtrate was concentrated in vacuo. The residue was recrystallized from isopropanol to provide the HCl salt of Cap-11 as a white solid (337.7 mg). ¹H NMR (DMSO-d$_6$, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26 (m, 1H). RT=0.28 (Condition II); >98% homogeneity index; LC-MS: Anal. Calcd. for [M+H]⁺ C$_6$H$_{11}$FNO$_2$: 148.08. found 148.06.

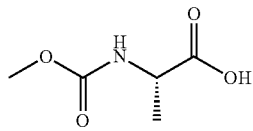

Cap-12 (same as Cap-52)

(S)-2-(Methoxycarbonylamino)propanoic acid

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH ~2-3. The resulting solutions was extracted with ethyl acetate (3×100 mL), and the combined organic phase was dried (Na$_2$SO$_4$), filtered, and concentrated in vacuo to provide a colorless oil (2.58 g). 500 mg of this material was purified by a reverse phase HPLC (H$_2$O/methanol/TFA) to provide 150 mg of Cap-12 as a colorless oil. ¹H NMR (DMSO-d$_6$, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

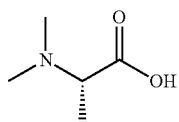

Cap-13

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (CELITE®) and the filtrate was concentrated in vacuo to provide the HCl salt of Cap-13 as an oil which solidified upon standing under vacuum (4.4 g; the mass is above theoretical yield). The product was used without further purification. $^1$H NMR (DMSO-$d_6$, δ=2.5, 500 MHz) δ 12.1 (br s, 1H), 4.06 (q, J=7.4, 1H), 2.76 (s, 6H), 1.46 (d, J=7.3, 3H).

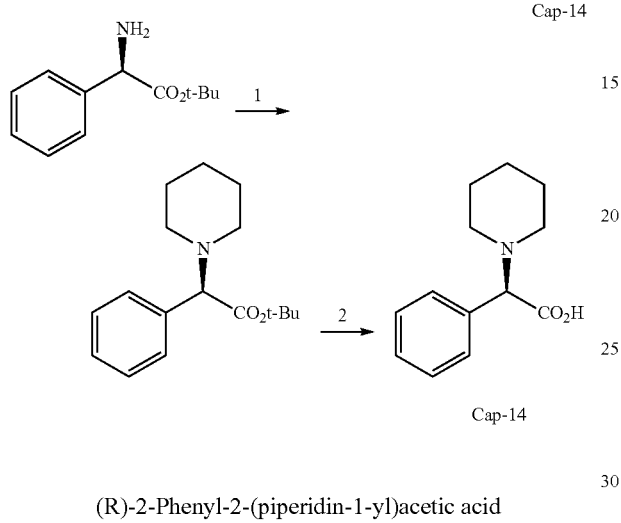

(R)-2-Phenyl-2-(piperidin-1-yl)acetic acid

Step 1: A mixture of (R)-(−)-D-phenylglycine tert-butyl ester (3.00 g, 12.3 mmol), NaBH$_3$CN (0.773 g, 12.3 mmol), KOH (0.690 g, 12.3 mmol) and acetic acid (0.352 mL, 6.15 mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried (MgSO$_4$), filtered and concentrated to dryness to provide a clear oil. This material was purified by reverse-phase preparative HPLC (Primesphere C-18, 30×100 mm; CH$_3$CN—H$_2$O-0.1% TFA) to give the intermediate ester (2.70 g, 56%) as a clear oil. $^1$H NMR (400 MHz, CDCl$_3$) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2 Hz, 1H), 2.59 (t, J=11.4 Hz, 1H), 2.07-2.02 (m, 2H), 1.82 (d, J=1.82 Hz, 3H), 1.40 (s, 9H). LC-MS: Anal. Calcd. for C$_{17}$H$_{25}$NO$_2$: 275. found: 276 (M+H)$^+$.

Step 2: To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; CH$_3$CN—H$_2$O-0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$H NMR (DMSO-$d_6$) δ 7.50 (s, 5H), 5.13 (s, 1H), 3.09 (br s, 2H), 2.92-2.89 (m, 2H), 1.74 (m, 4H), 1.48 (br s, 2H). LC-MS: Anal. Calcd. for C$_{13}$H$_{17}$NO$_2$: 219. found: 220 (M+H)$^+$.

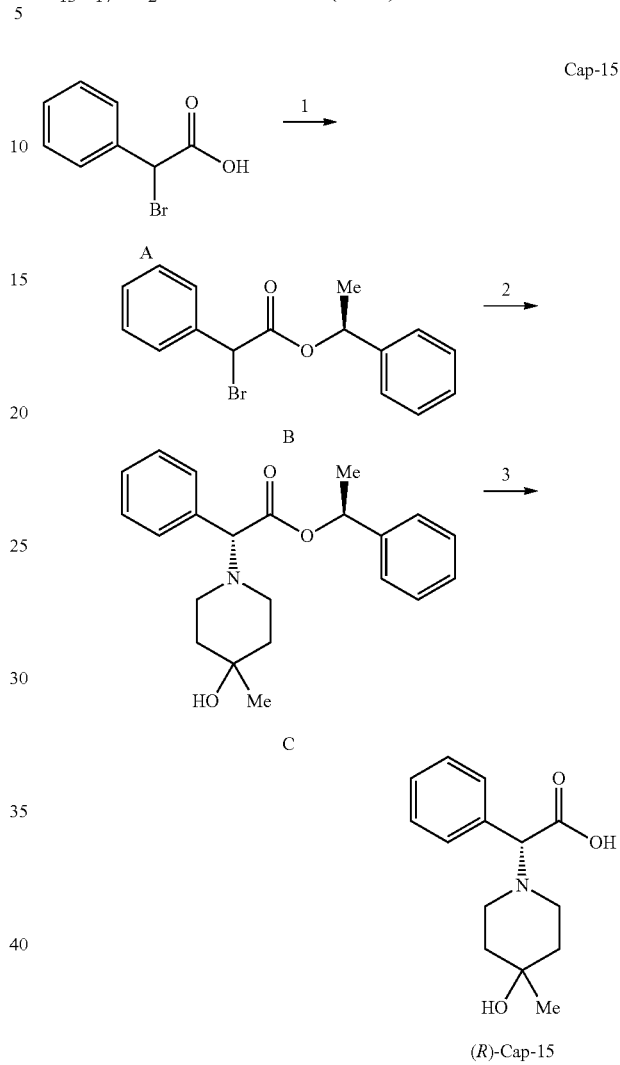

Step 1: (S)-1-Phenylethyl 2-bromo-2-phenylacetate. To a mixture of α-bromophenylacetic acid (10.75 g, 0.050 mol), (S)-(−)-1-phenylethanol (7.94 g, 0.065 mol) and DMAP (0.61 g, 5.0 mmol) in dry dichloromethane (100 mL) was added solid EDCI (12.46 g, 0.065 mol) all at once. The resulting solution was stirred at room temperature under Ar for 18 hours and then it was diluted with ethyl acetate, washed (H$_2$O×2, brine), dried (Na$_2$SO$_4$), filtered, and concentrated to give a pale yellow oil. Flash chromatography (SiO$_2$/hexane-ethyl acetate, 4:1) of this oil provided the title compound (11.64 g, 73%) as a white solid. $^1$H NMR (400 MHz, CDCl$_3$) δ 7.53-7.17 (m, 10H), 5.95 (q, J=6.6 Hz, 0.5H), 5.94 (q, J=6.6 Hz, 0.5H), 5.41 (s, 0.5H), 5.39 (s, 0.5H), 1.58 (d, J=6.6 Hz, 1.5H), 1.51 (d, J=6.6 Hz, 1.5H).

Step 2: (S)-1-Phenylethyl(R)-2-(4-hydroxy-4-methylpiperidin-1-yl)-2-phenylacetate. To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 mL) was added. The mixture was stirred for 1 hour at room temperature and then it was heated at 55-60° C. (oil bath temperature) for 4 hours. The cooled reaction mixture was then diluted with ethyl acetate (30 mL), washed (H₂O×2, brine), dried (MgSO₄), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid. (S,R)-isomer: ¹H NMR (CD₃OD) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), 1.71-1.49 (m, 4H), 1.38 (d, J=6.6 Hz, 3H), 1.18 (s, 3H). LC-MS: Anal. Calcd. for C₂₂H₂₇NO₃: 353. found: 354 (M+H)⁺. (S,S)-isomer: ¹H NMR (CD₃OD) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LC-MS: Anal. Calcd. for C₂₂H₂₇NO₃: 353. found: 354 (M+H)⁺.

Step 3: (R)-2-(4-Hydroxy-4-methylpiperidin-1-yl)-2-phenylacetic acid. To a solution of (S)-1-phenylethyl(R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; CH₃CN—H₂O-0.1% TFA) to give the title compound (as TFA salt) as a pale bluish solid (0.128 g, 98%). LC-MS: Anal. Calcd. for C₁₄H₁₉NO₃: 249. found: 250 (M+H)⁺.

and concentrated in vacuo. The residue was purified by silica gel chromatography (BIOTAGE®/0-20% ethyl acetate-hexane) to provide the title compound as a colorless oil (8.38 g, 92%). ¹H NMR (400 MHz, CD₃OD) δ 7.32-7.23 (m, 7H), 7.10-7.04 (m, 2), 5.85 (q, J=6.5 Hz, 1H), 3.71 (s, 2H), 1.48 (d, J=6.5 Hz, 3H).

Step 2: (R)—((S)-1-Phenylethyl) 2-(2-fluorophenyl)-2-(piperidin-1-yl)acetate. To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of CBr₄ (13.5 g, 40.7 mmol) in THF (100 mL) was added and the mixture was allowed to warm to −10° C. and stirred at this temperature for 2 hours. The reaction mixture was quenched with saturated aq. NH₄Cl and the layers were separated. The aqueous layer was back-extracted with ethyl acetate (2×) and the combined organic phases were washed (H₂O, brine), dried (Na₂SO₄), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (BIOTAGE®/0-30% diethyl ether-hexane) to provide a pure mixture of diastereomers (2:1 ratio by ¹H NMR) as a yellow oil (2.07 g, 31%), along with unreacted starting material (2.53 g, 51%). Further chromatography of the diastereomeric mixture (BIOTAGE®/0-10% diethyl ether-toluene) provided the title compound as a colorless oil (0.737 g, 11%). ¹H NMR (400 MHz, CD₃OD) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LC-MS: Anal. Calcd. for C₂₁H₂₄FNO₂: 341. found: 342 (M+H)⁺.

Step 3: (R)-2-(2-Fluorophenyl)-2-(piperidin-1-yl)acetic acid. A mixture of (R)—((S)-1-phenylethyl) 2-(2-fluorophenyl)-2-(piperidin-1-yl)acetate (0.737 g, 2.16 mmol) and 20% Pd(OH)₂/C (0.070 g) in ethanol (30 mL) was hydrogenated at room temperature and atmospheric pressure (H₂ balloon) for 2 hours. The solution was then purged with Ar, filtered through diatomaceous earth (CELITE®), and concentrated in vacuo. This provided the title compound as a colorless solid (0.503 g, 98%). ¹H NMR (400 MHz, CD₃OD) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LC-MS: Anal. Calcd. for C₁₃H₁₆FNO₂: 237. found: 238 (M+H)⁺.

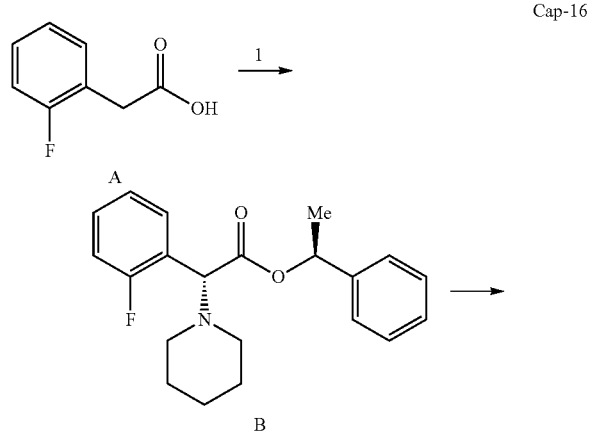

Cap-16

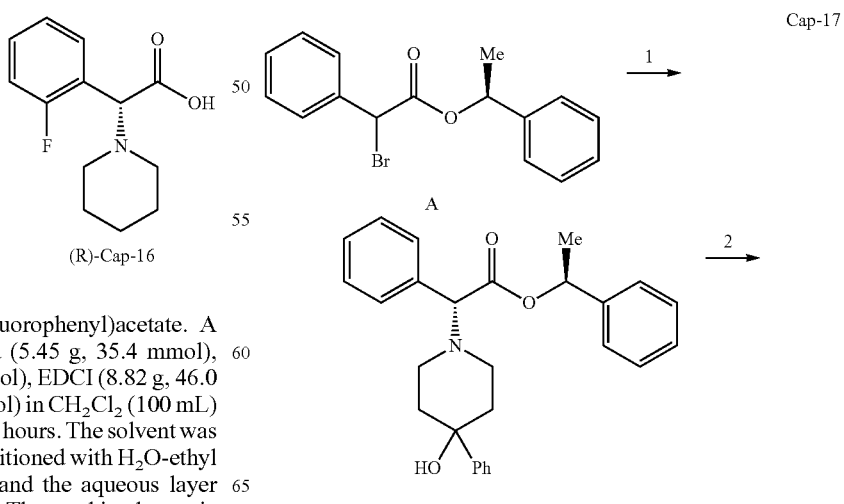

Cap-17

Step 1: (S)-1-Phenylethyl 2-(2-fluorophenyl)acetate. A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in CH₂Cl₂ (100 mL) was stirred at room temperature for 12 hours. The solvent was then concentrated and the residue partitioned with H₂O-ethyl acetate. The phases were separated and the aqueous layer back-extracted with ethyl acetate (2×). The combined organic phases were washed (H₂O, brine), dried (Na₂SO₄), filtered,

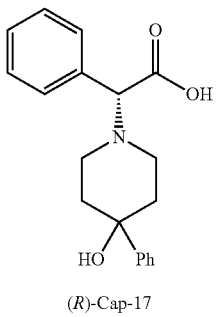

(R)-Cap-17

Step 1: (S)-1-Phenylethyl(R)-2-(4-hydroxy-4-phenylpiperidin-1-yl)-2-phenylacetate. To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed ($H_2O \times 2$, brine), dried ($MgSO_4$), filtered and concentrated. The residue was purified on a silica gel column (0-60% ethyl acetate-hexane) to provide an approximately 2:1 mixture of diastereomers, as judged by $^1$H NMR. Separation of these isomers was performed using supercritical fluid chromatography (CHIRALCEL® OJ-H, 30×250 mm; 20% ethanol in $CO_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$H NMR (400 MHz, $CD_3OD$) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LC-MS: Anal. Calcd. for $C_{27}H_{29}NO_3$: 415. found: 416 (M+H)$^+$; (S,S)-isomer: H$^1$NMR (400 MHz, $CD_3OD$) δ 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=11.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LC-MS: Anal. Calcd. for $C_{27}H_{29}NO_3$: 415. found: 416 (M+H)$^+$.

The following esters were prepared in similar fashion:

| Intermediate-17a | | |
|---|---|---|
| 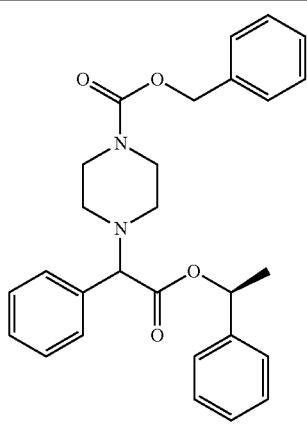 | Diastereomer 1: $^1$H NMR(500 MHz, DMSO-$d_6$) δ ppm 1.36(d, J = 6.41 Hz, 3H) 2.23-2.51 (m, 4H) 3.35(s, 4H) 4.25(s, 1H) 5.05(s, 2H) 5.82(d, J = 6.71 Hz, 1H) 7.15-7.52(m, 15H). LC-MS: Anal. Calcd. for: $C_{28}H_{30}N_2O_4$ 458.22; found: 459.44(M + H)$^+$. Diasteromer 2: $^1$H NMR(500 MHz, DMSO-$d_6$) δ ppm 1.45(d, J = 6.71 Hz, 3H) 2.27-2.44 (m, 4H) 3.39(s, 4H) 4.23(s, 1H) 5.06(s, 2H) 5.83(d, J = 6.71 Hz, 1H) 7.12(dd, J = 6.41, 3.05 Hz, 2H) 7.19-7.27(m, 3H) 7.27-7.44(m, 10H). LC-MS: Anal. Calcd. for: $C_{28}H_{30}N_2O_4$ 458.22; found: 459.44(M + H)$^+$. | |

| Intermediate-17b | | |
|---|---|---|
| 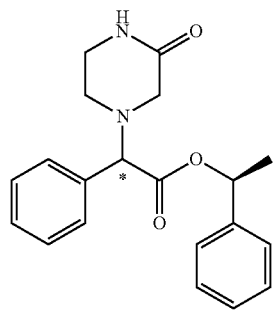 [SMILES: C[C@H](OC(=O)C(c1ccccc1)N1CCNC(=O)C1)c1ccccc1] | Diastereomer 1: RT = 11.76 minutes (Condition II); LC-MS: Anal. Calcd. for: $C_{20}H_{22}N_2O_3$ 338.16; found: 339.39(M + H)$^+$. Diastereomer 2: RT = 10.05 minutes (Condition II). LC-MS: Anal. Calcd. for: $C_{20}H_{22}N_2O_3$ 338.16; found: 339.39(M + H)$^+$. | |

| | | |
|---|---|---|
| Intermediate-17c | 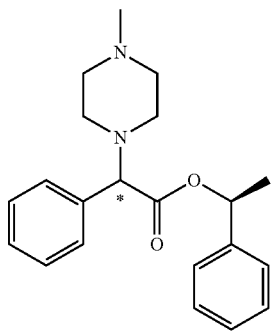 [SMILES: C[C@H](OC(=O)C(c1ccccc1)N1CCN(C)CC1)c1ccccc1] | Diastereomer 1: $T_R$ = 4.55 minutes(Condition I); LC-MS: Anal. Calcd. for: $C_{21}H_{26}N_2O_2$ 338.20; found: 339.45(M + H)$^+$. Diastereomer 2: $T_R$ = 6.00 minutes(Condition I). LC-MS: Anal. Calcd. for: $C_{21}H_{26}N_2O_2$ 338.20; found: 339.45(M + H)$^+$. |
| Intermediate-17d | 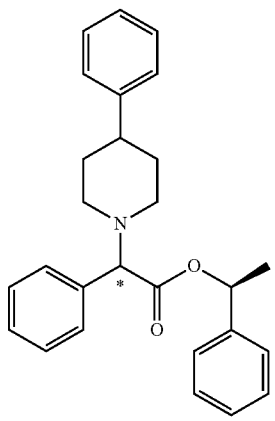 [SMILES: C[C@H](OC(=O)C(c1ccccc1)N1CCC(c2ccccc2)CC1)c1ccccc1] | Diastereomer 1: RT = 7.19 minutes(Condition I); LC-MS: Anal. Calcd. for: $C_{27}H_{29}NO_2$ 399.22; found; 400.48(M + H)$^+$. Diastereomer 2: RT = 9.76 minutes(Condition I); LC-MS: Anal. Calcd. for: $C_{27}H_{29}NO_2$ 399.22; found: 400.48(M + H)$^+$. |

Chiral SFC Conditions for determining retention time:
Condition I
Column: CHIRALPAK® AD-H Column, 4.62×50 mm, 5 μm
Solvents: 90% $CO_2$-10% methanol with 0.1% DEA
Temp: 35° C.
Pressure: 150 bar
Flow rate: 2.0 mL/min.
UV monitored at 220 nm
Injection: 1.0 mg/3 mL methanol
Condition II
Column: CHIRALCEL® OD-H Column, 4.62×50 mm, 5 μm
Solvents: 90% $CO_2$-10% methanol with 0.1% DEA
Temp: 35° C.
Pressure: 150 bar
Flow rate: 2.0 mL/min.
UV monitored at 220 nm
Injection: 1.0 mg/mL methanol Cap-17, Step 2: (R)-2-(4-Hydroxy-4-phenylpiperidin-1-yl)-2-phenylacetic acid. To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a white solid (0.230 g, 88%). LC-MS: Anal. Calcd. for $C_{19}H_{21}NO_3$: 311.15. found: 312 (M+H)$^+$.

The following carboxylic acids were prepared in optically pure form in a similar fashion:

| | | |
|---|---|---|
| Cap-17a | 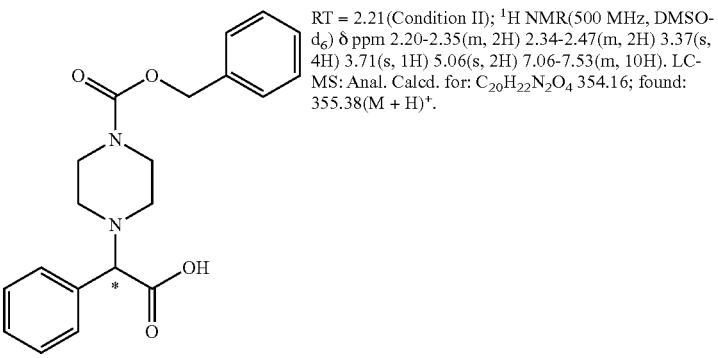 | RT = 2.21(Condition II); $^1$H NMR(500 MHz, DMSO-$d_6$) δ ppm 2.20-2.35(m, 2H) 2.34-2.47(m, 2H) 3.37(s, 4H) 3.71(s, 1H) 5.06(s, 2H) 7.06-7.53(m, 10H). LC-MS: Anal. Calcd. for: $C_{20}H_{22}N_2O_4$ 354.16; found: 355.38(M + H)$^+$. |

| | | |
|---|---|---|
| Cap-17b |  | RT = 0.27(Condition III); LC-MS: Anal. Calcd. for: $C_{12}H_{14}N_2O_3$ 234.10; found: 235.22(M + H)$^+$. |
| Cap-17c |  | RT = 0.48(Condition II); LC-MS: Anal. Calcd. for: $C_{13}H_{18}N_2O_2$ 234.14; found: 235.31(M + H)$^+$. |
| Cap-17d | 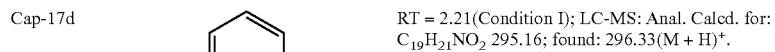 | RT = 2.21(Condition I); LC-MS: Anal. Calcd. for: $C_{19}H_{21}NO_2$ 295.16; found: 296.33(M + H)$^+$. |

LC-MS Conditions for determining retention time:
Condition I
Column: PHENOMENEX® Luna 4.6×50 mm S10
Start % B=0
Final % B=100
Gradient Time=4 min
Flow Rate=4 mL/min
Wavelength=220
Solvent A=10% methanol-90% H$_2$O-0.1% TFA
Solvent B=90% methanol-10% H$_2$O-0.1% TFA
Condition II
Column: Waters SunFire 4.6×50 mm S5
Start % B=0
Final % B=100
Gradient Time=2 min
Flow Rate=4 mL/min
Wavelength=220
Solvent A=10% methanol-90% H$_2$O-0.1% TFA
Solvent B=90% methanol-10% H$_2$O-0.1% TFA
Condition III
Column: PHENOMENEX® 10µ, 3.0×50 mm
Start % B=0
Final % B=100
Gradient Time=2 min
Flow Rate=4 mL/min
Wavelength=220
Solvent A=10% methanol-90% H$_2$O-0.1% TFA
Solvent B=90% methanol-10% H$_2$O-0.1% TFA

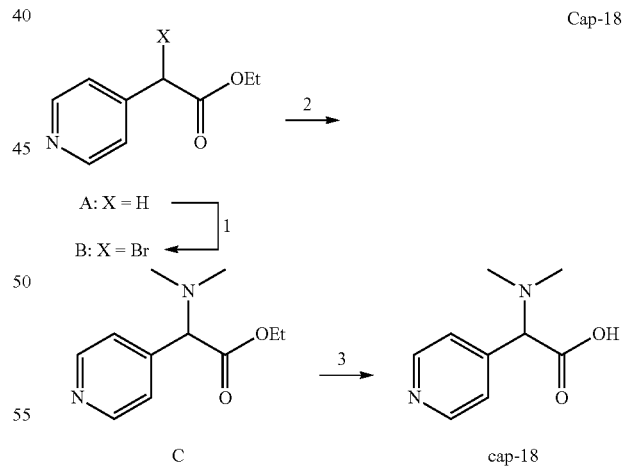

Step 1: (R,S)-Ethyl 2-(4-pyridyl)-2-bromoacetate. To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to −78° C. To this mixture was added CBr$_4$ (2.21 g, 6.66 mmol) and stirring was continued at −78° C. for 2 hours. The reaction mixture was then quenched with sat. aq. NH$_4$Cl and the phases were separated. The organic phase was washed (brine), dried (Na₂SO₄), filtered, and concentrated in vacuo. The resulting yellow oil was immediately purified by flash chromatography (SiO₂/hexane-ethyl acetate, 1:1) to provide the title compound (1.40 g, 95%) as a somewhat unstable yellow oil. $^1$H NMR (400 MHz, CDCl₃) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LC-MS: Anal. Calcd. for C₉H₁₀BrNO₂: 242, 244. found: 243, 245 (M+H)⁺.

Step 2: (R,S)-Ethyl 2-(4-pyridyl)-2-(N,N-dimethylamino) acetate. To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by thin layer chromatography) the volatiles were removed in vacuo and the residue was purified by flash chromatography (BIOTAGE®, 40+M SiO₂ column; 50%-100% ethyl acetate-hexane) to provide the title compound (0.539 g, 31%) as a light yellow oil. $^1$H NMR (400 MHz, CDCl₃) δ 8.58 (d, J=6.0 Hz, 2H), 7.36 (d, J=6.0 Hz, 2H), 4.17 (m, 2H), 3.92 (s, 1H), 2.27 (s, 6H), 1.22 (t, J=7.0 Hz). LC-MS: Anal. Calcd. for C₁₁H₁₆N₂O₂: 208. found: 209 (M+H)⁺.

Step 3: (R,S)-2-(4-Pyridyl)-2-(N,N-dimethylamino)acetic acid. To a solution of (R,S)-ethyl 2-(4-pyridyl)-2-(N,N-dimethylamino)acetate (0.200 g, 0.960 mmol) in a mixture of THF-methanol-H₂O (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. $^1$H NMR (400 MHz, DMSO-d₆) δ 8.49 (d, J=5.7 Hz, 2H), 7.34 (d, J=5.7 Hz, 2H), 3.56 (s, 1H), 2.21 (s, 6H).

The following examples were prepared in similar fashion using the method described above:

| | | |
|---|---|---|
| Cap-19 | 3-pyridyl-CH(NMe₂)-CO₂H | LC-MS: Anal. Calcd. for C₉H₁₂N₂O₂: 180; found: 181(M + H)⁺. |
| Cap-20 | 2-pyridyl-CH(NMe₂)-CO₂H | LC-MS: no ionization. $^1$H NMR(400 MHz, CD₃OD) δ 8.55(d, J = 4.3 Hz, 1H), 7.84(app t, J = 5.3 Hz, 1H), 7.61(d, J = 7.8 Hz, 1H), 7.37(app t, J = 5.3 Hz, 1H), 4.35(s, 1H), 2.60(s, 6H). |
| Cap-21 | 6-chloro-3-pyridyl-CH(NMe₂)-CO₂H | LC-MS: Anal. Calcd. for C₉H₁₁ClN₂O₂: 214, 216; found: 215, 217(M + H)⁺. |
| Cap-22 | 4-nitrophenyl-CH(NMe₂)-CO₂H | LC-MS: Anal. Calcd. for C₁₀H₁₂N₂O₄: 224; found: 225(M + H)⁺. |
| Cap-23 | 1-naphthyl-CH(NMe₂)-CO₂H | LC-MS: Anal. Calcd. for C₁₄H₁₅NO₂: 229; found: 230(M + H)⁺. |
| Cap-24 | 3-trifluoromethylphenyl-CH(NMe₂)-CO₂H | LC-MS: Anal. Calcd. for C₁₁H₁₂F₃NO₂: 247; found: 248(M + H)⁺. |

| | | -continued |
|---|---|---|
| Cap-25 | 2-(trifluoromethyl)phenyl-CH(NMe₂)-CO₂H | LC-MS: Anal. Calcd. for $C_{11}H_{12}F_3NO_2$: 247; found: 248(M + H)⁺. |
| Cap-26 | 2-fluorophenyl-CH(NMe₂)-CO₂H | LC-MS: Anal. Calcd. for $C_{10}H_{12}FNO_2$: 197; found: 198(M + H)⁺. |
| Cap-27 | 3-fluorophenyl-CH(NMe₂)-CO₂H | LC-MS: Anal. Calcd. for $C_{10}H_{12}FNO_2$: 247; found: 248(M + H)⁺. |
| Cap-28 | 3-chlorophenyl-CH(NMe₂)-CO₂H | LC-MS: Anal. Calcd. for $C_{10}H_{12}ClNO_2$: 213; found: 214(M + H)⁺. |
| Cap-29 | 2-chlorophenyl-CH(NMe₂)-CO₂H | LC-MS: Anal. Calcd. for $C_{10}H_{12}ClNO_2$: 213; found: 214(M + H)⁺. |
| Cap-30 | 4-chlorophenyl-CH(NMe₂)-CO₂H | LC-MS: Anal. Calcd. for $C_{10}H_{12}ClNO_2$: 213; found: 214(M + H)⁺. |
| Cap-31 | 2-methylthiazol-4-yl-CH(NMe₂)-CO₂H | LC-MS: Anal. Calcd. for $C_8H_{12}N_2O_2S$: 200; found: 201(M + H)⁺. |
| Cap-32 | thiophen-2-yl-CH(NMe₂)-CO₂H | LC-MS: Anal. Calcd. for $C_8H_{11}NO_2S$: 185; found: 186(M + H)⁺. |
| Cap-33 | thiophen-3-yl-CH(NMe₂)-CO₂H | LC-MS: Anal. Calcd. for $C_8H_{11}NO_2S$: 185; found: 186(M + H)⁺. |
| Cap-34 | benzo[d]isoxazol-3-yl-CH(NMe₂)-CO₂H | LC-MS: Anal. Calcd. for $C_{11}H_{12}N_2O_3$: 220; found: 221(M + H)⁺. |

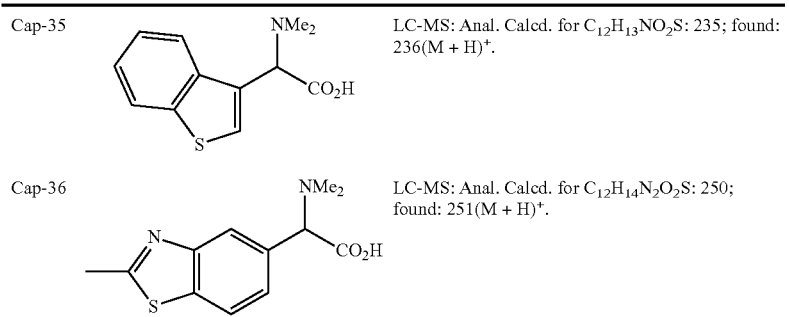

| Cap-35 | | LC-MS: Anal. Calcd. for $C_{12}H_{13}NO_2S$: 235; found: 236(M + H)⁺. |
| --- | --- | --- |
| Cap-36 | | LC-MS: Anal. Calcd. for $C_{12}H_{14}N_2O_2S$: 250; found: 251(M + H)⁺. |

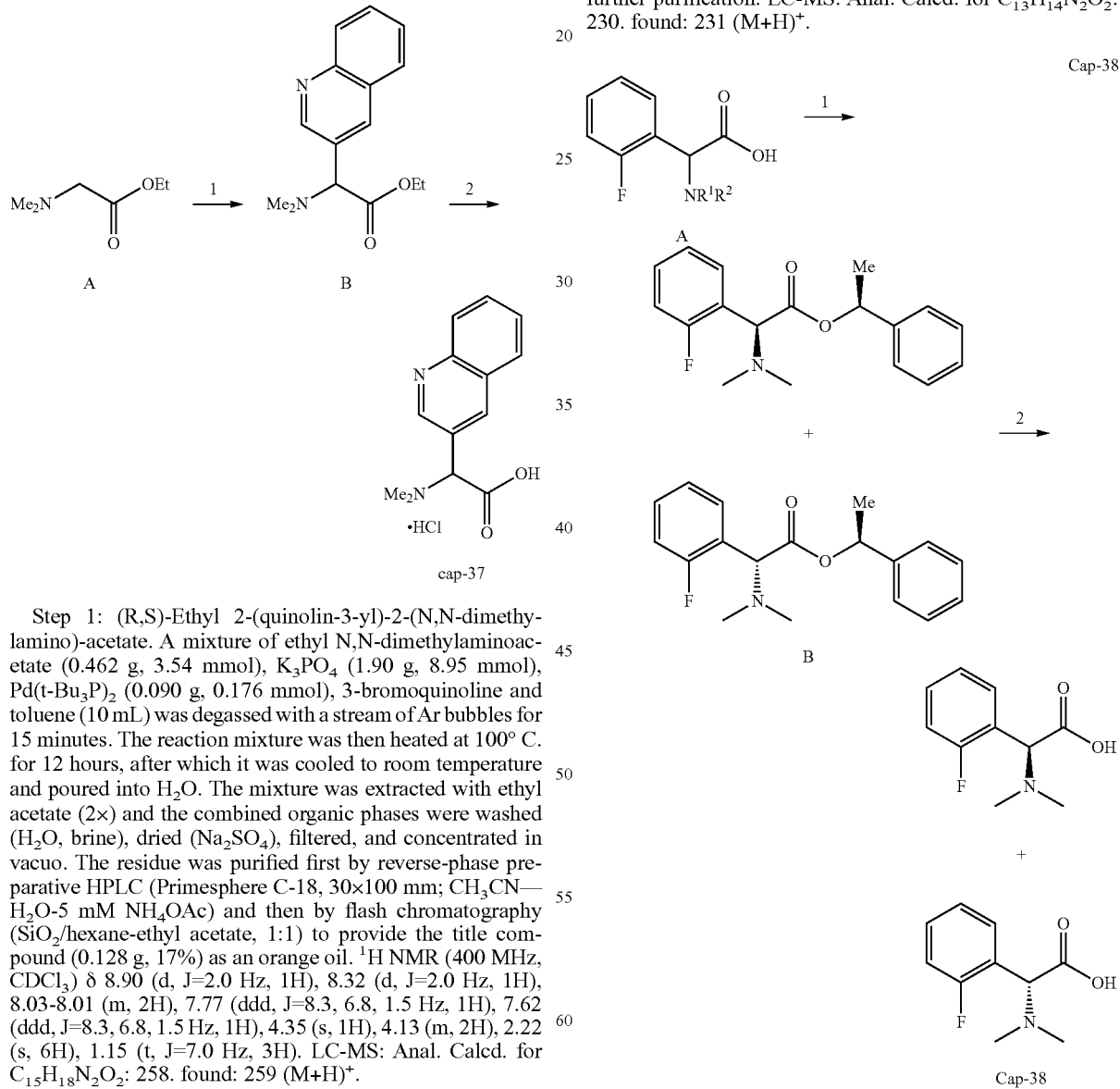

Step 1: (R,S)-Ethyl 2-(quinolin-3-yl)-2-(N,N-dimethylamino)-acetate. A mixture of ethyl N,N-dimethylaminoacetate (0.462 g, 3.54 mmol), $K_3PO_4$ (1.90 g, 8.95 mmol), $Pd(t-Bu_3P)_2$ (0.090 g, 0.176 mmol), 3-bromoquinoline and toluene (10 mL) was degassed with a stream of Ar bubbles for 15 minutes. The reaction mixture was then heated at 100° C. for 12 hours, after which it was cooled to room temperature and poured into $H_2O$. The mixture was extracted with ethyl acetate (2×) and the combined organic phases were washed ($H_2O$, brine), dried ($Na_2SO_4$), filtered, and concentrated in vacuo. The residue was purified first by reverse-phase preparative HPLC (Primesphere C-18, 30×100 mm; $CH_3CN$—$H_2O$-5 mM $NH_4OAc$) and then by flash chromatography ($SiO_2$/hexane-ethyl acetate, 1:1) to provide the title compound (0.128 g, 17%) as an orange oil. ¹H NMR (400 MHz, $CDCl_3$) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LC-MS: Anal. Calcd. for $C_{15}H_{18}N_2O_2$: 258. found: 259 (M+H)⁺.

Step 2: (R,S) 2-(Quinolin-3-yl)-2-(N,N-dimethylamino) acetic acid. A mixture of (R,S)-ethyl 2-(quinolin-3-yl)-2-(N, N-dimethylamino)acetate (0.122 g, 0.472 mmol) and 6M HCl (3 mL) was heated at 100° C. for 12 hours. The solvent was removed in vacuo to provide the dihydrochloride of the title compound (0.169 g, >100%) as a light yellow foam. The unpurified material was used in subsequent steps without further purification. LC-MS: Anal. Calcd. for $C_{13}H_{14}N_2O_2$: 230. found: 231 (M+H)⁺.

Step 1: (R)—((S)-1-Phenylethyl) 2-(dimethylamino)-2-(2-fluorophenyl)acetate and (S)—((S)-1-Phenylethyl) 2-(dimethylamino)-2-(2-fluorophenyl)acetate. To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in $CH_2Cl_2$ (40 mL) was added EDCI (3.29 g, 17.15 mmol) and the mixture was allowed to stir at room temperature for 12 hours. The solvent was then removed in vacuo and the residue partitioned with ethyl acetate-$H_2O$. The layers were separated, the aqueous layer was back-extracted with ethyl acetate (2×) and the combined organic phases were washed ($H_2O$, brine), dried ($Na_2SO_4$), filtered, and concentrated in vacuo. The residue was purified by silica gel chromatography (BIOTAGE®/0-50% diethyl ether-hexane). The resulting pure diastereomeric mixture was then separated by reverse-phase preparative HPLC (Primesphere C-18, 30×100 mm; $CH_3CN$—$H_2O$-0.1% TFA) to give first (S)-1-phenethyl(R)-2-(dimethylamino)-2-(2-fluorophenyl)acetate (0.501 g, 13%) and then (S)-1-phenethyl(S)-2-(dimethylamino)-2-(2-fluorophenyl)-acetate (0.727 g. 18%), both as their TFA salts. (S,R)-isomer: $^1H$ NMR (400 MHz, $CD_3OD$) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H). LC-MS: Anal. Calcd. for $C_{18}H_{20}FNO_2$: 301. found: 302 (M+H)$^+$; (S,S)-isomer: $^1H$ NMR (400 MHz, $CD_3OD$) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LC-MS: Anal. Calcd. for $C_{18}H_{20}FNO_2$: 301. found: 302 (M+H)$^+$.

Step 2: (R)-2-(Dimethylamino)-2-(2-fluorophenyl)acetic acid. A mixture of (R)—((S)-1-phenylethyl) 2-(dimethylamino)-2-(2-fluorophenyl)acetate TFA salt (1.25 g, 3.01 mmol) and 20% Pd(OH)$_2$/C (0.125 g) in ethanol (30 mL) was hydrogenated at room temperature and atmospheric pressure ($H_2$ balloon) for 4 hours. The solution was then purged with Ar, filtered through diatomaceous earth (CELITE®), and concentrated in vacuo. This gave the title compound as a colorless solid (0.503 g, 98%). $^1H$ NMR (400 MHz, $CD_3OD$) δ 7.53-7.63 (m, 2H), 7.33-7.38 (m, 2H), 5.36 (s, 1H), 2.86 (s, 6H). LC-MS: Anal. Calcd. for $C_{10}H_{12}FNO_2$: 197. found: 198 (M+H)$^+$.

The S-isomer could be obtained from (S)—((S)-1-phenylethyl) 2-(dimethylamino)-2-(2-fluorophenyl)acetate TFA salt in similar fashion.

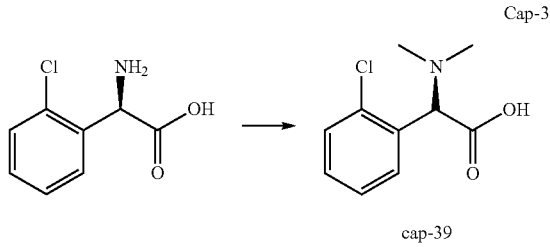

cap-39

A mixture of (R)-(2-chlorophenyl)glycine (0.300 g, 1.62 mmol), formaldehyde (35% aqueous solution, 0.80 mL, 3.23 mmol) and 20% Pd(OH)$_2$/C (0.050 g) was hydrogenated at room temperature and atmospheric pressure ($H_2$ balloon) for 4 hours. The solution was then purged with Ar, filtered through diatomaceous earth (CELITE®) and concentrated in vacuo. The residue was purified by reverse-phase preparative HPLC (Primesphere C-18, 30×100 mm; $CH_3CN$—$H_2O$-0.1% TFA) to give the TFA salt of the title compound (R)-2-(dimethylamino)-2-(2-chlorophenyl)acetic acid as a colorless oil (0.290 g, 55%). $^1H$ NMR (400 MHz, $CD_3OD$) δ 7.59-7.65 (m, 2H), 7.45-7.53 (m, 2H), 5.40 (s, 1H), 2.87 (s, 6H). LC-MS: Anal. Calcd. for $C_{10}H_{12}ClNO_2$: 213. found: 214 (M+H)$^+$.

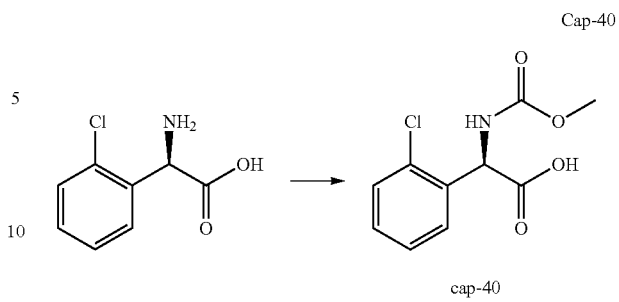

cap-40

To an ice-cold solution of (R)-(2-chlorophenyl)glycine (1.00 g, 5.38 mmol) and NaOH (0.862 g, 21.6 mmol) in $H_2O$ (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed ($H_2O$, brine), dried ($Na_2SO_4$), filtered, and concentrated in vacuo to give the title compound (R)-2-(methoxycarbonylamino)-2-(2-chlorophenyl)acetic acid as a yellow-orange foam (1.31 g, 96%). $^1H$ NMR (400 MHz, $CD_3OD$) δ 7.39-7.43 (m, 2H), 7.29-7.31 (m, 2H), 5.69 (s, 1H), 3.65 (s, 3H). LC-MS: Anal. Calcd. for $C_{10}H_{10}ClNO_4$: 243. found: 244 (M+H)$^+$.

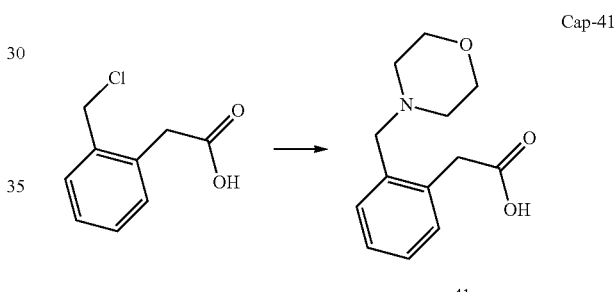

cap-41

To a suspension of 2-(2-(chloromethyl)phenyl)acetic acid (2.00 g, 10.8 mmol) in THF (20 mL) was added morpholine (1.89 g, 21.7 mmol) and the solution was stirred at room temperature for 3 hours. The reaction mixture was then diluted with ethyl acetate and extracted with $H_2O$ (2×). The aqueous phase was lyophilized and the residue was purified by silica gel chromatography (BIOTAGE®/0-10% methanol-$CH_2Cl_2$) to give the title compound 2-(2-(morpholinomethyl)phenyl)acetic acid as a colorless solid (2.22 g, 87%). $^1H$ NMR (400 MHz, $CD_3OD$) δ 7.37-7.44 (m, 3H), 7.29-7.33 (m, 1H), 4.24 (s, 2H), 3.83 (br s, 4H), 3.68 (s, 2H), 3.14 (br s, 4H). LC-MS: Anal. Calcd. for $C_{13}H_{17}NO_3$: 235. found: 236 (M+H)$^+$.

The following examples were similarly prepared using the method described for Cap-41:

| Cap-42 | 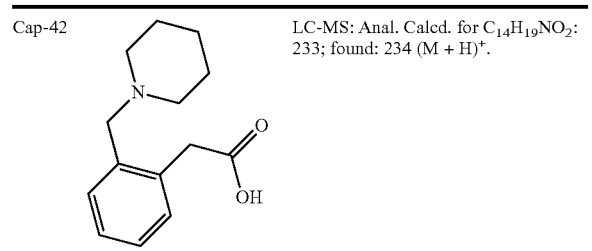 | LC-MS: Anal. Calcd. for $C_{14}H_{19}NO_2$: 233; found: 234 (M + H)$^+$. |
|---|---|---|

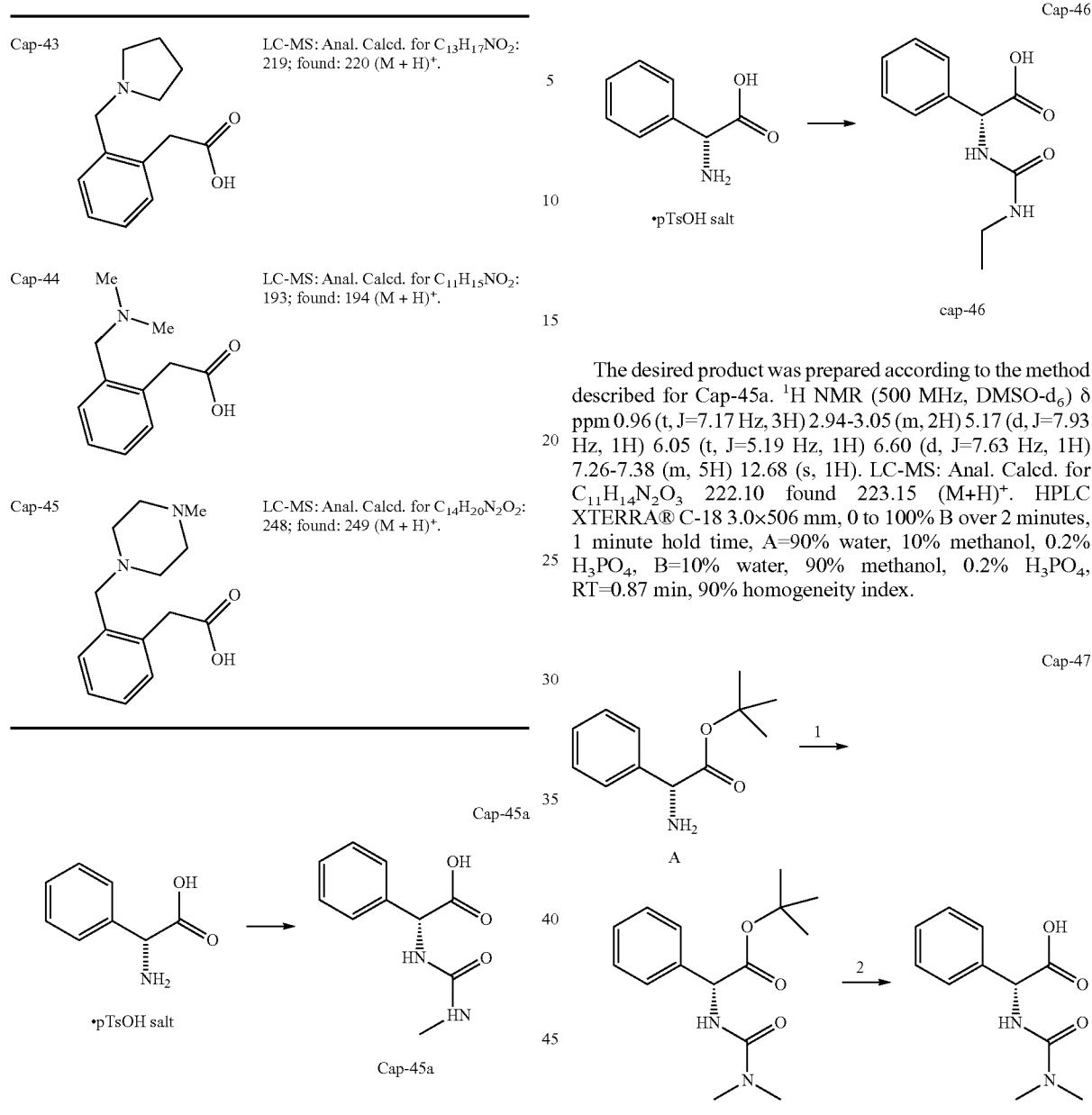

The desired product was prepared according to the method described for Cap-45a. $^1$H NMR (500 MHz, DMSO-d$_6$) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LC-MS: Anal. Calcd. for $C_{11}H_{14}N_2O_3$ 222.10 found 223.15 (M+H)$^+$. HPLC XTERRA® C-18 3.0×506 mm, 0 to 100% B over 2 minutes, 1 minute hold time, A=90% water, 10% methanol, 0.2% H$_3$PO$_4$, B=10% water, 90% methanol, 0.2% H$_3$PO$_4$, RT=0.87 min, 90% homogeneity index.

HMDS (1.85 mL, 8.77 mmol) was added to a suspension of (R)-2-amino-2-phenylacetic acid p-toluenesulfonate (2.83 g, 8.77 mmol) in CH$_2$Cl$_2$ (10 mL) and the mixture was stirred at room temperature for 30 minutes. Methyl isocyanate (0.5 g, 8.77 mmol) was added in one portion stirring continued for 30 minutes. The reaction was quenched by addition of H$_2$O (5 mL) and the resulting precipitate was filtered, washed with H$_2$O and n-hexanes, and dried under vacuum. (R)-2-(3-methylureido)-2-phenylacetic acid (1.5 g; 82%) was recovered as a white solid and it was used without further purification. $^1$H NMR (500 MHz, DMSO-d$_6$) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LC-MS: Anal. Calcd. for $C_{10}H_{12}N_2O_3$ 208.08 found 209.121 (M+H)$^+$; HPLC PHENOMENEX® C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

Step 1: (R)-tert-Butyl 2-(3,3-dimethylureido)-2-phenylacetate. To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with H$_2$O, 1N aq. HCl and brine, dried (MgSO$_4$), filtered and concentrated under reduced pressure. (R)-tert-butyl 2-(3,3-dimethylureido)-2-phenylacetate was obtained as a white solid (0.86 g; 75%) and used without further purification. $^1$H NMR (500 MHz, DMSO-d$_6$) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LC-MS: Anal. Calcd. for $C_{15}H_{22}N_2O_3$ 278.16 found 279.23 (M+H)$^+$; HPLC PHENOMENEX® Luna C-18 4.6×50 mm, 0 to 100% B over 4 minutes, 1 minute hold time, A=90% water, 10% methanol, 0.1% TFA, B=10% water, 90% methanol, 0.1% TFA, RT=2.26 min, 97% homogeneity index.

Step 2: (R)-2-(3,3-Dimethylureido)-2-phenylacetic acid. To a stirred solution of ((R)-tert-butyl 2-(3,3-dimethylureido)-2-phenylacetate (0.86 g, 3.10 mmol) in CH$_2$Cl$_2$ (250 mL) was added TFA (15 mL) dropwise and the resulting solution was stirred at rt for 3 hours. The desired compound was then precipitated out of solution with a mixture of EtOAC:Hexanes (5:20), filtered off and dried under reduced pressure. (R)-2-(3,3-dimethylureido)-2-phenylacetic acid was isolated as a white solid (0.59 g, 86%) and used without further purification. $^1$H NMR (500 MHz, DMSO-d$_6$) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=7.32 Hz, 2H) 7.38-7.43 (m, 2H) 12.65 (s, 1H). LC-MS: Anal. Calcd. for C$_{11}$H$_{14}$N$_2$O$_3$: 222.24. found: 223.21 (M+H)$^+$. HPLC XTERRA® C-18 3.0×50 mm, 0 to 100% B over 2 minutes, 1 minute hold time, A=90% water, 10% methanol, 0.2% H$_3$PO$_4$, B=10% water, 90% methanol, 0.2% H$_3$PO$_4$, RT=0.75 min, 93% homogeneity index.

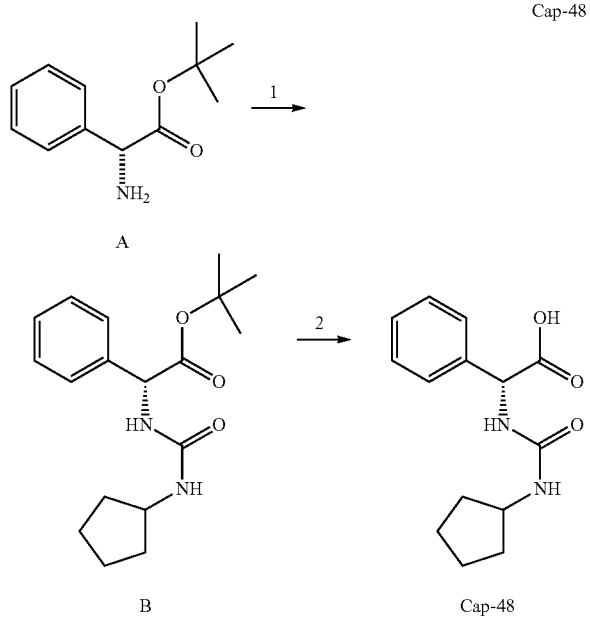

Step 1: (R)-tert-Butyl 2-(3-cyclopentylureido)-2-phenylacetate. To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes. After stirring at room temperature for 3 hours, the reaction was concentrated under reduced pressure and the resulting residue was taken up in ethyl acetate. The organic layer was washed with H$_2$O and brine, dried (MgSO$_4$), filtered, and concentrated under reduced pressure. (R)-tert-butyl 2-(3-cyclopentylureido)-2-phenylacetate was obtained as an opaque oil (1.32 g; 100%) and used without further purification. $^1$H NMR (500 MHz, CD$_3$Cl-D) δ ppm 1.50-1.57 (m, 2H) 1.58-1.66 (m, 2H) 1.87-1.97 (m, 2H) 3.89-3.98 (m, 1H) 5.37 (s, 1H) 7.26-7.38 (m, 5H). LC-MS: Anal. Calcd. for C$_{18}$H$_{26}$N$_2$O$_3$ 318.19 found 319.21 (M+H)$^+$; HPLC XTERRA® C-18 3.0×50 mm, 0 to 100% B over 4 minutes, 1 minute hold time, A=90% water, 10% methanol, 0.1% TFA, B=10% water, 90% methanol, 0.1% TFA, RT=2.82 min, 96% homogeneity index.

Step 2: (R)-2-(3-Cyclopentylureido)-2-phenylacetic acid. To a stirred solution of (R)-tert-butyl 2-(3-cyclopentylureido)-2-phenylacetate (1.31 g, 4.10 mmol) in CH$_2$Cl$_2$ (25 mL) was added TFA (4 mL) and triethylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). $^1$H NMR (500 MHz, DMSO-d$_6$) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LC-MS: Anal. Calcd. for C$_{14}$H$_{18}$N$_2$O$_3$: 262.31. found: 263.15 (M+H)$^+$. HPLC XTERRA® C-18 3.0×50 mm, 0 to 100% B over 2 minutes, 1 minute hold time, A=90% water, 10% methanol, 0.2% H$_3$PO$_4$, B=10% water, 90% methanol, 0.2% H$_3$PO$_4$, RT=1.24 min, 100% homogeneity index.

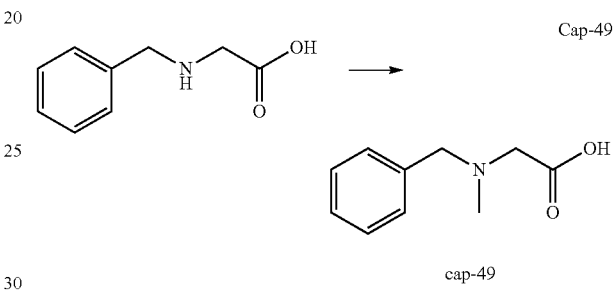

To a stirred solution of 2-(benzylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC (XTERRA® 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl(methyl)-amino)acetic acid as its TFA salt (723 mg, 33%) as a colorless wax. $^1$H NMR (300 MHz, DMSO-d$_6$) δ ppm 2.75 (s, 3H) 4.04 (s, 2H) 4.34 (s, 2H) 7.29-7.68 (m, 5H). LC-MS: Anal. Calcd. for: C$_{10}$H$_{13}$NO$_2$ 179.09. found: 180.20 (M+H)$^+$.

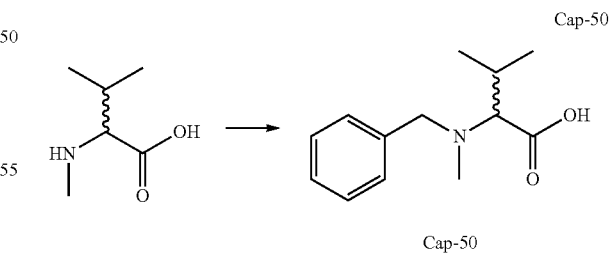

To a stirred solution of 3-methyl-2-(methylamino)butanoic acid (0.50 g, 3.81 mmol) in water (30 mL) was added K$_2$CO$_3$ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (XTERRA® 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. $^1$H NMR (500 MHz, DMSO-d$_6$) δ ppm 0.98 (d, 3H) 1.07 (d, 3H) 2.33-2.48 (m, 1H) 2.54-2.78 (m, 3H) 3.69 (s, 1H) 4.24 (s, 2H) 7.29-7.65 (m, 5H). LC-MS: Anal. Calcd. for: $C_{13}H_{19}NO_2$ 221.14. found: 222.28 (M+H)$^+$.

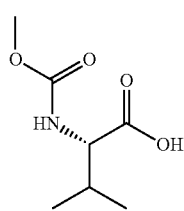

Cap-51

(S)-2-(Methoxycarbonylamino)-3-methylbutanoic acid

Na$_2$CO$_3$ (1.83 g, 17.2 mmol) was added to NaOH (33 mL of 1M/H$_2$O, 33 mmol) solution of L-valine (3.9 g, 33.29 mmol) and the resulting solution was cooled with ice-water bath. Methyl chloroformate (2.8 mL, 36.1 mmol) was added dropwise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with CH$_2$Cl$_2$ (50 mL, 3×). The organic phase was dried (MgSO$_4$) and evaporated in vacuo to afford Cap-51 as a white solid (6 g). $^1$H NMR for the dominant rotamer (DMSO-d$_6$, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for [M+H]$^+$ $C_2H_{14}NO_4$: 176.0923. found 176.0922.

Cap-51 (alternate route)

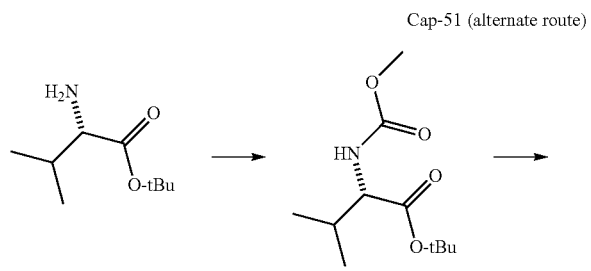

(S)-2-(Methoxycarbonylamino)-3-methylbutanoic acid

DIEA (137.5 mL, 0.766 mol) was added to a suspension of (S)-tert-butyl 2-amino-3-methylbutanoate hydrochloride (75.0 g, 0.357 mol) in THF (900 mL), and the mixture was cooled to 0° C. (ice/water bath). Methyl chloroformate (29.0 mL, 0.375 mol) was added dropwise over 45 min, the cooling bath was removed and the heterogeneous mixture was stirred at ambient temperature for 3 h. The solvent was removed under diminished pressure and the residue partitioned between EtOAc and water (1 L each). The organic layer was washed with H$_2$O (1 L) and brine (1 L), dried (MgSO$_4$), filtered and concentrated under diminished pressure. The crude material was passed through a plug of silica gel (1 kg), eluting with hexanes (4 L) and 15:85 EtOAc/hexanes (4 L) to afford (S)-tert-butyl 2-(methoxycarbonylamino)-3-methylbutanoate as a clear oil (82.0 g, 99% yield). $^1$H NMR (500 MHz, DMSO-d$_6$, δ=2.5 ppm) 7.34 (d, J=8.6, 1H), 3.77 (dd, J=8.6, 6.1, 1H), 3.53 (s, 3H), 1.94-2.05 (m, 1H), 1.39 (s, 9H), 0.83-0.92 (m, 6H). $^{13}$C-NMR (126 MHz, DMSO-d$_6$, δ=39.2 ppm) 170.92, 156.84, 80.38, 60.00, 51.34, 29.76, 27.62, 18.92, 17.95. LC-MS: [M+Na]$^+$ 254.17.

Trifluoroacetic acid (343 mL, 4.62 mol) and Et$_3$SiH (142 mL, 0.887 mol) were added sequentially to a solution of (S)-tert-butyl 2-(methoxycarbonylamino)-3-methylbutanoate (82.0 g, 0.355 mol) in CH$_2$Cl$_2$ (675 mL), and the mixture was stirred at ambient temperature for 4 h. The volatile component was removed under diminished pressure and the resultant oil triturated with petroleum ether (600 mL) to afford a white solid, which was filtered and washed with hexanes (500 mL) and petroleum ether (500 mL). Recrystallization from EtOAc/petroleum ether afforded Cap-51 as white flaky crystals (54.8 g, 88% yield). MP=108.5-109.5° C. $^1$H NMR (500 MHz, DMSO-d$_6$, δ=2.5 ppm) 12.52 (s, 1H), 7.31 (d, J=8.6, 1H), 3.83 (dd, J=8.6, 6.1, 1H), 3.53 (s, 3H), 1.94-2.07 (m, 1H), 0.86 (dd, J=8.9, 7.0, 6H). $^{13}$C NMR (126 MHz, DMSO-d$_6$, δ=39.2 ppm) 173.30, 156.94, 59.48, 51.37, 29.52, 19.15, 17.98. LC-MS: [M+H]$^+$=176.11. Anal. Calcd. for $C_7H_{13}NO_4$: C, 47.99; H, 7.48; N, 7.99. Found: C, 48.17; H, 7.55; N, 7.99. Optical Rotation: [α]$_D$=−4.16 (12.02 mg/mL; MeOH). Optical purity: >99.5% ee. Note: the optical purity assessment was made on the methyl ester derivative of Cap-51, which was prepared under a standard TMSCHN$_2$ (benzene/MeOH) esterification protocol. HPLC analytical conditions: column, CHIRALPAK® AD-H (4.6×250 mm, 5 μm); solvent, 95% heptane/5% IPA (isocratic); flow rate, 1 mL/min; temperature, 35° C.; UV monitored at 205 nm. [Note: Cap-51 could also be purchased from Flamm.]

Cap-52 (same as Cap-12)

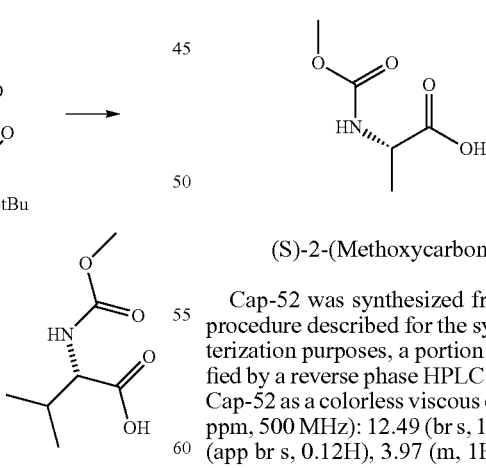

(S)-2-(Methoxycarbonylamino)propanoic acid

Cap-52 was synthesized from L-alanine according to the procedure described for the synthesis of Cap-51. For characterization purposes, a portion of the crude material was purified by a reverse phase HPLC (H$_2$O/methanol/TFA) to afford Cap-52 as a colorless viscous oil. $^1$H NMR (DMSO-d$_6$, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to Cap-64

Cap-53 to Cap-64 were prepared from appropriate starting materials according to the procedure described for the synthesis of Cap-51, with noted modifications if any.

| Cap | Structure | Data |
|---|---|---|
| Cap-53a: (R) Cap-53b: (S) ((S)-2-(methoxy-carbonyl-amino) butanoic acid) | | $^1$H NMR (DMSO-d$_6$, δ = 2.5 ppm, 500 MHz): δ 12.51 (br s, 1 H), 7.4 (d, J = 7.9, 0.9H), 7.06 (app s, 0.1H), 3.86-3.82 (m, 1H), 3.53 (s, 3H), 1.75-1.67 (m, 1H), 1.62-1.54 (m, 1H), 0.88 (d, J = 7.3, 3H). RT = 0.77 minutes (Cond. 2); LC-MS: Anal. Calcd. for [M + Na]$^+$ C$_6$H$_{11}$NNaO$_4$: 184.06; found 184.07. HRMS Calcd. for [M + Na]$^+$ C$_6$H$_{11}$NNaO$_4$: 184.0586; found 184.0592. |
| Cap-54a: (R) Cap-54b: (S) ((S)-2-cyclo-propyl-2-(methoxy-carbonyl-amino) acetic acid | | $^1$H NMR (DMSO-d$_6$, δ = 2.5 ppm, 500 MHz): δ 12.48 (s, 1H), 7.58 (d, J = 7.6, 0.9H), 7.25 (app s, 0.1H), 3.52 (s, 3H), 3.36-3.33 (m, 1H), 1.10-1.01 (m, 1H), 0.54-0.49 (m, 1H), 0.46-0.40 (m, 1H), 0.39-0.35 (m, 1H), 0.31-0.21 (m, 1H). HRMS Calcd. for [M + H]$^+$ C$_7$H$_{12}$NO$_4$: 174.0766; found 174.0771 |
| Cap-55 | 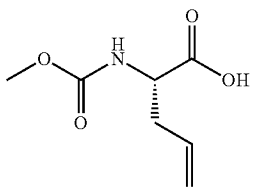 | $^1$H NMR (DMSO-d$_6$, δ = 2.5 ppm, 500 MHz): δ 12.62 (s, 1H), 7.42 (d, J = 8.2, 0.9H), 7.07 (app s, 0.1H), 5.80-5.72 (m, 1H), 5.10 (d, J = 17.1, 1H), 5.04 (d, J = 10.4, 1H), 4.01-3.96 (m, 1H), 3.53 (s, 3H), 2.47-2.42 (m, 1H), 2.35-2.29 (m, 1H). |
| Cap-56 (S)-3-methoxy-2-(methoxy-carbonyl-amino) propanoic acid | | $^1$H NMR (DMSO-d$_6$, δ = 2.5 ppm, 500 MHz): δ 12.75 (s, 1H), 7.38 (d, J = 8.3, 0.9H), 6.96 (app s, 0.1H), 4.20-4.16 (m, 1H), 3.60-3.55 (m, 2H), 3.54 (s, 3H), 3.24 (s, 3H). |
| Cap-57 | 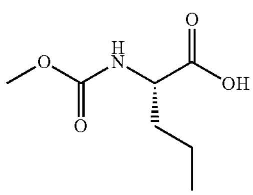 | $^1$H NMR (DMSO-d$_6$, δ = 2.5 ppm, 500 MHz): δ 12.50 (s, 1H), 8.02 (d, J = 7.7, 0.08H), 7.40 (d, J = 7.9, 0.76H), 7.19 (d, J = 8.2, 0.07H), 7.07 (d, J = 6.7, 0.09H), 4.21-4.12 (m, 0.08H), 4.06-3.97 (m, 0.07H), 3.96-3.80 (m, 0.85H), 3.53 (s, 3H), 1.69-1.51 (m, 2H), 1.39-1.26 (m, 2H), 0.85 (t, J = 7.4, 3H). LC (Cond. 2): RT = 1.39 LC-MS: Anal. Calcd. for [M + H]$^+$ C$_7$H$_{14}$NO$_4$: 176.09; found 176.06. |
| Cap-58 | 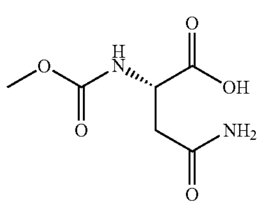 | $^1$H NMR (DMSO-d$_6$, δ = 2.5 ppm, 500 MHz): δ 12.63 (br s, 1H), 7.35 (s, 1H), 7.31 (d, J = 8.2, 1H), 6.92 (s, 1H), 4.33-4.29 (m, 1H), 3.54 (s, 3H), 2.54 (dd, J = 15.5, 5.4, 1H), 2.43 (dd, J = 15.6, 8.0, 1H). RT = 0.16 min (Cond. 2); LC-MS: Anal. Calcd. for [M + H]$^+$ C$_6$H$_{11}$N$_2$O$_5$: 191.07; found 191.14. |
| Cap-59a: (R) Cap-59b: (S) | | $^1$H NMR (DMSO-d$_6$, δ = 2.5 ppm, 400 MHz): δ 12.49 (br s, 1H), 7.40 (d, J = 7.3, 0.89H), 7.04 (br s, 0.11H), 4.00-3.95 (m, 3H), 1.24 (d, J = 7.3, 3H), 1.15 (t, J = 7.2, 3H). HRMS: Anal. Calcd. for [M + H]$^+$ C$_6$H$_{12}$NO$_4$: 162.0766; found 162.0771. |
| Cap-60 | 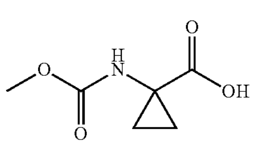 | The crude material was purified with a reverse phase HPLC (H$_2$O/MeOH/TFA) to afford a colorless viscous oil that crystallized to a white solid upon exposure to high vacuum. $^1$H NMR (DMSO-d$_6$, δ = 2.5 ppm, 400 MHz): δ 12.38 (br s, 1H), 7.74 (s, 0.82H), 7.48 (s, 0.18H), 3.54/3.51 (two s, 3H), 1.30 (m, 2H), 0.98 (m, 2H). HRMS: Anal. Calcd. for [M + H]$^+$ C$_6$H$_{10}$NO$_4$: 160.0610; found 160.0604. |

| Cap | Structure | Data |
|---|---|---|
| Cap-61 | 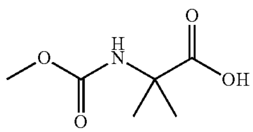 | ¹H NMR (DMSO-d₆, δ = 2.5 ppm, 400 MHz): δ 12.27 (br s, 1H), 7.40 (br s, 1H), 3.50 (s, 3H), 1.32 (s, 6H). HRMS: Anal. Calcd. for [M + H]⁺ C₆H₁₂NO₄: 162.0766; found 162.0765. |
| Cap-62 | 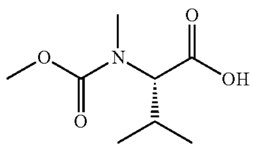 | ¹H NMR (DMSO-d₆, δ = 2.5 ppm, 400 MHz): δ 12.74 (br s, 1H), 4.21 (d, J = 10.3, 0.6H), 4.05 (d, J = 10.0, 0.4H), 3.62/3.60 (two singlets, 3H), 3.0 (s, 3H), 2.14-2.05 (m, 1H), 0.95 (d, J = 6.3, 3H), 0.81 (d, J = 6.6, 3H). LC-MS Anal. Calcd. for [M − H]⁻ C₈H₁₄NO₄: 188.09; found 188.05. |
| Cap-63 | 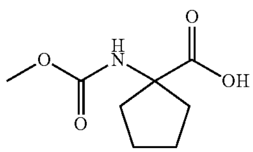 | [Note: the reaction was allowed to run for longer than what was noted for the general procedure.] ¹H NMR (DMSO-d₆, δ = 2.5 ppm, 400 MHz): 12.21 (br s, 1H), 7.42 (br s, 1H), 3.50 (s, 3H), 2.02-.185 (m, 4H), 1.66-1.58 (m, 4H). LC-MS: Anal. Calcd. for [M + H]⁺ C₈H₁₄NO₄: 188.09; found 188.19. |
| Cap-64 | 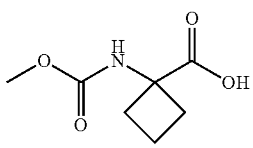 | [Note: the reaction was allowed to run for longer than what was noted for the general procedure.] ¹H NMR (DMSO-d₆, δ = 2.5 ppm, 400 MHz): 12.35 (br s, 1H), 7.77 (s, 0.82H), 7.56/7.52 (overlapping br s, 0.18H), 3.50 (s, 3H), 2.47-2.40 (m, 2H), 2.14-2.07 (m, 2H), 1.93-1.82 (m, 2H). |

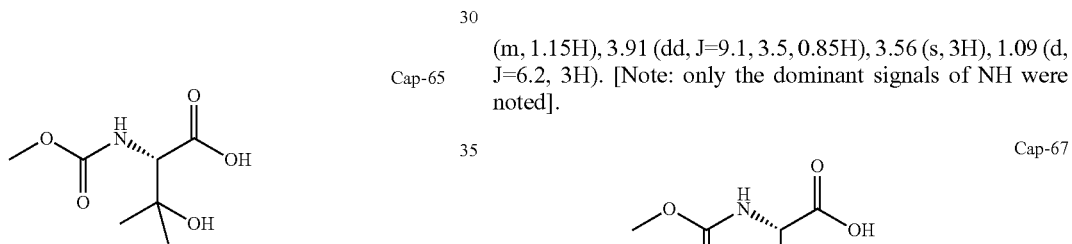

Cap-65

Methyl chloroformate (0.65 mL, 8.39 mmol) was added dropwise over 5 min to a cooled (ice-water) mixture of Na₂CO₃ (0.449 g, 4.23 mmol), NaOH (8.2 mL of 1M/H₂O, 8.2 mmol) and (S)-2-amino-3-hydroxy-3-methylbutanoic acid (1.04 g, 7.81 mmol). The reaction mixture was stirred for 45 min, and then the cooling bath was removed and stirring was continued for an additional 3.75 hr. The reaction mixture was washed with CH₂Cl₂, and the aqueous phase was cooled with ice-water bath and acidified with concentrated HCl to a pH region of 1-2. The volatile component was removed in vacuo and the residue was taken up in a 2:1 mixture of MeOH/CH₂Cl₂ (15 mL) and filtered, and the filtrate was rotervaped to afford Cap-65 as a white semi-viscous foam (1.236 g). ¹H NMR (DMSO-d₆, δ=2.5 ppm, 400 MHz): δ 6.94 (d, J=8.5, 0.9H), 6.53 (br s, 0.1H), 3.89 (d, J=8.8, 1H), 2.94 (s, 3H), 1.15 (s, 3H), 1.13 (s, 3H).

Cap-66 and Cap-67 were prepared from appropriate commercially available starting materials by employing the procedure described for the synthesis of Cap-65.

Cap-66

¹H NMR (DMSO-d₆, δ=2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted].

Cap-67

¹H NMR (DMSO-d₆, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted].

Cap-68

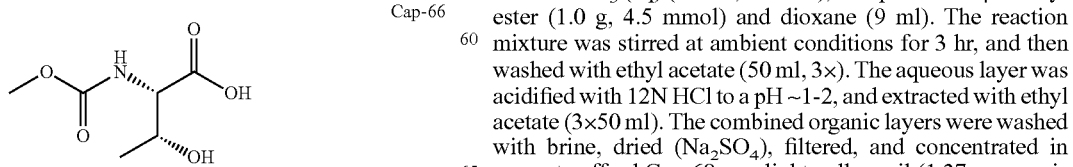

Methyl chloroformate (0.38 ml, 4.9 mmol) was added drop-wise to a mixture of 1N NaOH (aq) (9.0 ml, 9.0 mmol), 1M NaHCO₃ (aq) (9.0 ml, 9.0 mol), L-aspartic acid β-benzyl ester (1.0 g, 4.5 mmol) and dioxane (9 ml). The reaction mixture was stirred at ambient conditions for 3 hr, and then washed with ethyl acetate (50 ml, 3×). The aqueous layer was acidified with 12N HCl to a pH ~1-2, and extracted with ethyl acetate (3×50 ml). The combined organic layers were washed with brine, dried (Na₂SO₄), filtered, and concentrated in vacuo to afford Cap-68 as a light yellow oil (1.37 g; mass is above theoretical yield, and the product was used without further purification). ¹H NMR (DMSO-d₆, δ=2.5 ppm, 500

MHz): δ 12.88 (br s, 1H), 7.55 (d, J=8.5, 1H), 7.40-7.32 (m, 5H), 5.13 (d, J=12.8, 1H), 5.10 (d, J=12.9, 1H), 4.42-4.38 (m, 1H), 3.55 (s, 3H), 2.87 (dd, J=16.2, 5.5, 1H), 2.71 (dd, J=16.2, 8.3, 1H). LC (Cond. 2): RT=1.90 min; LC-MS: Anal. Calcd. for [M+H]$^+$ C$_{13}$H$_{16}$NO$_6$: 282.10. found 282.12.

Cap-69a and Cap-69b

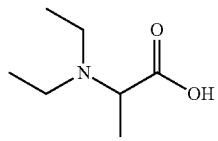

Cap-69a: (R)-enantiomer
Cap-69b: (S)-enantiomer

NaCNBH$_3$ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a DOWEX® 50WX8-100 ion-exchange resin (column was washed with water, and the compound was eluted with dilute NH$_4$OH, prepared by mixing 18 ml of NH$_4$OH and 282 ml of water) to afford Cap-69 (2.0 g) as an off-white soft hygroscopic solid. $^1$H NMR (DMSO-d$_6$, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to Cap-74x

Cap-70 to Cap-74x were prepared according to the procedure described for the synthesis of Cap-69 by employing appropriate starting materials.

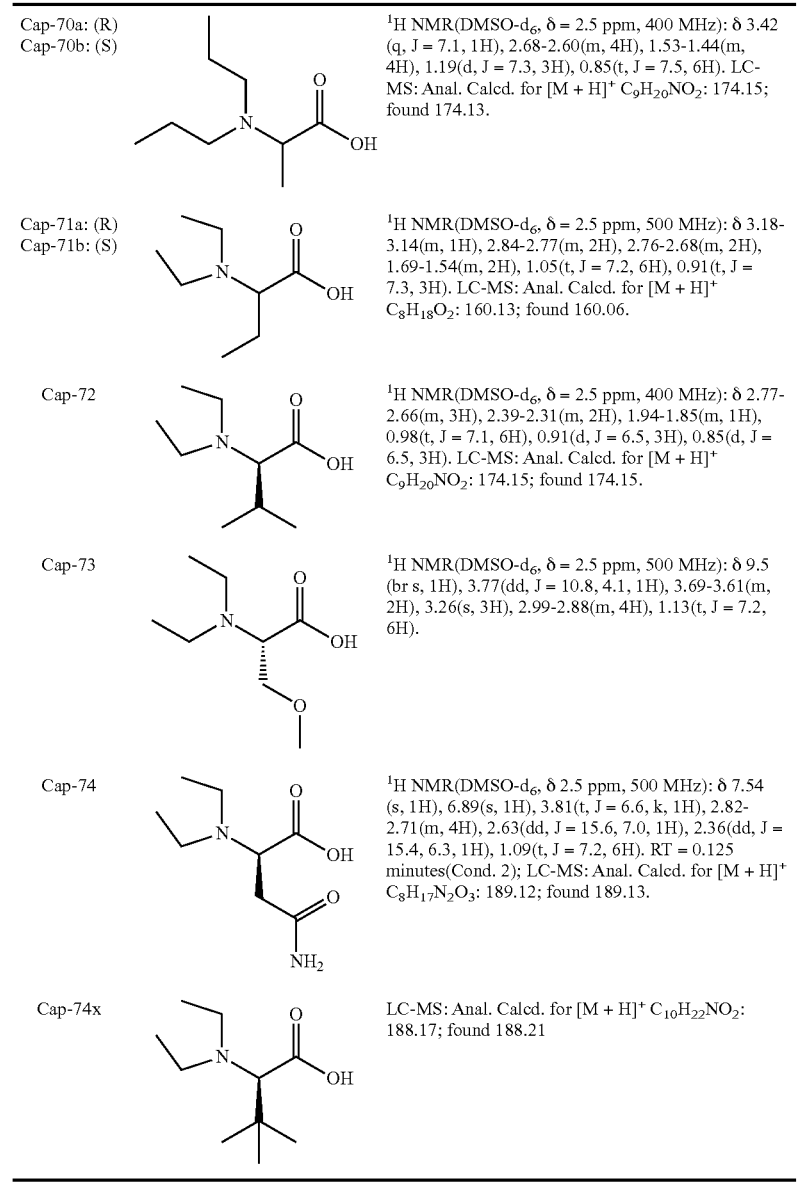

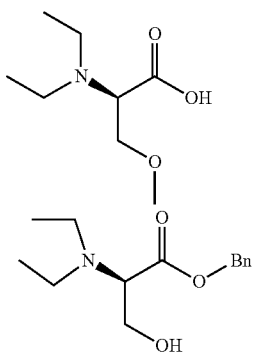

Cap-75, Step a

NaBH₃CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H₂O/TFA) to afford the TFA salt of (R)-benzyl 2-(diethylamino)-3-hydroxypropanoate as a colorless viscous oil (1.9 g). $^1$H NMR (DMSO-d$_6$, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21 (m, 4H), 1.23 (t, J=7.2, 6H). LC-MS (Cond. 2): RT=1.38 min; LC-MS: Anal. Calcd. for [M+H]$^+$ C$_{14}$H$_{22}$NO$_3$: 252.16. found 252.19.

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 μL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by compound elution with 2N NH₃/Methanol. Removal of the volatile component in vacuo afforded Cap-75, contaminated with (R)-2-(diethylamino)-3-hydroxypropanoic acid, as a yellow semi-solid (100 mg). The product was used as is without further purification.

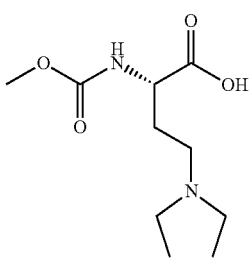

Cap-76

NaCNBH₃ (1.60 g, 24.2 mmol) was added in batches to a chilled (−15° C.) water/MeOH (12 mL each) solution of (S)-4-amino-2-(tert-butoxycarbonylamino) butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with DOWEX® 50WX8-100 ion-exchange resin (column was washed with water and the compound was eluted with dilute NH₄OH, prepared from 18 ml of NH₄OH and 282 ml of water) to afford intermediate (5)-2-amino-4-(diethylamino) butanoic acid as an off-white solid (1.73 g).

Methyl chloroformate (0.36 mL, 4.65 mmol) was added drop-wise over 11 min to a cooled (ice-water) mixture of Na₂CO₃ (0.243 g, 2.29 mmol), NaOH (4.6 mL of 1M/H₂O, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with CH₂Cl₂ (30 mL, 2×), and the aqueous phase was cooled with ice-water bath and acidified with concentrated HCl to a pH region of 2. The volatile component was then removed in vacuo and the crude material was free-based with MCX resin (6.0 g; column was washed with water, and sample was eluted with 2.0 M NH₃/MeOH) to afford impure Cap-76 as an off-white solid (704 mg). $^1$H NMR (MeOH-d$_4$, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC-MS: Anal. Calcd. for [M+H]$^+$ C$_{10}$H$_{21}$N$_2$O$_4$: 233.15. found 233.24.

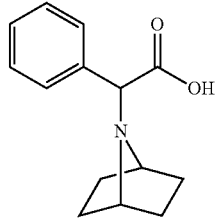

Cap-77a and Cap-77b

Cap-77a: enantiomer-1
Cap-77b: enantiomer-2

The synthesis of Cap-77 was conducted according to the procedure described for Cap-7 by using 7-azabicyclo[2.2.1]heptane for the SN₂ displacement step, and by effecting the stereoisomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% CO₂-10% EtOH at 70 mL/min, and a temperature of 35° C. to provide 124.5 mg of stereoisomer-1 and 133.8 mg of stereoisomer-2. These benzyl esters were hydrogenolysed according to the preparation of Cap-7 to provide Cap-77: $^1$H NMR (DMSO-d$_6$, δ=2.5 ppm, 400 MHz): δ 7.55 (m, 2H), 7.38-7.30 (m, 3H), 4.16 (s, 1H), 3.54 (app br s, 2H), 2.08-1.88 (m, 4H), 1.57-1.46 (m, 4H). LC (Cond. 1): RT=0.67 min; LC-MS: Anal. Calcd. for [M+H]$^+$ C$_{14}$H$_{18}$NO$_2$:

232.13. found 232.18. HRMS: Anal. Calcd. for [M+H]+ C14H18NO2: 232.1338. found 232.1340.

Cap-78

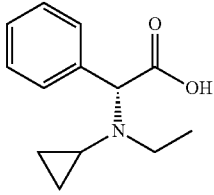

NaCNBH3 (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and NaCNBH3 (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC (H2O/MeOH/TFA) to afford the TFA salt of Cap-78 as a colorless viscous oil (353 mg). 1H NMR (DMSO-d6, δ=2.5 ppm, 400 MHz; after D2O exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H). LC (Cond. 1): RT=0.64 min; LC-MS: Anal. Calcd. for [M+H]+ C13H18NO2: 220.13. found 220.21. HRMS: Anal. Calcd. for [M+H]+ C13H18NO2: 220.1338. found 220.1343.

Cap-79

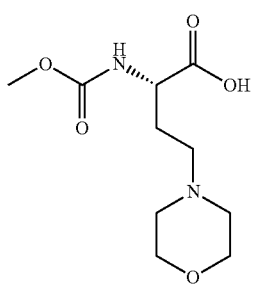

Ozone was bubbled through a cooled (–78° C.) CH2Cl2 (5.0 mL) solution Cap-55 (369 mg, 2.13 mmol) for about 50 min until the reaction mixture attained a tint of blue color. Me2S (10 pipette drops) was added, and the reaction mixture was stirred for 35 min. The –78° C. bath was replaced with a –10° C. bath and stirring continued for an additional 30 min, and then the volatile component was removed in vacuo to afford a colorless viscous oil.

NaBH3CN (149 mg, 2.25 mmol) was added to a MeOH (5.0 mL) solution of the above crude material and morpholine (500 µL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N NH3/MeOH elution) and a reverse phase HPLC (H2O/MeOH/TFA) to afford Cap-79 containing unknown amount of morpholine.

In order to consume the morpholine contaminant, the above material was dissolved in CH2Cl2 (1.5 mL) and treated with Et3N (0.27 mL, 1.94 mmol) followed by acetic anhydride (0.10 mL, 1.06 mmol) and stirred at ambient condition for 18 hr. THF (1.0 mL) and H2O (0.5 mL) were added and stirring continued for 1.5 hr. The volatile component was removed in vacuo, and the resultant residue was passed through MCX resin (MeOH wash; 2.0 N NH3/MeOH elution) to afford impure Cap-79 as a brown viscous oil, which was used for the next step without further purification.

Cap-80a and Cap-80b

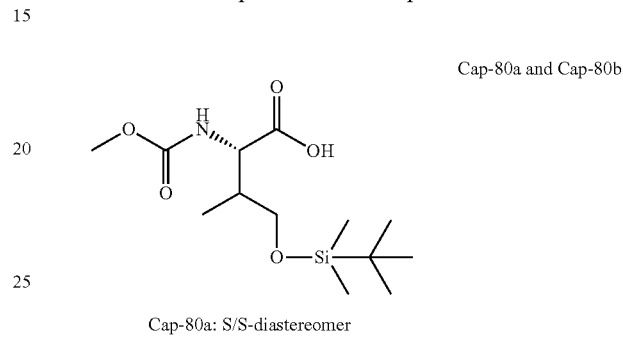

Cap-80a: S/S-diastereomer
Cap-80b: S/R-diastereomer

SOCl2 (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO3 solution. The aqueous phase was extracted with EtOAc (150 mL, 2×), and the combined organic phase was dried (MgSO4), filtered, and concentrated in vacuo to afford (S)-1-benzyl 4-methyl 2-aminosuccinate as a colorless oil (9.706 g). 1H NMR (DMSO-d6, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC-MS: Anal. Calcd. for [M+H]+ C12H16NO4: 238.11. found 238.22.

Pb(NO3)2 (6.06 g, 18.3 mmol) was added over 1 min to a CH2Cl2 (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et3N (3.0 mL, 21.5 mmol), and the heterogeneous mixture was stirred at ambient condition for 48 hr. The mixture was filtered and the filtrate was treated with MgSO4 and filtered again, and the final filtrate was concentrated. The resulting crude material was submitted to a BIOTAGE® purification (350 g silica gel, CH2Cl2 elution) to afford (S)-1-benzyl 4-methyl 2-(9-phenyl-9H-fluoren-9-ylamino)succinate as highly viscous colorless oil (7.93 g). 1H NMR (DMSO-d6, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC-MS: Anal. Calcd. for [M+H]+ C31H28NO4: 478.20. found 478.19.

LiHMDS (9.2 mL of 1.0 M/THF, 9.2 mmol) was added drop-wise over 10 min to a cooled (–78° C.) THF (50 mL) solution of (S)-1-benzyl 4-methyl 2-(9-phenyl-9H-fluoren-9-ylamino)succinate (3.907 g, 8.18 mmol) and stirred for ~1 hr.

Met (0.57 mL, 9.2 mmol) was added drop-wise over 8 min to the mixture, and stirring was continued for 16.5 hr while allowing the cooling bath to thaw to room temperature. After quenching with saturated NH$_4$Cl solution (5 mL), most of the organic component was removed in vacuo and the residue was partitioned between CH$_2$Cl$_2$ (100 mL) and water (40 mL). The organic layer was dried (MgSO$_4$), filtered, and concentrated in vacuo, and the resulting crude material was purified with a BIOTAGE® (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in 1.0:0.65 ratio ($^1$H NMR). The stereochemistry of the dominant isomer was not determined at this juncture, and the mixture was submitted to the next step without separation. Partial $^1$H NMR data (DMSO-d$_6$, δ=2.5 ppm, 400 MHz): major diastereomer, δ4.39 (d, J=12.3, 1H of CH$_2$), 3.33 (s, 3H, overlapped with H$_2$O signal), 3.50 (d, J=10.9, NH), 1.13 (d, J=7.1, 3H); minor diastereomer, δ 4.27 (d, J=12.3, 1H of CH$_2$), 3.76 (d, J=10.9, NH), 3.64 (s, 3H), 0.77 (d, J=7.0, 3H). LC (Cond. 1): RT=2.19 min; LC-MS: Anal. Calcd. for [M+H]$^+$ C$_{32}$H$_{30}$NO$_4$: 492.22. found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M H$_3$PO$_4$/H$_2$O (250 mL) with stirring, and the mixture was extracted with ether (100 mL, 2×). The combined organic phase was washed with brine, dried (MgSO$_4$), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-fluoren-9-ylamino)butanoate, contaminated with benzyl alcohol, as a colorless viscous oil and (2S,3R)-benzyl 4-hydroxy-3-methyl-2-(9-phenyl-9H-fluoren-9-ylamino)butanoate containing the (2S,3R) stereoisomer as an impurity. The later sample was resubmitted to the same column chromatography purification conditions to afford 750 mg of purified material as a white foam. [Note: the (2S,3S) isomer elutes before the (2S,3R) isomer under the above condition]. (2S,3S) isomer: $^1$H NMR (DMSO-d$_6$, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC-MS: Anal. Calcd. for [M+H]$^+$ C$_{31}$H$_{30}$NO$_3$: 464.45. found 464.22. (2S,3R) isomer: $^1$H NMR (DMSO-d$_6$, δ=2.5 ppm, 400 MHz): 7.81 (d, J=7.5, 2H), 7.39-7.10 (m, 16H), 4.63 (d, J=12.1, 1H), 4.50 (app t, J=4.9, 1H), 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H). LC (Cond. 1): RT=1.92 min; LC-MS: Anal. Calcd. for [M+H]$^+$ C$_{31}$H$_{30}$NO$_3$: 464.45. found 464.52.

The relative stereochemical assignments of the DIBAL-reduction products were made based on NOE studies conducted on lactone derivatives prepared from each isomer by employing the following protocol: LiHMDS (50 μL of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between CH$_2$Cl$_2$ (30 mL), water (20 mL) and saturated aqueous NH$_4$Cl solution (1 mL). The organic layer was dried (MgSO$_4$), filtered, and concentrated in vacuo, and the resulting crude material was submitted to a BIOTAGE® purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-d$_6$, δ=2.5 ppm, 400 MHz), 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC-MS: Anal. Calcd. for [M+Na]$^+$ C$_{24}$H$_{21}$NNaO$_2$: 378.15. found 378.42. (3S,4R)-lactone isomer: $^1$H NMR (DMSO-d$_6$, δ=2.5 ppm, 400 MHz), 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC-MS: Anal. Calcd. for [M+Na]$^+$ C$_{24}$H$_{21}$NNaO$_2$: 378.15. found 378.49.

TBDMS-Cl (48 mg, 0.312 mmol) followed by imidazole (28.8 mg, 0.423 mmol) were added to a CH$_2$Cl$_2$ (3 ml) solution of (2S,3 S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with CH$_2$Cl$_2$ (30 mL) and washed with water (15 mL), and the organic layer was dried (MgSO$_4$), filtered, and concentrated in vacuo. The resultant crude material was purified with a BIOTAGE® (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer: $^1$H NMR (DMSO-d$_6$, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC-MS: Anal. Calcd. for [M+H]$^+$ C$_{32}$H$_{44}$NO$_3$Si: 578.31. found 578.40. (2S,3R)-silyl ether isomer: $^1$H NMR (DMSO-d$_6$, δ=2.5 ppm, 400 MHz), 7.82 (d, J=3.0, 1H), 7.80 (d, J=3.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S,3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with H$_2$ as necessary. The reaction mixture was diluted with CH$_2$Cl$_2$ and filtered through a pad of diatomaceous earth (CELITE®-545), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/i-PrOH/H$_2$O) to afford (2S,3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9-ylamino)butanoate was similarly elaborated to (2S, 3R)-2-amino-4-(tert-butyldimethylsilyloxy)-3-methylbutanoic acid. (2S,3S)-amino acid isomer: $^1$H NMR (methanol-d$_4$, δ=3.29 ppm, 400 MHz), 3.76 (dd, J=10.5, 5.2, 1H), 3.73 (d, J=3.0, 1H), 3.67 (dd, J=10.5, 7.0, 1H), 2.37 (m, 1H), 0.97 (d, J=7.0, 3H), 0.92 (s, 9H), 0.10 (s, 6H). LC-MS: Anal. Calcd. for [M+H]$^+$ C$_{11}$H$_{26}$NO$_3$Si: 248.17. found 248.44. (2S, 3R)-amino acid isomer: $^1$H NMR (methanol-d$_4$, δ=3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal. Calcd. for [M+H]$^+$ C$_{11}$H$_{26}$NO$_3$Si: 248.17. found 248.44.

Water (1 mL) and NaOH (0.18 mL of 1.0 M/H$_2$O, 0.18 mmol) were added to a mixture of (2S,3S)-2-amino-4-(tert-butyldimethylsilyloxy)-3-methylbutanoic acid (41.9 mg, 0.169 mmol) and Na$_2$CO$_3$ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with CH$_2$Cl$_2$ (15 mL, 2×). The combined organic phase was dried (MgSO$_4$), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: $^1$H NMR (DMSO-d$_6$, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC-MS: Anal. Calcd. for [M+Na]$^+$ C$_{13}$H$_{27}$NNaO$_5$Si: 328.16. found 328.46. Cap-80b: $^1$H NMR (CDCl$_3$, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC-MS: Anal. Calcd. for [M+Na]$^+$ C$_{13}$H$_{27}$NNaO$_5$Si: 328.16. found 328.53. The crude products were utilized without further purification.

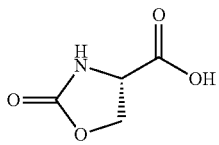

Cap-81

Prepared according to the protocol described by Falb et al., *Synthetic Communications*, 23:2839 (1993).

Cap-82 to Cap-85

Cap-82 to Cap-85 were synthesized from appropriate starting materials according to the procedure described for Cap-51 or Cap-13. The samples exhibited similar spectral profiles as that of their stereoisomers (i.e., Cap-4, Cap-13, Cap-51 and Cap-52, respectively).

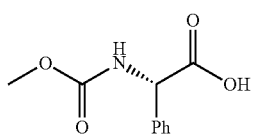

Cap-82

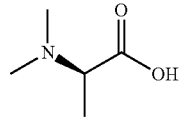

Cap-83

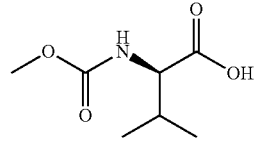

Cap-84

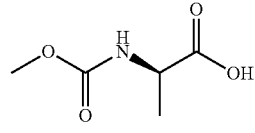

Cap-85

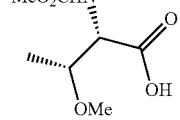

Cap-86

(2S,3R)-3-Methoxy-2-(methoxycarbonylamino)butanoic acid

To a mixture of O-methyl-L-threonine (3.0 g, 22.55 mmol), NaOH (0.902 g, 22.55 mmol) in H$_2$O (15 mL) was added ClCO$_2$Me (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in CH$_2$Cl$_2$ (250 mL) and the combined organic phases were concentrated under in vacuo to afford a colorless oil (4.18 g, 97%) which was of sufficient purity for use in subsequent steps. $^1$H NMR (400 MHz, CDCl$_3$) δ 4.19 (s, 1H), 3.92-3.97 (m, 1H), 3.66 (s, 3H), 1.17 (d, J=7.7 Hz, 3H). LC-MS: Anal. Calcd. for C$_7$H$_{13}$NO$_5$: 191. found: 190 (M–H)$^-$.

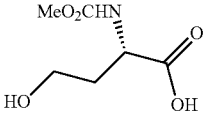

Cap-87

To a mixture of L-homoserine (2.0 g, 9.79 mmol), Na$_2$CO$_3$ (2.08 g, 19.59 mmol) in H$_2$O (15 mL) was added ClCO$_2$Me (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated in vacuo to afford a colorless solid (0.719 g, 28%) which was of sufficient purity for use in subsequent steps. $^1$H NMR (400 MHz, CDCl$_3$) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LC-MS: Anal. Calcd. for C$_7$H$_{13}$NO$_5$: 191. found: 192 (M+H)$^+$.

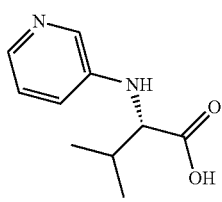

Cap-88

A mixture of L-valine (1.0 g, 8.54 mmol), 3-bromopyridine (1.8 mL, 18.7 mmol), K$_2$CO$_3$ (2.45 g, 17.7 mmol) and CuI (169 mg, 0.887 mmol) in DMSO (10 mL) was heated at 100° C. for 12 h. The reaction mixture was cooled to rt, poured into H$_2$O (ca. 150 mL) and washed with EtOAc (×2). The organic layers were extracted with a small amount of H$_2$O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H$_2$O (200 mL), MeOH (200 mL), and then NH$_3$ (3M in MeOH, 2×200 mL). The appropriate fractions was concentrated in vacuo and the residue (ca. 1.1 g) was dissolved in H$_2$O, frozen and lyophyllized. The title compound was obtained as a foam (1.02 g, 62%). $^1$H NMR (400 MHz, DMSO-d$_6$) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LC-MS: Anal. Calcd. for C$_{10}$H$_{14}$N$_2$O$_2$: 194. found: 195 (M+H)$^+$.

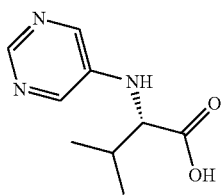

Cap-89

A mixture of L-valine (1.0 g, 8.54 mmol), 5-bromopyrimidine (4.03 g, 17.0 mmol), K$_2$CO$_3$ (2.40 g, 17.4 mmol) and CuI (179 mg, 0.94 mmol) in DMSO (10 mL) was heated at 100° C. for 12 h. The reaction mixture was cooled to RT, poured into H$_2$O (ca. 150 mL) and washed with EtOAc (×2). The organic layers were extracted with a small amount of H$_2$O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H$_2$O (200 mL), MeOH (200 mL), and then NH$_3$ (3M in MeOH, 2×200 mL). The appropriate fractions was concentrated in vacuo and the residue (ca. 1.1 g) was dissolved in H$_2$O, frozen and lyophyllized. The title compound was obtained as a foam (1.02 g, 62%). $^1$H NMR (400 MHz, CD$_3$OD) showed the mixture to contain valine and the purity could not be estimated. The material was used as is in subsequent reactions. LC-MS: Anal. Calcd. for C$_9$H$_{13}$N$_3$O$_2$: 195. found: 196 (M+H)$^+$.

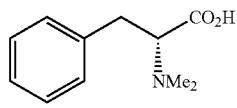

Cap-90

Cap-90 was prepared according to the method described for the preparation of Cap-1. The crude material was used as is in subsequent steps. LC-MS: Anal. Calcd. for C$_{11}$H$_{15}$NO$_2$: 193. found: 192 (M−H)$^−$.

Cap-91 to Cap-116

The following Caps were prepared according to the method used for preparation of Cap-51 unless noted otherwise:

| Cap | Structure | LC-MS |
|---|---|---|
| Cap-91 | ![structure] NHCO$_2$Me, CO$_2$H, phenyl | LC-MS: Anal. Calcd. for C$_{11}$H$_{13}$NO$_4$: 223; found: 222 (M − H)$^−$. |
| Cap-92 | ![structure] NHCO$_2$Me, CO$_2$H, phenyl | LC-MS: Anal Calcd. for C$_{11}$H$_{13}$NO$_4$: 223; found: 222 (M − H)$^−$. |
| Cap-93 | ![structure] pyridyl-CH$_2$-CH(NHCO$_2$Me)-COOH | LC-MS: Anal. Calcd. for C$_{10}$H$_{13}$N$_2$O$_4$: 224; found: 225 (M + H)$^+$. |
| Cap-94 | ![structure] imidazolyl-CH$_2$-CH(NHCO$_2$Me)-COOH | LC-MS: Anal. Calcd. for C$_8$H$_{11}$N$_3$O$_4$: 213; found: 214 (M + H)$^+$. |
| Cap-95 | ![structure] PhCH$_2$CH$_2$-CH(NHCO$_2$Me)-CH$_2$-COOH | LC-MS: Anal. Calcd. for C$_{13}$H$_{17}$NO$_4$: 251; found: 250 (M − H)$^−$. |

| Cap | Structure | LC-MS |
|---|---|---|
| Cap-96 | 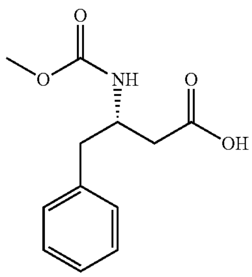 [SMILES: COC(=O)N[C@H](CC(=O)O)Cc1ccccc1] | LC-MS: Anal. Calcd. for C$_{12}$H$_{15}$NO$_4$: 237; found: 236 (M − H)$^-$. |
| Cap-97 | 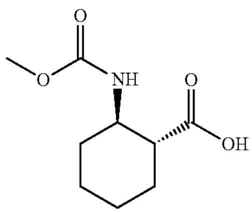 | LC-MS: Anal. Calcd. for C$_9$H$_{15}$NO$_4$: 201; found: 200 (M − H)$^-$. |
| Cap-98 | 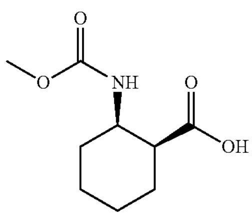 | LC-MS: Anal. Calcd. for C$_9$H$_{15}$NO$_4$: 201; found: 202 (M + H)$^+$. |
| Cap-99 | 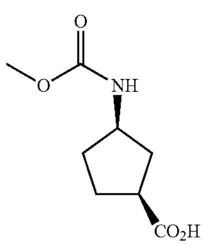 | $^1$H NMR (400 MHz, CD$_3$OD) δ 3.88-3.94 (m, 1H), 3.60, 3.61 (s, 3H), 2.80 (m, 1H), 2.20 (m, 1H), 1.82-1.94 (m, 3H), 1.45-1.71 (m, 2H). |
| Cap-99a | 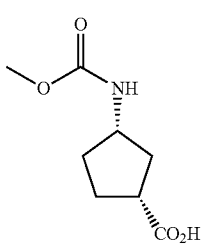 | $^1$H NMR (400 MHz, CD$_3$OD) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-100 | 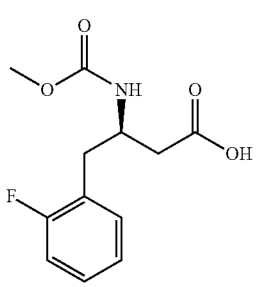 [SMILES: COC(=O)N[C@@H](CC(=O)O)Cc1ccccc1F] | LC-MS: Anal. Calcd. for C$_{12}$H$_{14}$NO$_4$F: 255; found: 256 (M + H)$^+$. |
| Cap-101 | | LC-MS: Anal. Calcd. for C$_{11}$H$_{13}$NO$_4$: 223; found: 222 (M − H)$^-$. |
| Cap-102 | | LC-MS: Anal. Calcd. for C$_{11}$H$_{13}$NO$_4$: 223; found: 222 (M − H)$^-$. |
| Cap-103 | | LC-MS: Anal. Calcd. for C$_{10}$H$_{12}$N$_2$O$_4$: 224; found: 225 (M + H)$^+$. |
| Cap-104 | | $^1$H NMR (400 MHz, CD$_3$OD) δ 3.60 (s, 3H), 3.50-3.53 (m, 1H), 2.66-2.69 and 2.44-2.49 (m, 1H), 1.91-2.01 (m, 2H), 1.62-1.74 (m, 4H), 1.51-1.62 (m, 2H). |
| Cap-105 | | $^1$H NMR (400 MHz, CD$_3$OD) δ 3.60 (s, 3H), 3.33-3.35 (m, 1H, partially obscured by solvent), 2.37-2.41 and 2.16-2.23 (m, 1H), 1.94-2.01 (m, 4H), 1.43-1.53 (m, 2H), 1.17-1.29 (m, 2H). |
| Cap-106 | | $^1$H NMR (400 MHz, CD$_3$OD) δ 3.16 (q, J = 7.3 Hz, 4H), 2.38-2.41 (m, 1H), 2.28-2.31 (m, 2H), 1.79-1.89 (m, 2H), 1.74 (app, ddd J = 3.5, 12.5, 15.9 Hz, 2H), 1.46 (app dt J = 4.0, 12.9 Hz, 2H), 1.26 (t, J = 7.3 Hz, 6H) |

Prepared from cis-4-aminocyclohexane carboxylic acid and acetaldehyde by employing a similar procedure described for the synthesis of Cap-2. The crude HCl salt was passed through MCX (MeOH/H$_2$O/CH$_2$Cl$_2$ wash; 2 N NH$_3$/MeOH elution) to afford an oil, which was dissolved in CH$_3$CN/H$_2$O and lyophilized to afford a tan solid.

| Cap | Structure | LC-MS |
|---|---|---|
| Cap-107 | (thiazol-4-yl methyl with NHCO2Me, CO2H) | LC-MS: Anal. Calcd. for $C_8H_{10}N_2O_4S$: 230; found: 231 $(M + H)^+$. |
| Cap-108 | (N-benzyl imidazolyl methyl with NHCO2Me, CO2H) | LC-MS: Anal. Calcd. for $C_{15}H_{17}N_3O_4$: 303; found: 304 $(M + H)^+$. |
| Cap-109 | (pyridin-3-yl methyl with NHCO2Me, CO2H) | LC-MS: Anal. Calcd. for $C_{10}H_{12}N_2O_4$: 224; found: 225 $(M + H)^+$. |
| Cap-110 | (pyridin-4-yl methyl with NHCO2Me, CO2H) | LC-MS: Anal. Calcd. for $C_{10}H_{12}N_2O_4$: 224; found: 225 $(M + H)^+$. |
| Cap-111 | (4-(methyl phosphate)phenyl methyl with NHCO2Me, CO2H) | LC-MS: Anal. Calcd. for $C_{12}H_{16}NO_8P$: 333; found: 334 $(M + H)^+$. |
| Cap-112 | (indol-3-yl methyl with NHCO2Me, CO2H) | LC-MS: Anal. Calcd. for $C_{13}H_{14}N_2O_4$: 262; found: 263 $(M + H)^+$. |
| Cap-113 | (4-benzyloxyphenyl methyl with NHCO2Me, CO2H) | LC-MS: Anal. Calcd. for $C_{18}H_{19}NO_5$: 329; found: 330 $(M + H)^+$. |
| Cap-114 | (azetidine-N-CO2Me, 2-CO2H) | $^1$H NMR (400 MHz, CDCl$_3$) δ 4.82-4.84 (m, 1H), 4.00-4.05 (m, 2H), 3.77 (s, 3H), 2.56 (s, br, 2H) |
| Cap-115 | (3-NHCO2Me, methyl, CO2H) | $^1$H NMR (400 MHz, CDCl$_3$) δ 5.13 (s, br, 1H), 4.13 (s, br, 1H), 3.69 (s, 3H), 2.61 (d, J = 5.0 Hz, 2H), 1.28 (d, J = 9.1 Hz, 3H). |
| Cap-116 | (3-NHCO2Me, isopropyl, CO2H) | $^1$H NMR (400 MHz, CDCl$_3$) δ 5.10 (d, J = 8.6 Hz, 1H), 3.74-3.83 (m, 1H), 3.69 (s, 3H), 2.54-2.61 (m, 2H), 1.88 (sept, J = 7.0 Hz, 1H), 0.95 (d, J = 7.0 Hz, 6H). |

Cap-117 to Cap-123

For the preparation of Cap-117 to Cap-123 the Boc amino acids were obtained from commercially sources and were deprotected by treatment with 25% TFA in CH$_2$Cl$_2$. After complete reaction as judged by LC-MS the solvents were removed in vacuo and the corresponding TFA salt of the amino acid was carbamoylated with methyl chloroformate according to the procedure described for Cap-51.

| Cap | Structure | LC-MS |
|---|---|---|
| Cap-117 | 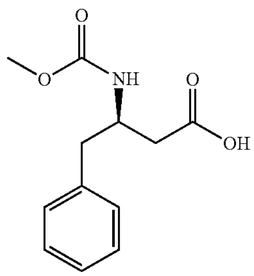 [SMILES: COC(=O)N[C@@H](CC(=O)O)Cc1ccccc1] | LC-MS: Anal. Calcd. for C$_{12}$H$_{15}$NO$_4$: 237; found: 238 (M + H)$^+$. |
| Cap-118 | 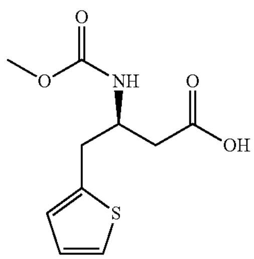 [SMILES: COC(=O)N[C@@H](CC(=O)O)Cc1cccs1] | LC-MS: Anal. Calcd. for C$_{10}$H$_{13}$NO$_4$S: 243; found: 244 (M + H)$^+$. |
| Cap-119 | 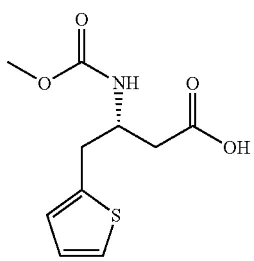 [SMILES: COC(=O)N[C@H](CC(=O)O)Cc1cccs1] | LC-MS: Anal. Calcd. for C$_{10}$H$_{13}$NO$_4$S: 243; found: 244 (M + H)$^+$. |
| Cap-120 | 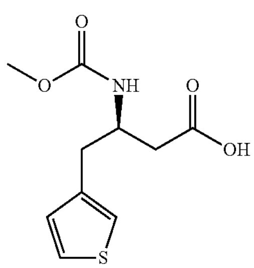 [SMILES: COC(=O)N[C@@H](CC(=O)O)Cc1ccsc1] | LC-MS: Anal. Calcd. for C$_{10}$H$_{13}$NO$_4$S: 243; found: 244 (M + H)$^+$. |
| Cap-121 | 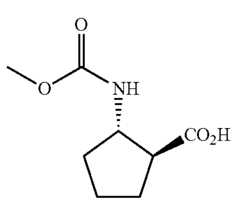 | $^1$H NMR (400 MHz, CDCl$_3$) δ 4.06-4.16 (m, 1H), 3.63 (s, 3H), 3.43 (s, 1H), 2.82 and 2.66 (s, br, 1H), 1.86-2.10 (m, 3H), 1.64-1.76 (m, 2H), 1.44-1.53 (m, 1H). |
| Cap-122 | 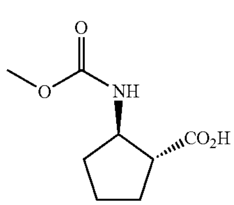 | $^1$H NMR profile is similar to that of its stereoisomer, Cap-121. |

| Cap | Structure | LC-MS |
|---|---|---|
| Cap-123 | 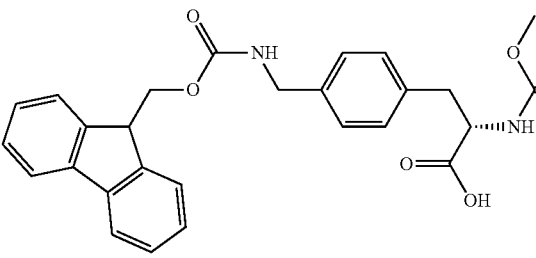 | LC-MS: Anal. Calcd. for $C_{27}H_{26}N_2O_6$: 474; found: 475 $(M + H)^+$. |

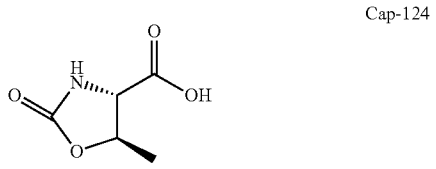

Cap-124

The hydrochloride salt of L-threonine tert-butyl ester was carbamoylated according to the procedure for Cap-51. The crude reaction mixture was acidified with 1N HCl to pH~1 and the mixture was extracted with EtOAc (2×50 mL). The combined organic phases were concentrated in vacuo to give a colorless oil which solidified on standing. The aqueous layer was concentrated in vacuo and the resulting mixture of product and inorganic salts was triturated with EtOAc-$CH_2Cl_2$-MeOH (1:1:0.1) and then the organic phase concentrated in vacuo to give a colorless oil which was shown by LC-MS to be the desired product. Both crops were combined to give 0.52 g of a solid. $^1$H NMR (400 MHz, $CD_3OD$) δ 4.60 (m, 1H), 4.04 (d, J=5.0 Hz, 1H), 1.49 (d, J=6.3 Hz, 3H). LC-MS: Anal. Calcd. for $C_5H_7NO_4$: 145. found: 146 $(M+H)^+$.

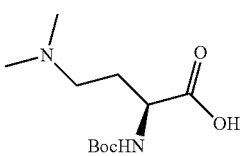

Cap-125

To a suspension of $Pd(OH)_2$, (20%, 100 mg), aqueous formaldehyde (37% wt, 4 ml), acetic acid, (0.5 mL) in methanol (15 mL) was added (S)-4-amino-2-(tert-butoxycarbonylamino)butanoic acid (1 g, 4.48 mmol). The reaction was purged several times with hydrogen and was stirred overnight with an hydrogen balloon room temperature. The reaction mixture was filtered through a pad of diatomaceous earth (CELITE®), and the volatile component was removed in vacuo. The resulting crude material was used as is for the next step. LC-MS: Anal. Calcd. for $C_{11}H_{22}N_2O_4$: 246. found: 247 $(M+H)^+$.


cj-25

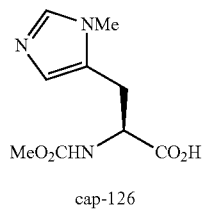

cap-126

This procedure is a modification of that used to prepare Cap-51. To a suspension of 3-methyl-L-histidine (0.80 g, 4.70 mmol) in THF (10 mL) and $H_2O$ (10 mL) at 0° C. was added $NaHCO_3$ (0.88 g, 10.5 mmol). The resulting mixture was treated with $ClCO_2Me$ (0.40 mL, 5.20 mmol) and the mixture allowed to stir at 0° C. After stirring for ca. 2 h LC-MS showed no starting material remaining. The reaction was acidified to pH 2 with 6 N HCl.

The solvents were removed in vacuo and the residue was suspended in 20 mL of 20% MeOH in $CH_2Cl_2$. The mixture was filtered and concentrated to give a light yellow foam (1.21 g,). LC-MS and $^1$H NMR showed the material to be a 9:1 mixture of the methyl ester and the desired product. This material was taken up in THF (10 mL) and $H_2O$ (10 mL), cooled to 0° C. and LiOH (249.1 mg, 10.4 mmol) was added. After stirring ca. 1 h LC-MS showed no ester remaining. Therefore the mixture was acidified with 6N HCl and the solvents removed in vacuo. LC-MS and $^1$H NMR confirm the absence of the ester. The title compound was obtained as its HCl salt contaminated with inorganic salts (1.91 g, >100%). The compound was used as is in subsequent steps without further purification. $^1$H NMR (400 MHz, $CD_3OD$) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H). LC-MS: Anal. Calcd. for $C_9H_{13}N_3O_4$: 227.09. found: 228.09 $(M+H)^+$.

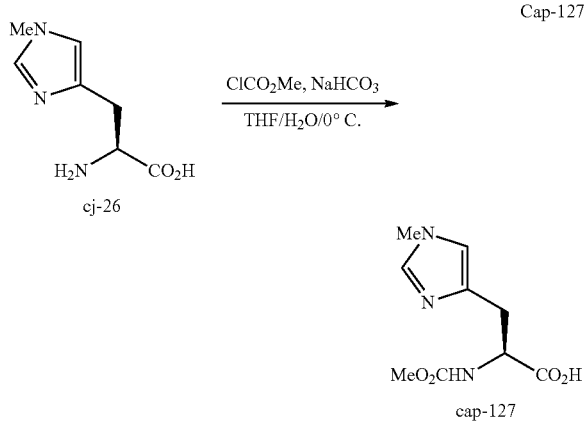

Cap-127 was prepared according to the method for Cap-126 above starting from (S)-2-amino-3-(1-methyl-1H-imidazol-4-yl)propanoic acid (1.11 g, 6.56 mmol), NaHCO$_3$ (1.21 g, 14.4 mmol) and ClCO$_2$Me (0.56 mL, 7.28 mmol). The title compound was obtained as its HCl salt (1.79 g, >100%) contaminated with inorganic salts. LC-MS and $^1$H NMR showed the presence of ca. 5% of the methyl ester. The crude mixture was used as is without further purification. $^1$H NMR (400 MHz, CD$_3$OD) δ 8.90 (s, 1H), 7.35 (s, 1H), 4.48 (dd, J=5.0, 8.6 Hz, 1H), 3.89 (s, 3H), 3.62 (s, 3H), 3.35 (m, 1H), 3.08 (m, 1H); LC-MS: Anal. Calcd. for C$_9$H$_{13}$N$_3$O$_4$: 227.09. found: 228 (M+H)$^+$.

Preparation of Cap-128

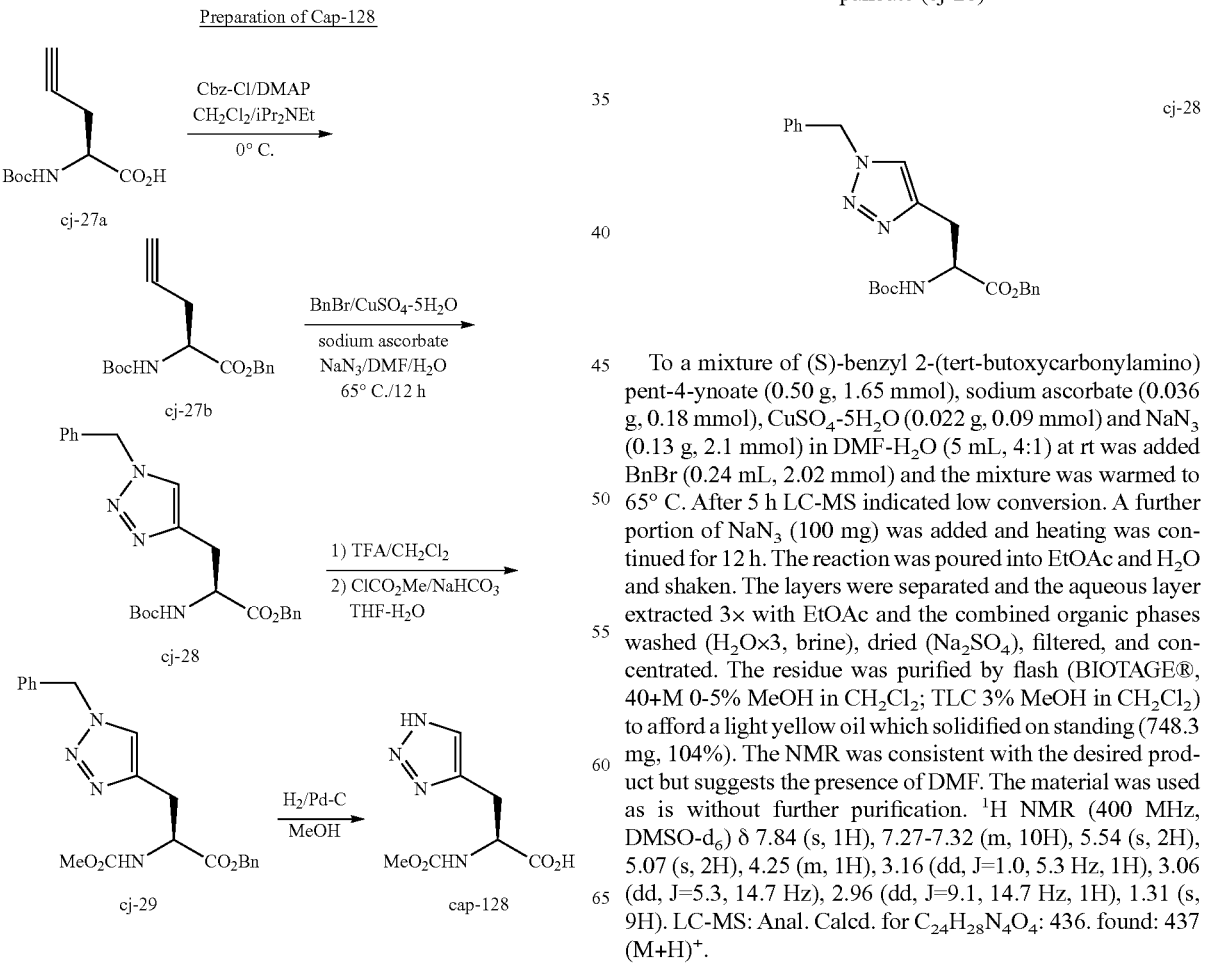

Step 1. Preparation of (S)-benzyl 2-(tert-butoxycarbonylamino)pent-4-ynoate (cj-27b)

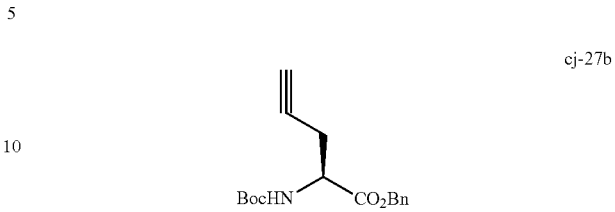

To a solution of cj-27a (1.01 g, 4.74 mmol), DMAP (58 mg, 0.475 mmol) and iPr$_2$NEt (1.7 mL, 9.8 mmol) in CH$_2$Cl$_2$ (100 mL) at 0° C. was added Cbz-Cl (0.68 mL, 4.83 mmol). The solution was allowed to stir for 4 h at 0° C., washed (1N KHSO$_4$, brine), dried (Na$_2$SO$_4$), filtered, and concentrated in vacuo. The residue was purified by flash column chromatography (TLC 6:1 hex:EtOAc) to give the title compound (1.30 g, 91%) as a colorless oil. $^1$H NMR (400 MHz, CDCl$_3$) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, 2H), 2.00 (t, J=2.5 Hz, 1H), 1.44 (s, 9H). LC-MS: Anal. Calcd. for C$_{17}$H$_{21}$Na$_4$: 303. found: 304 (M+H)$^+$.

Step 2. Preparation of (S)-benzyl 3-(1-benzyl-1H-1,2,3-triazol-4-yl)-2-(tert-butoxycarbonylamino)propanoate (cj-28)

To a mixture of (S)-benzyl 2-(tert-butoxycarbonylamino)pent-4-ynoate (0.50 g, 1.65 mmol), sodium ascorbate (0.036 g, 0.18 mmol), CuSO$_4$·5H$_2$O (0.022 g, 0.09 mmol) and NaN$_3$ (0.13 g, 2.1 mmol) in DMF-H$_2$O (5 mL, 4:1) at rt was added BnBr (0.24 mL, 2.02 mmol) and the mixture was warmed to 65° C. After 5 h LC-MS indicated low conversion. A further portion of NaN$_3$ (100 mg) was added and heating was continued for 12 h. The reaction was poured into EtOAc and H$_2$O and shaken. The layers were separated and the aqueous layer extracted 3× with EtOAc and the combined organic phases washed (H$_2$O×3, brine), dried (Na$_2$SO$_4$), filtered, and concentrated. The residue was purified by flash (BIOTAGE®, 40+M 0-5% MeOH in CH$_2$Cl$_2$; TLC 3% MeOH in CH$_2$Cl$_2$) to afford a light yellow oil which solidified on standing (748.3 mg, 104%). The NMR was consistent with the desired product but suggests the presence of DMF. The material was used as is without further purification. $^1$H NMR (400 MHz, DMSO-d$_6$) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz), 2.96 (dd, J=9.1, 14.7 Hz, 1H), 1.31 (s, 9H). LC-MS: Anal. Calcd. for C$_{24}$H$_{28}$N$_4$O$_4$: 436. found: 437 (M+H)$^+$.

Step 3. Preparation of (S)-benzyl 3-(1-benzyl-1H-1,2,3-triazol-4-yl)-2-(methoxycarbonylamino)propanoate (cj-29)

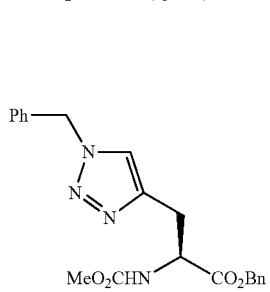

A solution of (S)-benzyl 3-(1-benzyl-1H-1,2,3-triazol-4-yl)-2-(tert-butoxycarbonylamino)propanoate (0.52 g, 1.15 mmol) in CH$_2$Cl$_2$ was added TFA (4 mL). The mixture was allowed to stir at room temperature for 2 h. The mixture was concentrated in vacuo to give a colorless oil which solidified on standing. This material was dissolved in THF-H$_2$O and cooled to 0° C. Solid NaHCO$_3$ (0.25 g, 3.00 mmol) was added followed by ClCO$_2$Me (0.25 mL, 3.25 mmol). After stirring for 1.5 h the mixture was acidified to pH~2 with 6N HCl and then poured into H$_2$O-EtOAc. The layers were separated and the aq phase extracted 2× with EtOAc. The combined org layers were washed (H$_2$O, brine), dried (Na$_2$SO$_4$), filtered, and concentrated in vacuo to give a colorless oil (505.8 mg, 111%, NMR suggested the presence of an unidentified impurity) which solidified while standing on the pump. The material was used as is without further purification. $^1$H NMR (400 MHz, DMSO-d$_6$) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09 (dd, J=5.6, 14.7 Hz, 1H), 2.98 (dd, J=9.6, 14.7 Hz, 1H). LC-MS: Anal. Calcd. for C$_{21}$H$_{22}$N$_4$O$_4$: 394. found: 395 (M+H)$^+$.

Step 4. Preparation of (S)-2-(methoxycarbonylamino)-3-(1H-1,2,3-triazol-4-yl)propanoic acid (Cap-128)

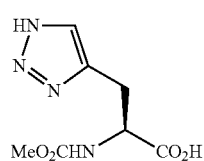

(S)-Benzyl 3-(1-benzyl-1H-1,2,3-triazol-4-yl)-2-(methoxycarbonylamino)propanoate (502 mg, 1.11 mmol) was hydrogenated in the presence of Pd—C (82 mg) in MeOH (5 mL) at atmospheric pressure for 12 h. The mixture was filtered through diatomaceous earth (CELITE®) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification. $^1$H NMR (400 MHz, DMSO-d$_6$) δ 12.78 (s, br, 1H), 7.59 (s, 1H), 7.50 (d, J=8.0 Hz, 1H), 4.19-4.24 (m, 1H), 3.49 (s, 3H), 3.12 (dd, J=4.8 Hz, 14.9 Hz, 1H), 2.96 (dd, J=9.9, 15.0 Hz, 1H). LC-MS: Anal. Calcd. for C$_7$H$_{10}$N$_4$O$_4$: 214. found: 215 (M+H)$^+$.

Preparation of Cap-129

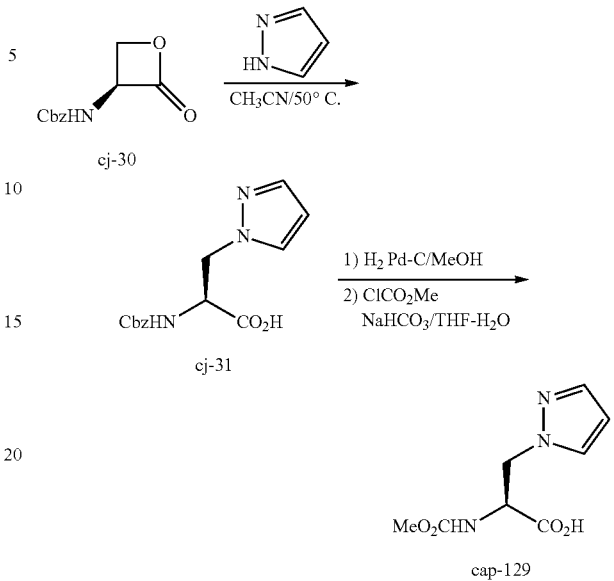

Step 1. Preparation of (S)-2-(benzyloxycarbonylamino)-3-(1H-pyrazol-1-yl)propanoic acid (cj-31)

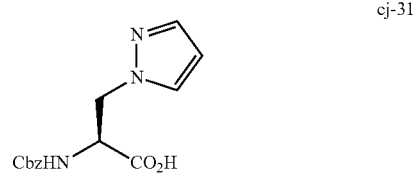 [SMILES: O=C(N[C@@H](Cn1cccn1)C(=O)O)OCc1ccccc1]

A suspension of (S)-benzyl 2-oxooxetan-3-ylcarbamate (0.67 g, 3.03 mmol), and pyrazole (0.22 g, 3.29 mmol) in CH$_3$CN (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of CH$_3$CN (ca. 4 mL) to afford a second crop (43.5 mg). Total yield 370.4 mg (44%). m.p. 165.5-168° C. lit m.p. 168.5-169.5 [Vederas et al., *J. Am. Chem. Soc.*, 107:7105 (1985)]. $^1$H NMR (400 MHz, CD$_3$OD) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LC-MS: Anal. Calcd. for C$_{14}$H$_{15}$N$_3$O$_4$: 289. found: 290 (M+H)$^+$.

Step 2. Preparation of (S)-2-(methoxycarbonylamino)-3-(1H-pyrazol-1-yl)propanoic acid (Cap-129)

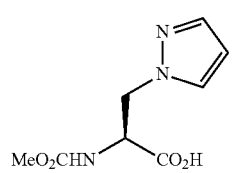

(S)-2-(Benzyloxycarbonylamino)-3-(1H-pyrazol-1-yl) propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the reaction mixture was diluted with 5 mL $H_2O$ and a few drops of 6N HCl. The homogeneous solution was filtered through diatomaceous earth (CELITE®), and the MeOH removed in vacuo. The remaining solution was frozen and lyophyllized to give a yellow foam (188.9 mg). This material was suspended in THF-$H_2O$ (1:1, 10 mL) and then cooled to 0° C. To the cold mixture was added $NaHCO_3$ (146.0 mg, 1.74 mmol) carefully (evolution of $CO_2$). After gas evolution had ceased (ca. 15 min) $ClCO_2Me$ (0.06 mL, 0.78 mmol) was added dropwise. The mixture was allowed to stir for 2 h and was acidified to pH~2 with 6N HCl and poured into EtOAc. The layers were separated and the aqueous phase extracted with EtOAC (×5). The combined organic layers were washed (brine), dried ($Na_2SO_4$), filtered, and concentrated to give the title compound as a colorless solid (117.8 mg, 79%). $^1$H NMR (400 MHz, DMSO-$d_6$) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LC-MS: Anal. Calcd. for $C_8H_{11}N_3O_4$: 213. found: 214 (M+H)$^+$.

Cap-130

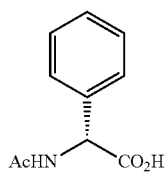

Cap-130 was prepared by acylation of commercially available (R)-phenylglycine analogous to the procedure given in: Calmes, M. et al., *Tetrahedron*, 43(10):2285 (1987).

Cap-131

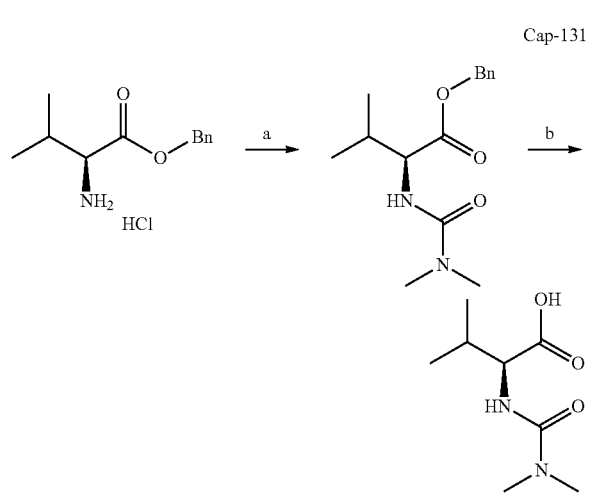

Step a: Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried ($MgSO_4$), filtered, and concentrated under reduced pressure. The resulting yellow oil was purified by flash chromatography, eluting with ethyl acetate:hexanes (1:1). Collected fractions were concentrated under vacuum providing 2.35 g (85%) of clear oil. $^1$H NMR (300 MHz, DMSO-$d_6$) δ ppm 0.84 (d, J=6.95 Hz, 3H), 0.89 (d, J=6.59 Hz, 3H), 1.98-2.15 (m, 1H), 2.80 (s, 6H), 5.01-5.09 (m, J=12.44 Hz, 1H), 5.13 (d, J=12.44 Hz, 1H), 6.22 (d, J=8.05 Hz, 1H), 7.26-7.42 (m, 5H). LC (Cond. 1): RT=1.76 min; MS: Anal. Calcd. for [M+H]$^+$ $C_{16}H_{22}N_2O_3$: 279.17. found 279.03.

Step b: To an MeOH (50 mL) solution of the intermediate prepared above (2.35 g; 8.45 mmol) was added Pd/C (10%; 200 mg) and the resulting black suspension was flushed with $N_2$ (3×) and placed under 1 atm of $H_2$. The mixture was stirred at room temperature overnight and filtered though a microfiber filter to remove the catalyst. The resulting clear solution was then concentrated under reduced pressure to obtain 1.43 g (89%) of Cap-131 as a white foam, which was used without further purification. $^1$H NMR (500 MHz, DMSO-$d_6$) δ ppm 0.87 (d, J=4.27 Hz, 3H), 0.88 (d, J=3.97 Hz, 3H), 1.93-2.11 (m, 1H), 2.80 (s, 6H), 3.90 (dd, J=8.39, 6.87 Hz, 1H), 5.93 (d, J=8.54 Hz, 1H), 12.36 (s, 1H). LC (Cond. 1): RT=0.33 min; MS: Anal. Calcd. for [M+H]$^+$ $C_8H_{17}N_2O_3$: 189.12. found 189.04.

Cap-132

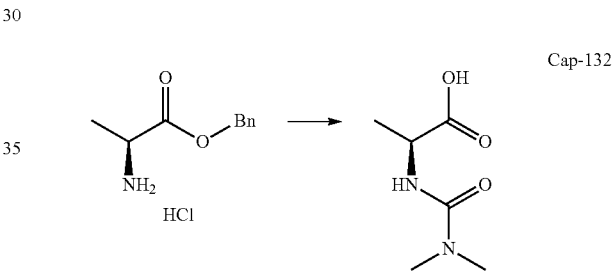

Cap-132 was prepared from (S)-benzyl 2-aminopropanoate hydrochloride according to the method described for Cap-131. $^1$H NMR (500 MHz, DMSO-$d_6$) δ ppm 1.27 (d, J=7.32 Hz, 3H), 2.80 (s, 6H), 4.06 (qt, 1H), 6.36 (d, J=7.32 Hz, 1H), 12.27 (s, 1H). LC (Cond. 1): RT=0.15 min; MS: Anal. Calcd. for [M+H]$^+$ $C_6H_{13}N_2O_3$: 161.09. found 161.00.

Cap-133

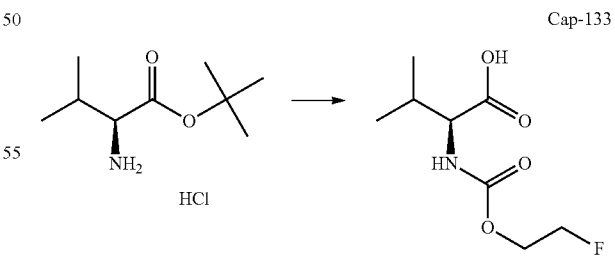

Cap-133 was prepared from (S)-tert-butyl 2-amino-3-methylbutanoate hydrochloride and 2-fluoroethyl chloroformate according to the method described for Cap-47. $^1$H NMR (500 MHz, DMSO-$d_6$) δ ppm 0.87 (t, J=6.71 Hz, 6H), 1.97-2.10 (m, 1H), 3.83 (dd, J=8.39, 5.95 Hz, 1H), 4.14-4.18 (m, 1H), 4.20-4.25 (m, 1H), 4.50-4.54 (m, 1H), 4.59-4.65 (m, 1H), 7.51 (d, J=8.54 Hz, 1H), 12.54 (s, 1H).

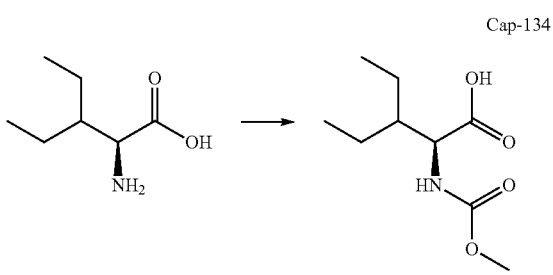

Cap-134

Cap-134 was prepared from (S)-diethylalanine and methyl chloroformate according to the method described for Cap-51. $^1$H NMR (500 MHz, DMSO-$d_6$) δ ppm 0.72-0.89 (m, 6H), 1.15-1.38 (m, 4H), 1.54-1.66 (m, 1H), 3.46-3.63 (m, 3H), 4.09 (dd, J=8.85, 5.19 Hz, 1H), 7.24 (d, J=8.85 Hz, 1H), 12.55 (s, 1H). LC (Cond. 2): RT=0.66 min; LC-MS: Anal. Calcd. for [M+H]$^+$ C$_9$H$_{18}$NO$_4$: 204.12. found 204.02.

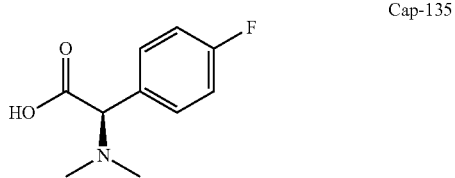

Cap-135

A solution of D-2-amino-(4-fluorophenyl)acetic acid (338 mg, 2.00 mmol), 1N HCl in diethylether (2.0 mL, 2.0 mmol) and formalin (37%, 1 mL) in methanol (5 mL) was subjected to balloon hydrogenation over 10% palladium on carbon (60 mg) for 16 h at 25° C. The mixture was then filtered through CELITE® to afford the HCl salt of Cap-135 as a white foam (316 mg, 80%). $^1$H NMR (300 MHz, MeOH-$d_4$) δ 7.59 (dd, J=8.80, 5.10 Hz, 2H), 7.29 (t, J=8.6 Hz, 2H), 5.17 (s, 1H), 3.05 (v br s, 3H), 2.63 (v br s, 3H); R$_f$=0.19 min (Cond.-MS-WS); 95% homogenity index; LRMS: Anal. Calcd. for [M+H]$^+$ C$_{10}$H$_{13}$FNO$_2$: 198.09. found: 198.10.

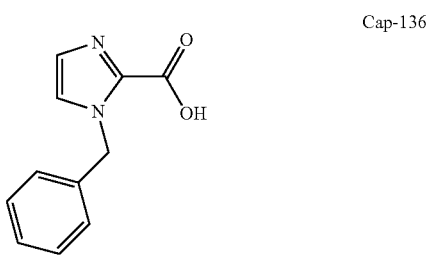 [SMILES: O=C(O)c1nccn1Cc1ccccc1]

Cap-136

To a cooled (−50° C.) suspension of 1-benzyl-1H-imidazole (1.58 g, 10.0 mmol) in anhydrous diethyl ether (50 mL) under nitrogen was added n-butyl lithium (2.5 M in hexanes, 4.0 mL, 10.0 mmol) dropwise. After being stirred for 20 min at −50° C., dry carbon dioxide (passed through Drierite) was bubbled into the reaction mixture for 10 min before it was allowed to warm up to 25° C. The heavy precipitate which formed on addition of carbon dioxide to the reaction mixture was filtered to yield a hygroscopic, white solid which was taken up in water (7 mL), acidified to pH=3, cooled, and induced to crystallize with scratching. Filtration of this precipitate gave a white solid which was suspended in methanol, treated with 1N HCl/diethyl ether (4 mL) and concentrated in vacuo. Lyophilization of the residue from water (5 mL) afforded the HCl salt of Cap-136 as a white solid (817 mg, 40%). $^1$H NMR (300 MHz, DMSO-$d_6$) δ 7.94 (d, J=1.5 Hz, 1H), 7.71 (d, J=1.5 Hz, 1H), 7.50-7.31 (m, 5H), 5.77 (s, 2H); R$_f$=0.51 min (Cond.-MS-W5); 95% homogenity index; LRMS: Anal. Calc. for [M+H]$^+$ C$_{11}$H$_{12}$N$_2$O$_2$: 203.08. found: 203.11.

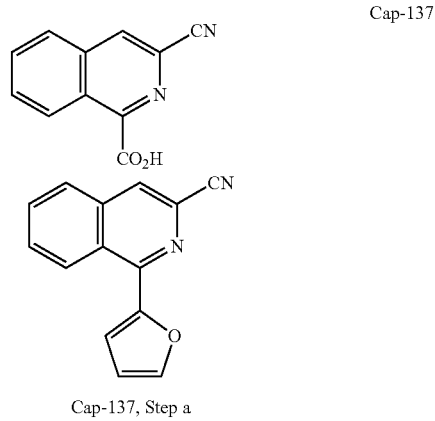

Cap-137

Cap-137, Step a

A suspension of 1-chloro-3-cyanoisoquinoline (188 mg, 1.00 mmol; prepared according to the procedure in WO 2003/099274) (188 mg, 1.00 mmol), cesium fluoride (303.8 mg, 2.00 mmol), bis(tri-tert-butylphosphine)palladium dichloride (10 mg, 0.02 mmol) and 2-(tributylstannyl)furan (378 μL, 1.20 mmol) in anhydrous dioxane (10 mL) under nitrogen was heated at 80° C. for 16 h before it was cooled to 25° C. and treated with saturated, aqueous potassium fluoride solution with vigorous stirring for 1 h. The mixture was partitioned between ethyl acetate and water and the organic phase was separated, washed with brine, dried over Na$_2$SO$_4$, filtered and concentrated. Purification of the residue on silica gel (elution with 0% to 30% ethyl acetate/hexanes) afforded Cap-137, Step a as a white solid which was used as is (230 mg, 105%). R$_f$=1.95 min (Cond.-MS-W2); 90% homogeneity index; LRMS: Anal. Calc. for [M+H]$^+$ C$_{14}$H$_8$N$_2$O: 221.07. found: 221.12.

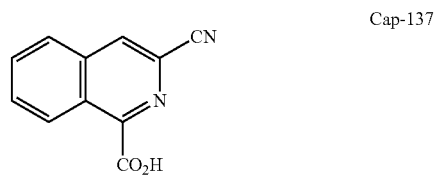 [SMILES: N#Cc1cc2ccccc2c(C(=O)O)n1]

Cap-137

To a suspension of Cap-137, Step a (110 mg, 0.50 mmol) and sodium periodate (438 mg, 2.05 mmol) in carbon tetrachloride (1 mL), acetonitrile (1 mL) and water (1.5 mL) was added ruthenium trichloride hydrate (2 mg, 0.011 mmol). The mixture was stirred at 25° C. for 2 h and then partitioned between dichloromethane and water. The aqueous layer was separated, extracted twice more with dichloromethane and the combined dichloromethane extracts were dried over Na$_2$SO$_4$, filtered and concentrated. Trituration of the residue with hexanes afforded Cap-137 (55 mg, 55%) as a grayish-colored solid. R$_f$=1.10 min (Cond.-MS-W2); 90% homogeneity index; LC-MS: Anal. Calc. for [M+H]$^+$ C$_{11}$H$_8$N$_2$O$_2$: 200.08. found: 200.08.

Cap-138 to Cap-158

Synthetic Strategy. Method A.

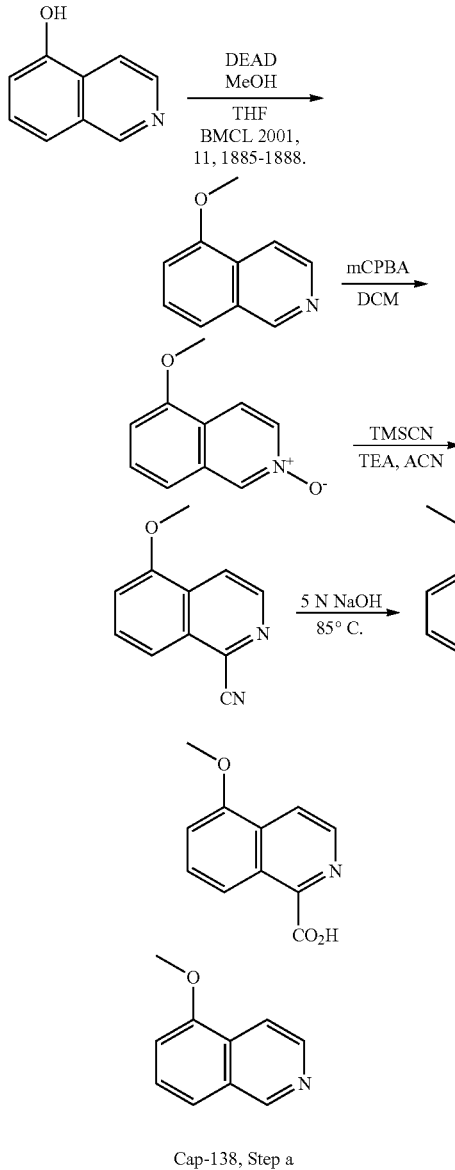

Cap-138, Step a

To a stirred suspension of 5-hydroxisoquinoline (prepared according to the procedure in WO 2003/099274) (2.0 g, 13.8 mmol) and triphenylphosphine (4.3 g, 16.5 mmol) in dry tetrahydrofuran (20 mL) was added dry methanol (0.8 mL) and diethyl azodicarboxylate (3.0 mL, 16.5 mmol) portionwise. The mixture was stirred at room temperature for 20 h before it was diluted with ethyl acetate and washed with brine, dried over $Na_2SO_4$, filtered and concentrated. The residue was preabsorbed onto silica gel and purified (elution with 40% ethyl acetate/hexanes) to afford Cap-138, Step a as a light yellow solid (1.00 g, 45%). $^1$H NMR ($CDCl_3$, 500 MHz) δ 9.19 (s, 1H), 8.51 (d, J=6.0 Hz, 1H), 7.99 (d, J=6.0 Hz, 1H), 7.52-7.50 (m, 2H), 7.00-6.99 (m, 1H), 4.01 (s, 3H); $R_f$=0.66 min (Cond. D2); 95% homogeneity index; LC-MS: Anal. Calc. for $[M+H]^+$ $C_{10}H_{10}NO$: 160.08. found 160.10.

Cap-138, Step b

To a stirred solution of Cap-138, Step a (2.34 g, 14.7 mmol) in anhydrous dichloromethane (50 mL) at room temperature was added meta-chloroperbenzoic acid (77%, 3.42 g, 19.8 mmol) in one portion. After being stirred for 20 h, powdered potassium carbonate (2.0 g) was added and the mixture was stirred for 1 h at room temperature before it was filtered and concentrated to afford Cap-138, Step b as a pale, yellow solid which was sufficiently pure to carry forward (2.15 g, 83.3%). $^1$H NMR ($CDCl_3$, 400 MHz) δ 8.73 (d, J=1.5 Hz, 1H), 8.11 (dd, J=7.3, 1.7 Hz, 1H), 8.04 (d, J=7.1 Hz, 1H), 7.52 (t, J=8.1 Hz, 1H), 7.28 (d, J=8.3 Hz, 1H), 6.91 (d, J=7.8 Hz, 1H), 4.00 (s, 3H); $R_f$=0.92 min, (Cond.-D1); 90% homogenity index; LC-MS: Anal. Calc. for $[M+H]^+$ $C_{10}H_{10}NO_2$: 176.07. found: 176.0.

Cap-138, Step c

To a stirred solution of Cap-138, Step b (0.70 g, 4.00 mmol) and triethylamine (1.1 mL, 8.00 mmol) in dry acetonitrile (20 mL) at room temperature under nitrogen was added trimethylsilylcyanide (1.60 mL, 12.00 mmol). The mixture was heated at 75° C. for 20 h before it was cooled to room temperature, diluted with ethyl acetate and washed with saturated sodium bicarbonate solution and brine prior to drying over $Na_2SO_4$ and solvent concentration. The residue was flash chromatographed on silica gel (elution with 5% ethyl acetate/hexanes) to 25% ethyl acetate/hexanes to afford Cap-138, Step c (498.7 mg) as a white, crystalline solid along with 223 mg of additional Cap-138, Step c recovered from the filtrate. $^1$H NMR ($CDCl_3$, 500 MHz) δ 8.63 (d, J=5.5 Hz, 1H), 8.26 (d, J=5.5 Hz, 1H), 7.88 (d, J=8.5 Hz, 1H), 7.69 (t, J=8.0 Hz, 1H), 7.08 (d, J=7.5 Hz, 1H), 4.04 (s, 3H); $R_f$=1.75 min, (Cond.-D1); 90% homogeneity index; LC-MS: Anal. Calc. for $[M+H]^+$ $C_{11}H_9N_2O$: 185.07. found: 185.10.

Cap-138

Cap-138, Step c (0.45 g, 2.44 mmol) was treated with 5N sodium hydroxide solution (10 mL) and the resulting suspension was heated at 85° C. for 4 h, cooled to 25° C., diluted with dichloromethane and acidified with 1N hydrochloric acid. The organic phase was separated, washed with brine, dried over Na$_2$SO$_4$, concentrated to ¼ volume and filtered to afford Cap-138 as a yellow solid (0.44 g, 88.9%). $^1$H NMR (DMSO-d$_6$, 400 MHz) δ 13.6 (br s, 1H), 8.56 (d, J=6.0 Hz, 1H), 8.16 (d, J=6.0 Hz, 1H), 8.06 (d, J=8.8 Hz, 1H), 7.71-7.67 (m, 1H), 7.30 (d, J=8.0 Hz, 1H), 4.02 (s, 3H); R$_t$=0.70 min (Cond.-D1); 95% homogenity index; LC-MS: Anal. Calc. for [M+H]$^+$ C$_{11}$H$_{10}$NO$_3$: 204.07. found: 204.05.

Synthetic Strategy. Method B (derived from *Tetrahedron Letters*, 42:6707 (2001)).

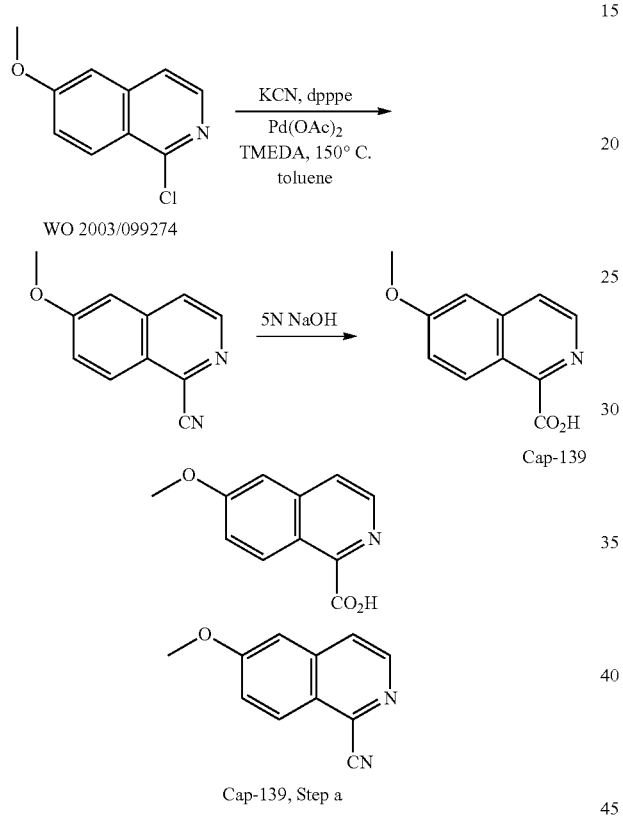

Cap-139, Step a

To a thick-walled, screw-top vial containing an argon-degassed suspension of 1-chloro-6-methoxyisoquinoline (1.2 g, 6.2 mmol; prepared according to the procedure in WO 2003/099274), potassium cyanide (0.40 g, 6.2 mmol), 1,5-bis(diphenylphosphino)pentane (0.27 g, 0.62 mmol) and palladium (II) acetate (70 mg, 0.31 mmol) in anhydrous toluene (6 mL) was added N,N,N',N'-tetramethylethylenediamine (0.29 mL, 2.48 mmol). The vial was sealed, heated at 150° C. for 22 h and then allowed to cool to 25° C. The reaction mixture was diluted with ethyl acetate, washed with water and brine, dried over Na$_2$SO$_4$, filtered and concentrated. The residue was purified on silica gel eluting with 5% ethyl acetate/hexanes to 25% ethyl acetate/hexanes to afford Cap-139, Step a as a white solid (669.7 mg). $^1$H NMR (CDCl$_3$, 500 MHz) δ 8.54 (d, J=6.0 Hz, 1H), 8.22 (d, J=9.0 Hz, 1H), 7.76 (d, J=5.5 Hz, 1H), 7.41-7.39 (m, 1H), 7.13 (d, J=2.0 Hz, 1H), 3.98 (s, 3H); R$_t$=1.66 min (Cond.-D1); 90% homogenity index; LC-MS: Anal. Calc. for [M+H]$^+$ C$_{11}$H$_9$N$_2$O: 185.07. found: 185.20.

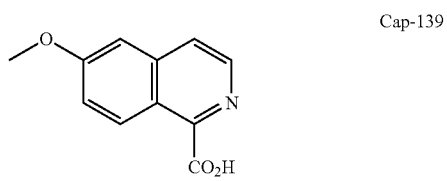

Cap-139

Cap-139 was prepared from the basic hydrolysis of Cap-139, Step a with 5N NaOH according to the procedure described for Cap-138. $^1$H NMR (400 MHz, DMSO-d$_6$) δ 13.63 (v br s, 1H), 8.60 (d, J=9.3 Hz, 1H), 8.45 (d, J=5.6 Hz, 1H), 7.95 (d, J=5.9 Hz, 1H), 7.49 (d, J=2.2 Hz, 1H), 7.44 (dd, J=9.3, 2.5 Hz, 1H), 3.95 (s, 3H); R$_t$=0.64 min (Cond.-D1); 90% homogenity index; LC-MS: Anal. Calc. for [M+H]$^+$ C$_{11}$H$_{10}$NO$_3$: 204.07. found: 204.05.

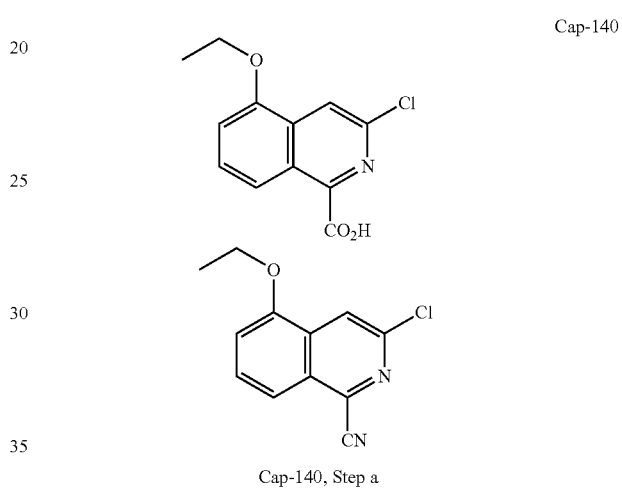

Cap-140, Step a

To a vigorously-stirred mixture of 1,3-dichloro-5-ethoxy-isoquinoline (482 mg, 2.00 mmol; prepared according to the procedure in WO 2005/051410), palladium (II) acetate (9 mg, 0.04 mmol), sodium carbonate (223 mg, 2.10 mmol) and 1,5-bis(diphenylphosphino)pentane (35 mg, 0.08 mmol) in dry dimethylacetamide (2 mL) at 25° C. under nitrogen was added N,N,N',N'-tetramethylethylenediamine (60 mL, 0.40 mmol). After 10 min, the mixture was heated to 150° C., and then a stock solution of acetone cyanohydrin (prepared from 457 μL of acetone cyanohydrin in 4.34 mL DMA) was added in 1 mL portions over 18 h using a syringe pump. The mixture was then partitioned between ethyl acetate and water and the organic layer was separated, washed with brine, dried over Na$_2$SO$_4$, filtered and concentrated. The residue was purified on silica gel eluting with 10% ethyl acetate/hexanes to 40% ethyl acetate/hexanes to afford Cap-140, Step a as a yellow solid (160 mg, 34%). R$_t$=2.46 min (Cond.-MS-W2); 90% homogenity index; LC-MS: Anal. Calc. for [M+H]$^+$ C$_{12}$H$_9$ClN$_2$O: 233.05. found: 233.08.

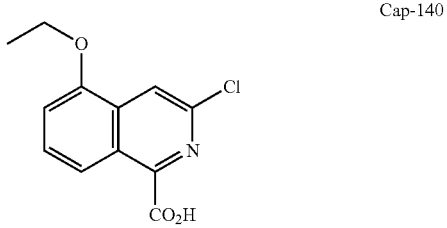

Cap-140

Cap-140 was prepared by the acid hydrolysis of Cap-140, Step a with 12N HCl as described in the procedure for the preparation of Cap-141, described below. $R_f$=2.24 min (Cond.-MS-W2); 90% homogenity index; LC-MS: Anal. Calc. for [M+H]$^+$ C$_{12}$H$_{11}$ClNO$_3$: 252.04. found: 252.02.

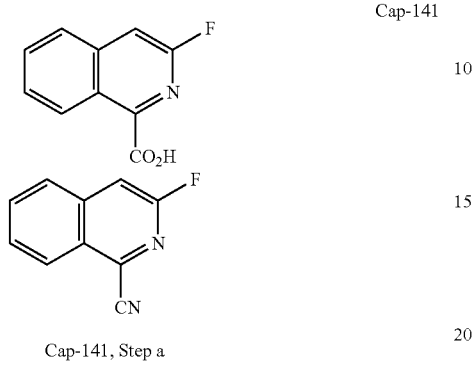

Cap-141

Cap-141, Step a

Cap-141, Step a was prepared from 1-bromo-3-fluoroisoquinoline (prepared from 3-amino-1-bromoisoquinoline using the procedure outlined in *J. Med. Chem.*, 13:613 (1970)) as described in the procedure for the preparation of Cap-140, Step a (vide supra). $^1$H NMR (500 MHz, CDCl$_3$) δ 8.35 (d, J=8.5 Hz, 1H), 7.93 (d, J=8.5 Hz, 1H), 7.83 (t, J=7.63 Hz, 1H), 7.77-7.73 (m, 1H), 7.55 (s, 1H); $R_f$=1.60 min (Cond.-D1); 90% homogenity index; LC-MS: Anal. Calc. for [M+H]$^+$ C$_{10}$H$_6$FN$_2$: 173.05. found: 172.99.

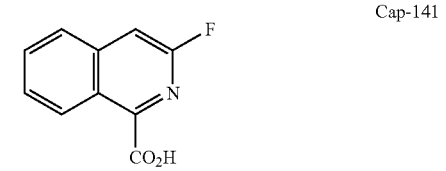 [SMILES: O=C(O)c1nc(F)cc2ccccc12]

Cap-141

Cap-141, Step a (83 mg, 0.48 mmol) was treated with 12N HCl (3 mL) and the resulting slurry was heated at 80° C. for 16 h before it was cooled to room temperature and diluted with water (3 mL). The mixture was stirred for 10 min and then filtered to afford Cap-141 as an off-white solid (44.1 mg, 47.8%). The filtrate was diluted with dichloromethane and washed with brine, dried over Na$_2$SO$_4$, and concentrated to afford additional Cap-141 which was sufficiently pure to be carried forward directly (29.30 mg, 31.8%). $^1$H NMR (DMSO-d$_6$, 500 MHz) δ 14.0 (br s, 1H), 8.59-8.57 (m, 1H), 8.10 (d, J=8.5 Hz, 1H), 7.88-7.85 (m, 2H), 7.74-7.71 (m, 1H); $R_f$=1.33 min (Cond.-D1); 90% homogenity index; LC-MS: Anal. Calc. for [M+H]$^+$ C$_{10}$H$_7$FNO$_2$: 192.05. found: 191.97.

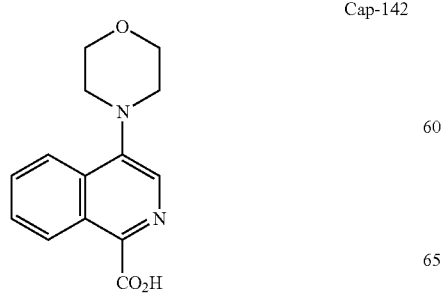

Cap-142

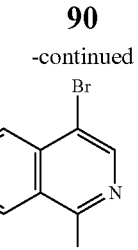

Cap-142, Step a

Cap-142, Step a was prepared from 4-bromoisoquinoline N-oxide as described in the two-step procedure for the preparation of Cap-138, steps b and c. $R_f$=1.45 min (Cond.-MS-W1); 90% homogenity index; LC-MS: Anal. Calc. for [M+H]$^+$ C$_{10}$H$_6$BrN$_2$: 232.97. found: 233.00.

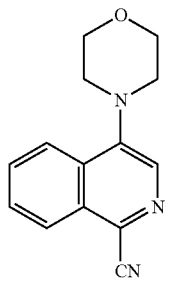

Cap-142, Step b

To an argon-degassed suspension of Cap-142, Step a (116 mg, 0.50 mmol), potassium phosphate tribasic (170 mg, 0.80 mmol), palladium (II) acetate (3.4 mg, 0.015 mmol) and 2-(dicyclohexylphosphino)biphenyl (11 mg, 0.03 mmol) in anhydrous toluene (1 mL) was added morpholine (61 μL, 0.70 mmol). The mixture was heated at 100° C. for 16 h, cooled to 25° C. and filtered through diatomaceous earth (CELITE®). Purification of the residue on silica gel, eluting with 10% to 70% ethyl acetate/hexanes afforded Cap-142, Step b (38 mg, 32%) as a yellow solid, which was carried forward directly. $R_f$=1.26 min (Cond.-MS-W1); 90% homogenity index; LC-MS: Anal. Calc. for [M+H]$^+$ C$_{14}$H$_{14}$N$_3$O: 240.11. found: 240.13.

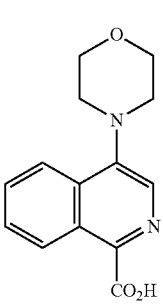

Cap-142

Cap-142 was prepared from Cap-142, Step b with 5N sodium hydroxide as described in the procedure for Cap-138. $R_f$=0.72 min (Cond.-MS-W1); 90% homogenity index; LC-MS: Anal. Calc. for [M+H]$^+$ C$_{14}$H$_{15}$N$_2$O$_3$: 259.11. found: 259.08.

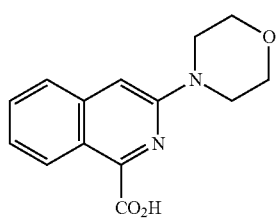

Cap-143

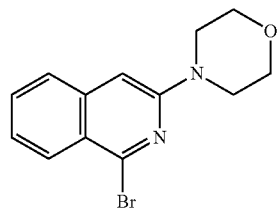

Cap-143, Step a

To a stirred solution of 3-amino-1-bromoisoquinoline (444 mg, 2.00 mmol) in anhydrous dimethylformamide (10 mL) was added sodium hydride (60%, unwashed, 96 mg, 2.4 mmol) in one portion. The mixture was stirred at 25° C. for 5 min before 2-bromoethyl ether (90%, 250 µL, 2.00 mmol) was added. The mixture was stirred further at 25° C. for 5 h and at 75° C. for 72 h before it was cooled to 25° C., quenched with saturated ammonium chloride solution and diluted with ethyl acetate. The organic layer was separated, washed with water and brine, dried over $Na_2SO_4$, filtered and concentrated. Purification of the residue on silica gel eluting with 0% to 70% ethyl acetate/hexanes afforded Cap-143, Step a as a yellow solid (180 mg, 31%). $R_f$=1.75 min (Cond.-MS-W1); 90% homogenity index; LC-MS: Anal. Calc. for $[M+H]^+$ $C_{13}H_{14}BrN_2O$: 293.03. found: 293.04.

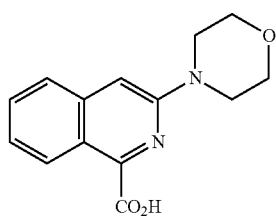

Cap-143

To a cold (−60° C.) solution of Cap-143, Step a (154 mg, 0.527 mmol) in anhydrous tetrahydrofuran (5 mL) was added a solution of n-butyllithium in hexanes (2.5 M, 0.25 mL, 0.633 mmol). After 10 min, dry carbon dioxide was bubbled into the reaction mixture for 10 min before it was quenched with 1N HCl and allowed to warm to 25° C. The mixture was then extracted with dichloromethane (3×30 mL) and the combined organic extracts were concentrated in vacuo. Purification of the residue by a reverse phase HPLC (MeOH/water/TFA) afforded Cap-143 (16 mg, 12%). $R_f$=1.10 min (Cond.-MS-W1); 90% homogenity index; LC-MS: Anal. Calc. for $[M+H]^+$ $C_{14}H_{15}N_2O_3$: 259.11. found: 259.08.

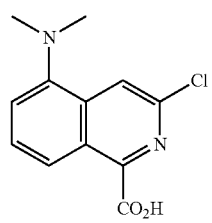

Cap-144

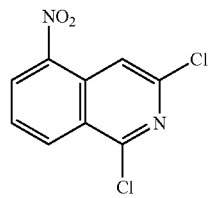

Cap-144, Step a 1,3-Dichloroisoquinoline (2.75 g, 13.89 mmol) was added in small portions to a cold (0° C.) solution of fuming nitric acid (10 mL) and concentrated sulfuric acid (10 mL). The mixture was stirred at 0° C. for 0.5 h before it was gradually warmed to 25° C. where it stirred for 16 h. The mixture was then poured into a beaker containing chopped ice and water and the resulting suspension was stirred for 1 h at 0° C. before it was filtered to afford Cap-144, Step a (2.73 g, 81%) as a yellow solid which was used directly. $R_f$=2.01 min. (Cond.-D1); 95% homogenity index; LC-MS: Anal. Calc. for $[M+H]^+$ $C_9H_5Cl_2N_2O_2$: 242.97. found: 242.92.

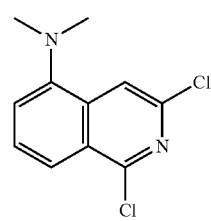

Cap-144, Step b

Cap-144, Step a (0.30 g, 1.23 mmol) was taken up in methanol (60 mL) and treated with platinum oxide (30 mg), and the suspension was subjected to Parr hydrogenation at 7 psi $H_2$ for 1.5 h. Then formalin (5 mL) and additional platinum oxide (30 mg) were added, and the suspension was resubjected to Parr hydrogenation at 45 psi $H_2$ for 13 h. It was then suction-filtered through diatomaceous earth (CELITE®) and concentrated down to ¼ volume. Suction-filtration of the ensuing precipitate afforded the title compound as a yellow solid which was flash chromatographed on silica gel eluting with 5% ethyl acetate in hexanes to 25% ethyl acetate in hexanes to afford Cap-144, Step b (231 mg, 78%) as a pale yellow solid. $R_f$=2.36 min (Cond.-D1); 95% homogenity index; $^1$H NMR (400 MHz, $CDCl_3$) δ 8.02 (s, 1H), 7.95 (d, J=8.6 Hz, 1H), 7.57-7.53 (m, 1H), 7.30 (d, J=7.3 Hz, 1H), 2.88 (s, 6H); LC-MS: Anal. Calc. for $[M+H]^+$ $C_{11}H_{11}Cl_2N_2$:

241.03. found: 241.02. HRMS: Anal. Calc. for [M+H]$^+$ C$_{11}$H$_{11}$Cl$_2$N$_2$: 241.0299. found: 241.0296.

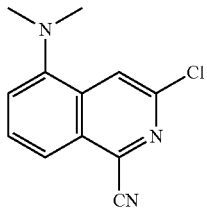

Cap-144, Step c

Cap-144, Step c was prepared from Cap-144, Step b according to the procedure described for the preparation of Cap-139, Step a. R$_t$=2.19 min (Cond.-D1); 95% homogenity index; LC-MS: Anal. Calc. for [M+H]$^+$ C$_{12}$K$_1$ClN$_3$: 232.06. found: 232.03. HRMS: Anal. Calc. for [M+H]$^+$ C$_{12}$K$_1$ClN$_3$: 232.0642. found: 232.0631.

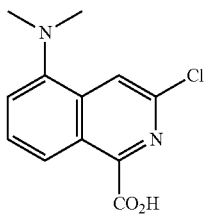

Cap-144

Cap-144 was prepared according to the procedure described for Cap-141. R$_t$=2.36 min (Cond.-D1); 90%; LC-MS: Anal. Calc. for [M+H]$^+$ C$_{12}$H$_{12}$ClN$_2$O$_2$: 238.01. found: 238.09.

Cap-145 to Cap-162

Cap-145 to Cap-162 were prepared from the appropriate 1-chloroisoquinolines according to the procedure described for the preparation of Cap-138 (Method A) or Cap-139 (Method B) unless noted otherwise as outlined below.

| Cap-# | Cap | Method | Hydrolysis | R$_t$ (LC-Cond.); % homogeneity index; MS data |
|---|---|---|---|---|
| Cap-145 | 3-chloroisoquinoline-1-carboxylic acid<br>Prepared from commercially available 1,3-dichloroisoquinoline | B | 12N HCl | 1.14 min (Cond.-MS-W1); 90%; LC-MS: Anal. Calc. for [M + H]$^+$ C$_{10}$H$_7$ClNO$_2$: 208.02; found: 208.00. |
| Cap-146 | 3-methoxyisoquinoline-1-carboxylic acid<br>Prepared from commercially available 3-hydroxyisoquinoline | A | 5N NaOH | 1.40 min (Cond.-D1); 95%; LC-MS: Anal. Calc. for [M + H]$^+$ C$_{11}$H$_{10}$NO$_3$: 204.07; found: 204.06. |
| Cap-147 | 4-methoxyisoquinoline-1-carboxylic acid<br>Prepared from commercially available 1-chloro-4-hydroxyisoquinoline | B | 5N NaOH | 0.87 min (Cond.-D1); 95%; LC-MS: Anal. Calc. for [M + H]$^+$ C$_{11}$H$_{10}$NO$_3$: 204.07; found: 204.05. |

-continued

| Cap-# | Cap | Method | Hydrolysis | $R_t$ (LC-Cond.); % homogeneity index; MS data |
|---|---|---|---|---|
| Cap-148 | 7-methoxyisoquinoline-1-carboxylic acid structure. Prepared from commercially available 7-hydroxyisoquinoline | A | 5N NaOH | 0.70 min (Cond.-D1); 95%; LC-MS: Anal. Calc. for $[M + H]^+$ $C_{11}H_{10}NO_3$: 204.07; found: 204.05. |
| Cap-149 | 5-methoxyisoquinoline-1-carboxylic acid structure. Prepared from commercially available 5-hydroxyisoquinoline | A | 5N NaOH | 0.70 min (Cond.-D1); 95%; LC-MS: Anal. Calc. for $[M + H]^+$ $C_{11}H_{10}NO_3$: 204.07; found: 204.05. |
| Cap-150 | 8-methoxyisoquinoline-1-carboxylic acid · TFA structure. Prepared from 8-methoxy-1-chloroisoquinoline, which can be synthesized following the procedure in WO 2003/099274 | A | 12N HCl | 0.26 min (Cond.-D1); 95%; LC-MS: Anal. Calc. for $[M + H]^+$ $C_{11}H_{10}NO_3$: 204.07; found: 204.04. |
| Cap-151 3-chloro-5-methoxyisoquinoline-1-carboxylic acid | Structure. Prepared from 5-methoxy-1,3-dichloroisoquinoline, which can be synthesized following the procedure in WO 2005/051410 | B | 12N HCl | 1.78 min (Cond.-D1); 90%; LC-MS: Anal. Calc. for $[M + H]^+$ $C_{11}H_9ClNO_3$: 238.03; found: 238.09. |
| Cap-152 | Structure. Prepared from commercially available 6-methoxy-1,3-dichloroisoquinoline | B | 12N HCl | 1.65 min (Cond.-D1); 95%; LC-MS: Anal. Calc. for $[M + H]^+$ $C_{11}H_9ClNO_3$: 238.00; found: 238.09. |

| Cap-# | Cap | Method | Hydrolysis | $R_t$ (LC-Cond.); % homogeneity index; MS data |
|---|---|---|---|---|
| Cap-153 | 4-bromoisoquinoline-1-carboxylic acid. Prepared from 4-bromoisoquinoline, which can be synthesized following the procedure in WO 2003/062241 | A | 6N HCl | 1.18 min (Cond.-MS-W1); 95%; LC-MS: Anal. Calc. for $[M+H]^+$ $C_{10}H_7BrNO_2$: 251.97; found: 251.95. |
| Cap-154 | 7-fluoroisoquinoline-1-carboxylic acid. Prepared from 7-fluoro-1-chloroisoquinoline, which can be synthesized following the procedure in WO 2003/099274 | B | 5N NaOH | 0.28 min (Cond.-MS-W1); 90%; LC-MS: Anal. Calc. for $[M+H]^+$ $C_{10}H_7FNO_2$: 192.05; found: 192.03. |
| Cap-155 | 7-chloroisoquinoline-1-carboxylic acid. Prepared from 1,7-dichloroisoquinoline, which can be synthesized following the procedure in WO 2003/099274 | B | 5N NaOH | 0.59 min (Cond.-MS-W1); 90%; LC-MS: Anal. Calc. for $[M+H]^+$ $C_{10}H_7ClNO_2$: 208.02; found: 208.00. |
| Cap-156 | 6-chloroisoquinoline-1-carboxylic acid. Prepared from 1,6-dichloroisoquinoline, which can be synthesized following the procedure in WO 2003/099274 | B | 5N NaOH | 0.60 min (Cond.-MS-W1); 90%; LC-MS: Anal. Calc. for $[M+H]^+$ $C_{10}H_7ClNO_2$: 208.02; found: 208.03. |

-continued

| Cap-# | Cap | Method | Hydrolysis | $R_t$ (LC-Cond.); % homogeneity index; MS data |
|---|---|---|---|---|
| Cap-157 | 4-chloroisoquinoline-1-carboxylic acid<br><br>Prepared from 1,4-dichloroisoquinoline, which can be synthesized following the procedure in WO 2003/062241 | B | 12N HCl | 1.49 min (Cond.-D1); 95%; LC-MS: Anal. Calc. for $[M + H]^+$ $C_{10}H_{17}ClNO$: 208.02; found: 208.00. |
| Cap-158 | 5-chloroisoquinoline-1-carboxylic acid<br><br>Prepared from 1,5-dichloroisoquinoline, which can be synthesized following the procedure in WO 2003/099274 | B | 5N NaOH | 0.69 min (Cond.-MS-W1); 90%; LC-MS: Anal. Calc. for $[M + H]^+$ $C_{10}H_7ClNO_2$: 208.02; found: 208.01. |
| Cap-159 | 5-fluoroisoquinoline-1-carboxylic acid<br><br>Prepared from 5-fluoro-1-chloroisoquinoline, which can be synthesized following the procedure in WO 2003/099274 | B | 5N NaOH | 0.41 min (Cond.-MS-W1); 90%; LC-MS: Anal. Calc. for $[M + H]^+$ $C_{10}H_7FNO_2$: 192.05; found: 192.03. |
| Cap-160 | 6-fluoroisoquinoline-1-carboxylic acid<br><br>Prepared from 6-fluoro-1-chloroisoquinoline, which can be synthesized following the procedure in WO 2003/099274 | B | 5N NaOH | 0.30 min (Cond.-MS-W1); 90%; LC-MS: Anal. Calc. for $[M + H]^+$ $C_{10}H_7FNO_2$: 192.05; found: 192.03. |

| Cap-# | Cap | Method | Hydrolysis | $R_f$ (LC-Cond.); % homogeneity index; MS data |
|---|---|---|---|---|
| Cap-161 | ![structure] Prepared from 4-bromoquinoline-2-carboxylic acid and dimethylamine (DMSO, 100° C. | — | — | 0.70 min (Cond.-D1); 95%; LC-MS: Anal. Calc. for [M + H]$^+$ $C_{12}H_{13}N_2O_2$: 217.10; found: 217.06. |
| Cap-162 | ![structure] Prepared from m-anisidine following the procedure described in *J. Hetero. Chem.*, 17 (1993) and *Heterocycles*, 60: 953 (2003). | — | — | 0.65 min (Cond.-M3); 95%; LC-MS: Anal. Calc. for [M + H]$^+$ $C_{11}H_{10}NO_3$: 204.07; found: 203.94. |

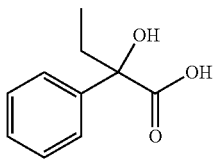

Cap-163

To a solution of 2-ketobutyric acid (1.0 g, 9.8 mmol) in diethylether (25 ml) was added phenylmagnesium bromide (22 ml, 1M in THF) dropwise. The reaction was stirred at ~25° C. under nitrogen for 17.5 h. The reaction was acidified with 1N HCl and the product was extracted with ethyl acetate (3×100 ml). The combined organic layer was washed with water followed by brine and dried over MgSO$_4$. After concentration in vacuo, a white solid was obtained. The solid was recrystallized from hexanes/ethyl acetate to afford Cap-163 as white needles (883.5 mg). $^1$H NMR (DMSO-d$_6$, δ=2.5 ppm, 500 MHz): 12.71 (br s, 1H), 7.54-7.52 (m, 2H), 7.34-7.31 (m, 2H), 7.26-7.23 (m, 1H), 5.52-5.39 (br s, 1H), 2.11 (m, 1H), 1.88 (m, 1H), 0.79 (app t, J=7.4 Hz, 3H).

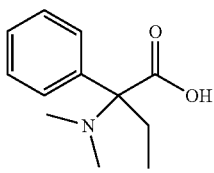

Cap-164

A mixture of 2-amino-2-phenylbutyric acid (1.5 g, 8.4 mmol), formaldehyde (14 mL, 37% in water), 1N HCl (10 mL) and 10% Pd/C (0.5 mg) in MeOH (40 mL) was exposed to H$_2$ at 50 psi in a Parr bottle for 42 h. The reaction was filtered over CELITE® and concentrated in vacuo, the residue was taken up in MeOH (36 mL) and the product was purified with a reverse phase HPLC (MeOH/H$_2$O/TFA) to afford the TFA salt of Cap-164 as a white solid (1.7 g). $^1$H NMR (DMSO-d$_6$, δ=2.5 ppm, 500 MHz) 7.54-7.47 (m, 5H), 2.63 (m, 1H), 2.55 (s, 6H), 2.31 (m, 1H), 0.95 (app t, J=7.3 Hz, 3H).

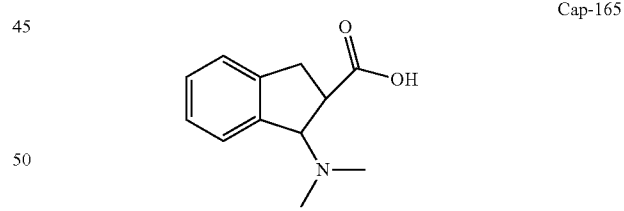

Cap-165

To a mixture of 2-amino-2-indanecarboxylic acid (258.6 mg, 1.46 mmol) and formic acid (0.6 ml, 15.9 mmol) in 1,2-dichloroethane (7 ml) was added formaldehyde (0.6 ml, 37% in water). The mixture was stirred at ~25° C. for 15 min then heated at 70° C. for 8 h. The volatile component was removed in vacuo, and the residue was dissolved in DMF (14 mL) and purified by a reverse phase HPLC (MeOH/H$_2$O/TFA) to afford the TFA salt of Cap-165 as a viscous oil (120.2 mg). $^1$H NMR (DMSO-d$_6$, δ=2.5 ppm, 500 MHz): 7.29-7.21 (m, 4H), 3.61 (d, J=17.4 Hz, 2H), 3.50 (d, J=17.4 Hz, 2H), 2.75 (s, 6H). LC-MS: Anal. Calcd. for [M+H]$^+$ $C_{12}H_{16}NO_2$: 206.12. found: 206.07.

Cap-166a and Cap-166b

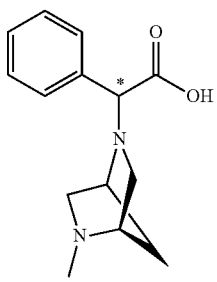

Cap-166a: Diastereomer-1
Cap-166b: Diastereomer-2

Cap-166a and Cap-166b were prepared from (1S,4S)-(+)-2-methyl-2,5-diazabicyclo[2.2.1]heptane (2HBr) according to the method described for the synthesis of Cap-7a and Cap-7b, with the exception that the benzyl ester intermediate was separated using a semi-prep Chrialcel OJ column, 20×250 mm, 10 μm eluting with 85:15 heptane/ethanol mixture at 10 mL/min elution rate for 25 min. Cap-166b: $^1$H NMR (DMSO-d$_6$, δ=2.5 ppm, 500 MHz): 7.45 (d, J=7.3 Hz, 2H), 7.27-7.19 (m, 3H), 4.09 (s, 1H), 3.34 (app br s, 1H), 3.16 (app br s, 1H), 2.83 (d, J=10.1 Hz, 1H), 2.71 (m, 2H), 2.46 (m, 1H), 2.27 (s, 3H), 1.77 (d, J=9.8 Hz, 1H), 1.63 (d, J=9.8 Hz, 1H). LC-MS: Anal. Calcd. for [M+H]$^+$ C$_{14}$H$_{19}$N$_2$O$_2$: 247.14. found: 247.11.

Cap-167

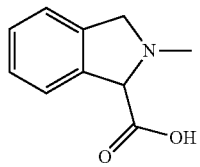

A solution of racemic Boc-1,3-dihydro-2H-isoindole carboxylic acid (1.0 g, 3.8 mmol) in 20% TFA/CH$_2$Cl$_2$ was stirred at ~25° C. for 4 h. All the volatile component was removed in vacuo. A mixture of the resultant crude material, formaldehyde (15 mL, 37% in water), 1N HCl (10 mL) and 10% Pd/C (10 mg) in MeOH was exposed to H$_2$ (40 PSI) in a Parr bottle for 23 h. The reaction mixture was filtered over CELITE® and concentrated in vacuo to afford Cap-167 as a yellow foam (873.5 mg). $^1$H NMR (DMSO-d$^6$, δ=2.5 ppm, 500 MHz) 7.59-7.38 (m, 4H), 5.59 (s, 1H), 4.84 (d, J=14 Hz, 1H), 4.50 (d, J=14.1 Hz, 1H), 3.07 (s, 3H). LC-MS: Anal. Calcd. for [M+H]$^+$ C$_{10}$H$_{12}$NO$_2$: 178.09. found: 178.65.

Cap-168

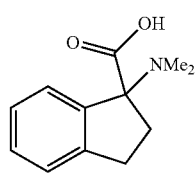

Racemic Cap-168 was prepared from racemic Boc-aminoindane-1-carboxylic acid according to the procedure described for the preparation of Cap-167. The crude material was employed as such.

Cap-169

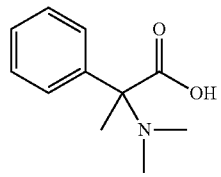

A mixture of 2-amino-2-phenylpropanoic acid hydrochloride (5.0 g, 2.5 mmol), formaldehyde (15 ml, 37% in water), 1N HCl (15 ml), and 10% Pd/C (1.32 g) in MeOH (60 mL) was placed in a Parr bottle and shaken under hydrogen (55 PSI) for 4 days. The reaction mixture was filtered over CELITE® and concentrated in vacuo. The residue was taken up in MeOH and purified by reverse phase prep-HPLC (MeOH/water/TFA) to afford the TFA salt of Cap-169 as a viscous semi-solid (2.1 g). $^1$H NMR (CDCl$_3$, δ=7.26 ppm, 500 MHz): 7.58-7.52 (m, 2H), 7.39-7.33 (m, 3H), 2.86 (br s, 3H), 2.47 (br s, 3H), 1.93 (s, 3H). LC-MS: Anal. Calcd. for [M+H]$^+$ C$_{11}$H$_{16}$NO$_2$: 194.12. found: 194.12.

Cap-170

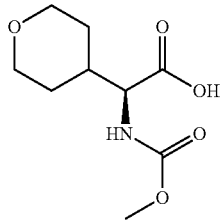

(S)-2-(Methoxycarbonylamino)-2-(tetrahydro-2H-pyran-4-yl)acetic acid

To (S)-2-amino-2-(tetrahydro-2H-pyran-4-yl)acetic acid (505 mg; 3.18 mmol; obtained from Astatech) in water (15 ml) was added sodium carbonate (673 mg; 6.35 mmol), and the resultant mixture was cooled to 0° C. and then methyl chloroformate (0.26 ml; 3.33 mmol) was added dropwise over 5 minutes. The reaction was allowed to stir for 18 hours while allowing the bath to thaw to ambient temperature. The reaction mixture was then partitioned between 1N HCl and ethyl acetate. The organic layer was removed and the aqueous layer was further extracted with 2 additional portions of ethyl acetate. The combined organic layers were washed with brine, dried over magnesium sulfate, filtered and concentrated in vacuo to afford Cap-170a colorless residue. $^1$H NMR (500 MHz, DMSO-d$_6$) δ ppm 12.65 (1H, br s), 7.44 (1H, d, J=8.24 Hz), 3.77-3.95 (3H, m), 3.54 (3H, s), 3.11-3.26 (2H, m), 1.82-1.95 (1H, m), 1.41-1.55 (2H, m), 1.21-1.39 (2H, m); LC-MS: Anal. Calcd. for [M+H]$^+$ C$_9$H$_{16}$NO$_5$: 218.1. found 218.1.

Cap-171

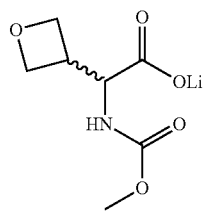

A solution of methyl 2-(benzyloxycarbonylamino)-2-(oxetan-3-ylidene)acetate (200 mg, 0.721 mmol; *Il Farmaco*, 56:609-613 (2001)) in ethyl acetate (7 ml) and CH$_2$Cl$_2$ (4.00 ml) was degassed by bubbling nitrogen for 10 min. Dimethyl dicarbonate (0.116 ml, 1.082 mmol) and Pd/C (20 mg, 0.019 mmol) were then added, the reaction mixture was fitted with a hydrogen balloon and allowed to stir at ambient temperature overnight at which time TLC (95:5 $CH_2Cl_2$/MeOH: visualized with stain made from 1 g $Ce(NH_4)_2SO_4$, 6 g ammonium molybdate, 6 ml sulfuric acid, and 100 ml water) indicated complete conversion. The reaction was filtered through CELITE® and concentrated. The residue was purified via BIOTAGE® (load with dichloromethane on 25 samples; elute on 25S column with dichloromethane for 3CV then 0 to 5% MeOH/dichloromethane over 250 ml then hold at 5% MeOH/dichloromethane for 250 ml; 9 ml fractions). Collected fractions containing desired material and concentrated to 120 mg (81%) of methyl 2-(methoxycarbonylamino)-2-(oxetan-3-yl)acetate as a colorless oil. $^1$H NMR (500 MHz, chloroform-d) δ ppm 3.29-3.40 (m, J=6.71 Hz, 1H) 3.70 (s, 3H) 3.74 (s, 3H) 4.55 (t, J=6.41 Hz, 1H) 4.58-4.68 (m, 2H) 4.67-4.78 (m, 2H) 5.31 (br s, 1H). LC-MS: Anal. Calcd. for $[M+H]^+$ $C_8H_{14}NO_5$: 204.2. found 204.0.

To methyl 2-(methoxycarbonylamino)-2-(oxetan-3-yl)acetate (50 mg, 0.246 mmol) in THF (2 mL) and water (0.5 mL) was added lithium hydroxide monohydrate (10.33 mg, 0.246 mmol). The resultant solution was allowed to stir overnight at ambient temperature. TLC (1:1 EA/Hex; Hanessian stain [1 g $Ce(NH_4)_2SO_4$, 6 g ammonium molybdate, 6 ml sulfuric acid, and 100 ml water]) indicated ~10% starting material remaining. Added an additional 3 mg LiOH and allowed to stir overnight at which time TLC showed no starting material remaining. Concentrated in vacuo and placed on high vac overnight providing 55 mg lithium 2-(methoxycarbonylamino)-2-(oxetan-3-yl)acetate as a colorless solid. $^1$H NMR (500 MHz, MeOD) δ ppm 3.39-3.47 (m, 1H) 3.67 (s, 3 H) 4.28 (d, J=7.93 Hz, 1H) 4.64 (t, J=6.26 Hz, 1H) 4.68 (t, J=7.02 Hz, 1H) 4.73 (d, J=7.63 Hz, 2H).

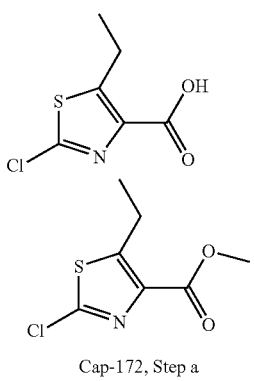

Cap-172, Step a

The following diazotization step was adapted from Barton, A. et al., *J.C.S. Perkin Trans I*, 159-164 (1982): A solution of $NaNO_2$ (166 mg, 2.4 mmol) in water (0.6 mL) was added slowly to a stirred, cold (0° C.) solution of methyl 2-amino-5-ethyl-1,3-thiazole-4-carboxylate (186 mg, 1.0 mmol), $CuSO_4$·$5H_2O$ (330 mg, 1.32 mmol), NaCl (260 mg, 4.45 mmol) and $H_2SO_4$ (5.5 mL) in water (7.5 mL). The mixture was stirred at 0° C. for 45 min and allowed to warm up to room temperature where it stirred further for 1 h before CuCl (118 mg) was added. This mixture was stirred further at room temperature for 16 h before it was diluted with brine and extracted with ether twice. The organic layers were combined, dried over $MgSO_4$ and concentrated to give methyl 2-chloro-5-ethylthiazole-4-carboxylate (i.e., Cap-172, Step a) (175 mg, 85%) as an orange oil (80% pure) which was used directly in the next reaction. $R_t$=1.99 min (Cond.-MD1); LC-MS: Anal. Calcd. for $[M+H]^+$ $C_7H_9ClNO_2S$: 206.01. found: 206.05.

Cap-172

To a solution of methyl 2-chloro-5-ethylthiazole-4-carboxylate (175 mg) in THF/$H_2O$/MeOH (20 mL/3 mL/12 mL) was added LiOH (305 mg, 12.76 mmol). The mixture was stirred at room temperature overnight before it was concentrated down and neutralized with 1N HCl in ether (25 mL). The residue was extracted twice with ethyl acetate and the organic layers were combined, dried over $MgSO_4$ and evaporated to yield Cap-172 (60 mg, 74%) as a red solid which was used without further purification. $^1$H NMR (300 MHz, DMSO-$d_6$) δ ppm 13.03-13.42 (1H, m), 3.16 (2H, q, J=7.4 Hz), 1.23 (3H, t, J=7.5 Hz). $R_t$=1.78 min (Cond.-MD1); LC-MS: Anal. Calcd. for $[M+H]^+$ $C_6H_7ClNO_2S$: 191.99. found: 191.99.

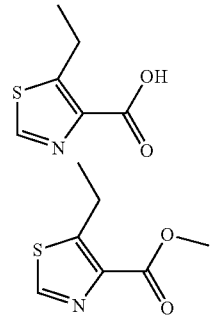

Cap-173, Step a

The following diazotization step was adapted from Barton, A. et al., *J.C.S. Perkin Trans I*, 159-164 (1982): A solution of $NaNO_2$ (150 mg, 2.17 mmol) in water (1.0 mL) was added dropwise to a stirred, cold (0° C.) solution of methyl 2-amino-5-ethyl-1,3-thiazole-4-carboxylate (186 mg, 1.0 mmol) in 50% $H_3PO_2$ (3.2 mL). The mixture was stirred at 0° C. for 1 h and allowed to warm up to room temperature where it stirred further for 2 h. After recooling to 0° C., the mixture was treated slowly with a solution of NaOH (85 mg) in water (10 mL). The mixture was then diluted with saturated $NaHCO_3$ solution and extracted twice with ether. The organic layers were combined, dried over $MgSO_4$ and concentrated to give methyl 5-ethylthiazole-4-carboxylate (i.e., Cap-173, Step a) (134 mg, 78%) as an orange oil (85% pure) which was used directly in the next reaction. $R_t$=1.58 min (Cond.-MD1); LC-MS: Anal. Calcd. for $[M+H]^+$ $C_2H_{10}NO_2S$: 172.05. found: 172.05.

Cap-173

To a solution of methyl 5-ethylthiazole-4-carboxylate (134 mg) in THF/$H_2O$/MeOH (18 mL/2.7 mL/11 mL) was added LiOH (281 mg, 11.74 mmol). The mixture was stirred at room temperature overnight before it was concentrated down and neutralized with 1N HCl in ether (25 mL). The residue was extracted twice with ethyl acetate and the organic layers were combined, dried over $MgSO_4$ and evaporated to yield Cap-173 (90 mg, 73%) as an orange solid which was used without further purification. $^1$H NMR (300 MHz, DMSO-$d_6$) δ ppm 12.74-13.04 (1H, m), 3.20 (2H, q, J=7.3 Hz), 1.25 (3H, t, J=7.5 Hz). $R_t$=1.27 min (Cond.-MD1); LC-MS: Anal. Calcd. for [M+H]$^+$ C$_6$H$_8$NO$_2$S: 158.03. found: 158.04.

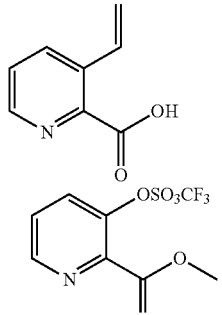

Cap-174, Step a

Triflic anhydride (5.0 g, 18.0 mmol) was added dropwise to a cold (0° C.) solution of methyl 3-hydroxypicolinate (2.5 g, 16.3 mmol) and TEA (2.5 mL, 18.0 mmol) in CH$_2$Cl$_2$ (80 mL). The mixture was stirred at 0° C. for 1 h before it was allowed to warm up to room temperature where it stirred for an additional 1 h. The mixture was then quenched with saturated NaHCO$_3$ solution (40 mL) and the organic layer was separated, washed with brine, dried over MgSO$_4$ and concentrated to give methyl 3-(trifluoromethylsulfonyloxy)picolinate (i.e., Cap-174, Step a) (3.38 g, 73%) as a dark brown oil (>95% pure) which was used directly without further purification. $^1$H NMR (300 MHz, CDCl$_3$) δ ppm 8.72-8.79 (1H, m), 7.71 (1H, d, J=1.5 Hz), 7.58-7.65 (1H, m), 4.04 (3H, s). $R_t$=1.93 min (Cond.-MD1); LC-MS: Anal. Calcd. for [M+H]$^+$ C$_8$H$_7$F$_3$NO$_5$S: 286.00. found: 286.08.

Cap-174

To a solution of methyl 3-(trifluoromethylsulfonyloxy)picolinate (570 mg, 2.0 mmol) in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. overnight before a saturated solution of KF (20 mL) was added to the reaction mixture at room temperature. This mixture was stirred for 4 h before it was filtered through CELITE® and the pad of CELITE® was washed with ethyl acetate. The aqueous phase of the filtrate was then separated and concentrated down in vacuo. The residue was treated with 4N HCl in dioxanes (5 mL) and the resulting mixture was extracted with methanol, filtered and evaporated to afford Cap-174 (260 mg) as a green solid which was slightly contaminated with inorganic salts but was used without further purification. $^1$H NMR (300 MHz, DMSO-d$_6$) δ ppm 8.21 (1H, d, J=3.7 Hz), 7.81-7.90 (1H, m), 7.09 (1H, dd, J=7.7, 4.8 Hz), 6.98 (1H, dd, J=17.9, 11.3 Hz), 5.74 (1H, dd, J=17.9, 1.5 Hz), 5.20 (1H, d, J=11.0 Hz). $R_t$=0.39 min (Cond.-MD1); LC-MS: Anal. Calcd. for [M+H]$^+$ C$_8$H$_8$NO$_2$: 150.06. found: 150.07.

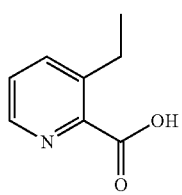

Cap-175

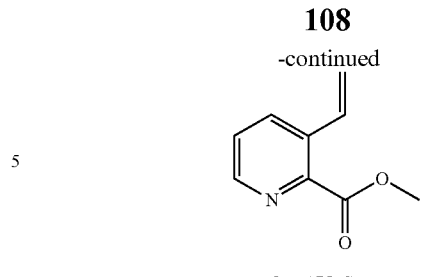

Cap-175, Step a

To a solution of methyl 3-(trifluoromethylsulfonyloxy)picolinate (i.e., Cap-174, Step a) (570 mg, 2.0 mmol), an intermediate in the preparation of Cap-174, in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. for 4 h before the solvent was removed in vacuo. The residue was taken up in acetonitrile (50 mL) and hexanes (50 mL) and the resulting mixture was washed twice with hexanes. The acetonitrile layer was then separated, filtered through CELITE®, and evaporated. Purification of the residue by flash chromatography on a Horizon instrument (gradient elution with 25% ethyl acetate in hexanes to 65% ethyl acetate in hexanes) afforded methyl 3-vinylpicolinate (i.e., Cap-175, Step a) (130 mg, 40%) as a yellow oil. $^1$H NMR (300 MHz, CDCl$_3$) δ ppm 8.60 (1H, dd, J=4.6, 1.7 Hz), 7.94 (1H, d, J=7.7 Hz), 7.33-7.51 (2H, m), 5.72 (1H, d, J=17.2 Hz), 5.47 (1H, d, J=11.0 Hz), 3.99 (3H, s). $R_t$=1.29 min (Cond.-MD1); LC-MS: Anal. Calcd. for [M+H]$^+$ C$_9$H$_{10}$NO$_2$: 164.07. found: 164.06.

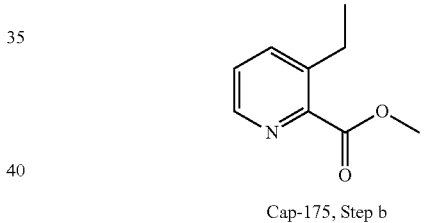

Cap-175, Step b

Palladium on carbon (10%, 25 mg) was added to a solution of methyl 3-vinylpicolinate (120 mg, 0.74 mmol) in ethanol (10 mL). The suspension was stirred at room temperature under an atmosphere of hydrogen for 1 h before it was filtered through CELITE® and the pad of CELITE® was washed with methanol. The filtrate was concentrated down to dryness to yield methyl 3-ethylpicolinate (i.e., Cap-175, Step b) which was taken directly into the next reaction. $R_t$=1.15 min (Cond.-MD1); LC-MS: Anal. Calcd. for [M+H]$^+$ C$_9$H$_{12}$NO$_2$: 166.09. found: 166.09.

Cap-175

To a solution of methyl 3-ethylpicolinate in THF/H$_2$O/MeOH (5 mL/0.75 mL/3 mL) was added LiOH (35 mg, 1.47 mmol). The mixture was stirred at room temperature for 2 d before additional LiOH (80 mg) was added. After an additional 24 h at room temperature, the mixture was filtered and the solvent was removed in vacuo. The residue was then treated with 4N HCl in dioxanes (5 mL) and the resulting suspension was concentrated down to dryness to yield Cap-175 as a yellow solid which was used without further purification. $^1$H NMR (300 MHz, DMSO-d$_6$) δ ppm 8.47 (1H, dd, J=4.8, 1.5 Hz), 7.82-7.89 (1H, m), 7.53 (1H, dd, J=7.7, 4.8

Hz), 2.82 (2H, q, J=7.3 Hz), 1.17 (3H, t, J=7.5 Hz). $R_f$=0.36 min (Cond.-MD1); LC-MS: Anal. Calcd. for $[M+H]^+$ $C_8H_{10}NO_2$: 152.07. found: 152.10.

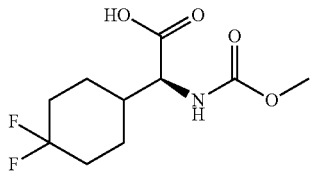

Cap-176

(S)-2-(4,4-Difluorocyclohexyl)-2-(methoxycarbonylamino)acetic acid

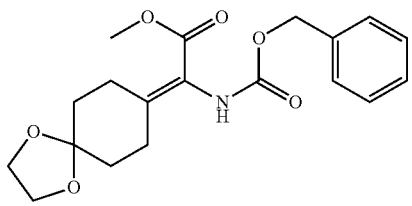

Cap-176, Step a

A solution of 1,4-dioxaspiro[4.5]decan-8-one (15 g, 96 mmol) in EtOAc (150 mL) was added to a solution of methyl 2-(benzyloxycarbonylamino)-2-(dimethoxyphosphoryl)acetate (21.21 g, 64.0 mmol) in 1,1,3,3-tetramethylguanidine (10.45 mL, 83 mmol) and EtOAc (150 mL). The resulting solution was the stirred at ambient temperature for 72 h and then it was diluted with EtOAc (25 mL). The organic layer was washed with 1N HCl (75 mL), $H_2O$ (100 mL) and brine (100 mL), dried ($MgSO_4$), filtered and concentrated. The residue was purified via BIOTAGE® (5% to 25% EtOAc/Hexanes; 300 g column). The combined fractions containing the product were then concentrated under vacuum and the residue was re-crystallized from hexanes/EtOAc to give white crystals that corresponded to methyl 2-(benzyloxycarbonylamino)-2-(1,4-dioxaspiro[4.5]decan-8-ylidene)acetate (6.2 g) $^1$H NMR (400 MHz, $CDCl_3$-d) δ ppm 7.30-7.44 (5H, m), 6.02 (1H, br. s.), 5.15 (2H, s), 3.97 (4H, s), 3.76 (3H, br. s.), 2.84-2.92 (2H, m), 2.47 (2H, t, J=6.40 Hz), 1.74-1.83 (4H, m). LC (Cond. OL1): $R_f$=2.89 min. LC-MS: Anal. Calcd. for $[M+Na]^+$ $C_{19}H_{23}NNaO_6$: 745.21. found: 745.47.

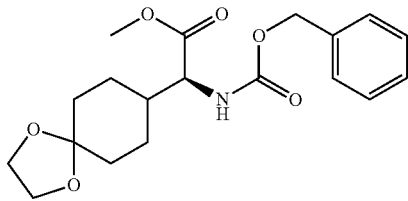

Cap-176, Step b

Ester Cap-176, Step b was prepared from alkene Cap-176, Step a according to the method of Burk, M. J. et al. (*J. Am. Chem. Soc.*, 117:9375-9376 (1995)) and references therein: A 500 mL high-pressure bottle was charged with alkene Cap-176, Step a (3.5 g, 9.68 mmol) in degassed MeOH (200 mL) under a blanket of $N_2$. The solution was then charged with (−)-1,2-Bis((2S,5S)-2,5-dimethylphospholano)ethane(cyclooctadiene) rhodium (I) tetrafluoroborate (0.108 g, 0.194 mmol) and the resulting mixture was flushed with $N_2$ (3×) and charged with $H_2$ (3×). The solution was shaken vigorously under 70 psi of $H_2$ at ambient temperature for 72 h. The solvent was removed under reduced pressure and the remaining residue was taken up in EtOAc. The brownish solution was then filtered through a plug of Silica Gel and eluted with EtOAc. The solvent was concentrated under vacuum to afford a clear oil corresponding to ester Cap-176, Step b (3.4 g). $^1$H NMR (500 MHz, $CDCl_3$-d) δ ppm 7.28-7.43 (5H, m), 5.32 (1H, d, J=9.16 Hz), 5.06-5.16 (2H, m), 4.37 (1H, dd, J=9.00, 5.04 Hz), 3.92 (4H, t, J=3.05 Hz), 3.75 (3H, s), 1.64-1.92 (4H, m), 1.37-1.60 (5H, m). LC (Cond. OL1): $R_f$=1.95 min. LC-MS: Anal. Calcd. for $[M+H]^+$ $C_{19}H_{26}NO_6$: 364.18. found: 364.27.

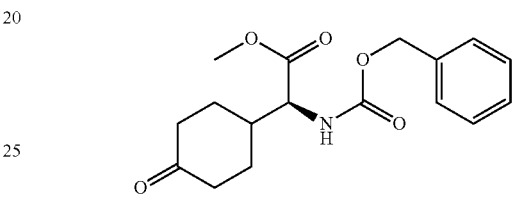

Cap-176, Step c

Ester Cap-176, Step b (4.78 g, 13.15 mmol) was dissolved in THF (15 mL) followed by sequential addition of water (10 mL), glacial acetic acid (26.4 mL, 460 mmol) and dichloroacetic acid (5.44 mL, 65.8 mmol). The resulting mixture was stirred for 72 h at ambient temperature, and the reaction was quenched by slow addition of solid $Na_2CO_3$ with vigorous stirring until the release of gas was no longer visible. Crude product was extracted into 10% ethyl acetate-dichloromethane and the organic layers were combined, dried ($MgSO_4$) filtered and concentrated. The resulting residue was purified via BIOTAGE® (0 to 30% EtOAc/Hex; 25 g column) to afford ketone Cap-176, Step c (3.86 g) as a clear oil. $^1$H NMR (400 MHz, $CDCl_3$-d) δ ppm 7.28-7.41 (5H, m), 5.55 (1H, d, J=8.28 Hz), 5.09 (2H, s), 4.46 (1H, dd, J=8.16, 5.14 Hz), 3.74 (3H, s), 2.18-2.46 (5H, m), 1.96-2.06 (1H, m), 1.90 (1H, ddd, J=12.99, 5.96, 2.89 Hz), 1.44-1.68 (2H, m, J=12.36, 12.36, 12.36, 12.36, 4.77 Hz). LC (Cond. OL1): $R_f$=1.66 min. LC-MS: Anal. Calcd. for $[M+Na]^+$ $C_{12}H_{21}NNaO_5$: 342.13. found: 342.10.

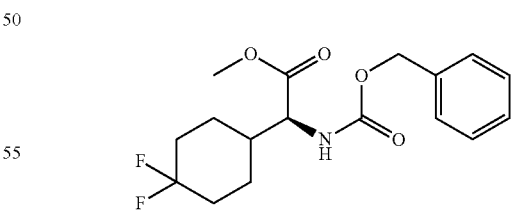

Cap-176, Step d

DEOXO-FLUOR® (3.13 mL, 16.97 mmol) was added to a solution of ketone Cap-176, Step c (2.71 g, 8.49 mmol) in $CH_2Cl_2$ (50 mL) followed by addition of a catalytic amount of EtOH (0.149 mL, 2.55 mmol). The resulting yellowish solution was stirred at rt overnight. The reaction was quenched by addition of sat. aq. $NaHCO_3$ (25 mL) and the mixture was extracted with EtOAc (3×75 mL)). The combined organic layers were dried (MgSO$_4$), filtered and dried to give a yellowish oil. The residue was purified via BIOTAGE® chromatography (2% to 15% EtOAc/Hex; 90 g column) and a white solid corresponding to the difluoro amino acid difluoride Cap-176, Step d (1.5 g) was recovered. $^1$H NMR (400 MHz, CDCl$_3$-d) δ ppm 7.29-7.46 (5H, m), 5.34 (1H, d, J=8.28 Hz), 5.12 (2H, s), 4.41 (1H, dd, J=8.66, 4.89 Hz), 3.77 (3H, s), 2.06-2.20 (2H, m), 1.83-1.98 (1H, m), 1.60-1.81 (4H, m), 1.38-1.55 (2H, m). $^{19}$F NMR (376 MHz, CDCl$_3$-d) δ ppm −92.15 (1F, d, J=237.55 Hz), −102.44 (1F, d, J=235.82 Hz). LC (Cond. OL1): R$_t$=1.66 min. LC-MS: Anal. Calcd. for [2M+Na]$^+$ C$_{34}$H$_{42}$F$_4$N$_2$NaO$_8$: 705.28. found: 705.18.

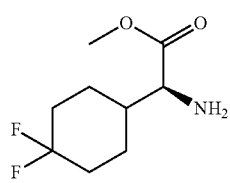

Cap-176, Step e

Difluoride Cap-176, Step d (4 g, 11.72 mmol) was dissolved in MeOH (120 mL) and charged with Pd/C (1.247 g, 1.172 mmol). The suspension was flushed with N$_2$ (3×) and the reaction mixture was placed under 1 atm of H$_2$ (balloon). The mixture was stirred at ambient temperature for 48 h. The suspension was then filtered though a plug of CELITE® and concentrated under vacuum to give an oil that corresponded to amino acid Cap-176, Step e (2.04 g) and that was used without further purification. $^1$H NMR (400 MHz, DMSO-d$_6$) δ ppm 3.62 (3H, s), 3.20 (1H, d, J=5.77 Hz), 1.91-2.09 (2H, m), 1.50-1.88 (7H, m), 1.20-1.45 (2H, m). $^{19}$F NMR (376 MHz, DMSO-d$_6$) δ ppm −89.39 (1F, d, J=232.35 Hz), −100.07 (1F, d, J=232.35 Hz). $^{13}$C NMR (101 MHz, DMSO-d$_6$) δ ppm 175.51 (1C, s), 124.10 (1C, t, J=241.21, 238.90 Hz), 57.74 (1C, s), 51.39 (1C, s), 39.23 (1C, br. s.), 32.02-33.83 (2C, m), 25.36 (1C, d, J=10.02 Hz), 23.74 (1C, d, J=9.25 Hz). LC (Cond. OL2): R$_t$=0.95 min. LC-MS: Anal. Calcd. for [2M+H]$^+$ C$_{18}$H$_{31}$F$_4$N$_2$O$_2$: 415.22. found: 415.40.

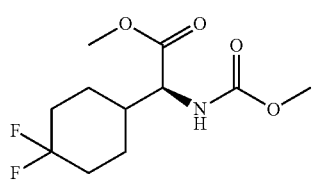

Cap-176, Step f

Methyl chloroformate (1.495 mL, 19.30 mmol) was added to a solution of amino acid Cap-176, Step e (2 g, 9.65 mmol) and DIEA (6.74 mL, 38.6 mmol) in CH$_2$Cl$_2$ (100 mL). The resulting solution was stirred at rt for 3 h and volatiles were removed under reduced pressure. The residue was purified via BIOTAGE® (0% to 20% EtOAc/Hex; 90 g column) A clear oil that solidified upon standing under vacuum and corresponding to carbamate Cap-176, Step f (2.22 g) was recovered. $^1$H NMR (500 MHz, CDCl$_3$-d) δ ppm 5.27 (1H, d, J=8.55 Hz), 4.39 (1H, dd, J=8.85, 4.88 Hz), 3.77 (3H, s), 3.70 (3H, s), 2.07-2.20 (2H, m), 1.84-1.96 (1H, m), 1.64-1.82 (4H, m), 1.39-1.51 (2H, m). $^{19}$F NMR (471 MHz, CDCl$_3$-d) δ ppm −92.55 (1F, d, J=237.13 Hz), −102.93 (1F, d, J=237.12 Hz). $^{13}$C NMR (126 MHz, CDCl$_3$-d) δ ppm 171.97 (1C, s), 156.69 (1C, s), 119.77-125.59 (1C, m), 57.24 (1C, br. s.), 52.48 (1C, br. s.), 52.43 (1C, s), 39.15 (1C, s), 32.50-33.48 (2C, m), 25.30 (1C, d, J=9.60 Hz), 24.03 (1C, d, J=9.60 Hz). LC (Cond. OL1): R$_t$=1.49 min. LC-MS: Anal. Calcd. for [M+Na]$^+$ C$_{11}$H$_{17}$F$_2$NNaO$_4$: 288.10. found: 288.03.

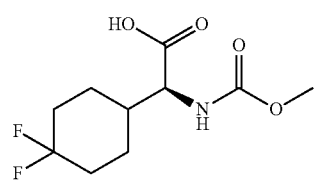

Cap-176

(S)-2-(4,4-Difluorocyclohexyl)-2-(methoxycarbonylamino)acetic acid

A solution of LiOH (0.379 g, 15.83 mmol) in water (25 mL) was added to a solution of carbamate Cap-176, Step f (2.1 g, 7.92 mmol) in THF (75 mL) and the resulting mixture was stirred at ambient temperature for 4 h. THF was removed under vacuum and the remaining aqueous phase was acidified with 1N HCl solution (2 mL) and then extracted with EtOAc (2×50 mL). The combined organic layers were dried (MgSO$_4$), filtered and concentrated to give a white foam corresponding to Cap-176 (1.92 g). $^1$H NMR (400 MHz, DMSO-d$_6$) δ ppm 12.73 (1H, s), 7.50 (1H, d, J=8.78 Hz), 3.97 (1H, dd, J=8.53, 6.02 Hz), 3.54 (3H, s), 1.92-2.08 (2H, m), 1.57-1.90 (5H, m), 1.34-1.48 (1H, m), 1.27 (1H, qd, J=12.72, 3.26 Hz). $^{19}$F NMR (376 MHz, DMSO-d$_6$) δ ppm −89.62 (1F, d, J=232.35 Hz), −99.93 (1F, d, J=232.35 Hz). LC (Cond. OL2): R$_t$=0.76 min. LC-MS: Anal. Calcd. for [M−H]$^+$ C$_{10}$H$_{14}$F$_2$NO$_4$: 250.09. found: 250.10.

Cap-177a-d

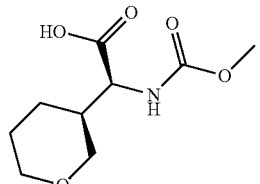

Cap 177a

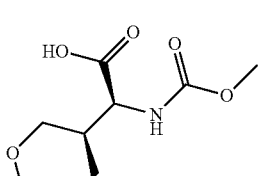

Cap 177b

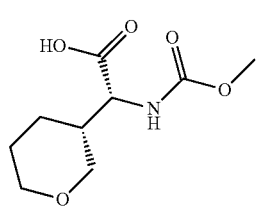

Cap 177c

-continued

Cap 177d

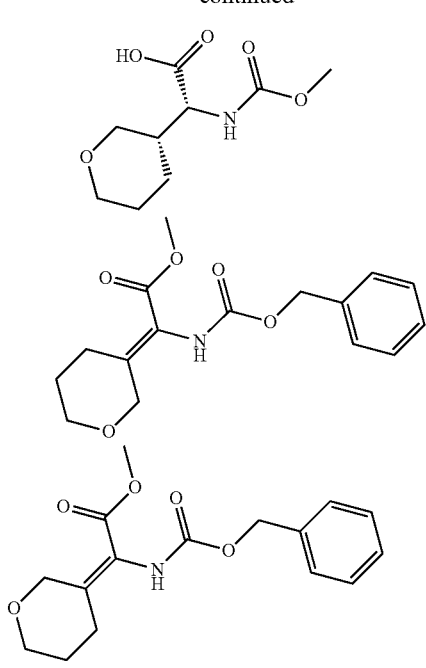

Cap-177a-d, Step a 1,1,3,3-Tetramethylguanidine (0.985 mL, 7.85 mmol) was added to a stirred solution of methyl 2-(benzyloxycarbonylamino)-2-(dimethoxyphosphoryl)acetate (2.0 g, 6.0 mmol) in EtOAc (40 mL) and the mixture was stirred at rt under $N_2$ for 10 min. Then dihydro-2H-pyran-3(4H)-one [23462-75-1] (0.604 g, 6.04 mmol) was added and the mixture was stirred at rt for 16 h. The reaction mixture was then cooled in freezer for 10 min and neutralized with aq. citric acid (1.5 g in 20 mL water). The two phases were partitioned and the organic layer was washed with 0.25 N aq.HCl and brine, and then dried ($MgSO_4$) and concentrated to a colorless oil. The crude material was purified by flash silica chromatography (loading solvent: DCM, eluted with EtOAc/Hexanes, gradient from 20% to 30% EtOAc) to yield two isomeric products: The first eluted product was (Z)-methyl 2-(benzyloxycarbonylamino)-2-(2H-pyran-3(4H,5H,6H)-ylidene)acetate (490 mg) (white solid), and the second was (E)-methyl 2-(benzyloxycarbonylamino)-2-(2H-pyran-3(4H,5H,6H)-ylidene)acetate (433 mg) (white solid). LC-MS retention time 1.398 min (for Z-isomer) and 1.378 min (for E-isomer); m/z 304.08 (for Z-isomer) and 304.16 (for E-isomer) (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) (for Z-isomer) δ ppm 7.30-7.44 (m, 5H), 6.18 (br. s., 1H), 5.10-5.17 (m, 2H), 4.22 (s, 2H), 3.78 (br. s., 3H), 2.93-3.02 (m, 2H), 1.80 (dt, J=11.7, 5.8 Hz, 2H), 1.62 (s, 2H). $^1$H NMR (400 MHz, chloroform-d) (for E-isomer) δ ppm 7.31-7.44 (m, 5H), 6.12 (br. s., 1H), 5.13-5.17 (m, 2H), 4.64 (br. s., 2H), 3.70-3.82 (m, 5H), 2.49 (t, J=6.5 Hz, 2H), 1.80 (br. s., 2H). (Note: the absolute regiochemistry was determined by $^1$H NMR shifts and coupling constants).

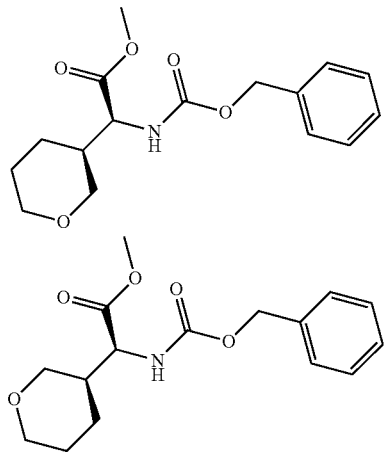

Cap-177a-d, Step b (−)-1,2-Bis((2S,5S)-2,5-dimethylphospholano)ethane(cyclooctadiene)-rhodium(I) tetrafluoroborate (28.2 mg, 0.051 mmol) was added to a stirred solution of (Z)-methyl 2-(benzyloxycarbonylamino)-2-(2H-pyran-3(4H,5H,6H)-ylidene) acetate (310 mg, 1.015 mmol) in MeOH (10 mL) and the mixture was vacuum flushed with $N_2$, followed by $H_2$, and then the reaction was stirred under $H_2$ (60 psi) at rt for 2d. The reaction mixture was concentrated and the residue was purified by flash silica chromatography (loading solvent: DCM, eluted with 20% EtOAc in hexanes) to yield (S)-methyl 2-(benzyloxycarbonylamino)-2-((S)-tetrahydro-2H-pyran-3-yl)acetate (204 mg) as clear colorless oil. LC-MS retention time 1.437 min; m/z 307.89 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) δ ppm 7.30-7.46 (m, 5H), 5.32 (d, J=8.8 Hz, 1H), 5.12 (s, 2H), 4.36 (dd, J=8.9, 5.6 Hz, 1H), 3.84-3.98 (m, 2H), 3.77 (s, 3H), 3.28-3.37 (m, 1H), 3.23 (dd, J=11.3, 10.5 Hz, 1H), 2.04-2.16 (m, 1H), 1.61-1.75 (m, 3H), 1.31-1.43 (m, 1H).

The other stereoisomer ((E)-methyl 2-(benzyloxycarbonylamino)-2-(2H-pyran-3(4H,5H,6H)-ylidene)acetate) (360 mg, 1.18 mmol) was reduced in a similar manner to yield (S)-methyl 2-(benzyloxycarbonylamino)-2-((R)-tetrahydro-2H-pyran-3-yl)acetate (214 mg) as clear colorless oil. LC-MS retention time 1.437 min; m/z 308.03 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) δ ppm 7.30-7.44 (m, 5H), 5.31 (d, J=9.0 Hz, 1H), 5.12 (s, 2H), 4.31 (dd, J=8.7, 6.9 Hz, 1H), 3.80-3.90 (m, 2H), 3.77 (s, 3H), 3.37 (td, J=10.8, 3.5 Hz, 1H), 3.28 (dd, J=11.3, 9.8 Hz, 1H), 1.97-2.10 (m, 1H), 1.81 (d, J=11.5 Hz, 1H), 1.61-1.72 (m, 2H), 1.33-1.46 (m, 1H).

The individual enantiomers of Cap-177a, Step b (Cap-177c, Step b) and Cap-177b, Step b (Cap-177d, Step b) were prepared in the same manner and in similar yields utilizing (−)-1,2-Bis((2R,5R)-2,5-dimethylphospholano)ethane (cyclooctadiene)-rhodium(I)tetrafluoroborate as the hydrogenation catalyst for the olefin reductions of the individual stereoisomer starting materials.

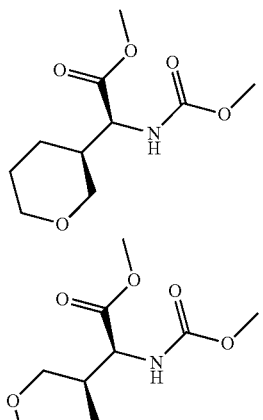

Cap-177a and Cap-177b, Step c

10% Pd/C (69.3 mg, 0.065 mmol) was added to a solution of (S)-methyl 2-(benzyloxycarbonylamino)-2-((S)-tetrahydro-2H-pyran-3-yl)acetate (200 mg, 0.651 mmol) and dimethyl dicarbonate [4525-33-1] (0.104 mL, 0.976 mmol) in MeOH (10 mL). The reaction mixture was vacuum flushed with N$_2$, followed by H$_2$, and then the reaction was stirred under H$_2$ (55 psi) at rt for 5 h. The reaction mixture was filtered through CELITE®/silica pad and the filtrate was concentrated to a colorless oil. The crude oil was purified by flash silica chromatography (loading solvent: DCM, eluted with 30% EtOAc in hexanes) to yield product (S)-methyl 2-(methoxycarbonylamino)-2-((S)-tetrahydro-2H-pyran-3-yl)acetate (132 mg) as colorless oil. LC-MS retention time 0.92 min; m/z 231.97 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) δ ppm 5.24 (d, J=8.5 Hz, 1H), 4.34 (dd, J=8.9, 5.6 Hz, 1H), 3.84-3.97 (m, 2H), 3.77 (s, 3H), 3.70 (s, 3H), 3.29-3.38 (m, 1H), 3.23 (dd, J=11.2, 10.4 Hz, 1H), 2.03-2.14 (m, 1H), 1.56-1.75 (m, 3H), 1.32-1.43 (m, 1H).

Another diastereomer ((S)-methyl 2-(benzyloxycarbonylamino)-2-((R)-tetrahydro-2H-pyran-3-yl)acetate) was transformed in a similar manner to yield (S)-methyl 2-(methoxycarbonylamino)-2-((R)-tetrahydro-2H-pyran-3-yl)acetate as clear colorless oil. LC-MS retention time 0.99 min; m/z 231.90 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) δ ppm 5.25 (d, J=8.0 Hz, 1H), 4.29 (dd, J=8.4, 7.2 Hz, 1H), 3.82-3.90 (m, 2H), 3.77 (s, 3H), 3.70 (s, 3H), 3.37 (td, J=10.8, 3.3 Hz, 1H), 3.28 (t, J=10.5 Hz, 1H), 1.96-2.08 (m, 1H), 1.81 (dd, J=12.9, 1.6 Hz, 1H), 1.56-1.72 (m, 2H), 1.33-1.46 (m, 1H).

The individual enantiomers of Cap-177a, Step c (Cap-177c, Step c) and Cap-177b, Step c (Cap-177d, Step c) were prepared in a similar manner and is similar yields using the appropriate starting materials from Cap-177a-d, Step b.

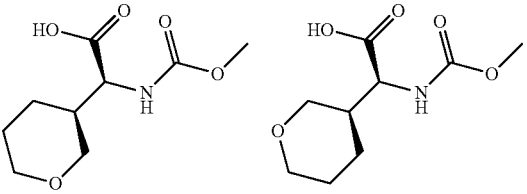

Cap-177a and Cap-177b, Step d

To a solution of (S)-methyl 2-(methoxycarbonylamino)-2-((S)-tetrahydro-2H-pyran-3-yl)acetate (126 mg, 0.545 mmol) in THF (4 mL) stirring at rt was added a solution of 1M LiOH (1.090 mL, 1.090 mmol) in water. The reaction was stirred at rt for 3 h, neutralized with 1M HCl (1.1 mL) and extracted with EtOAc (3×10 mL). The organics were dried, filtered and concentrated to yield (S)-2-(methoxycarbonylamino)-2-((S)-tetrahydro-2H-pyran-3-yl)acetic acid (Cap-177a) (125 mg) as a clear colorless oil. LC-MS retention time 0.44 min; m/z 218.00 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) δ ppm 5.28 (d, J=8.8 Hz, 1H), 4.38 (dd, J=8.7, 5.6 Hz, 1H), 3.96-4.04 (m, 1H), 3.91 (d, J=11.0 Hz, 1H), 3.71 (s, 3 H), 3.33-3.41 (m, 1H), 3.24-3.32 (m, 1H), 2.10-2.24 (m, 1H), 1.74-1.83 (m, 1H), 1.63-1.71 (m, 2H), 1.35-1.49 (m, 1H).

Another diastereomer ((S)-methyl 2-(methoxycarbonylamino)-2-((R)-tetrahydro-2H-pyran-3-yl)acetate) was transformed in a similar manner to yield (S)-2-(methoxycarbonylamino)-2-((R)-tetrahydro-2H-pyran-3-yl)acetic acid (Cap-177b) as clear colorless oil. LC-MS retention time 0.41 min; m/z 217.93 (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% $H_2O$/10 mM ammonium acetate and Solvent B was 5% $H_2O$/95% MeOH/10 mM ammonium acetate. MS data was determined using a MICROMASS® Platform for LC in electrospray mode. $^1$H NMR (400 MHz, chloroform-d) δ ppm 6.18 (br. s., 1H), 5.39 (d, J=8.5 Hz, 1H), 4.27-4.37 (m, 1H), 3.82-3.96 (m, 2H), 3.72 (s, 3H), 3.42 (td, J=10.8, 3.3 Hz, 1H), 3.35 (t, J=10.4 Hz, 1H), 2.01-2.18 (m, 1H), 1.90 (d, J=11.8 Hz, 1H), 1.59-1.76 (m, 2H), 1.40-1.54 (m, 1H).

The individual enantiomers of Cap-177a (Cap-177c) and Cap-177b (Cap-177d) were prepared in a similar manner and is similar yields using the appropriate starting materials from Cap-177a-d, Step c.

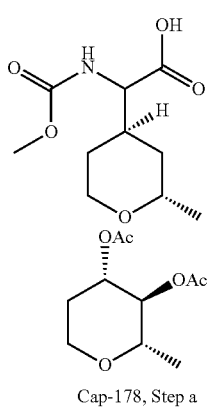

Cap-178

To a solution of (2S,3S,4S)-2-methyl-3,4-dihydro-2H-pyran-3,4-diyl diacetate (5 g, 23.34 mmol) in 20 mL of MeOH in a hydrogenation tank was added Pd/C (150 mg, 0.141 mmol). The resulting mixture was hydrogenated at 40 psi on Parr Shaker for 1 hour. The mixture was then filtered and the filtrate was concentrated to afford Cap-178, Step a (5.0 g) as a clear oil, which solidified while standing. $^1$H NMR (500 MHz, CDCl$_3$) δ ppm 4.85-4.94 (1H, m), 4.69 (1H, t, J=9.46 Hz), 3.88-3.94 (1H, m), 3.44 (1H, td, J=12.21, 1.83 Hz), 3.36 (1H, dq, J=9.42, 6.12 Hz), 2.03-2.08 (1H, m), 2.02 (3H, s), 2.00 (3H, s), 1.70-1.80 (1H, m), 1.16 (3H, d, J=6.10 Hz).

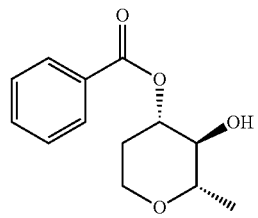

Cap-178, Step b

To a solution of Cap-178, Step a (5.0 g, 23 mmol) in 50 mL of MeOH was added several drops of sodium methoxide. After stirring at room temperature for 30 min, sodium methoxide (0.1 mL, 23.12 mmol) was added and the solution was stirred at room temperature overnight. The solvent was then removed under vacuum. The residue was diluted with benzene and concentrated to afford the corresponding diol as a yellow solid. The solid was dissolved in 50 mL of pyridine and to this solution at −35° C. was added benzoyl chloride (2.95 mL, 25.4 mmol) dropwise. The resulting mixture was stirred at −35° C. for 1 hour then at room temperature overnight. The mixture was diluted with Et$_2$O and washed with water. The aqueous layer was extracted with EtOAc (2×). The combined organic layers were dried with MgSO$_4$ and concentrated. The crude product was purified by flash chromatography (silica gel, 5%45% EtOAc/Hex) to afford Cap-178, Step b (4.5 g) as clear oil which slowly crystallized upon prolonged standing. LC-MS: Anal. Calcd. for [M+Na]$^+$ $C_{13}H_{16}NaO_4$ 259.09. found 259.0; $^1$H NMR (500 MHz, CDCl$_3$) δ ppm 8.02-8.07 (2H, m), 7.55-7.61 (1H, m), 7.45 (2H, t, J=7.78 Hz), 5.01 (1 H, ddd, J=11.44, 8.70, 5.49 Hz), 3.98 (1H, ddd, J=11.90, 4.88, 1.53 Hz), 3.54 (1H, td, J=12.36, 2.14 Hz), 3.41 (1H, t, J=9.00 Hz), 3.31-3.38 (1H, m), 2.13-2.19 (1H, m), 1.83-1.94 (1H, m), 1.36 (3H, d, J=5.80 Hz).

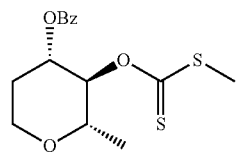

Cap-178, Step c

To a mixture of NaH (1.143 g, 28.6 mmol) (60% in mineral oil) in 6 mL of CS$_2$ was added Cap-178, Step b (4.5 g, 19 mmol) in 40 mL of CS$_2$ dropwise over 15 min. The resulting mixture was stirred at room temperature for 30 min. The mixture turned light orange with some solid. MeI (14.29 mL, 229 mmol) was then added dropwise over 20 min. The mixture was then stirred at room temperature overnight. The reaction was carefully quenched with saturated NH$_4$Cl solution. The mixture was extracted with EtOAc (3×). The combined organic layers were dried with MgSO$_4$ and concentrated. The crude product was purified by flash chromatography (silica gel, 6% EtOAc/Hex) to afford Cap-178, Step c (3.13 g) as clear oil. LC-MS: Anal. Calcd. for [M+Na]$^+$ $C_{15}H_{18}NaO_4S_2$ 349.05. found 349.11; $^1$H NMR (500 MHz, CDCl$_3$) δ ppm 7.94-8.00 (2 H, m), 7.50-7.58 (1H, m), 7.41 (2H, t, J=7.78 Hz), 5.96 (1H, t, J=9.46 Hz), 5.28 (1H, ddd, J=11.37, 9.38, 5.49 Hz), 4.02 (1H, ddd, J=11.98, 4.96, 1.68 Hz), 3.54-3.68 (2H, m), 2.48 (3H, s), 2.31 (1H, dd), 1.88-1.99 (1H, m), 1.28 (3H, d).

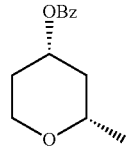

Cap-178, Step d

To a mixture of Cap-178, Step c (3.13 g, 9.59 mmol) and AIBN (120 mg, 0.731 mmol) in 40 mL of benzene at 80° C. was added tri-n-butyltin hydride (10.24 mL, 38.4 mmol). The resulting mixture was stirred at reflux temperature for 20 min then cooled to room temperature. The mixture was diluted with diethyl ether and 100 mL of KF (10 g) aqueous solution was added and the mixture was stirred vigorously for 30 min. The two layers were then separated and the aqueous phase was extracted with EtOAc (2×). The organic layer was dried with MgSO₄ and concentrated. The crude product was purified by flash chromatography (silica gel, deactivated with 3% Et₃N in Hexanes and flushed with 3% Et₃N in Hexanes to remove tributyltin derivative and then eluted with 15% EtOAc/Hex) to afford Cap-178, Step d (1.9 g) as clear oil. ¹H NMR (500 MHz, CDCl₃) δ ppm 7.98-8.07 (2H, m), 7.52-7.58 (1H, m), 7.43 (2H, t, J=7.63 Hz), 5.08-5.17 (1H, m), 4.06 (1H, ddd, J=11.90, 4.88, 1.53 Hz), 3.50-3.59 (2H, m), 2.08-2.14 (1H, m), 1.99-2.06 (1H, m), 1.69-1.80 (1H, m), 1.41-1.49 (1H, m), 1.24 (3H, d, J=6.10 Hz).

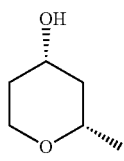

Cap-178, Step e

To a mixture of Cap-178, Step d (1.9 g, 8.63 mmol) in 10 mL of MeOH was added sodium methoxide (2 mL, 4.00 mmol) (2 M in methanol). The resulting mixture was stirred at room temperature for 5 hours. The solvent was removed under vacuum. The mixture was neutralized with saturated NH₄Cl solution and extracted with EtOAc (3×). The organic layers were dried with MgSO₄ and concentrated to afford Cap-178, Step e (0.8 g) as clear oil. The product was used in the next step without further purification. ¹H NMR (400 MHz, CDCl₃) δ ppm 4.01 (1H, ddd, J=11.80, 5.02, 1.76 Hz), 3.73-3.83 (1H, m), 3.36-3.46 (2H, m), 1.92-2.00 (1H, m), 1.88 (1H, m), 1.43-1.56 (1H, m), 1.23 (3H, d), 1.15-1.29 (1H, m).

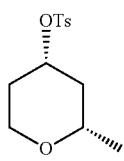

Cap-178, Step f

Tosyl-Cl (2.63 g, 13.77 mmol) was added to a solution of Cap-178, Step e (0.8 g, 6.89 mmol) and pyridine (2.23 mL, 27.5 mmol) in 100 mL of CH₂Cl₂. The resulting mixture was stirred at room temperature for 3 days. 10 mL of water was then added into the reaction mixture and the mixture was stirred at room temperature for an hour. The two layers were separated and the organic phase was washed with water and 1 N HCl aq. solution. The organic phase was dried with MgSO₄ and concentrated to afford Cap-178, Step f (1.75 g) as a light yellow solid. The product was used in the next step without further purification. Anal. Calcd. for [M+H]⁺ C₁₃H₁₉O₄S 271.10. found 270.90; ¹H NMR (500 MHz, CDCl₃) δ ppm 7.79 (2H, d, J=8.24 Hz), 7.34 (2H, d, J=7.93 Hz), 4.53-4.62 (1H, m), 3.94 (1H, ddd, J=12.13, 4.96, 1.83 Hz), 3.29-3.41 (2H, m), 2.45 (3H, s), 1.90-1.97 (1H, m), 1.79-1.85 (1H, m), 1.64-1.75 (1H, m), 1.38-1.48 (1H, m), 1.17 (3H, d, J=6.10 Hz).

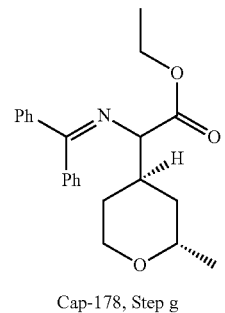 [SMILES: CCOC(=O)C(N=C(c1ccccc1)c1ccccc1)[C@@H]1CCO[C@@H](C)C1]

Cap-178, Step g

To a microwave tube was placed ethyl 2-(diphenylmethyleneamino)acetate (1.6 g, 5.92 mmol) and Cap-178, Step f (1.6 g, 5.92 mmol). 10 mL of toluene was added. The tube was sealed and LiHMDS (7.1 mL, 7.10 mmol) (1 N in toluene) was added dropwise under N₂. The resulting dark brown solution was heated at 100° C. under microwave radiation for 6 hours. To the mixture was then added water and the mixture was extracted with EtOAc (3×). The combined organic layers were washed with brine, dried with MgSO₄ and concentrated to afford a diastereomeric mixture of Cap-3, Step g (3.1 g) as an orange oil. The crude mixture was submitted to the next step without separation. LC-MS: Anal. Calcd. for [M+H]⁺ C₂₃H₂₈NO₃ 366.21. found 366.3.

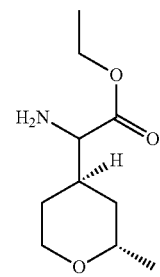

Cap-178, Step h

To a solution of the diastereomeric mixture of ethyl Cap-178, Step g in 20 mL of THF was added HCl (30 ml, 60.0 mmol) (2 N aqueous). The resulting mixture was stirred at room temperature for 1 hour. The mixture was extracted with EtOAc and the aqueous layer was concentrated to afford an HCl salt of Cap-178, Step h (1.9 g) as an orange oil. The salt was used in the next step without further purification. LC-MS: Anal. Calcd. for [M+H]⁺ C₁₀H₂₀NO₃ 202.14. found 202.1.

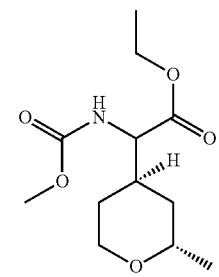

Cap-178, Step i

A solution of 1.9 g Cap-178, Step h (HCl salt), DiPEA (4.19 mL, 24.0 mmol) and methyl chloroformate (1.24 mL, 16.0 mmol) in 20 mL of CH₂Cl₂ was stirred at room temperature for 1 hour. The mixture was diluted with $CH_2Cl_2$ and washed with water. The organic layer was dried with $Na_2SO_4$ and concentrated. The crude product was purified by flash chromatography (silica gel, 0-20% EtOAc/Hex) to afford Cap-178, Step (1.1 g) as a yellow oil. Anal. Calcd. for $[M+Na]^+$ $C_{12}H_{21}NNaO_5$ 282.13. found 282.14; $^1H$ NMR (400 MHz, $CDCl_3$) δ ppm 5.16 (1H, br. s.), 4.43-4.58 (1H, m), 4.17-4.28 (2H, m), 3.89-4.03 (1H, m), 3.72-3.78 (2H, m), 3.67-3.72 (3H, m), 2.07-2.19 (1H, m), 1.35-1.77 (4H, m), 1.30 (3H, td, J=7.09, 2.89 Hz), 1.19 (3H, d, J=6.53 Hz).

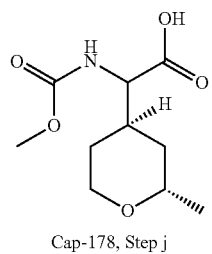 [SMILES: COC(=O)NC(C(=O)O)[C@@H]1CCO[C@@H](C)C1]

Cap-178, Step j

To a mixture of Cap-178, Step i (1.1 g, 4.2 mmol) in 5 mL of THF and 2 mL of water was added LiOH (6.36 mL, 12.7 mmol) (2 N aq.). The resulting mixture was stirred at room temperature overnight. The mixture was then neutralized with 1 N HCl aq. and extracted with EtOAc (3×). The combined organic layers were dried with $MgSO_4$ and concentrated to afford Cap-178, Step j (0.8 g) as a clear oil. LC-MS: Anal. Calcd. for $[M+H]^+$ $C_{10}H_{18}NO_5$ 232.12. found 232.1; $^1H$ NMR (400 MHz, $CDCl_3$) δ ppm 5.20 (1H, d, J=8.28 Hz), 4.54 (1H, t, J=8.16 Hz), 3.95-4.10 (1H, m), 3.66-3.85 (5H, m), 2.15-2.29 (1H, m), 1.41-1.85 (4H, m), 1.23 (3H, dd, J=6.53, 1.76 Hz).

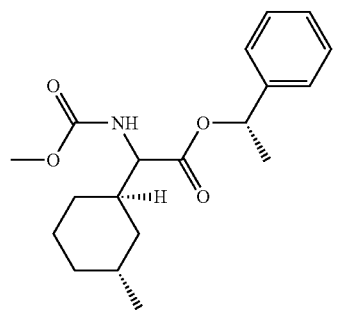

Cap-178, Step k

To a solution of Cap-178, Step j (240 mg, 1.04 mmol), (S)-1-phenylethanol (0.141 mL, 1.142 mmol) and EDC (219 mg, 1.14 mmol) in 10 mL of $CH_2Cl_2$ was added DMAP (13.95 mg, 0.114 mmol). The resulting solution was stirred at room temperature overnight and the solvent was removed under vacuum. The residue was taken up into EtOAc, washed with water, dried with $MgSO_4$ and concentrated. The crude product was purified by chromatography (silica gel, 0-15% EtOAc/Hexanes) to afford Cap-178, Step k as a mixture of two diastereomers. The mixture was separated by chiral HPLC (CHIRALPAK® AS column, 21×250 mm, 10 um) eluting with 90% 0.1% diethylamine/Heptane-10% EtOH at 15 mL/min to afford Cap-178, Step k stereoisomer 1 (eluted first) and Cap-178, Step k stereoisomer 2 (eluted second) as white solids. The stereochemistry of the isomers was not assigned.

Cap-178, Step k stereoisomer 1 (130 mg): LC-MS: Anal. Calcd. for $[M+Na]^+$ $C_{18}H_{25}NNaO_5$ 358.16. found 358.16; $^1H$ NMR (500 MHz, $CDCl_3$) δ ppm 7.28-7.38 (5 H, m), 5.94 (1H, q, J=6.71 Hz), 5.12 (1H, d, J=9.16 Hz), 4.55 (1H, t, J=9.00 Hz), 3.72-3.81 (1H, m), 3.67 (3H, s), 3.60-3.70 (2H, m), 1.98-2.08 (1H, m), 1.59 (3H, d, J=6.71 Hz), 1.38-1.47 (2H, m), 1.30 (2H, t, J=5.34 Hz), 0.93 (3H, d, J=6.41 Hz).

Cap-178, Stereoisomer 1

To a solution of Cap-178, Step k stereoisomer 1 ((S)-2-(methoxycarbonylamino)-2-((2S,4R)-2-methyltetrahydro-2H-pyran-4-yl)acetic acid) (150 mg, 0.447 mmol) in 10 mL of EtOH was added Pd/C (20 mg, 0.188 mmol) and the mixture was hydrogenated on Parr shaker at 40 psi overnight. The mixture was then filtered and the filtrate was concentrated to afford Cap-178, stereoisomer 1 (100 mg) as a sticky white solid. LC-MS: Anal. Calcd. for $[M+H]^+$ $C_{10}H_{18}NO_5$ 232.12. found 232.1; $^1H$ NMR (500 MHz, $CDCl_3$) δ ppm 5.14-5.27 (1H, m), 4.51 (1H, t, J=8.39 Hz), 3.90-4.07 (1H, m), 3.60-3.83 (5H, m), 2.06-2.27 (1H, m), 1.45-1.77 (4H, m), 1.21 (3H, d, J=6.41 Hz).

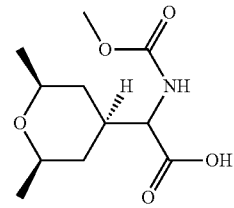

Cap-179 (Enantiomer-1 and Enantiomer-2)

179 stereoisomer 1
179 stereoisomer 2

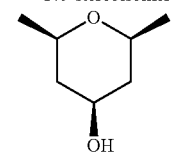

Cap-179, Step a 2,6-Dimethyl-4H-pyran-4-one (10 g, 81 mmol) was dissolved in ethanol (125 mL) and Pd/C (1 g, 0.94 mmol) was added. The mixture was hydrogenated in a Parr shaker under $H_2$ (0.325 g, 161 mmol) (70 psi) at room temperature for 12 hrs. The catalyst was filtered through a pad of CELITE® and washed with ethanol. The filtrate was concentrated in vacuum and the residue was purified via BIOTAGE® (2% to 25% EtOAc/Hex; 160 g column) Two fractions of clear oils were isolated. The first eluting one corresponded to (2R,6S)-2,6-dimethyldihydro-2H-pyran-4(3H)-one (1.8 g) while the second one corresponded to Cap-179, Step a (1.8 g).

(2R,6S)-2,6-Dimethyldihydro-2H-pyran-4(3H)-one data: $^1H$ NMR (500 MHz, $CDCl_3$) δ ppm 3.69 (2H, ddd, J=11.29, 5.95, 2.29 Hz), 2.24-2.36 (2H, m), 2.08-2.23 (2H, m), 1.18-1.34 (6H, m); $^{13}C$ NMR (126 MHz, $CDCl_3$) δ ppm 206.96 (1C, br. s.), 72.69 (2C, s), 48.70 (2C, s), 21.72 (2C, s).

Cap-179, Step a data: $^1H$ NMR (500 MHz, $CDCl_3$) δ ppm 3.69-3.78 (1H, m), 3.36-3.47 (2H, m), 2.10 (1H, br. s.), 1.88 (2H, dd, J=12.05, 4.73 Hz), 1.19 (6H, d, J=6.10 Hz), 1.10 (2H, q, J=10.70 Hz); $^{13}C$ NMR (126 MHz, $CDCl_3$) δ ppm 71.44 (2C, s), 67.92 (1C, s), 42.59 (2C, s), 21.71 (2C, s).

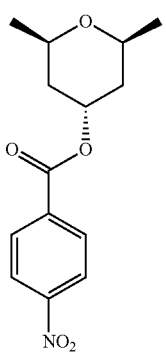

Cap-179, Step b

DEAD (2.311 mL, 14.59 mmol) was added drop wise to a solution of Cap-179, Step a (0.38 g, 2.92 mmol), 4-nitrobenzoic acid (2.195 g, 13.14 mmol) and Ph₃P (3.83 g, 14.59 mmol) in benzene (25 mL). Heat evolution was detected and the resulting amber solution was stirred at ambient temperature for 6 h. Solvent was removed under reduced pressure and the residue was purified via BIOTAGE® (0 to 15% EtOAc/Hex; 80 g column) A white solid corresponding to Cap-179, Step b (0.77 g) was isolated. LC-MS: Anal. Calcd. for [M]⁺ $C_{14}H_{17}NO_5$: 279.11. found 279.12. ¹H NMR (500 MHz, CDCl₃) δ ppm 8.27-8.32 (2H, m), 8.20-8.24 (2H, m), 5.45 (1H, quin, J=2.82 Hz), 3.92 (2H, dqd, J=11.90, 6.10, 6.10, 1.53 Hz), 1.91 (2H, dd, J=14.80, 2.29 Hz), 1.57 (3H, dt, J=14.65, 3.05 Hz), 1.22 (6H, d, J=6.10 Hz).

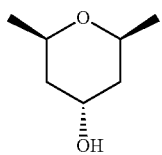

Cap-179, Step c

A solution LiOH (0.330 g, 13.8 mmol) in water (8 mL) was added to a solution of Cap-179, Step b (0.77 g, 2.76 mmol) in THF (30 mL) and the resulting mixture was stirred at ambient temperature for 16 h. THF was removed under reduced pressure and the aqueous layer was diluted with more water (20 mL) and extracted with EtOAc (3×15 mL). The combined organic layers were dried (MgSO₄), filtered and concentrated under vacuum. An oily residue with a white solid was recovered. The mixture was triturated with hexanes and the solid was filtered off to yield a clear oil corresponding to Cap-179, Step c (0.34 g). ¹H NMR (500 MHz, CDCl₃) δ ppm 4.21 (1H, quin, J=2.82 Hz), 3.87-3.95 (2H, m), 1.72 (1H, br. s.), 1.63 (2H, dd, J=14.34, 2.14 Hz), 1.39-1.47 (2H, m), 1.17 (6H, d, J=6.41 Hz).

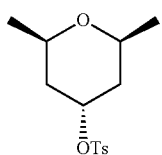

Cap-179, Step d p-Tosyl chloride (3.98 g, 20.89 mmol) was added to a solution of Cap-179, Step c (1.36 g, 10.5 mmol) and Pyridine (3.38 mL, 41.8 mmol) in CH₂Cl₂ (150 mL) at room temperature and stirred for 24 h and then concentrated to a yellow oil. The remaining residue was added to pyridine (20 mL) and water (30 mL) and the resulting mixture was stirred at ambient temperature for 1½ h. The mixture was extracted with Et₂O (75 mL) and the separated organic layer was the washed thoroughly with 1 N aq. HCl (4×50 mL). The organic layer was then dried (MgSO₄), filtered and concentrated. A white solid corresponding to Cap-179, Step d (2.2 g) was isolated. LC-MS: Anal. Calcd. for [2M+H]⁺ $C_{28}H_{41}O_8S_2$: 569.22. found 569.3. ¹H NMR (400 MHz, CDCl₃) δ ppm 7.80 (2H, d, J=8.28 Hz), 7.35 (2H, d, J=8.03 Hz), 4.89 (1H, quin, J=2.82 Hz), 3.77-3.88 (2H, m), 2.46 (3H, s), 1.77 (2H, dd, J=14.93, 2.89 Hz), 1.36 (2H, ddd, J=14.31, 11.54, 2.76 Hz), 1.13 (6H, d, J=6.27 Hz).

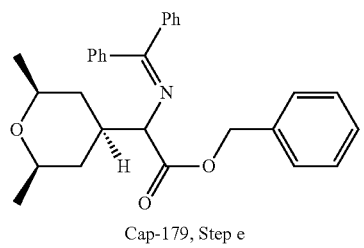 [SMILES: C[C@@H]1C[C@H](C(N=C(c2ccccc2)c2ccccc2)C(=O)OCc2ccccc2)C[C@H](C)O1]

Cap-179, Step e

LiHMDS (4.30 mL, 4.30 mmol) was added to a solution of Cap-179, Step d (1.02 g, 3.59 mmol) and benzyl 2-(diphenylmethyleneamino)acetate (1.181 g, 3.59 mmol) in toluene (25 mL) at room temperature in a sealed microwave vial and the resulting mixture was then stirred for 5 h at 100° C. under microwave radiation. The reaction was quenched with water (10 mL), extracted with EtOAc, washed with water, dried over MgSO₄, filtrated, and concentrated in vacuum. The residue was purified via BIOTAGE® (0% to 6% EtOAc/Hex; 80 g column) and a yellow oil corresponding to Cap-179, Step e (1.2 g) was isolated. Anal. Calcd. for [2M+Na]⁺ $C_{58}H_{62}N_2NaO_6$: 905.45. found 905.42. ¹H NMR (400 MHz, CDCl₃) δ ppm 7.64-7.70 (4H, m), 7.29-7.44 (29H, m), 7.06 (4H, dd, J=7.65, 1.63 Hz), 5.18 (2H, d, J=2.01 Hz), 3.89 (2H, d, J=6.53 Hz), 3.79-3.87 (1H, m), 3.46 (5H, dquind, J=11.26, 5.87, 5.87, 5.87, 5.87, 1.88 Hz), 2.47 (2H, s), 2.35-2.46 (2H, m), 1.78 (1H, dd, J=14.81, 3.01 Hz), 1.62-1.65 (1H, m), 1.61 (2H, s), 1.36-1.43 (3H, m), 1.19 (7H, d, J=6.27 Hz), 1.14 (11H, dd, J=6.15, 2.89 Hz), 0.86-0.96 (3H, m).

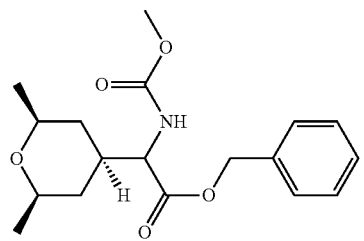

Cap-179, Step f (Enantiomer-1 and Enantiomer-2)

Cap-179, Step e (2.08 g, 4.71 mmol) was dissolved in THF (100 mL) and treated with 2 N HCl (9.42 mL, 18.84 mmol). The resulting clear solution was stirred at ambient temperature for 4 h and then THF was removed under reduced pressure. The remaining aqueous layer was extracted with hexanes (3×20 ml) and after diluting with H₂O (20 mL), the aqueous phase was basified with 1 N NaOH to pH=10 and extracted with EtOAc (3×10 mL). The combined organic layers were dried (MgSO₄), filtered and concentrated under vacuum. The resulting residue was taken up in CH₂Cl₂ (100 mL) and charged with DIEA (2.468 mL, 14.13 mmol) and methyl chloroformate (0.401 mL, 5.18 mmol). The resulting solution was stirred at ambient temperature for 2 h. The reaction mixture was quenched with water (10 mL) and the organic layer was removed under reduced pressure. The aqueous layer was then extracted with EtOAc (3×10 mL) and the combined organic layers were dried (MgSO₄), filtered and concentrated. The residue was purified via BIOTAGE® (10% EtOAc/Hex; 25 g column) A clear colorless oil corresponding to Cap-179, Step f (1.05 g) was recovered. LC-MS: Anal. Calcd. for [M+H]⁺ $C_{18}H_{26}NO_5$: 336.18. found 336.3. ¹H NMR (500 MHz, CDCl₃) δ ppm 7.32-7.40 (5H, m), 5.26 (1H, d, J=8.24 Hz), 5.13-5.24 (2H, m), 4.36 (1H, dd, J=8.85, 4.88 Hz), 3.68 (3H, s), 3.32-3.46 (2H, m), 2.02-2.14 (1H, m), 1.52 (1H, d, J=12.82 Hz), 1.32 (1H, d, J=12.51 Hz), 1.11-1.18 (6H, m), 0.89-1.07 (2H, m).

A chiral SFC method was developed to separate the racemic mixture by using 12% methanol as the modifier on a CHIRALPAK® AD-H column (30×250 mm, 5 μm) (Temp=35° C., Pressure=150 bar, Wavelength=210 nm, Flow rate=70 mL/min for 8 min, Solvent A=CO₂, Solvent B=MeOH). The two separated isomers, Cap-179 Step f (Enantiomer-1) (first eluting) and Cap-179 Step f (Enantiomer-2) (second eluting) exhibited the same analytical data as the corresponding mixture (see above).

Cap-179

Enantiomer-1 and Enantiomer-2

Cap-179 Step f (Enantiomer-1) (0.35 g, 1.044 mmol) was dissolved in MeOH (50 mL) in a Parr bottle and charged with Pd/C (0.111 g, 1.044 mmol). The suspension was then placed in a Parr shaker and the mixture was flushed with N₂ (3×), placed under 40 psi of H₂ (2.104 mg, 1.044 mmol) and shaken at room temperature for 2 h. The catalyst was filtered off through a pad of CELITE® and the solvent was removed under reduced pressure, to yield an amber solid corresponding to Cap-179 Enantiomer-1 (0.25 g). ¹H NMR (500 MHz, DMSO-d₆) δ ppm 12.74 (4H, br. s.), 7.35 (4H, d, J=6.10 Hz), 3.85 (4H, br. s.), 3.53 (3H, s), 3.35 (2H, ddd, J=15.95, 9.99, 6.10 Hz), 1.97 (1H, br. s.), 1.48 (2H, t, J=13.28 Hz), 1.06 (6H, d, J=6.10 Hz), 0.82-1.00 (2H, m).

Cap-179 Enantiomer-2 was prepared similarly: ¹H NMR (500 MHz, DMSO-d₆) δ ppm 12.50 (1H, br. s.), 7.31 (1H, br. s.), 3.84 (1H, t, J=7.32 Hz), 3.53 (3H, s), 3.29-3.41 (2H, m), 1.99 (1H, s), 1.48 (2H, t, J=14.34 Hz), 1.06 (6H, d, J=6.10 Hz), 0.95 (1H, q, J=12.21 Hz), 0.87 (1H, q, J=11.80 Hz). [Note: the minor variation in the ¹H NMR profile of the enantiomers is likely a result of a difference in sample concentration.]

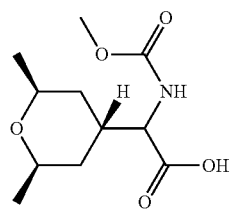

Cap-180 (racemic mixture)

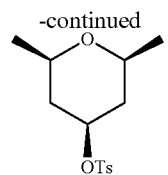

Cap-180, Step a p-Tosyl-Cl (4.39 g, 23.0 mmol) was added to a solution of Cap-179, Step a (1.50 g, 11.5 mmol) and pyridine (3.73 mL, 46.1 mmol) in CH₂Cl₂ (50 mL) at room temperature and stirred for 2 days. The reaction was diluted with CH₂Cl₂, washed with water, then 1 N HCl. The organic layer was dried (MgSO₄) and concentrated to a yellow oil which was purified via BIOTAGE® (5% to 20% EtOAc/Hex; 40 g column) A clear oil that solidified under vacuum and corresponding to Cap-180, Step a (2.89 g) was isolated. LC-MS: Anal. Calcd. for [2M+Na]⁺ $C_{28}H_{40}NaO_8S_2$: 591.21. found 591.3. ¹H NMR (500 MHz, CDCl₃) δ ppm 7.80 (2H, d, J=8.24 Hz), 7.35 (2H, d, J=7.93 Hz), 4.59 (1H, tt, J=11.37, 4.96 Hz), 3.36-3.46 (2H, m), 2.46 (3H, s), 1.91 (2H, dd, J=12.05, 5.04 Hz), 1.37 (2H, dt, J=12.67, 11.52 Hz), 1.19 (6H, d, J=6.10 Hz).

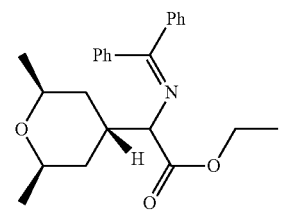

Cap-180, Step b

LiHMDS 1 N (7.09 mL, 7.09 mmol) was added to a solution of Cap-180, Step a (1.68 g, 5.91 mmol) and ethyl 2-(diphenylmethyleneamino)acetate (1.579 g, 5.91 mmol) in toluene (30 mL) at room temperature and the resulting mixture was then stirred for 16 h at 85° C. The reaction was quenched with water (50 mL), extracted with EtOAc, washed with water, dried over MgSO₄, filtrated, and concentrated in vacuo. The residue was purified via BIOTAGE® (0% to 15% EtOAc/Hex; 40 g column) A clear yellowish oil corresponding to Cap-180, Step b (racemic mixture; 0.64 g) was isolated. LC-MS: Anal. Calcd. for [M+H]⁺ $C_{24}H_{30}NO_3$: 380.22. found 380.03. ¹H NMR (400 MHz, CDCl₃) δ ppm 7.64-7.70 (2H, m), 7.45-7.51 (3H, m), 7.38-7.44 (1H, m), 7.31-7.37 (2H, m), 7.13-7.19 (2H, m), 4.39 (1H, d, J=10.54 Hz), 4.16-4.26 (2H, m), 3.29-3.39 (1H, m), 2.93-3.03 (1H, m), 2.70 (1H, m, J=9.41, 4.14 Hz), 1.42-1.49 (2H, m), 1.31-1.37 (1H, m), 1.29 (4H, t, J=7.15 Hz), 1.04 (6H, dd, J=7.78, 6.27 Hz).

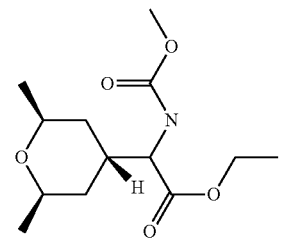

Cap-180, Step c

Cap-180, Step b (0.36 g, 0.949 mmol) was dissolved in THF (10 mL) and treated with 2 N HCl (1.897 mL, 3.79 mmol). The resulting clear solution was stirred at ambient temperature for 20 h and THF was removed under reduced pressure. The remaining aqueous layer was extracted with hexanes (3×20 mL) and after diluting with $H_2O$ (20 mL), the aqueous phase was basified with 1 N NaOH to pH=10 and extracted with EtOAc (3×10 mL). The combined organic layers were dried ($MgSO_4$), filtered and concentrated under vacuum. The resulting residue was taken up in $CH_2Cl_2$ (10.00 mL) and charged with DIEA (0.497 mL, 2.85 mmol) and methyl chloroformate (0.081 mL, 1.044 mmol). The resulting solution was stirred at ambient temperature for 2 h and the reaction mixture was quenched with water (10 mL) and the organic layer was removed under reduced pressure. Aqueous layer was extracted with EtOAc (3×10 mL) and the combined organic layers were dried ($MgSO_4$), filtered and concentrated. An amber oil corresponding to Cap-180, Step c (0.21 g) was recovered and it was used without further purification. LC-MS: Anal. Calcd. for $[M+H]^+ C_{13}H_{24}NO_5$: 273.17. found 274.06. $^1H$ NMR (400 MHz, $CDCl_3$) δ ppm 5.20 (1H, d, J=8.03 Hz), 4.59 (1H, t, J=10.16 Hz), 4.11-4.27 (3H, m), 3.69-3.82 (2H, m), 3.64 (3H, s), 1.95-2.07 (1H, m), 1.63 (1H, d, J=13.80 Hz), 1.41 (2H, dd, J=8.03, 4.02 Hz), 1.31-1.37 (1H, m), 1.26 (3H, t, J=7.15 Hz), 1.16 (1H, d, J=6.27 Hz), 1.12 (6H, dd, J=6.15, 3.89 Hz).

Cap-180

Racemic Mixture

Cap-180, Step c (0.32 g, 1.2 mmol) was dissolved in THF (10 mL) and charged with LiOH (0.056 g, 2.342 mmol) in water (3.33 mL) at 0° C. The resulting solution was stirred at rt for 2 h. THF was removed under reduced pressure and the remaining residue was diluted with water (15 mL) and washed with $Et_2O$ (2×10 mL). The aqueous layer was then acidified with 1N HCl to pH ~2 and extracted with EtOAc (3×15 mL). The combined organic layers were dried ($MgSO_4$), filtered and concentrated under vacuum to yield Cap-180 (racemic mixture) (0.2 g) as a white foam. LC-MS: Anal. Calcd. for $[M+H]^+ C_{11}H_{20}NO_5$: 246.13. found 246.00. $^1H$ NMR (400 MHz, $CDCl_3$) δ ppm 5.14 (1H, d, J=9.03 Hz), 4.65 (1H, t, J=9.91 Hz), 3.63-3.89 (5H, m), 1.99-2.13 (1H, m), 1.56-1.73 (2H, m), 1.48-1.55 (1H, m), 1.35-1.48 (1H, m), 1.27 (1H, br. s.), 1.17 (6H, d, J=6.02 Hz).

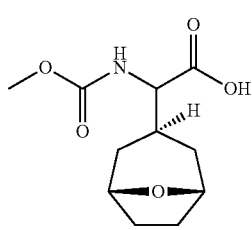

Cap-185

(Enantiomer-1 and Enantiomer-2)

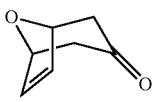

Cap-185, Step a

To a mixture of furan (1.075 mL, 14.69 mmol) and zinc (1.585 g, 24.24 mmol) in 1 mL of THF was added 1,1,3,3-tetrabromopropan-2-one (8.23 g, 22.03 mmol) and triethyl borate (5.25 mL, 30.8 mmol) in 4 mL of THF dropwise during 1 hour in dark. The resulting mixture was stirred at room temperature in dark for 17 hours. The resulting dark brown mixture was cooled to −15° C., and 6 mL of water was added. The mixture was warmed to 0° C. and stirred at this temperature for 30 min. The mixture was then filtered and washed with ether. The filtrate was diluted with water and extracted with ether (3×). The combined organic layers were dried with $MgSO_4$ and concentrated to afford dark brown oil. The dark brown oil was dissolved in 6 mL of MeOH and the solution was added dropwise to a mixture of zinc (4.99 g, 76 mmol), copper (I) chloride (0.756 g, 7.64 mmol) and ammonium chloride (5.4 g, 101 mmol) in 20 mL of MeOH. The reaction temperature was maintained below 15° C. during addition. The mixture was then stirred at room temperature for 20 hours, filtered, and the filtrate was diluted with water and extracted with $CH_2Cl_2$ (3×). The combined organic layers were dried with $MgSO_4$ and concentrated. The crude product was purified by flash chromatography (silica gel, 0-14% EtOAc/Hex) to afford Cap-185, Step a as a white solid (1.0 g) as a white solid, which turned yellow soon. $^1H$ NMR (500 MHz, $CDCl_3$) δ ppm 6.24 (2H, s), 5.01 (2H, d, J=4.88 Hz), 2.73 (2H, dd, J=16.94, 5.04 Hz), 2.31 (2H, d, J=16.79 Hz).

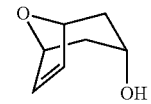

Cap-185, Step b

To a solution of Cap-185, Step a (240 mg, 1.933 mmol) in 2 mL of THF at −78° C. was added L-selectride (3.87 mL, 3.87 mmol) (1 M in THF) dropwise over 100 min. The resulting mixture was stirred at −78° C. for 1 hour and then at room temperature overnight. The mixture was then cooled to 0° C., 4 mL of 20% NaOH aqueous solution was added, followed by 2 mL of $H_2O_2$ (30% water solution) dropwise. The resulting mixture was stirred for 1 hour and then neutralized with 6N HCl (~5 mL). The aqueous layer was saturated with NaCl and extracted with $CH_2Cl_2$ (3×). The combined organic layers were dried with $MgSO_4$ and concentrated. The crude product was purified by flash chromatography (silica gel, 0-40% EtOAc/Hex) to afford Cap-185, Step b (180 mg) as clear oil. $^1H$ NMR (400 MHz, $CDCl_3$) δ ppm 6.49 (2H, s), 4.76 (2H, d, J=4.27 Hz), 3.99 (1H, t, J=5.77 Hz), 2.29 (2H, ddd, J=15.18, 5.65, 4.02 Hz), 1.70-1.78 (2H, m).

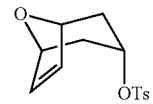

Cap-185, Step c p-Tosyl-Cl (544 mg, 2.85 mmol) was added to a solution of Cap-185, Step b (180 mg, 1.427 mmol) and pyridine (0.462 mL, 5.71 mmol) in 5 mL of $CH_2Cl_2$ (5 mL) and the mixture was stirred at room temperature for 2 days. The reaction was diluted with $CH_2Cl_2$ and washed with 1 N aq. HCl. The aqueous layer was extracted with $CH_2Cl_2$ (2×). The combined organic layers were dried with $MgSO_4$ and concentrated. The crude product was purified by flash chromatography (silica gel, 0-15% EtOAc/Hex) to afford Cap-185, Step c (210 mg) as a white solid. $^1$H NMR (500 MHz, CDCl$_3$) δ ppm 7.73 (2H, d, J=8.24 Hz), 7.32 (2H, d, J=8.24 Hz), 6.25 (2H, s), 4.76 (1H, t, J=5.65 Hz), 4.64 (2H, d, J=3.66 Hz), 2.44 (3H, s), 2.18 (2H, td, J=10.07, 5.49 Hz), 1.71 (2H, d, J=15.56 Hz).

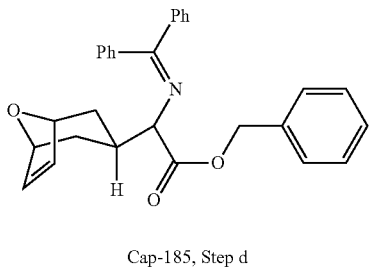 [SMILES: O=C(OCc1ccccc1)C(N=C(c1ccccc1)c1ccccc1)C1CC2C=CC(C1)O2]

Cap-185, Step d

A microwave tube was charged with benzyl 2-(diphenylmethyleneamino)acetate (1.5 g, 4.57 mmol) and Cap-185, Step c (1.28 g, 4.57 mmol) in 5 mL of toluene. The tube was sealed and LiHMDS (5.5 mL, 5.5 mmol) (1 N in toluene) was added dropwise under N$_2$. The resulting dark brown solution was heated at 100° C. in microwave for 5 hours. To the mixture was then added water and EtOAc. The layers were separated and the water phase was extracted with EtOAc (2×). The combined organic layers were concentrated to afford Cap-185, Step d as a racemic mixture of. The crude mixture was submitted to the next step without purification or separation. LC-MS: Anal. Calcd. for [M+H]$^+$ C$_{29}$H$_{28}$NO$_3$ 438.21. found 438.4.

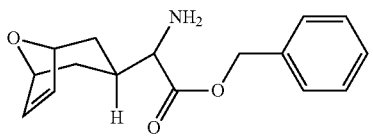

Cap-185, Step e

To a solution of the racemic mixture of Cap-185, Step d in 30 mL of THF was added HCl (20 mL) (2 N aq.). The resulting mixture was stirred at room temperature for 2 hours. After the reaction was done as judged by TLC, the two layers were separated. The aqueous layer was washed with EtOAc, neutralized with sat. NaHCO$_3$ aq. solution and then extracted with EtOAc (3×). The combined organic layers were dried with MgSO$_4$ and concentrated to afford Cap-185, Step e. LC-MS: Anal. Calcd. for [M+H]$^+$ C$_{16}$H$_{20}$NO$_3$ 274.14. found 274.12.

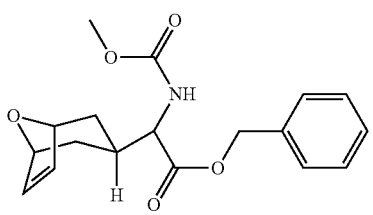

Cap-185, Step f

A solution of the crude Cap-185, Step e, DiPEA (1.24 mL, 7.1 mmol) and methyl chloroformate (0.55 mL, 7.1 mmol) in 5 mL of CH$_2$Cl$_2$ was stirred at room temperature for 1 hour. The mixture was then diluted with CH$_2$Cl$_2$ and washed with water. The organic layer was dried with Na$_2$SO$_4$ and concentrated. The crude product was purified by flash chromatography (silica gel, 0-40% EtOAc/Hex) to afford 700 mg of the racemic mixture. The mixture was then separated by chiral HPLC (CHIRALPAK® AD-H column, 30×250 mm, 5 um) eluting with 88% CO$_2$-12% EtOH at 70 mL/min to afford 240 mg of Enantiomer-1 and 310 mg of Enantiomer-2 of Cap-1, Step f as white solids. Enantiomer-1: LC-MS: Anal. Calcd. for [M+H]$^+$ C$_{18}$H$_{22}$NO$_5$ 332.15. found 332.3. $^1$H NMR (500 MHz, CDCl$_3$) δ ppm 7.30-7.40 (5H, m), 6.03-6.16 (2H, m), 5.09-5.26 (3 H, m), 4.65-4.74 (2H, m), 4.33 (1H, dd, J=9.16, 4.88 Hz), 3.67 (3H, s), 2.27-2.38 (1 H, m), 1.61-1.69 (1H, m), 1.45-1.56 (1H, m), 1.34 (1H, dd, J=13.43, 5.19 Hz), 1.07 (1H, dd, J=13.12, 5.19 Hz). Enantiomer-2: LC-MS: Anal. Calcd. for [M+H]$^+$ C$_{18}$H$_{22}$NO$_5$ 332.15. found 332.06.

Cap-185

Enantiomer-1 and Enantiomer-2

To a hydrogenation bottle containing a solution Cap-185, Step f (Enantiomer-2) (300 mg, 0.905 mmol) in 10 mL of MeOH was added Pd/C (15 mg, 0.141 mmol) under a cover of nitrogen. The mixture was hydrogenated on a Parr shaker at 40 psi for 3 hours. The mixture was then filtered and the filtrate was concentrated to afford Cap-185 (Enantiomer-2) (200 mg) as a white solid. LC-MS: Anal. Calcd. for [M+H]$^+$ C$_{11}$H$_{18}$NO$_5$ 244.12. found 244.2. $^1$H NMR (500 MHz, CDCl$_3$) δ ppm 5.33 (1H, br. s.), 4.46 (2H, d), 4.28 (1H, br. s.), 3.68 (3H, s), 2.35 (1H, br. s.), 1.91-2.03 (2H, m), 1.56-1.80 (4H, m), 1.36-1.55 (2H, m). [Note: Cap-185 (Enantiomer-1) can be obtained in a similar fashion.]

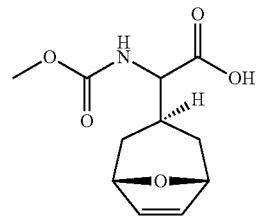

Cap-186

To a solution of the ester Cap-185, Step f (Enantiomer-2) (150 mg, 0.453 mmol) in 4 mL of MeOH was added NaOH (4 mL of 1 N in water, 4.00 mmol). The resulting mixture was stirred at room temperature for 3 hours. The methanol was then removed under vacuum, and the residue was neutralized with 1 N HCl solution and extracted with EtOAc (3×). The combined organic layers were dried with MgSO$_4$ and concentrated to afford Cap-186 that was contaminated with some benzyl alcohol (sticky white solid; 115 mg). LC-MS: Anal. Calcd. for [M+H]$^+$ C$_{11}$H$_{16}$NO$_5$ 242.10. found 242.1. $^1$H NMR (500 MHz, CDCl$_3$) δ ppm 6.10-6.19 (2H, m), 5.36 (1H, d, J=8.85 Hz), 4.75-4.84 (2H, m), 4.28 (1H, dd, J=8.55, 4.58 Hz), 3.68 (3H, s), 2.33-2.45 (1H, m), 1.60-1.72 (2H, m), 1.30-1.48 (2H, m).

Cap-187

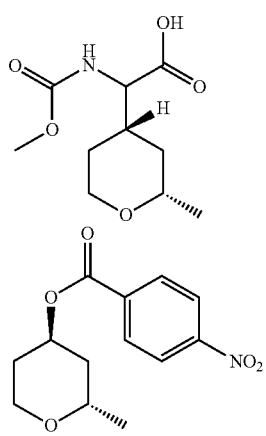

Cap-187, Step a

To a solution of Cap-178, Step e (2.2 g, 18.94 mmol), PPh₃ (24.84 g, 95 mmol) and 4-nitrobenzoic acid (14.24 g, 85 mmol) in 30 mL of benzene was added DEAD (42.9 mL, 95 mmol) dropwise. The resulting light orange solution was stirred at room temperature overnight. The solvent was then removed under vacuum and the residue was purified by flash chromatography (silica gel, 0-15% EtOAc/Hex) to afford Cap-187, Step a (2.3 g) as a white solid. $^1$H NMR (500 MHz, CDCl₃) δ ppm 8.27-8.34 (2H, m), 8.20-8.26 (2H, m), 5.45 (1H, t, J=2.90 Hz), 3.83-3.96 (3H, m), 1.90-2.03 (2H, m), 1.80-1.88 (1H, m), 1.61-1.70 (1H, m), 1.21 (3H, d, J=6.10 Hz).

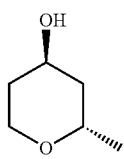

Cap-187, Step b

To a solution of Cap-187, Step a (2.3 g, 8.67 mmol) in 10 mL of MeOH was added sodium methoxide (2.372 mL, 8.67 mmol) (25% in Methanol). The resulting mixture was stirred at room temperature for 3 hours. Water was added, and the mixture was extracted with EtOAc (5×). The combined organic layers were dried with MgSO₄ and concentrated. The crude product was purified by flash chromatography (silica gel, 0-15% EtOAc/Hex, then 15-50% EtOAc/Hex) to afford Cap-187, Step b (0.85 g) as clear oil. $^1$H NMR (500 MHz, CDCl₃) δ ppm 4.19-4.23 (1H, m), 3.82-3.91 (2H, m), 3.73-3.79 (1H, m), 1.79-1.88 (1H, m), 1.62-1.68 (1H, m), 1.46-1.58 (2H, m), 1.14 (3H, d, J=6.10 Hz).

Cap-187

The individual enantiomers of Cap-187 were synthesized from Cap-187, Step b according to the procedure described for Cap-178. LC-MS: Anal. Calcd. for [M+H]⁺ C₁₀H₁₈NO₅ 232.12. found 232.1. $^1$H NMR (400 MHz, CDCl₃) δ ppm 5.26 (1H, d, J=7.78 Hz), 4.32-4.43 (1H, m), 4.07 (1H, dd, J=11.54, 3.51 Hz), 3.72 (3H, s), 3.39-3.50 (2 H, m), 2.08-2.23 (1H, m), 1.54-1.68 (1H, m), 1.38-1.52 (1H, m), 1.11-1.32 (5H, m).

Cap-188

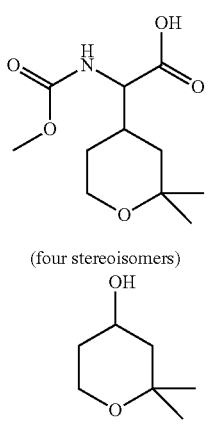

(four stereoisomers)

Cap-188, Step a

To a solution of 2,2-dimethyldihydro-2H-pyran-4(3H)-one (2 g, 15.60 mmol) in 50 ml of MeOH was slowly added sodium borohydride (0.649 g, 17.16 mmol). The resulting mixture was stirred at room temperature for 3 hours. To the mixture was then added 1 N HCl aqueous solution until it crosses into acidic pH range and then extracted with EtOAc (3×). The combined organic layers were dried with MgSO₄ and concentrated to afford Cap-188, Step a (1.9 g) as clear oil. The product was used in the next step without purification. $^1$H NMR (400 MHz, CDCl₃) δ ppm 3.91-4.02 (1H, m), 3.79-3.86 (1H, m), 3.63 (1H, td, J=12.05, 2.51 Hz), 1.82-1.93 (2H, m), 1.40-1.53 (1H, m), 1.29-1.38 (1H, m), 1.27 (3H, s), 1.20 (3H, s).

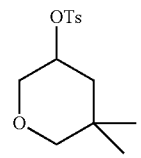

Cap-188.1 and Cap-188.2, Step b p-Tosyl-Cl (5.56 g, 29.2 mmol) was added to a solution of Cap-188, Step a (1.9 g, 14.59 mmol) and pyridine (4.72 mL, 58.4 mmol) in 100 mL of CH₂Cl₂. The resulting mixture was stirred at room temperature for 3 days. To the reaction was added 10 mL of water, and the mixture was stirred at room temperature for an additional hour. The two layers were separated and the organic phase was washed with water and 1 N HCl aqueous solution. The organic phase was dried with MgSO₄ and concentrated to afford the mixture of two enantiomers as a light yellow solid. The mixture was then separated by chiral HPLC (CHIRALPAK® AD column, 21×250 mm, 10 um) eluting with 92% 0.1% diethylamine/Heptane-8% EtOH at 15 mL/min to afford Cap-188.1, Step b (1.0 g) and Cap-188.2, Step b (1.0 g). The absolute stereochemistry of the two enantiomers was not assigned. Cap-188.1, Step b: LC-MS: Anal. Calcd. for [2M+Na]⁺ C₂₈H₄₀NaO₈S₂ 591.21. found 591.3. $^1$H NMR (500 MHz, CDCl₃) δ ppm 7.79 (2H, d, J=8.24 Hz), 7.34 (2H, d, J=8.24 Hz), 4.72-4.81 (1H, m), 3.78 (1H, dt, J=12.44, 4.16 Hz), 3.53-3.61 (1 H, m), 2.45 (3H, s), 1.75-1.86 (2H, m), 1.61-1.71 (1H, m), 1.52-1.60 (1H, m), 1.22 (3H, s), 1.14 (3H, s). Cap-188.2, Step b: LC-MS: Anal. Calcd. for [2M+Na]⁺ C₂₈H₄₀NaO₈S₂ 591.21. found 591.3;

Cap-188

The four stereoisomers of Cap-188 could be synthesized from Cap-188.1, Step b and Cap-188.2, Step b, according to the procedure described for the preparation of Cap-178. Cap-188 (Steroisomer-1): LC-MS: Anal. Calcd. for [M+Na]⁺ C₁₁H₁₉NNaO₅ 268.12. found 268.23. ¹H NMR (500 MHz, CDCl₃) δ ppm 5.32 (1H, d, J=8.55 Hz), 4.26-4.35 (1H, m), 3.57-3.82 (5H, m), 2.11-2.34 (1H, m), 1.25-1.58 (4H, m), 1.21 (6H, d, J=6.10 Hz). Cap-188 (Stereoisomer-2): LC-MS: Anal. Calcd. for [M+H]⁺ C₁₁H₂₀NO₅ 246.13. found 246.1. ¹H NMR (500 MHz, CDCl₃) δ ppm 5.25 (1H, d, J=8.55 Hz), 4.33 (1H, dd, J=8.39, 5.04 Hz), 3.80 (1H, dd, J=11.90, 3.97 Hz), 3.62-3.76 (4H, m), 2.20-2.32 (1H, m), 1.52-1.63 (1H, m), 1.27-1.49 (3H, m), 1.22 (6H, d, J=14.04 Hz).

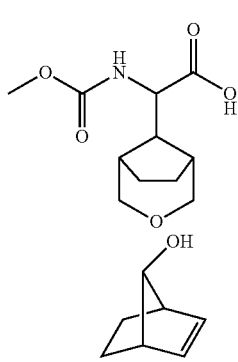

Cap-189

Cap-189, Step a

To a solution of phenylmagnesium bromide (113 mL, 340 mmol) (3 M in ether) in 100 mL of ether was added dropwise exo-2,3-epoxynorbornane (25 g, 227 mmol) in 50 mL of ether. After the initial exotherm, the mixture was heated to reflux overnight. The reaction was then cooled to room temperature and quenched carefully with water (~10 mL). The mixture was diluted with ether and washed with a 3 N HCl aqueous solution (~160 mL). The aqueous layer was extracted with ether (2×) and the combined organic layers were dried with MgSO₄ and concentrated. The crude product was purified by flash chromatography (silica gel, 0-18% EtOAc/Hex) to afford Cap-189, Step a (11 g). ¹H NMR (400 MHz, CDCl₃) δ ppm 6.03-6.11 (2H, m), 3.76 (1H, d, J=11.29 Hz), 2.72-2.81 (2H, m), 1.98 (1H, d, J=11.29 Hz), 1.67-1.76 (2H, m), 0.90-0.97 (2H, m).

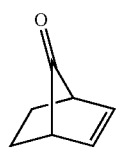

Cap-189, Step b

To a solution of oxalyl chloride (59.9 mL, 120 mmol) in 200 mL of CH₂Cl₂ at −78° C. was added DMSO (17.01 mL, 240 mmol) in 100 mL of CH₂Cl₂. The mixture was stirred for 10 min, and Cap-189, Step a (11 g, 100 mmol) in 150 mL of CH₂Cl₂ was added followed by Et₃N (72.4 mL, 519 mmol) in 30 mL of CH₂Cl₂. The mixture was stirred at −78° C. for 30 min and then warmed to room temperature. Water (150 mL) was added and the mixture was stirred at room temperature for 30 mins. The two layers were then separated, and the aqueous layer was extracted with CH₂Cl₂ (2×). The organic layers were combined, dried with MgSO₄ and concentrated. The crude product was purified by flash chromatography (silica gel, 0-5% EtOAc/Hex) to afford Cap-189, Step b (5.3 g) as a light yellow oil. ¹H NMR (500 MHz, CDCl₃) δ ppm 6.50-6.55 (2H, m), 2.78-2.84 (2 H, m), 1.92-1.99 (2H, m), 1.17-1.23 (2H, m).

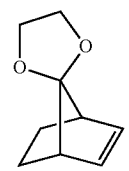

Cap-189, Step c

A mixture of Cap-189, Step b (5.3 g, 49.0 mmol), p-toluenesulfonic acid monohydrate (1.492 g, 7.84 mmol) and ethylene glycol (4.10 mL, 73.5 mmol) in 100 mL of benzene was refluxed for 4 hours and then stirred at room temperature overnight. The reaction was partitioned between Et₂O and aqueous sat. NaHCO₃ solution and the two layers were separated. The organic layer was washed with brine, dried with MgSO₄ and concentrated. The crude product was purified by flash chromatography (silica gel, 0-6% EtOAc/Hex) to afford Cap-189, Step c (5.2 g) as a clear oil. ¹H NMR (400 MHz, CDCl₃) δ ppm 6.20 (2H, t, J=2.13 Hz), 3.90-3.97 (2H, m), 3.81-3.89 (2H, m), 2.54 (2H, m), 1.89-1.99 (2H, m), 0.95-1.03 (2H, m).

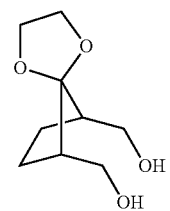

Cap-189, Step d

A solution of Cap-189, Step c (5.2 g, 34.2 mmol) in 60 mL of MeOH and 50 mL of CH₂Cl₂ was cooled to −78° C. and treated with ozone gas until a light blue color was apparent. The reaction was then bubbled with N₂ to remove the excess ozone gas (blue color disappeared) and sodium borohydride (1.939 g, 51.3 mmol) was added into the reaction. The reaction was then warmed to 0° C. Acetone was added into the mixture to quench the excess sodium borohydride. The mixture was concentrated and the residue was purified by flash chromatography (silica gel, 100% EtOAc) to afford Cap-189, Step d (5.0 g) as a clear oil. ¹H NMR (400 MHz, CDCl₃) δ ppm 3.99-4.09 (4H, m), 3.68 (4H, m), 2.17-2.29 (2H, m), 1.92-2.10 (2H, m), 1.77-1.88 (2H, m), 1.57-1.70 (2H, m).

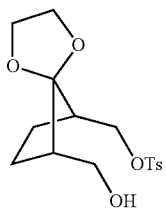

Cap-189, Step e

To a solution of Cap-189, Step d (1 g, 5.31 mmol) in 20 mL of CH$_2$Cl$_2$ was added silver oxide (3.8 g), p-Ts-Cl (1.215 g, 6.38 mmol) and KI (0.176 g, 1.063 mmol). The resulting solution was stirred at room temperature for 3 days. The mixture was then filtered and the filtrate was concentrated. The crude product was purified by flash chromatography (silica gel, 60% EtOAc/Hex) to afford Cap-189, Step e (0.79 g) as clear oil. LC-MS: Anal. Calcd. for [M+Na]$^+$ C$_{16}$H$_{22}$NaO$_6$S 365.10. found 365.22. $^1$H NMR (400 MHz, CDCl$_3$) δ ppm 7.80 (2H, d, J=8.28 Hz), 7.36 (2H, d, J=8.03 Hz), 4.11-4.17 (1H, m), 3.85-4.06 (5H, m), 3.64-3.71 (1H, m), 3.55-3.63 (1H, m), 2.47 (3H, s), 2.32-2.43 (1H, m), 2.15-2.27 (1H, m), 1.70-1.89 (2H, m), 1.52-1.66 (1H, m), 1.35-1.47 (1H, m).

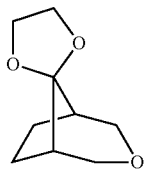

Cap-189, Step f

To a solution of Cap-189, Step e (2.2 g, 6.43 mmol) in 40 mL of MeOH was added potassium carbonate (1.776 g, 12.85 mmol). The resulting mixture was stirred at room temperature overnight. The mixture was then diluted with water and EtOAc. The two layers were separated. The aqueous layer was extracted with EtOAc (2×). The combined organic layers were washed with brine, dried with MgSO$_4$ and concentrated. The crude product was purified by flash chromatography (silica gel, 0-15% EtOAc/Hex) to afford Cap-189, Step f (0.89 g, 5.23 mmol, 81%) as clear oil. $^1$H NMR (400 MHz, CDCl$_3$) δ ppm 3.89-4.02 (6H, m), 3.58 (2H, dd, J=10.79, 2.51 Hz), 1.69-1.89 (6H, m).

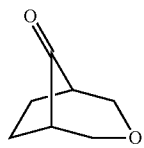

Cap-189, Step g

To the solution of Cap-189, Step f (890 mg, 5.23 mmol) in 15 mL of THF was added HCl (15 mL, 45.0 mmol) (3 M aqueous). The resulting mixture was stirred at room temperature overnight. The mixture was then diluted with ether and the two layers were separated. The aqueous phase was extracted with ether (2×) and the combined organic layers were dried with MgSO$_4$ and concentrated to afford Cap-189, Step g (0.95 g, containing some residual solvents). The product was used in the next step without purification. $^1$H NMR (500 MHz, CDCl$_3$) δ ppm 3.95-4.00 (2H, m), 3.85 (2H, d, J=10.68 Hz), 2.21-2.28 (2H, m), 1.99-2.04 (2H, m), 1.90-1.96 (2H, m).

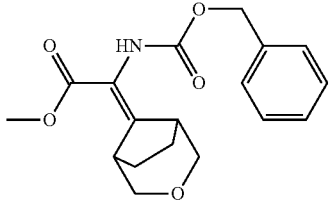

Cap-189, Step h
(Enantiomer-1 and Enantiomer-2)

To a solution of (+/−)-benzyloxycarbonyl-α-phosphonoglycine trimethyl ester (1733 mg, 5.23 mmol) in 6 mL of THF at −20° C. was added 1,1,3,3-tetramethylguanidine (0.723 mL, 5.75 mmol). The resultant light yellow mixture was stirred at −20° C. for 1 hour, and Cap-189, Step g (660 mg, 5.23 mmol) in 3 mL of THF was added and mixture was then stirred at room temperature for 3 days. The reaction mixture was then diluted with EtOAc, washed with a 0.1 N HCl aq. solution. The aqueous layer was extracted with EtOAc (2×) and the combined organic layers were dried with MgSO$_4$ and concentrated. The crude product was purified by flash chromatography (silica gel, 0-4% EtOAc/CH$_2$Cl$_2$) to afford 960 mg of the racemic mixture. The mixture was separated by chiral HPLC (CHIRALPAK® AD column, 21×250 mm, 10 um) eluting with 90% 0.1% diethylamine/Heptane-10% EtOH at 15 mL/min to afford Cap-189, Step h (Enantiomer-1; 300 mg) and Cap-189, Step h (Enantiomer-2; 310 mg) as white solids. Cap-189, Step h (Enantiomer-1): LC-MS: Anal. Calcd. for [M+H]$^+$ C$_{18}$H$_{22}$NO$_5$ 332.15. found 332.2. $^1$H NMR (500 MHz, CDCl$_3$) δ ppm 7.29-7.41 (5H, m), 6.00 (1H, br. s.), 5.13 (2H, s), 3.63-3.87 (8H, m), 2.84 (1H, br. s.), 1.84-2.02 (2H, m), 1.63-1.84 (2H, m). Cap-189, Step h (Enantiomer-2): LC-MS: Anal. Calcd. for [M+H]$^+$ C$_{18}$H$_{22}$NO$_5$ 332.15. found 332.2.

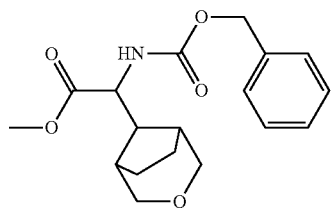

Cap-189, Step i

N$_2$ was bubbled through a solution of Cap-189, Step h (Enantiomer-2; 290 mg, 0.875 mmol) in 10 mL of MeOH in a 500 mL hydrogenation bottle for 30 mins. To the solution was added (S,S)-Me-BPE-Rh (9.74 mg, 0.018 mmol), and the mixture was then hydrogenated at 60 psi for 6 days. The mixture was concentrated, and chiral analytical HPLC (CHIRALPAK® OJ column) indicated that there were a small amount of remaining starting material and one major product. The residue was then separated by chiral HPLC (CHIRALPAK® OJ column, 21×250 mm, 10 um) eluting with 70% 0.1% diethylamine/Heptane-30% EtOH at 15 mL/min to afford Cap-189, Step i, (150 mg) as clear oil. LC-MS: Anal. Calcd. for [M+H]$^+$ C$_{18}$H$_{24}$NO$_5$ 334.17. found 334.39. $^1$H NMR (500 MHz, CDCl$_3$) δ ppm 7.28-7.41 (5H, m), 5.12-5.18 (1H, m), 5.09 (2H, s), 4.05 (1H, t, J=10.07 Hz), 3.75 (3H, s), 3.60-3.72 (2H, m), 3.41-3.50 (2H, m), 2.10 (1H, br. s.), 1.72-1.99 (6H, m).

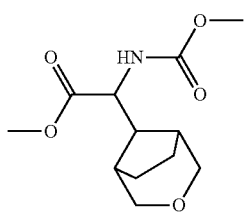

Cap-189, Step j

To a solution of Cap-189, Step i (130 mg, 0.430 mmol) in 10 mL of MeOH in a hydrogenation bottle were added dimethyl dicarbonate (0.072 mL, 0.675 mmol) and 10% Pd/C (23.94 mg, 0.022 mmol) under a cover of nitrogen cover. The mixture was then hydrogenated on Parr-shaker at 45 psi overnight. The mixture was filtered and the filtrate was concentrated to afford Cap-189, Step j (110 mg) as a clear oil. LC-MS: Anal. Calcd. for [M+H]$^+$ C$_{12}$H$_{20}$NO$_5$ 258.13. found 258.19. $^1$H NMR (500 MHz, CDCl$_3$) δ ppm 5.08 (1H, d, J=9.16 Hz), 4.03 (1H, t, J=10.07 Hz), 3.75 (3H, s), 3.60-3.72 (5H, m), 3.46 (2H, t, J=10.38 Hz), 2.11 (1H, br. s.), 1.72-1.99 (6H, m).

Cap-189

To a mixture of Cap-189, Step j (110 mg, 0.428 mmol) in 2 mL of THF and 1 mL of water was added LiOH (0.641 mL, 1.283 mmol) (2 N aq.). The resulting mixture was stirred at room temperature overnight. The mixture was neutralized with a 1 N HCl aq. solution and extracted with EtOAc (3×). The combined organic layers were dried with MgSO$_4$ and concentrated to afford Cap-189 (100 mg) as a white solid. LC-MS: Anal. Calcd. for [M+Na]$^+$ C$_{11}$H$_{17}$NNaO$_5$ 266.10. found 266.21. $^1$H NMR (500 MHz, CDCl$_3$) δ ppm 5.10 (1H, d, J=9.16 Hz), 4.02 (1H, t, J=10.07 Hz), 3.62-3.78 (5H, m), 3.49 (2H, d, J=10.68 Hz), 2.07-2.22 (2H, m), 1.72-1.98 (6H, m).

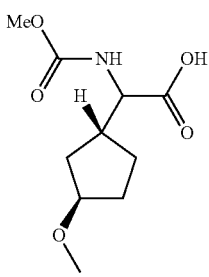

Cap-190
(diastereomeric mixture)

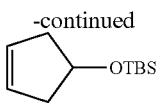

Cap-190, Step a

To a mixture of cyclopent-3-enol (2.93 g, 34.8 mmol) and imidazole (5.22 g, 77 mmol) in 30 mL of DMF at 0° C. was added t-butyldimethylchlorosilane (6.30 g, 41.8 mmol). The resulting colorless mixture was stirred at room temperature overnight. Hexanes and water were then added to the mixture and the two layers were separated. The aqueous layer was extracted with EtOAc (2×) and the combined organic layers were washed with brine, dried with MgSO$_4$ and concentrated. The crude product was purified by flash chromatography (silica gel, 2% EtOAc/Hex) to afford Cap-190, Step a (6.3 g) as a clear oil. $^1$H NMR (500 MHz, CDCl$_3$) δ ppm 5.65 (2H, s), 4.49-4.56 (1H, m), 2.56 (2 H, dd, J=15.26, 7.02 Hz), 2.27 (2H, dd, J=15.26, 3.36 Hz), 0.88 (9H, s), 0.06 (6H, s).

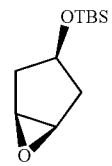

Cap-190, Step b

To a solution of Cap-190, Step a (2.3 g, 11.59 mmol) in 40 mL of CH$_2$Cl$_2$ at 0° C. was added m-CPBA (5.60 g, 16.23 mmol) in 5 portions. The reaction mixture was stirred at room temperature overnight. Hexanes and water were then added to the mixture and the two layers were separated. The organic layer was washed with 50 mL aq. 10% NaHSO$_3$ and brine, dried with MgSO$_4$ and concentrated. The crude product was purified by flash chromatography (silica gel, 3%-6% EtOAc/Hex) to afford Cap-190, Step b (1.42 g) and its trans diastereomer (0.53 g) as clear oils. Cap-190, Step b (cis): $^1$H NMR (400 MHz, CDCl$_3$) δ ppm 4.39-4.47 (1H, m), 3.47 (2H, s), 2.01-2.10 (2H, m), 1.93-2.00 (2H, m), 0.88 (9H, s), 0.04 (6H, s). Cap-190, Step b (trans): $^1$H NMR (400 MHz, CDCl$_3$) δ ppm 4.04-4.14 (1H, m), 3.47 (2H, s), 2.41 (2H, dd, J=14.05, 7.28 Hz), 1.61 (2H, dd, J=14.18, 6.90 Hz), 0.87 (9H, s), 0.03 (6H, s).

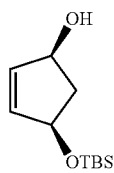

Cap-190, Step c

To a solution of (S)-1,2'-methylenedipyrrolidine (0.831 g, 5.39 mmol) in 15 mL of benzene at 0° C. was added dropwise n-butyllithium (4.90 mL, 4.90 mmol) (1 M in hexane). The solution turned bright yellow. The mixture was stirred at 0° C. for 30 min. Cap-190, Step b (cis-isomer; 0.7 g, 3.27 mmol) in 10 mL of benzene was then added and the resulting mixture was stirred at 0° C. for 3 hours. EtOAc and sat. NH$_4$Cl aq. solution were added into the mixture, and the two layers were separated. The organic layer was washed with water and brine, dried with MgSO$_4$ and concentrated. The crude product was purified by flash chromatography (silica gel, 15%

EtOAc/Hex) to afford Cap-190, Step c (400 mg) as a light yellow oil. $^1$H NMR (500 MHz, CDCl$_3$) δ ppm 5.84-5.98 (2H, m), 4.53-4.69 (2H, m), 2.63-2.73 (1H, m), 1.51 (1H, dt, J=13.73, 4.43 Hz), 0.89 (9H, s), 0.08 (6H, s).

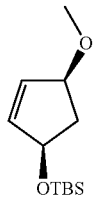

Cap-190, Step d

To a solution of Cap-190, Step c (400 mg, 1.866 mmol), MeI (1.866 mL, 3.73 mmol) (2 M in t-butyl methyl ether) in 5 mL of THF at 0° C. was added NaH (112 mg, 2.80 mmol) (60% in mineral oil). The resulting mixture was allowed to warm up to room temperature and stirred at room temperature overnight. The reaction was then quenched with water and extracted with EtOAc (3×). The combined organic layers were washed with brine, dried with MgSO$_4$ and concentrated. The crude product was purified by flash chromatography (silica gel, 5% EtOAc/Hex) to afford Cap-190, Step d (370 mg) as light yellow oil. $^1$H NMR (500 MHz, CDCl$_3$) δ ppm 5.92-5.96 (1H, m), 5.87-5.91 (1H, m), 4.64-4.69 (1H, m), 4.23-4.28 (1H, m), 3.32 (3H, s), 2.62-2.69 (1H, m), 1.54 (1H, dt, J=13.12, 5.49 Hz), 0.89 (9H, s), 0.07 (5H, d, J=1.83 Hz).

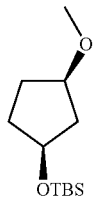

Cap-190, Step e

To a solution of Cap-190, Step d (400 mg, 1.751 mmol) in 10 mL of EtOAc in a hydrogenation bottle was added platinum(IV) oxide (50 mg, 0.220 mmol). The resulting mixture was hydrogenated at 50 psi on Parr shaker for 2 hours. The mixture was then filtered through CELITE®, and the filtrate was concentrated to afford Cap-190, Step e (400 mg) as a clear oil. LC-MS: Anal. Calcd. for [M+H]$^+$ C$_{12}$H$_{27}$O$_2$Si 231.18. found 231.3. $^1$H NMR (500 MHz, CDCl$_3$) δ ppm 4.10-4.17 (1H, m), 3.65-3.74 (1H, m), 3.27 (3H, s), 1.43-1.80 (6H, m), 0.90 (9H, s), 0.09 (6H, s).

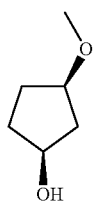

Cap-190, Step f

To a solution of Cap-190, Step e (400 mg, 1.736 mmol) in 5 mL of THF was added TBAF (3.65 mL, 3.65 mmol) (1 N in THF). The color of the mixture turned brown after several min., and it was stirred at room temperature overnight. The volatile component was removed under vacuum, and the residue was purified by flash chromatography (silica gel, 0-25% EtOAc/Hex) to afford Cap-190, Step f (105 mg) as light yellow oil. $^1$H NMR (500 MHz, CDCl$_3$) δ ppm 4.25 (1H, br. s.), 3.84-3.92 (1H, m), 3.29 (3H, s), 1.67-2.02 (6H, m).

Cap-190

Cap-190 was then synthesized from Cap-190, Step f according to the procedure described for Cap-182. LC-MS: Anal. Calcd. for [M+Na]$^+$ C$_{10}$H$_{17}$NNaO$_5$ 254.10. found 254.3. $^1$H NMR (500 MHz, CDCl$_3$) δ ppm 5.25 (1H, d, J=8.55 Hz), 4.27-4.41 (1H, m), 3.81-3.90 (1H, m), 3.69 (3H, s), 3.26 (3H, s), 2.46-2.58 (1H, m), 1.76-1.99 (3H, m), 1.64-1.73 (1H, m), 1.40-1.58 (1H, m), 1.22-1.38 (1H, m).

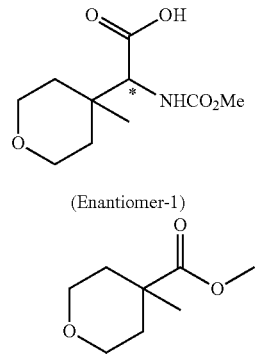

Cap-191

(Enantiomer-1)

Cap-191, Step a

To a solution of diisopropylamine (3 ml, 21.05 mmol) in THF (3 ml) at −78° C. under nitrogen was added n-butyl lithium (2.5 M in hexanes; 8.5 ml, 21.25 mmol). The reaction was stirred at −78° C. for 10 min then brought up to 0° C. for 25 min. The reaction was cooled down again to −78° C., methyl tetrahydro-2H-pyran-4-carboxylate (3 g, 20.81 mmol) in THF (3 ml) was added. The reaction was stirred at −78° C. for 15 min then brought up to 0° C. for 30 min. The reaction was cooled down to −78° C., methyl iodide (1.301 ml, 20.81 mmol) was added. After the addition, the cold bath was removed and the reaction was allowed to slowly warm up to ~25° C. and stirred for 22 h. Ethyl acetate and aqueous HCl (0.1N) were added, and the organic layer was separated and washed with brine and dried (MgSO$_4$), filtered, and concentrated in vacuo. The residue was loaded on a Thomson's silica gel cartridge eluting with 10% ethyl acetate/hexanes to afford a light yellow oil (2.83 g). $^1$H NMR (400 MHz, DMSO-d$_6$) δ ppm 3.73-3.66 (m, 2H), 3.66 (s, 3H), 3.40-3.30 (m, 2H), 1.95-1.93 (dm, 1H), 1.92-1.90 (dm, 1H), 1.43 (ddd, J=13.74, 9.72, 3.89, 2H), 1.18 (s, 3H).

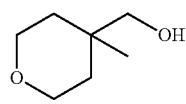

Cap-191, Step b

To a solution of Cap-191, Step a (3 g, 18.96 mmol) in toluene (190 ml) at −78° C. under nitrogen was added diisobutylaluminum hydride (1.5M in toluene; 26.5 ml, 39.8 mmol) dropwise. The reaction was continued to stir at −78° C. for 1.5 h., and the bath was removed and was stirred for 18 h. The reaction was quenched with MeOH (20 mL). HCl (1M, 150 mL) was added and the mixture was extracted with EtOAc (4×40 mL). The combined organic phases were washed with brine, dried (MgSO$_4$), filtered, and concentrated in vacuo. The residue was purified with flash chromatography (silica gel; 40% ethyl acetate/hexanes) to afford a colorless oil (1.36 g). $^1$H NMR (400 MHz, CDCl$_3$) δ ppm 3.77 (dt, J=11.73, 4.55, 2H), 3.69-3.60 (m, 2H), 3.42 (s, 2H), 1.71-1.40 (bs, 1H) 1.59 (ddd, J=13.74, 9.72, 4.39, 2H), 1.35-1.31 (m, 1H), 1.31-1.27 (m, 1H), 1.06 (s, 3H).

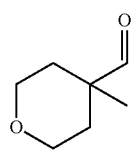

Cap-191, Step c

To a solution of DMSO (5.9 ml, 83 mmol) in CH$_2$Cl$_2$ (85 ml) at −78° C. under nitrogen was added oxalyl chloride (3.8 ml, 43.4 mmol) and stirred for 40 min. A solution of Cap-191, Step b (4.25 g, 32.6 mmol) in CH$_2$Cl$_2$ (42.5 ml) was then added. The reaction was continued to be stirred at −78° C. under nitrogen for 2 h. The reaction was quenched with cold 20% K$_2$HPO$_4$ (aq) (10 mL) and water. The mixture was stirred at ~25° C. for 15 min, diluted with diethyl ether (50 mL) and the layers were separated. The aqueous layer was extracted with diethyl ether (2×50 mL). The combined organic layers were washed with brine, dried (MgSO$_4$), filtered, and concentrated in vacuo. The residue was taken up in CH$_2$Cl$_2$ (4 mL) and purified with flash chromatography (silica gel, eluting with CH$_2$Cl$_2$) to afford a colorless oil (2.1 g). $^1$H NMR (400 MHz, CDCl$_3$) δ ppm 9.49 (s, 1H), 3.80 (dt, J=11.98, 4.67, 2H), 3.53 (ddd, J=12.05, 9.41, 2.89, 2H), 1.98 (ddd, J=4.71, 3.20, 1.38, 1H), 1.94 (ddd, J=4.71, 3.20, 1.38, 1H), 1.53 (ddd, J=13.87, 9.60, 4.14, 2H), 1.12 (s, 3H).

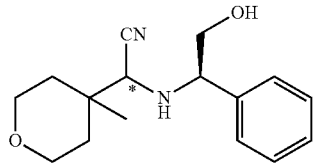

Cap-191, Step d

To a solution of Cap-191c (2.5 g, 19.51 mmol) in CHCl$_3$ (20 ml) under nitrogen at ~25° C. was added (R)-2-amino-2-phenylethanol (2.94 g, 21.46 mmol) and stirred for 5 h. The reaction was cooled to 0° C., trimethylsilyl cyanide (3.8 ml, 30.4 mmol) was added dropwise. The cold bath was removed and the reaction was allowed to stir at ~25° C. under nitrogen for 15.5 h. The reaction was treated with 3N HCl (20 mL) and water (20 mL), and the product was extracted with CHCl$_3$ (3×50 mL). The combined organic layers were dried (NaSO$_4$), filtered, and concentrated in vacuo. The residue was purified with flash chromatography (silica gel; 40% ethyl acetate/hexanes) to afford two diastereomers: Cap-191, Step d1 (diastereomer 1) as a colorless oil which solidified into a white solid upon standing (3 g). $^1$H NMR (400 MHz, DMSO-d$_6$) δ ppm 7.42-7.26 (m, 5H), 5.21 (t, J=5.77, 1H), 3.87 (dd, J=8.53, 4.52, 1H), 3.61-3.53 (m, 1H), 3.53-3.37 (m, 5H), 3.10 (d, J=13.05, 1H), 2.65 (d, J=13.05, 1H), 1.64-1.55 (m, 1H), 1.55-1.46 (m, 1H), 1.46-1.39 (m, 1H), 1.31-1.23 (m, 1H), 1.11 (s, 3H). LC-MS: Anal. Calcd. for [M+H]$^+$ C$_{16}$H$_{23}$N$_2$O$_2$: 275.18. found 275.20. Cap-191, Step d2 (diastereomer 2) as a light yellow oil (0.5 g). $^1$H NMR (400 MHz, DMSO-d$_6$) δ ppm 7.44-7.21 (m, 5H), 4.82 (t, J=5.40, 1H), 3.82-3.73 (m, 1H), 3.73-3.61 (m, 3H), 3.61-3.37 (m, 5H), 2.71 (dd, J=9.29, 4.77, 1H), 1.72-1.55 (m, 2H), 1.48-1.37 (m, 1H), 1.35-1.25 (m, 1H), 1.10 (s, 3H). LC-MS: Anal. Calcd. for [M+H]$^+$ C$_{16}$H$_{23}$N$_2$O$_2$: 275.18. found 275.20.

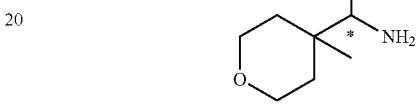

Cap-191, Step e

To a solution of Cap-191, Step d2 (diastereomer 2) (0.4472 g, 1.630 mmol) in CH$_2$Cl$_2$ (11 ml) and MeOH (5.50 ml) at 0° C. under nitrogen was added lead tetraacetate (1.445 g, 3.26 mmol). The reaction was stirred for 1.5 h, the cold bath was removed and stirring was continued for 20 h. The reaction was treated with a phosphate buffer (pH=7; 6 mL) and stirred for 45 min. The reaction was filtered over CELITE®, washed with CH$_2$Cl$_2$ and the layers were separated. The aqueous layer was extracted with CH$_2$Cl$_2$ (3×25 mL), and the combined organic layers was washed with brine, dried (MgSO$_4$), filtered and concentrated in vacuo. The residue was purified with flash chromatography (silica gel; 15% ethyl acetate/hexanes) to afford the imine intermediate as a colorless oil (181.2 mg). $^1$H NMR (400 MHz, DMSO-d$_6$) δ ppm 8.55 (d, J=1.00, 1H), 7.89-7.81 (m, 2H), 7.61-7.46 (m, 3H), 4.80 (d, J=1.00, 1H), 3.74 (tt, J=11.80, 4.02, 2H), 3.62-3.46 (m, 2H), 1.79-1.62 (m, 2H), 1.46-1.30 (m, 2H), 1.15 (s, 3H).

The imine intermediate was taken up in 6N HCl (10 mL) and heated at 90° C. for 10 days. The reaction was removed from the heat, allowed to cool to room temperature and extracted with ethyl acetate (3×25 mL). The aqueous layer was concentrated in vacuo to afford an off-white solid. The solid was taken up in MeOH and loaded on a pre-conditioned MCX (6 g) cartridge, washed with MeOH followed by elution with 2N NH$_3$/MeOH solution and concentrated in vacuo to afford an off-white solid (79.8 mg). $^1$H NMR (400 MHz, DMSO-d$_6$) δ ppm 14.33-13.51 (bs, 1H), 8.30 (bs, 3H), 3.82-3.75 (m, 1H), 3.70 (dt, J=11.80, 4.02, 2H), 3.58-3.43 (m, 2H), 1.76-1.60 (m, 2H), 1.47-1.36 (m, 1H), 1.36-1.27 (m, 1H), 1.08 (s, 3H). LC-MS: Anal. Calcd. for [M+H]$^+$ C$_8$H$_{16}$NO$_3$: 174.11. found 174.19.

Cap-191

Enantiomer-1

To a solution of Cap-191, Step e (0.0669 g, 0.386 mmol) and sodium carbonate (0.020 g, 0.193 mmol) in sodium hydroxide (1M aq.; 0.4 ml, 0.40 mmol) at 0° C. was added methyl chloroformate (0.035 ml, 0.453 mmol) dropwise. The reaction was removed from the cold bath and allowed to stir at ~25° C. for 3 h. The reaction was washed with diethyl ether (3×20 mL). The aqueous layer was acidified with 12 N HCl (pH ~1-2), and extracted with ethyl acetate (2×20 mL). The combined organic layers were dried (MgSO₄), filtered, and concentrated in vacuo to afford Cap-191 as a colorless film (66.8 mg). ¹H NMR (400 MHz, DMSO-d₆) δ ppm 13.10-12.37 (bs, 1H), 7.37 (d, J=9.04, 1H), 4.02 (d, J=9.29, 1H), 3.72-3.57 (m, 2H), 3.56 (s, 3H), 3.54-3.44 (m, 2H), 1.65 (ddd, J=13.61, 9.72, 4.27, 1H), 1.53 (ddd, J=13.68, 9.66, 4.27, 1H), 1.41-1.31 (m, 1H), 1.31-1.22 (m, 1H), 1.00 (s, 3H). LC-MS: Anal. Calcd. for [M+Na]⁺ $C_{10}H_{17}NO_5Na$: 254.10. found 254.11.

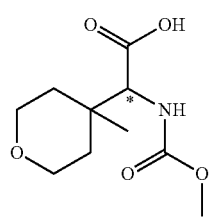

Cap-192 (Enantiomer-2)

Cap-192 (Enantiomer-2) was prepared from Cap-191, Step d1 according to the procedure described for the preparation of its enantiomer Cap-191.

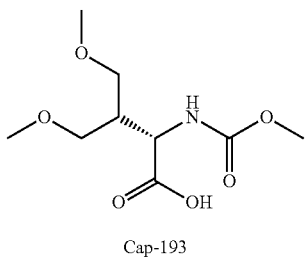

Cap-193

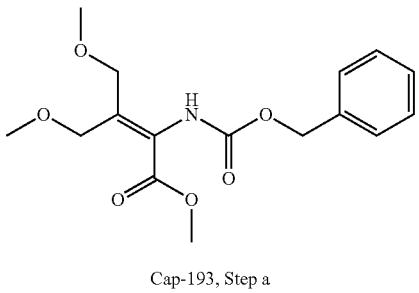 [SMILES: COCC(COC)[C@H](NC(=O)OCc1ccccc1)C(=O)OC]

Cap-193, Step a

To a solution of methyl 2-(benzyloxycarbonylamino)-2-(dimethoxyphosphoryl)acetate (1.45 g, 4.2 mmol) in DCM was added DBU (0.70 ml, 4.7 mmol). The reaction mixture was stirred for 10 min, followed by addition of a solution of 1,3-dimethoxypropan-2-one (0.5 g, 4.2 mmol) in DCM. The reaction mixture was stirred at room temperature for 18 hrs. The reaction mixture was charged to an 80 g silica gel cartridge which was eluted with an 18 min gradient of 0-70% EtOAc in hexane to afford Cap-193, Step a (0.8 g) as a thick oil. ¹H NMR (400 MHz, MeOD) ppm 7.23-7.43 (5H, m), 4.99-5.18 (2H, m), 4.16 (2H, s), 4.06 (2H, s), 3.66-3.78 (3H, s), 3.26 (3H, s), 3.23 (3H, s). LC-MS: Anal. Calcd. For [M+Na]⁺ $C_{16}H_{21}NNaO_6$: 346.14. found: 346.12.

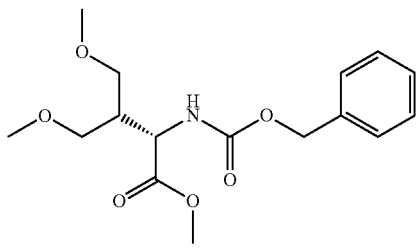

Cap-193, Step b

A reaction mixture of ester Cap-193, Step a (0.5 g) and (+)-1,2-bis((2S,5S)-2,5-diethylphospholano)benzene(cyclooctadiene)rhodium (I) tetrafluoroborate (0.1 g) in MeOH was stirred under 55 psi of H₂ for 18 hrs. The reaction mixture was concentrated to dryness. The residue was charged to a 25 g silica gel cartridge and eluted with an 18 min gradient of 0-80% EtOAc in hexane to afford Cap-193, Step b (0.49 g) as a clear oil. LC-MS: Anal. Calcd. For [M+Na]⁺ $C_{16}H_{23}NNaO_6$: 348.15. found: 348.19.

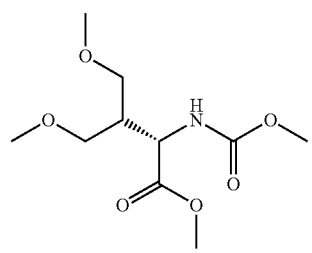

Cap-193, Step c

A reaction mixture of Cap-193, Step b (0.16 g), dimethyl dicarbonate (0.13 g) and 10% Pd/C (0.026 g) in EtOAc was stirred under H₂ at room temperature for 2 hrs. The reaction mixture was filtered and concentrated to yield the methyl carbamate Cap-193, Step c. LC-MS: Anal. Calcd. For [M+Na]⁺ $C_{10}H_{19}NNaO_6$: 272.12. found: 272.07.

Cap-193

To a solution of ester Cap-193, Step c in THF (1 mL) and MeOH (0.25 mL) was added 1 N NaOH (1 mL). The reaction mixture was stirred at room temperature for 2 hrs. The reaction mixture was concentrated and diluted with EtOAc and 1 N HCl. The aqueous phase was extracted with EtOAc, and the combined organic phase was washed with sat. NaCl, dried over anhydrous Na₂SO₄, filtered and concentrated to yield Cap-193 (0.082 g). ¹H NMR (400 MHz, CDCl₃) 5.99 (1H, d, J=8.56 Hz), 4.57 (1H, dd, J=8.56, 3.27 Hz), 3.67 (3H, s), 3.49 (2H, d, J=4.28 Hz), 3.45-3.44 (2H, m), 3.26-3.35 (6H, m). LC-MS: Anal. Calcd. For [M+Na]⁺ $C_9H_{12}NNaO_6$: 258.11. found: 258.13.

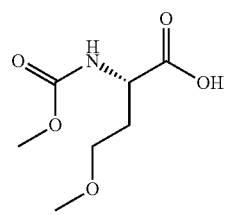

Cap-194

Piperidine (1.0 mL, 10 mmol) was added to a solution of (S)-2-(((9H-fluoren-9-yl)methoxy)carbonylamino)-4-methoxybutanoic acid (0.355 g, 1 mmol) in DMF (3 mL), and the mixture was stirred at rt for 3 h. The volatiles were removed and the residue was partitioned between sat. $NaHCO_3$ (aq.) (5 mL) and EtOAc (5 mL). The aqueous layer was further washed with EtOAc and $Et_2O$. To the aqueous solution was added $Na_2CO_3$ (212 mg, 2.0 mmol) followed by methyl chloroformate (0.16 mL, 2.0 mmol) and the reaction mixture was stirred at rt for 16 h. The reaction mixture was acidified with 1 N HCl (aq.) until pH <7 and then extracted with EtOAc (2×10 mL). The combined organic layers were dried ($Na_2SO_4$), filtered and concentrated. The residue was purified by flash silica chromatography (EtOAc/hexanes, gradient from 20% to 70%) to yield (S)-4-methoxy-2-(methoxycarbonylamino)butanoic acid (Cap-194) (91.5 mg) as viscous colorless oil. LC-MS retention time=0.61 min; m/z 214 [M+Na]$^+$. (Column: PHENOMENEX® Luna 3.0×50 mm S10. Solvent A=90% Water: 10% Methanol: 0.1% TFA. Solvent B=10% Water: 90% Methanol: 0.1% TFA. Flow Rate=4 mL/min. Start % B=0. Final % B=100. Gradient Time=3 min. Wavelength=220). $^1$H NMR (400 MHz, chloroform-d) δ ppm 7.41 (br. s., 1H), 5.74-6.02 (m, 1H), 4.32-4.56 (m, 1H), 3.70 (s, 3H), 3.54 (t, J=5.0 Hz, 2H), 3.34 (s, 3H), 1.99-2.23 (m, 2H).

EXAMPLE SECTION

Low resolution mass analysis was conducted on a Shimadzu LC system coupled with Waters MICROMASS® ZQ MS system (Cond. 1) or Waters Acquity HPLC with Waters PDA UV-Vis detection and Waters ZQ MS (Cond. 2). Retention time ($R_t$) were derived by employing the following conditions, and it should be noted that retention times may vary slightly between instruments:

Condition 1a
Column=PHENOMENEX® Luna 4.6×30 mm S10
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition 1b
Column=Waters Acquity BEH C18; 1.7 μm; 150×2.1 mm ID; (at 35 C)
Hold 10% B=0-1 min
10-50% B=0-25 min
50-98% B=25-33 min
Hold 98% B=32-35 min
98-10% B=35.0-35.5 min
Hold 10% B=35.5-40 min
Flow rate=0.35 ml/min
Wavelength=254 nm
Solvent A=0.05% TFA in water
Solvent B=0.05% TFA in $CH_3CN$
Condition 1c
Column=Waters Acquity BEH C18; 1.7 μm; 150×2.1 mm ID; (at 35° C.)
Hold 10% B=0-1 min
10-60% B=1-4 min
60-98% B=4-21 min
Hold 98% B=21-21.5 min
98-10% B=21.5-22 min
Hold 10% B=22-25 min
Flow rate=0.35 ml/min
Wavelength=315 nm
Solvent A=0.05% TFA in water
Solvent B=0.05% TFA in $CH_3CN$
Condition 2a
Column=Waters SunFire C18, 4.6×150 mm, 3.5 μm
Start % B=10
Final % B=50
Gradient time=20 min
Stop time=varies 25 to 40 min
Flow Rate=1 mL/min
Wavelength=220 & 254 nm
Solvent A=0.1% TFA in 5% $CH_3CN/95\%$ $H_2O$
Solvent B=0.1% TFA in 95% $CH_3CN/5\%$ $H_2O$
Condition 2b
Column=Waters Xbridge phenyl, 4.6×150 mm, 3 μm
Start % B=10
Final % B=50
Gradient time=20 min
Stop time=varies 25 to 40 min
Flow Rate=1 mL/min
Wavelength=220 & 254 nm
Solvent A=0.1% TFA in 5% $CH_3CN/95\%$ $H_2O$
Solvent B=0.1% TFA in 95% $CH_3CN/5\%$ $H_2O$
Condition 3
Column=PHENOMENEX® Luna C18 (2), 3u, 150×4.6 mm
Start % B=0
Final % B=100
Gradient time: =10 min
Flow rate=1 mL/min
Wavelength=220 and 256 nm
Solvent A=$H_2O/CH_3CN$ (95:5)+0.05% TFA
Solvent B=$H_2O/CH_3CN$ (5:95)+0.05% TFA
Condition OL1
Column=PHENOMENEX® Luna 3.0×50 mm S10
Start % B=0
Final % B=100
Gradient time=4 min
Stop time=5 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition OL2
Column=PHENOMENEX® Luna 50×2 mm 3u
Start % B=0
Final % B=100
Gradient time=4 min
Stop time=5 min
Flow Rate=0.8 mL/min
Oven Temp=40° C.
Wavelength=220 nm
Solvent A=0.1% TFA in 10% Acetonitrile/90% $H_2O$
Solvent B=0.1% TFA in 90% Acetonitrile/10% $H_2O$ Condition OL3
Column=Waters Acquity BEH C18; 1.7 μm; 150×2.1 mm ID; (at 35° C.)
Hold 10% B=0-1 min
10-60% B=1-4 min
60-98% B=4-21 min
Hold 98% B=21-21.5 min
98-10% B=21.5-22 min
Hold 10% B=22-25 min
Flow rate=0.35 ml/min
Wavelength=315 nm
Solvent A=0.05% TFA in water
Solvent B=0.05% TFA in $CH_3CN$
Condition OL4a
Column=Waters SunFire C18, 4.6×150 mm, 3.5 μm
Start % B=10
Final % B=100
Gradient time=15 min
Stop time=18 min
Flow Rate=1 mL/min
Wavelength=220 & 254 nm
Solvent A=0.1% TFA in 5% $CH_3CN$/95% $H_2O$
Solvent B=0.1% TFA in 95% $CH_3CN$/5% $H_2O$
Condition OL4b
Column=Waters Xbridge phenyl, 4.6×150 mm, 3 μm
Start % B=10
Final % B=50
Gradient time=15 min
Stop time=18 min
Flow Rate=1 mL/min
Wavelength=220 & 254 nm
Solvent A=0.1% TFA in 5% $CH_3CN$/95% $H_2O$
Solvent B=0.1% TFA in 95% $CH_3CN$/5% $H_2O$
Condition OL4c
Column=Waters Acquity BEH C18; 1.7 μm; 50×2.1 mm ID; (at 35° C.)
Hold 2% B=0-1 min
2-98% B=1-1.5 min
98% B=1.5-2.2 min
Flow rate=0.8 ml/min
Wavelength=2 nm
Solvent A=0.05% TFA in water
Solvent B=0.05% TFA in $CH_3CN$
Condition OL5a
Column=PHENOMENEX® Luna 3.0×50 mm S10
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition OL5b
Column=PHENOMENEX® Luna 3.0×50 mm S10
Start % B=0
Final % B=100
Gradient time=3 min
Stop time=4 min
Flow Rate=4 mL/min
Wavelength=220 nm
Solvent A=10 mM $NH_4OAc$ in 5% methanol/95% $H_2O$
Solvent B=10 mM $NH_4OAc$ in 95% methanol/5% $H_2O$
Condition-D4
Column=PHENOMENEX® Luna, 3.0×50 mm S10
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition J4
Column=PHENOMENEX® Luna 4.6×50 mm S10
Start % B=0
Final % B=100
Gradient time=4 min
Stop time=5 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition PY1
Column=PHENOMENEX®, 2.0×50 mm, 3 nm
Start % B=0
Final % B=100
Gradient time=4 min
Stop time=5 min
Flow Rate=0.8 mL/min
Wavelength=220 nm
Solvent A=0.1% TFA in 10% methanol/90% water
Solvent B=0.1% TFA in 90% methanol/10% water
Oven temp.=40° C.

Examples 1 and 2

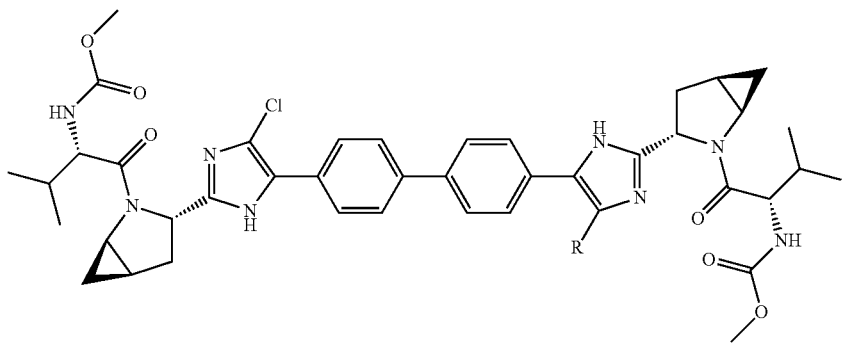

Example-1: R = H
Example-2: R = Cl

Example 1

Step a

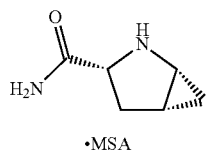

·MSA

Amide 1a (CH₃SO₃H) was prepared according to the procedure described for the synthesis of its enantiomer in patent WO 2004/052850.

Example 1

Step b

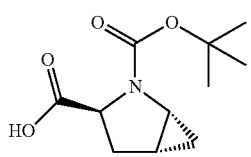 [SMILES: CC(C)(C)OC(=O)N1[C@@H]2C[C@@H]2C[C@H]1C(=O)O]

A 1 L round bottom flask equipped with a nitrogen inlet, overhead agitator, thermocouple and heating mantle was charged with 50 g (225 mmol) amide 1a (.CH₃SO₃H) and 250 mL isopropanol. The resulting slurry was then charged with 252 mL of 23 wt % NaOEt in EtOH (2.68 M, 675 mmol, 3.0 equiv) and stirred at 50° C. for ca. 1 h. The mixture was charged with 12.2 mL (675 mmol, 3 equiv) of water and heated to 60° C. The resulting slurry was allowed to stir at 60° C. for ca. 18 h. The slurry was cooled to rt and charged with 250 mL water and 98.2 g (450 mmol, 2.0 equiv) di-t-butyldicarbonate. Ethanol and isopropanol were removed via vacuum distillation and the aqueous mixture cooled to 0° C. The mixture was neutralized with 76 mL (456 mmol) 6M aqueous HCl while maintaining an internal temperature <5° C. The product was extracted with 500 mL MTBE and the rich organic layer was washed with 100 mL water. The clear solution was concentrated down to 150 mL via vacuum distillation and the resulting slurry was charged with 600 mL heptane while maintaining an internal temperature >45° C. The slurry was cooled to rt over ca. 30 min and allowed to stir at rt for ca. 2 h. The product was filtered, washed with 250 mL 4:1 heptane:MTBE and dried under vacuum at 70° C. to give 40.5 g (178 mmol, 79% yield, 99.8 AP at 205 nm) of acid 1b: $^1$H NMR (400 MHz, DMSO-d$_6$) δ 12.48 (s, 1H), 4.02-3.80 (m, 1H), 3.45-3.15 (m, 1H), 2.40-2.19 (m, 1H), 2.19-2.0 (m, 1H), 1.70-1.50 (m, 1H), 1.50-1.20 (m, 9H), 0.83-0.60 (m, 1H), 0.33-0.55 (m, 1H); $^{13}$C NMR (100 MHz, DMSO-d$_6$) δ 173.7, 173.2, 155.0, 154.3, 79.4, 60.5, 60.2, 37.6, 32.6, 31.8, 28.4, 28.2, 15.6, 15.2, 14.4; HRMS calcd for C$_{11}$H$_{18}$NO$_4$ (M+H; ESI$^+$): 228.1236. Found: 228.1234.

Alternative Synthesis of Acid 1b

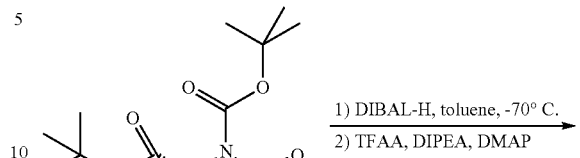

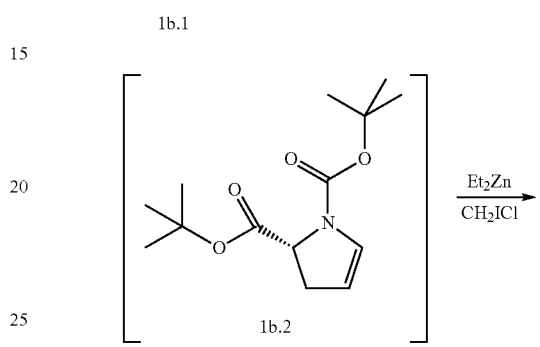

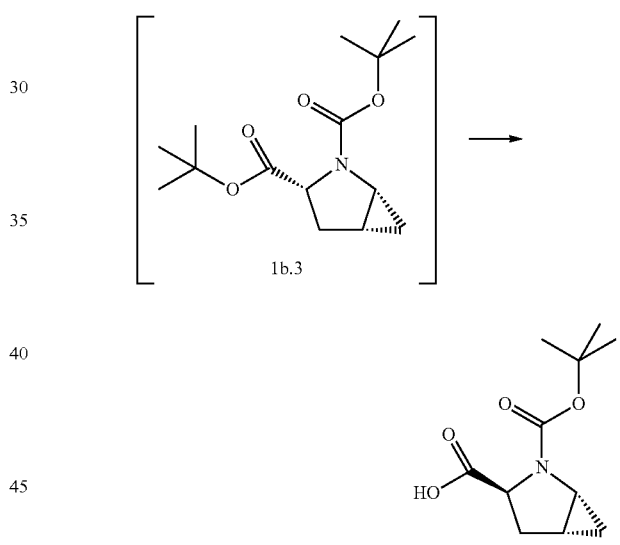

Acid 1b

In a 500-mL reactor ester 1b.1 (commercially available, 17.5 g, 1.00 equiv) was dissolved in THF (87.5 mL). The resulting solution was cooled to −75° C. and 1.5M DIBAL-H in toluene (61.3 mL, 1.5 equiv) was charged while maintaining the temperature below −70° C. The resulting solution was stirred at −70° C. for 1 hour. Trifluoroacetic acid (2.3 mL, 0.5 equiv) was charged over 10 minutes maintaining the internal temperature below −70° C. Triethylamine (51.3 mL, 6 equiv) was then charged over 15 minutes maintaining the internal temperature below −70° C. Trifluoroacetic anhydride (11.2 mL, 1.3 equiv) was charged over 10 minutes maintaining the internal temperature below −70° C. The reaction was then allowed to warm to room temperature over 90 minutes and quenched via inverse addition to a solution of 20 wt % aqueous citric acid monohydrate (96.6 g, 1.5 equiv) while maintaining a temperature below 15° C. The resulting mixture was stirred at room temperature for 2 hours then the lower aqueous layer was discarded. The product rich organic layer was washed twice with 70 mL saturated aqueous sodium bicarbonate. Solid sodium bicarbonate (1.7 g, 0.1 g/g Example 146) was charged and the solution was solvent exchanged into pure toluene under vacuum to provide 1b.2 as a solution in 2 L/kg toluene.

A solution of 1b.2 (16.5 g theoretical from Example 151) in 33 mL toluene was polish filtered into a 250 mL reactor. Trifluorotoluene (50 mL) and chloroiodomethane (43.2 g, 4.0 equiv) were then charged and the resulting solution cooled to −20° C. 1.1M Diethylzinc in toluene (111 mL, 2.0 equiv) was charged while maintaining the internal temperature <−8° C. The resulting solution was stirred at −15 to −20° C. for 14 hours. The reaction mixture was warmed to 0° C. then quenched via inverse addition to a solution of 20 wt % aqueous citric acid (135.7 g, 2.3 equiv). The reactor was rinsed with toluene (82 mL) and the rinse added to the quench solution. The resulting biphasic mixture was stirred for 20 minutes then the lower aqueous layer was split and discarded. The rich organic was washed twice with 60 mL 13 wt % aqueous NaCl followed by 60 mL saturated NaHCO₃. The resulting solution was solvent exchanged into pure IPA under vacuum to provide 1b.3 as a solution in 10 L/kg IPA.

A 250 mL reactor was charged with a solution of 1b.3 (147 mL, 14.7 g theoretical from ester 1b.1) in IPA. The solution was warmed to 35° C. and solid sodium hydroxide (6.2 g, 3.0 equiv) was added. The resulting mixture was stirred at 35° C. overnight. Water (44 mL) was added and the organic solvents removed under vacuum. MTBE (145 ml) was added and the pH adjusted to 3.0 with 6N aqueous HCl. The aqueous layer was split and discarded. The product rich organic was washed with 60 mL water then azeotropically dried under vacuum via constant volume addition of MTBE. The solution was concentrated to 55 mL and stirred at 50° C. for 30 minutes. The solution was cooled to room temperature over 1 hour during which time a slurry formed. Heptane (90 mL) was charged over 90 min and the resulting slurry aged for 1 h. The solids were collected on a medium glass frit and washed with 22.5 mL 3:1 heptane:MTBE followed by 22.5 mL heptane. The tan solid was dried in a 50° C. vacuum oven to provide 5.48 g (46%) acid 1b with 94.9 LCAP purity. The crude acid 1b was dissolved in 55 mL MTBE at 50° C. The resulting solution was concentrated to 20 mL and cooled to room temperature over 1 hour. Heptane (33 mL) was then added over 90 minutes. The resulting solids were collected on a medium glass frit, washed with heptane (15 mL), and dried in a 50° C. vacuum oven to provide 4.45 g of acid 1b as a tan powder (98.8 AP, 98.8% chiral purity, 37% from ester 1b.1).

Example 1

Step c

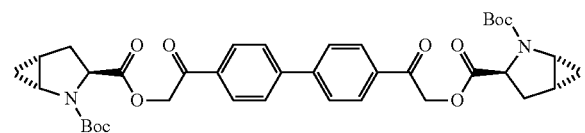

A 250 mL round bottom flask equipped with a nitrogen inlet, overhead agitator and thermocouple was charged with 20.0 g (88.0 mmol, 2.11 equiv) acid 1b, 16.5 g (41.7 mmol, 1 equiv) 1,1'-(biphenyl-4,4'-diyl)bis(2-bromoethanone), 110 mL acetonitrile and 55 mL tetrahydrofuran. Diisopropylethylamine (15.1 mL, 86.6 mmol, 2.08 equiv) was then charged while maintaining an internal temperature <25° C. The mixture was allowed to stir at 20-25° C. for ca. 5 h and charged with 83 mL ethyl acetate and 90 mL 13 wt % aqueous NaCl. The resulting biphasic mixture was separated and the rich organic layer was washed with an additional 90 mL 13 wt % aqueous NaCl. The rich organic layer was diluted with 20 mL tetrahydrofuran and washed with an aqueous mixture of NaHCO₃ and NaCl (45 mL 1M aqueous NaHCO₃ and 45 mL 26% aqueous NaCl). The rich organic layer was solvent exchanged into toluene via vacuum distillation to a target volume of ca. 160 mL. The resulting toluene solution of ketoester 1c was used as is in the next step.

[Note: for the preparation of 1,1'-(biphenyl-4,4'-diyl)bis(2-bromoethanone), see process patent application WO 2009/020825].

Example 1

Step d

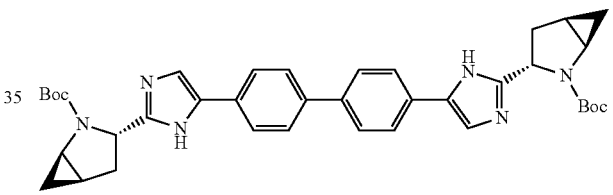

The above toluene solution of ketoester 1c was charged with 64.2 g (832.9 mmol, 20.0 equiv) NH₄OAc and allowed to stir at 90-100° C. for ca. 18 h. Cooled to 60° C. and charged 255 mL 2:1 AcOH:water. The resulting biphasic mixture was separated and the toluene layer was washed with 58 mL 1:1 AcOH:water. The rich aqueous layers were combined and residual toluene was removed via vacuum distillation. The aqueous solution was diluted with 60 mL methanol and heated to 50-60° C. Charged 106 mL (1060 mmol, 25.4 equiv) 10 N NaOH while maintaining an internal temperature <60° C. The resulting slurry was then cooled to rt. The slurry was filtered and washed with 100 mL water followed by 400 mL methanol to give 26.1 g of crude imidazole 1d. The wet, crude imidazole 1d was then charged into a 500 mL round bottom flask equipped with a nitrogen inlet, overhead agitator and thermocouple. Charged 165 mL N-methyl-2-pyrrolidinone and heated to 50° C. The resulting clear solution was charged with 30 mL Methanol and allowed to stir at 50° C. for ca. 18 h. The resulting slurry was charged with an additional 130 mL methanol while maintaining an internal temperature >45° C. The slurry was allowed to stir at 50° C. for ca. 30 min and cooled to rt. The slurry was filtered and the solids were washed with 90 mL 1:1 methanol:N-methyl-2-pyrrolidinone followed by 200 mL methanol. The solids were dried under vacuum at 70° C. to give 22.7 g (31.5 mmol, 76% yield, 95 AP at 254 nm) imidazole 1d: $^1$H NMR (400 MHz, DMSO-d$_6$) δ 11.95 (s, 2H), 7.89-7.76 (d, 4H), 7.74-7.60 (d, 4H), 7.50 (s, 2H) 4.62 (s, 2H), 3.55-3.30 (m, 2H), 2.45-2.20 (m, 4H), 1.70-1.59 (m, 2H), 1.59-0.90 (s, 18H), 0.83-0.69 (m, 2H), 0.65-0.49 (m, 2H); HRMS calcd for C$_{38}$H$_{45}$N$_6$O$_4$ (M+H; ESI$^+$): 649.3502. Found: 649.3524.

Example 1

Step e

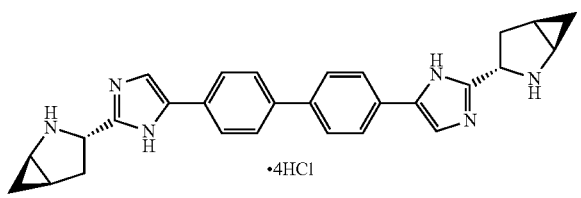 [SMILES: c1cc(-c2cnc([C@@H]3C[C@H]4C[C@H]4N3)[nH]2)ccc1-c1ccc(-c2cnc([C@@H]3C[C@H]4C[C@H]4N3)[nH]2)cc1]

A 250 mL round bottom flask equipped with a nitrogen inlet and overhead agitator was charged with 7.0 g (10.8 mmol) imidazole 1d, 105 mL methanol and 3.7 mL (20.8 mmol, 1.93 equiv) 5.6 M HCl in isopropanol. The resulting solution was treated with charcoal and filtered. The charcoal was washed with 140 mL methanol and combined with the filtrate. The rich organic stream was concentrated down to ca. 70 mL and charged into a round bottom flask equipped with a nitrogen inlet, overhead agitator and thermocouple. The solution was then charged with 14.75 mL (88.5 mmol, 8.2 equiv) 6M HCl and allowed to stir at 50° C. After ca. 12 h at 50° C., the mixture was charged with 50 mL isopropanol and the resulting slurry was allowed to stir at 50° C. for 1 h. The slurry was cooled to rt and aged for ca. 15 h. The product was filtered and washed with 35 mL 4:1 isopropanol:methanol followed by 70 mL isopropanol. The solids were dried at 55° C. under vacuum to give 5.3 g (8.9 mmol, 83%, 99.8 AP at 254 nm) pyrrolidine 1e/4HCl: $^1$H NMR (400 MHz, DMSO-d$_6$) δ 14.00-9.38 (bs, 8H), 8.31 (s, 2H), 8.06-7.96 (d, 4H), 7.94-7.84 (d, 4H), 5.05-4.89 (dd, 2H), 3.55-3.42 (m, 2H), 2.87-2.69 (dt, 2H), 2.64-2.53 (dd, 2H), 2.05-1.89 (m, 2H), 1.17-0.98 (m, 2H), 0.96-0.82 (dd, 2H); $^{13}$C NMR (100 MHz, DMSO-d$_6$) δ 140.0, 139.3, 133.6, 127.2, 126.6, 125.8, 116.6, 49.8, 34.3, 29.9, 15.2, 5.3; HRMS calcd for C$_{28}$H$_{29}$N$_6$ (M+H; ESI$^+$): 449.2454. Found: 449.2470.

Example 1

Step f

A 250 mL jacketed reactor equipped with a nitrogen inlet, overhead agitator and thermocouple was charged with 4.24 g (24.2 mmol, 2.4 equiv) (S)-2-(methoxycarbonylamino)-3-methylbutanoic acid, 3.86 g (25.21 mmol, 2.5 equiv) 1-hydroxybenzotriazole monohydrate, 4.55 g (23.73 mmol, 2.35 equiv) 1-(3-dimethylaminopropyl)-3-ethylcarbodiimide hydrochloride and 60 mL acetonitrile. The mixture was stirred for ca. 1 h and charged with 6 g (10.1 mmol) pyrrolidine 1e/4HCl. The resulting slurry was cooled to 10° C. and charged with 7.92 mL (45.41 mmol, 4.5 equiv) diisopropylethylamine. The mixture was allowed to warm to rt and stirred for ca. 19 h. The resulting organic solution was washed with 36 mL 13 wt % aqueous NaCl. The rich organic was charged with 12 mL acetonitrile and washed with 36 mL of an aqueous solution containing 13 wt % aqueous NaCl and 1 M NaOH. The rich organic was then charged with 12 mL methanol and heated to 50° C. Water (60 mL) was added over a period of 2 h and the resulting slurry was cooled to rt and aged for ca. 2 h. The solids were filtered, washed with 36 mL 1:1 acetonitrile:water and dried under vacuum. A 250 mL jacketed reactor equipped with a nitrogen inlet, overhead agitator and thermocouple was charged with the above solids and dissolved with 240 mL SDA3A grade ethanol. The solution was concentrated down to ca. 50 mL via vacuum distillation and charged with 4.24 mL (23.19 mmol, 2.30 equiv) 5.47 M HCl in isopropanol and an additional 30 mL SDA3A ethanol. The mixture was concentrated to ca. 50 mL, diluted with 40 mL SDA3A ethanol and treated with charcoal. The charcoal was filtered and washed with 90 mL SDA3A ethanol. The rich filtrate and wash were combined and concentrated down to 40 mL. Charged 16 mL ethyl acetate and heated to 40° C. Charged 60 mg amide 1f/2HCl seed crystals and stirred at 40° C. for 1 h. Charged an additional 68 mL ethyl acetate over 1.5 h while maintaining an internal temperature of 40° C. Stirred the resulting slurry at 40° C. for ca. 18 h and cooled to rt. The slurry was filtered and washed with 24 mL 3:1 ethyl acetate: SDA3A ethanol and 30 mL ethyl acetate. The solids were dried under vacuum at 50° C. to give 6.83 g (8.17 mmol, 81%, 99.5 AP at 300 nm) amide 1f/2HCl: $^1$H NMR (600 MHz, DMSO-d$_6$) δ 15.51 (s, 2H), 14.95 (s, 2H) 8.19 (s, 2H), 8.05 (d, 4H), 7.91 (d, 4H), 7.25 (d, 2H), 5.18 (t, 2H), 4.44 (t, 2H), 3.77 (s, 2H), 3.55 (s, 6H), 2.50 (m, 2H), 2.39 (m, 2H), 2.24 (m, 2H), 1.91 (m, 2H), 0.95 (m, 2H), 0.92 (d, 6H), 0.81 (d, 6H), 0.75 (s, 2H); $^{13}$C NMR (125 MHz, DMSO-d$_6$) δ 172.7, 156.9, 148.5, 139.1, 131.7, 127.1, 126.5, 125.9, 115.1, 57.8, 54.5, 51.5, 37.3, 32.9, 29.2, 19.7, 17.5, 17.5, 15.7; Calculated Elemental

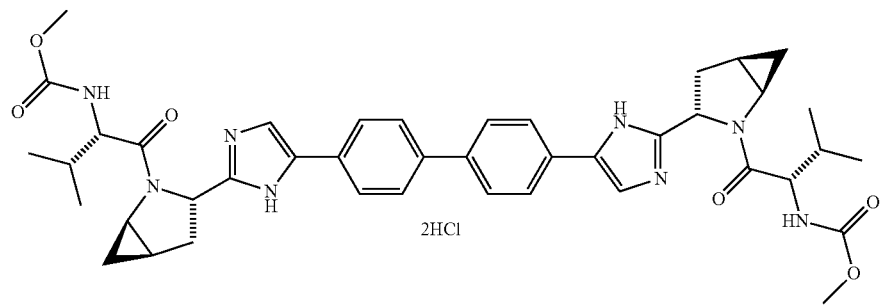

Analysis (corrected for 0.81% water): C=59.86%, H=6.30%, N=13.29%, Cl=8.41%. Found: C=59.99%, H=6.27%, N=13.12%, Cl=8.42%.

Preparation of Seed for amide 1f/2HCl: Amide 1f was prepared according to the basic procedure outlined above using 504 mg (0.8 mmol) pyrrolidine 1e.4HCl. After reaction completion, the rich acetonitrile solution was washed with 3 mL 13% aqueous NaCl, 2×3 mL of an aqueous solution containing 13% NaCl and 1M NaOH, and 3 mL 13% aqueous NaCl. The rich organic was concentrated down to a residue and diluted with 10 mL acetonitrile. The hazy mixture was filtered and the clear filtrate was concentrated down to a residue. The residue was diluted with 10 mL SDA3A ethanol and charged with 2.1 mL (1.9 mmol, 2.4 equiv) 0.88 M HCl in ethanol. The mixture was concentrated down to a residue and diluted with 1.8 mL isopropanol. The resulting solution was heated to 50° C. and allowed to stir for ca. 18 h. The resulting slurry was cooled to rt, filtered and washed with 2:1 acetone:ethanol to give 476 mg (0.57 mmol, 78%) amide 1f/2HCl.

[Note: (S)-2-(methoxycarbonylamino)-3-methylbutanoic acid was purchased from Flamma.]

Examples 1 and 2

A sample of amide 1f/2HCl (106.9 mg) was free-based (2 g MCX column; MeOH wash; 2 N NH$_3$/MeOH elution) and dried in vacuo. NCS (0.0195 g, 0.146 mmol) was added to a DMF (2.5 mL) solution of the resultant material and heated with an oil bath at 50° C. for 16.5 hr. Most of the volatile component was removed in vacuo and the residue was dissolved in MeOH and submitted to a reverse phase HPLC purification (MeOH/water/TFA; column: PHENOMENEX® Luna, 30×100 mm S10 Axia) to retrieve the TFA salts of Example 1 (white foam; 56.1 mg) and Example 2 (white foam; 22.3 mg). Example 1: $^1$H NMR (DMSO-d$_6$, δ=2.50 ppm, 400 MHz): 12.61 (br s, 1H), 8.13 (s, 1H), 7.93 (d, J=8.5, 2H), 7.90-7.86 (m, 4H), 7.82 (d, J=8.5, 2H), 7.27 (d, J=8.3, 1H), 7.17 (d, J=8.5, 1H), 5.02-4.94 (m, 2H), 4.44-4.38 (m, 1.80H), 4.31 (app br s, 0.2H), 3.75 (m, 1H), 3.62 (m, 1H), 3.55 (s, 3H), 3.54 (s, 3H), 2.56-2.50 ('m' partially overlapped with solvent signal, 1H), 2.41-2.23 (m, 3H), 2.17-2.09 (m, 1H), 2.07-2.00 (m, 1H), 1.97-1.91 (m, 1H), 1.88-1.81 (m, 1H), 1.01-0.81 (m, 15H), 0.71 (m, 1H). LC (Cond. 2a and 2b): >95% homogeneity index. LC-MS (Cond. 1a): R$_t$=1.80 min. LC-MS: Anal. Calcd. for [M+H]$^+$ C$_{42}$H$_{50}$ClN$_8$O$_6$: 797.35. found 797.33. Example 2: $^1$H NMR (DMSO-d$_6$, δ=2.50 ppm, 400 MHz): 7.86 (d, J=8.6, 4H), 7.80 (d, J=8.5, 4H), 7.17 (d, J=8.5, 2H), 4.96 (dd, J=7.5, 6.0, 2H), 4.40 (app t, J=7.8, 2H), 3.61 (m, 2H), 3.54 (s, 6H), 2.33-2.23 (m, 4H), 2.09-1.98 (m, 2H), 1.90-1.82 (m, 2H), 1.01-0.82 (overlapped 'm' and two 'd' at 0.96 ppm and 0.87 ppm with J=6.8 and J=6.5, respectively; 14H); 0.71 (m, 1.7H), 0.62 (m, 0.3H). LC (Cond. 2a and 2b): >95% homogeneity index. LC-MS (Cond. 1a): R$_t$=2.79 min. LC-MS: Anal. Calcd. for [M+H]$^+$ C$_{42}$H$_{49}$Cl$_2$N$_8$O$_6$: 831.32. found 831.26.

Example 3

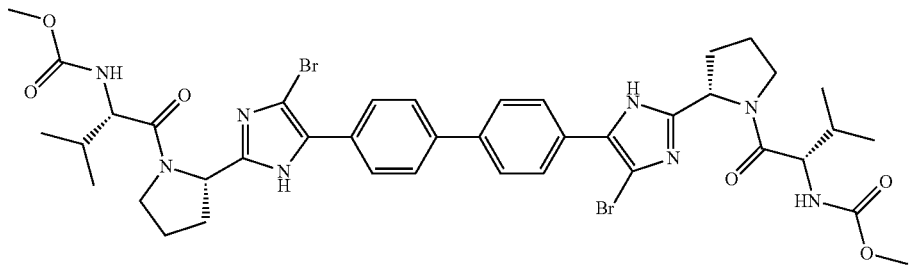

Example 3

Step a

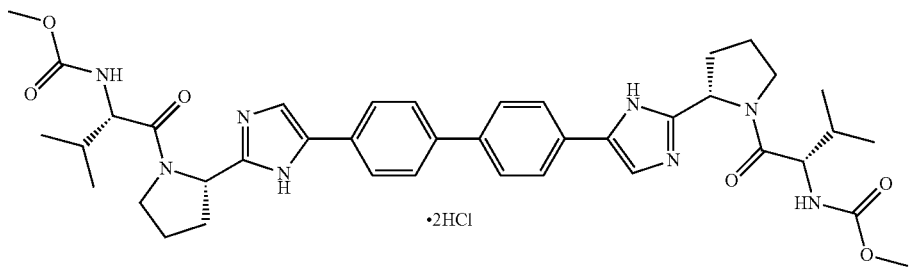

For the synthesis of amide 3a/2HCl, see the process patent application WO 2009/020825.

Example 3

To a solution of amide 3a (32 mg, 0.043 mmol) in acetic acid (2 mL) was added 2 eqv. of 1M bromine in acetic acid and the reaction was stirred for 30 min. An additional 1 eqv. bromine was added (solids formed), and the reaction was neutralized with 5% NaHCO$_3$ and extracted with EtOAc (2×10 mL). The combined extracts were washed with sat'd Na$_2$S$_2$O$_3$ soln and brine and concentrated. The residue was dried under high vacuum to afford Example 3 (41 mg). LC-MS (Cond.-J4): RT=3.54 min. LC-MS Anal. Calcd. for [M+H]$^+$ C$_{40}$H$_{49}$Br$_2$N$_8$O$_6$: 897.22. found 897.28.

Examples 4 and 5

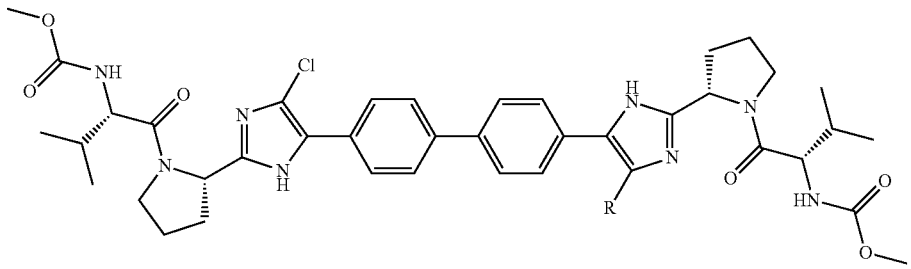

Example 4 (R = H)
Example 5 (R = Cl)

Diisopropylethyl amine (100 ul, 74.2 mg, 0.574 mmol) was added to a mixture of amide 3a (197 mg, 0.243 mmol) and N-chlorosuccinamide (39 mg, 0.292 mmol) in acetonitrile (2 mL) and stirred for overnight. An additional portion of N-chlorosuccinamide (66 mg, 0.494 mmol) was then added to the reaction mixture and stirred until the consumption of the starting material was confirmed by HPLC analysis. The crude reaction mixture was then purified by reverse phase HPLC (Solvent A=H$_2$O/CH$_3$CN (95:5)+0.05% TFA; Solvent B=H$_2$O/CH$_3$CN (5:95)+0.05% TFA; Column. Luna C18, 5u, 100×21.5 mm; Flow rate: 20 mL/min) to afford the TFA salts of Example 4 (yellowish amorphous powder, 60 mg) and Example 3 (yellowish amorphous powder, 115 mg). Example 5: LC-MS (Cond. 3): R$_t$=6.13 min. $^1$H NMR (DMSO-d$_6$, TMS, 600 MHz): 8.16 (s, 1H), 7.95-7.91 (m, 7H), 7.85 (d, J=8.8, 2H), 7.35 (d, J=8.4, 1H), 7.32 (d, J=8.4, 1H), 5.19 (t, J=7.3, 1H), 5.05 (m, 1H), 4.15 (t, J=7.7, 1H). 4.08 (t, J=8.1, 1H), 3.88-3.81 (m, 4H), 3.56 (s, 6H), 2.43 (m, 1H), 2.21-2.11 (m, 4H), 2.08-2.05 (m, 2H), 1.97 (m, 3H), 0.91 (d, J=6.5, 3H), 0.87 (d, J=7.0, 3H), 0.85 (d, J=7.0, 3H), 0.80 (d, J=6.6, 3H). HRMS: Calcd. for [M+H]$^+$ C$_{40}$H$_{50}$ClN$_8$O$_6$: 773.3542. found 773.3530. Example 4: LC-MS (Cond. 3): R$_t$=8.61 min $^1$H NMR (DMSO-d$_6$, TMS, 600 MHz): 7.89 (d, J=8.3, 4H), 7.83 (d, J=8.3, 4H), 7.33 (d, J=8.4, 2H), 5.05 (m, 2H), 4.09 (t, J=8.3, 2H), 3.84-3.81 (m, 4H), 3.56 (s, 6H), 2.24-2.15 (m, 4H), 2.00-1.95 (m, 6H), 0.91 (d, J=6.7, 6H), 0.87 (d, J=6.6, 6H). HRMS: Calcd. for [M+H]$^+$ C$_{40}$H$_{49}$Cl$_2$N$_8$O$_6$: 807.3152. found 807.3138.

Examples 6 and 7

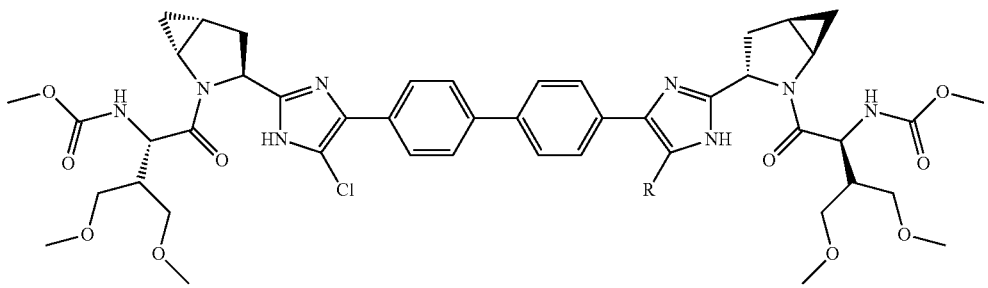

Example-6: R = H
Example-7: R = Cl

Example 6

Step a

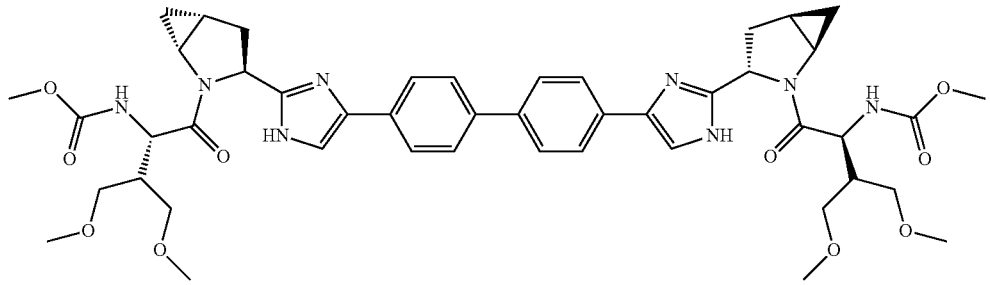

To a mixture of pyrrolidine 1e/4HCl (0.104 g, 0.174 mmol), HATU (0.133 g, 0.349 mmol) and Cap-193 (0.082 g, 0.349 mmol) in DMF was added DIEA (0.183 mL). The reaction mixture was stirred at room temperature for 3 hrs. The reaction mixture was purified by preparatory HPLC (PHENOMENEX® Axia 5u column, 35 min gradient from 0-90% B. A=H$_2$O/CH$_3$CN/10 mM NH$_4$OAc, 95:5. B=CH$_3$CN/H$_2$O/10 mM NH$_4$OAc 95:5) to afford Example 6, Step a (0.064 g). LC-MS: Anal. Calcd. For [M+H]$^+$ C$_{46}$H$_{59}$N$_8$O$_m$: 883.43. found: 883.26. $^1$H NMR (400 MHz, MeOD) ppm 7.90 (2H, s), 7.78-7.86 (8H, m), 5.13 (2H, dd, J=9.2, 6.9 Hz), 4.96 (2H, d, J=5.0 Hz), 3.73-3.79 (2 H, m), 3.63 (6H, s), 3.39-3.49 (6H, m), 3.35 (1H, d, J=4.8 Hz), 3.32-3.34 (1H, m), 3.30 (6H, s), 3.15 (6H, s), 2.66 (2H, dd, J=13.5, 9.4 Hz), 2.37-2.51 (4H, m), 2.02-2.09 (2H, m), 1.03-1.14 (2H, m), 0.81-0.93 (2H, m).

Examples 6 and 7

To a solution of Example 6, Step a (0.057 g) in DMF was added NCS (10.34 mg, 0.077 mmol). The reaction mixture was heated at 60° C. for 3 hrs. The reaction mixture was purified by preparatory HPLC (PHENOMENEX® Axia 5u 30×100 mm column, 20 min gradient from 0-100% B. A=H$_2$O/CH$_3$OH/TFA 90:10:0.1. B=CH$_3$OH/H$_2$O/TFA 90:10:0.1) to afford Example 6 (0.022 g) and Example 7 (0.017 g). Example 6: LC (Cond.-J5): R$_f$=3.46 min. LC-MS: Anal. Calcd. For [M+H]$^+$ C$_{46}$H$_{58}$ClN$_8$O$_{10}$: 917.39. found: 917.12. $^1$H NMR (400 MHz, MeOD) ppm 7.87-7.91 (1H, m), 7.77-7.86 (8H, m), 5.14 (1H, dd, J=9.2, 6.9 Hz), 5.05 (1H, dd, J=8.1, 6.3 Hz), 4.96 (2H, t, J=5.7 Hz), 3.73-3.79 (1H, m), 3.67-3.72 (1H, m), 3.57-3.66 (6H, m), 3.32-3.51 (8H, m), 3.29 (6H, d, J=1.8 Hz), 3.19 (3H, s), 3.12-3.16 (3H, m), 2.60-2.72 (1H, m), 2.32-2.54 (5H, m), 2.02 (2H, d, J=6.3 Hz), 1.00-1.19 (2H, m), 0.88 (1H, br. s.), 0.82 (1H, br. s.). Example 7: LC (Cond. PY1): R$_f$=4.083 min. LC-MS: Anal. Calcd. For [M+H]$^+$ C$_{46}$H$_{56}$Cl$_2$N$_8$O$_m$: 951.35. found: 951.09. $^1$H NMR (400 MHz, MeOD) ppm 7.74-7.84 (8H, m), 5.05 (2H, t, J=7.2 Hz), 4.95 (2H, d, J=5.5 Hz), 3.66-3.72 (2H, m), 3.63 (6H, s), 3.37-3.53 (8H, m), 3.30 (6H, s), 3.19 (6H, s), 2.32-2.51 (6H, m), 1.92-2.06 (2H, m), 1.08 (2H, dt, J=8.6, 5.8 Hz), 0.81 (2H, d, J=1.8 Hz).

Example V1

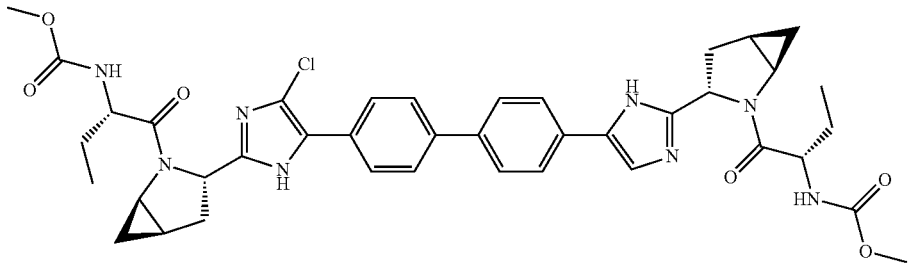

Example V1

Step a

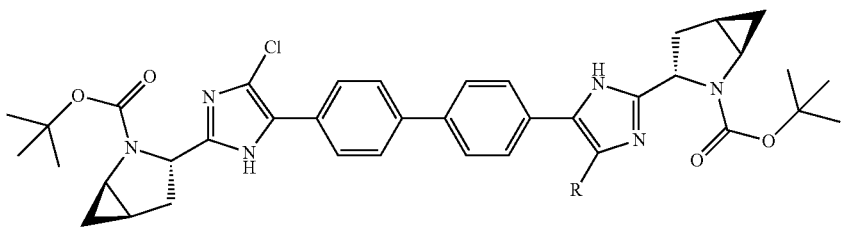

V1a-1 R = H
V1a-2 R = Cl

A solution of carbamate 1d (0.80 g, 1.23 mmol) and NCS (0.214 g, 1.603 mmol) in DMF (12 mL) was heated at 50° C. for 17 h. After it was allowed to cool to ambient temperature, volatile components were removed in vacuo. The residue was dissolved in MeOH (36 mL) and the two products were separated by prep-HPLC (Column: XTERRA®, 30×100 mm, S5; Start % B=50, Final % B=100; Gradient time=10 min; Stop time=12 min; Flow rate=30 ml/min; Wavelength=220; Solvent A=10% MeOH-90% $H_2O$-0.1% TFA; Solvent B=90% MeOH-10% $H_2O$-0.1% TFA). Each of the two fractions were neutralized with an excess solution of 2N $NH_3$/MeOH and concentrated in vacuo to remove most of the methanol, and the residue was partitioned between 20% MeOH/$CHCl_3$ and water. The organic layer was dried ($MgSO_4$), filtered, and concentrated in vacuo to afford chloride V1a-1 (light yellow foam; 288.4 mg) and dichloride V1a-2 (light yellow solid; 400.4 mg). Chloride V1a-1: $^1H$ NMR (DMSO-$d_6$, δ=2.5 ppm, 400 MHz): 12.62-12.60 (m, 1H), 12.23 (s, 0.2H), 11.92 (s, 0.8H), 7.85-7.32 (m, 9H), 4.68-4.42 (m, 2H), 3.47-3.38 (m, 2H), 2.40-2.35 (m, 2H), 2.26-2.20 (m, 2H), 1.71-1.58 (m, 2H), 1.55-0.96 (app br s, 18H), 0.82-0.69 (m, 2H), 0.64-0.51 (m, 2H). LC (V-Cond. 1): $R_t$=2.44 min. LC-MS: Anal. Calcd. for [M+H]+$C_{38}H_{44}ClN_6O_4$: 683.31. found: 683.31. Dichloride V1a-2: $^1H$ NMR (DMSO-$d_6$, 6=2.5 ppm, 400 MHz): 12.62 (s, 2H), 7.85 (d, J=8.8, 4H), 7.82 (d, J=8.9, 4H), 4.61-4.42 (m, 2H), 3.53-3.38 (m, 2H), 2.41-2.35 (m, 2H), 2.27-2.20 (m, 2H), 1.70-1.59 (m, 2H), 1.53-0.94 (app br s, 18H), 0.80-0.70 (m, 2H), 0.64-0.53 (m, 2H). LC (Cond. 1a): $R_t$=2.89 min. LC-MS: Anal. Calcd. For [M+H]$^+$ $C_{38}H_{43}Cl_2N_6O_4$: 717.27. found: 717.31.

Example V1

Step b

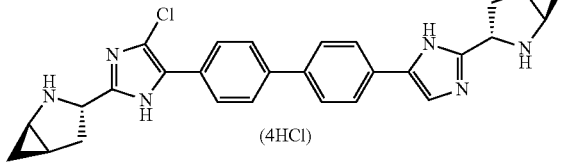

(4HCl)

To a suspension of chloride V1a-1 (0.2741 g, 0.401 mmol) in MeOH (1 mL) was added 4M HCl in dioxane (4 mL). The mixture was stirred at room temperature for 7 h, and then the volatile component was removed in vacuo to afford the HCl salt of V1b as a tan solid (231.7 mg). The product was used without further purification. $^1H$ NMR (DMSO-$d_6$, δ=2.5 ppm, 400 MHz): 13.51 (br s, 1H), 10.53-10.30 (m, 2H), 9.87-9.72 (m, 1H), 8.02-7.85 (m, 9H), 4.72-4.68 (m, 1H), 4.65-4.53 (m, 1H), 3.42-3.30 (m, 2H), 2.68-2.37 ('m' partially overlapped with solvent signal, 4H), 1.97-1.87 (m, 2H), 1.16-1.07 (m, 2H), 0.89-0.80 (m, 2H). LC (Cond. 1a): $R_t$=1.66 min. LC-MS: Anal. Calcd. for [M+H]$^+$ $C_{28}H_{28}ClN_6$: 483.21. found: 483.20. [Note: the exact HCl content of the product was not determined].

Example V1

To a solution of chloride V1b/4HCl (0.045 g, 0.072 mmol), (S)-2-(methoxycarbonylamino)butanoic acid (0.025 g, 0.157 mmol), and N,N-diisopropylethylamine (0.075 mL, 0.429 mmol) in DMF (1.5 mL) was added HATU (0.057 g, 0.150 mmol). The reaction mixture was stirred at ~25° C. for 1 h. It was diluted with MeOH (2.5 mL) and the product was purified by prep-HPLC (Column: XTERRA®, 30×100 mm, S5; Start % B=30, Final % B=90; Gradient time=10 min; Stop time=12 min; Flow rate=30 ml/min; Wavelength=220; Solvent A=10% MeOH-90% $H_2O$-0.1% TFA; Solvent B=90% MeOH-10% $H_2O$-0.1% TFA) to afford the TFA salts of Example V1 as a light yellow solid (39.4 mg). $^1H$ NMR (DMSO-$d_6$, δ=2.5 ppm, 400 MHz): 14.80-14.36 (br m, 1.4H), 12.58 (app br s, 0.6H), 8.14 (s, 1H), 7.94 (d, J=8.5, 2H), 7.89 (d, J=8.3, 2H), 7.87 (d, J=8.4, 2H), 7.82 (d, J=8.6, 2H), 7.38 (d, J=7.8, 0.9H), 7.28 (d, J=7.8, 0.9H), 7.07 (app br s, 0.1H), 6.96 (app br s, 0.1H), 5.02 (dd, J=8.8, 6.8, 1H), 4.96 (dd, J=7.0, 6.0, 1H), 4.50-4.39 (m, 2H), 3.74-3.67 (m, 1H), 3.59-3.48 (m, 7H), 2.60-2.47 ('m' partially overlapped with solvent signal, 1H), 2.42-2.22 (m, 3H), 2.01-1.65 (m, 4H), 1.65-1.52 (m, 2H), 1.06-0.84 (m, 8H), 0.83-0.77, (m, 1H), 0.74-0.66 (m, 1H). LC (Cond. 2a and 2b): >95% homogeneity index. LC (Cond. 1a): $R_t$=1.66 min. LC-MS: Anal. Calcd. for [M+H]$^+$ $C_{40}H_{46}ClN_8O_6$: 769.32. found: 769.35.

Example V2

Example V2 (TFA salt) was prepared from pyrrolidine V1b/4HCl and (S)-2-(methoxycarbonylamino)-2-(tetrahydro-2H-pyran-4-yl)acetic acid according to the procedure described for the synthesis of Example V1.

| Example | | $R_t$ (LC-Cond.); LC (Cond. 2a and 2b): % homogeneity index; MS data |
|---|---|---|
| V2 | (S)-methyl (1-oxo-1-(tetrahydro-2H-pyran-4-yl)methyl carbamate structure | 2.06 min (Cond. 1a); >95%; LC-MS: Anal. Calcd. for [M + H]$^+$ $C_{46}H_{54}ClN_8O_8$: 881.38; found: 881.36. |

Example V3

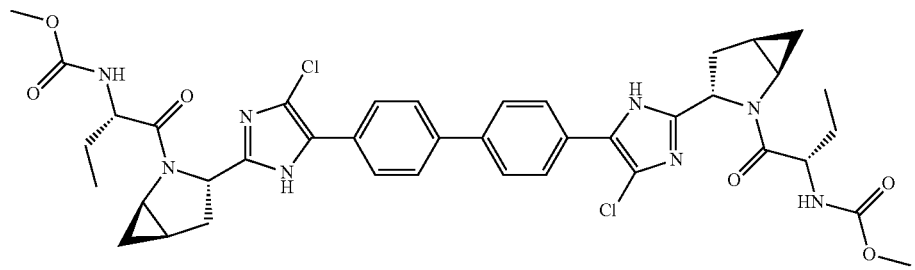

Example V3

Step a

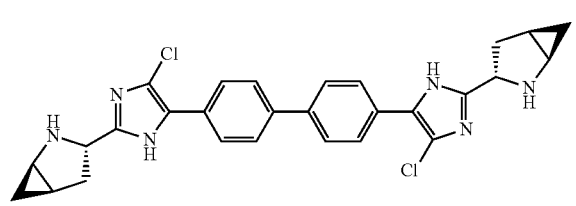 [SMILES: Clc1nc([C@@H]2C[C@H]3C[C@H]3N2)[nH]c1-c1ccc(-c2ccc(-c3[nH]c([C@@H]4C[C@H]5C[C@H]5N4)nc3Cl)cc2)cc1]

Intermediate V3a was prepared as HCl salt from carbamate V1a-2 according to the procedure described for the preparation of pyrrolidine V1b. $^1$H NMR (DMSO-d$_6$, δ=2.5 ppm, 400 MHz): 10.62-10.48 (m, 2H), 9.92-9.75 (m, 2H), 7.92 (d, J=8.8, 4H), 7.89 (d, J=9.1, 4H), 4.68-4.57 (m, 2H), 3.40-3.31 (m, 2H), 2.54-2.50 ('m' partially overlapped with solvent signal, 2H), 2.46-2.39 (m, 2H), 1.91-1.85 (m, 2H), 1.16-1.07 (m, 2H), 0.85-080 (m, 2H). LC (Cond. 1a): R$_t$=2.01 min. LC-MS: Anal. Calcd. for [M+H]$^+$ C$_{28}$H$_{27}$Cl$_2$N$_6$: 517.17. found: 517.06. [Note: the exact HCl salt content of the product was not determined].

Example V3

Example V3 (TFA salt) was prepared from the HCl salt of pyrrolidine V3a according to the procedure described for the synthesis of Example V1. $^1$H NMR (DMSO-d$_6$, δ=2.5 ppm, 400 MHz): 12.59 (very br s, ~2H), 7.86 (d, J=8.5, 4H), 7.80 (d, J=8.3, 4H), 7.46 (app br s, 0.13H), 7.37 (d, J=7.6, 1.73H), 6.97 (app br s, 0.14H), 4.97-4.94 (m, 2H), 4.52-4.35 (m, 2H), 3.63-3.45 (m, 8H), 2.36-2.23 (m, 4H), 1.96-1.83 (m, 2H), 1.82-1.67 (m, 2H), 1.64-1.49 (m, 2H), 1.13-0.82 (m, 8H), 0.78-0.61 (m, 2H). LC (Cond. 2a and 2b): >95% homogeneity index. LC (Cond. 1a): R$_t$=2.66 min. LC-MS: Anal. Calcd. for [M+H]$^+$ C$_{40}$H$_{45}$Cl$_2$N$_8$O$_6$: 803.28. found: 803.28.

Examples V4 to V6

Examples V4 to V6 (TFA salt) were prepared from the HCl salt of pyrrolidine V3a and the appropriate acids according to the procedure described for the synthesis of Example V1.

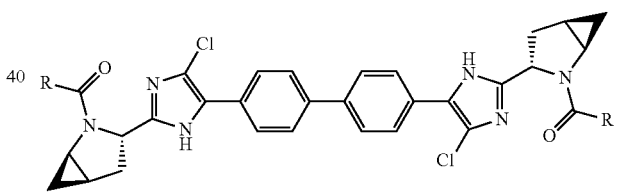

| Example | ![R structure] | R$_t$ (LC-Cond.); LC (Cond. 2a and 2b): % homogeneity index; MS data |
|---|---|---|
| V4 | methyl carbamate-THP-glycyl | 2.64 min (Cond. 1a); >95%; LC-MS: Anal. Calcd. for [M + H]$^+$ C$_{46}$H$_{53}$Cl$_2$N$_8$O$_8$: 915.34; found: 915.70. $^1$H NMR (DMSO-d$_6$, δ = 2.5 ppm, 400 MHz): 12.63 (very br s, ~2H), 7.87 (d, J = 8.6, 4H), 7.78 (d, J = 8.5, 4H), 7.42 (app br s, 0.1H), 7.26 (d, J = 8.6, 1.75H), 6.97 (app br s, 0.14H), 4.95 (dd, J = 8.4, 5.1, 2H), 4.48 (app t, J = 8.1, 2H), 3.85 (m, 4H), 3.73-3.64 (m, 2H), 3.54 (s, 6H), 3.32-3.18 (m, 4H), 2.37-2.19 (m, 4H), 2.05-1.91 (m, 2H), 1.91-1.78 (m, 2H), 1.71-1.58 (m, 2H), 1.56-1.39 (m, 4H), 1.39-1.25, (m, 2H), 1.05-0.93 (m, 2H), 0.77-0.66 (m, 2H) |

-continued

| Example | 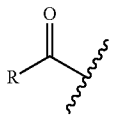 R | $R_t$ (LC-Cond.); LC (Cond. 2a and 2b): % homogeneity index; MS data |
|---|---|---|
| V5 | 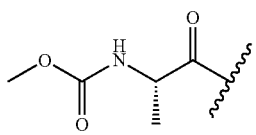 [SMILES: *C(=O)[C@H](C)NC(=O)OC] | 2.59 min (Cond. 1a); >95%; LC-MS: Anal. Calcd. for $[M + H]^+$ $C_{38}H_{41}Cl_2N_8O_6$: 775.25; found: 775.29. $^1$H NMR (DMSO-$d_6$, δ = 2.5 ppm, 400 MHz): 12.56 (very br s, ~2H), 7.86 (d, J = 8.5, 4H), 7.80 (d, J = 8.5, 4H), 7.37 (d, J = 7.6, 1.70H), 7.02 (app br s, 0.3H), 4.95 (app t, J = 6.8, 2H), 4.63-4.54 (m, 2H), 3.62-3.34 (overlapped 'm' and 's'; s is at 3.52; 8H), 2.31-2.28 (m, 4H), 1.91-1.84 (m, 2H), 1.28 (s, 3H). 1.27 (d, J = 7, 6H), 1.02-0.97 (m, 2H), 0.76-0.61 (m, 2H). |
| V5.1 | 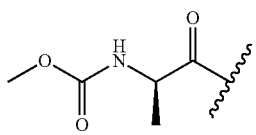 [SMILES: *C(=O)[C@@H](C)NC(=O)OC] | 2.65 min (Cond. 1a); >95%; LC-MS: Anal. Calcd. for $[M + H]^+$ $C_{38}H_{41}Cl_2N_8O_6$: 775.25; found: 775.35. |
| V5.2 | 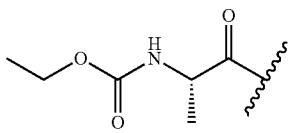 [SMILES: *C(=O)[C@H](C)NC(=O)OCC] | 2.72 min (Cond. 1a); >95%; LC-MS: Anal. Calcd. for $[M + H]^+$ $C_{40}H_{45}Cl_2N_8O_6$: 803.28; found: 803.38. |
| V5.3 | 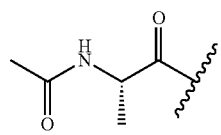 [SMILES: *C(=O)[C@H](C)NC(C)=O] | 2.50 min (Cond. 1a); >95%; LC-MS: Anal. Calcd. for $[M + H]^+$ $C_{38}H_{41}Cl_2N_8O_4$: 743.26; found: 743.36. |
| V6 | 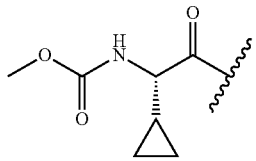 [SMILES: *C(=O)[C@@H](NC(=O)OC)C1CC1] | 2.75 min (Cond. 1a); >95%; LC-MS: Anal. Calcd. for $[M + H]^+$ $C_{42}H_{45}Cl_2N_8O_6$: 827.28; found: 827.33. |

Examples V7 and V8

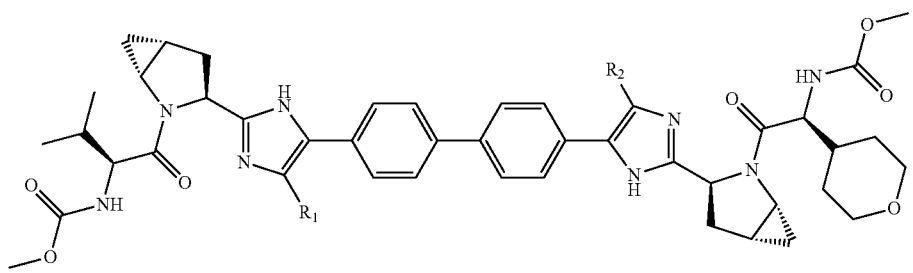

V7 ($R_1$ = H, $R_2$ = Cl)
V8 ($R_1$ = Cl, $R_2$ = H)

Example V7

Step a

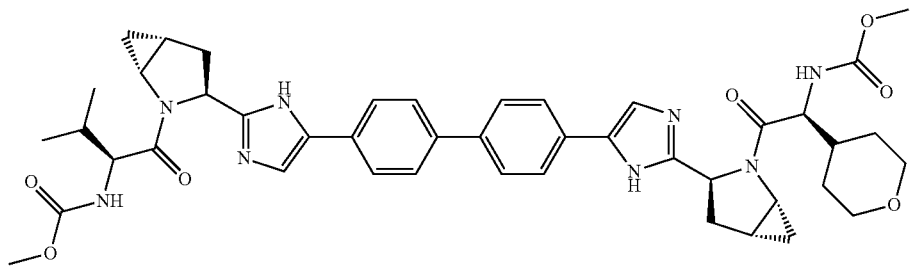

To a solution of pyrrolidine 1e/4HCl (0.350 g, 0.589 mmol), (S)-2-(methoxycarbonylamino)-3-methylbutanoic acid (0.103 g, 0.589 mmol), (S)-2-(methoxycarbonylamino)-2-(tetrahydro-2H-pyran-4-yl)acetic acid (0.128 g, 0.589 mmol) and N,N-diisopropylethylamine (0.720 mL, 4.12 mmol) in DMF (3 mL) was added HATU (0.493 g, 1.295 mmol). The reaction mixture was stirred at ~25° C. for 4 h, and then was diluted with MeOH and purified by prep-HPLC (Column: XTERRA®, 30×100 mm, S5; Start % B=30, Final % B=75; Gradient time=15 min; Stop time=15 min; Flow rate=30 ml/min; Wavelength=220; Solvent A=10% MeOH-90% $H_2O$-0.1% TFA; Solvent B=90% MeOH-10% $H_2O$-0.1% TFA) to isolate product V7a out of the three possible products. Product V7a was dissolved in MeOH and free-based (6 g MCX cartridge; MeOH wash; 2N $NH_3$/MeOH elution) and concentrated in vacuo to afford a tan solid (103.2 mg). LC (Cond. 1a): $R_t$=1.63 min. LC-MS: Anal. Calcd. for $[M+H]^+$ $C_{44}H_{53}N_8O_7$: 805.40. found: 805.49.

Examples V7 and V8

A solution of product V7a (0.103 g, 0.128 mmol) and NCS (0.022 g, 0.167 mmol) in DMF (1.5 mL) was heated at 50° C. for 24 h. After it was allowed to cool to ambient temperature, the reaction mixture was diluted with MeOH and purified by prep-HPLC (Column: XTERRA®, 30×100 mm, S5; Start % B=40, Final % B=100; Gradient time=15 min; Stop time=17 min; Flow rate=30 ml/min; Wavelength=220; Solvent A=10% MeOH-90% $H_2O$-0.1% TFA; Solvent B=90% MeOH-10% $H_2O$-0.1% TFA) to isolate a mixture of regioisomers V7 and V8. The mixture was dissolved in MeOH and submitted to a different prep-HPLC purification condition (Column: Waters SunFire, 30×100 mm, S5; Start % B=10, Final % B=50; Gradient time=20 min; Stop time=20 min; Flow rate=30 ml/min; Wavelength=220; Solvent A=10% Acetonitrile-90% $H_2O$-0.1% TFA; Solvent B=90% Acetonitrile-10% $H_2O$-0.1% TFA) to separate the two regioisomers as TFA salts. Example V7 (off-white solid, 17.3 mg): $^1$H NMR (DMSO-$d_6$, δ=2.5 ppm, 400 MHz): 14.52 (app br s, too broad to integrate), 12.64 (app br s, too broad to integrate), 8.14 (s, 1H), 7.95-7.79 (m, 8H), 7.26 (two overlapped 'd', J=~8.6, 1.70H), 7.10 (app br s, 0.08H), 6.98 (app br s, 0.22H), 5.01-4.97 (m, 1H), 4.96-4.92 (m, 1H), 4.50-4.46 (m, 1H), 4.43-4.40 (m, 1H), 3.90-3.81 (m, 2H), 3.79-3.72 (m, 1H), 3.71-3.64 (m, 1H), 3.54 (app s, 6H), 3.31-3.18 (m, 2H), 2.65-2.50 ('m' partially overlapped with solvent, 1H), 2.45-2.19 (m, 3H), 2.18-2.08 (m, 1H), 2.04-1.89 (m, 2H), 1.89-1.79 (m, 1H), 1.69-1.59 (m, 1H), 1.55-1.41 (m, 2H), 1.38-1.23 (m, 1H), 1.04-0.77 (m, 9H), 0.74-0.67 (m, 1H). LC (Cond. 2a and 2b): >95% homogeneity index. LC (Cond. 1a): $R_t$=2.15 min. LC-MS: Anal. Calcd. for $[M+H]^+$ $C_{44}H_{51}Cl_1N_8O_7$: 839.36. found: 839.35. Example V8 (off-white solid, 16.8 mg): $^1$H NMR (DMSO-$d_6$, δ=2.5 ppm, 400 MHz): 14.53 (br s, too broad to integrate), 12.61 (br s, too broad to integrate), 8.13 (s, 1H), 7.94 (d, J=8.3, 2H), 7.90 (d, J=8.6, 2H), 7.85 (d, J=8.5, 2H), 7.82 (d, J=8.6, 2H), 7.36 (d, J=8.8, ~1H), 7.17 (d, J=8.5, ~1H), 5.00-4.94 (m, 2H), 4.49 (app t, J=7.7, 1H), 4.40 (app t, J=7.9, 1H), 3.90-3.78 (m, 3H), 3.65-3.59 (m, 1H), 3.55 (s, 3H), 3.54 (s, 3H), 3.35-3.19 (m, 2H), 2.64-2.50 ('m' partially overlapped with solvent signal, 1H), 2.41-2.34 (m, 1H), 2.33-2.22 (m, 2H), 2.12-1.99 (m, 2H), 1.99-1.90 (m, 1H), 1.89-1.81 (m, 1H), 1.52-1.27 (m, 4H), 1.07-0.84 (m, 8H), 0.84-0.77 (m, 1H), 0.75-0.65 (m, 1H). LC (Cond. 2a and 2b): >95% homogeneity index. LC (Cond. 1a): $R_t$=2.15 min. LC-MS: Anal. Calcd. for $[M+H]^+$ $C_{44}H_{51}Cl_1N_8O_7$: 839.36. found: 839.38.

Example V9

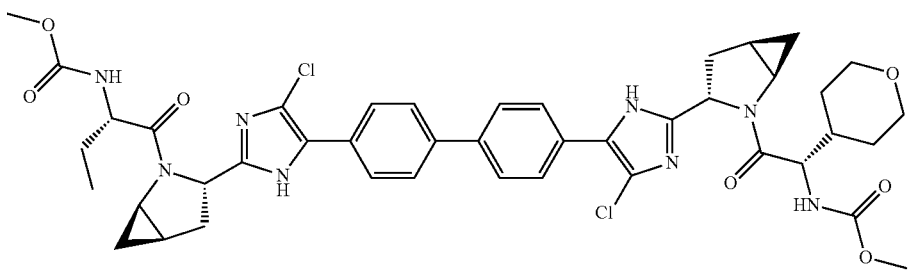

Example V9

Step a

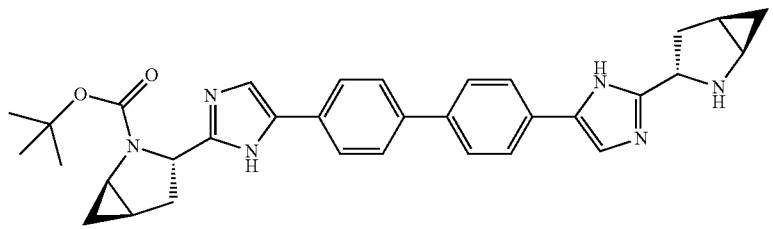 [SMILES: CC(C)(C)OC(=O)N1[C@@H]2C[C@@H]2C[C@H]1c1ncc(-c2ccc(-c3ccc(-c4cnc([C@@H]5C[C@H]6C[C@H]6N5)[nH]4)cc3)cc2)[nH]1]

Boc$_2$O (0.734 g, 3.36 mmol) followed DMAP (0.021 g, 0.168 mmol) were added to a mixture of pyrrolidine 1e/4HCl (2.00 g, 3.36 mmol) and Et$_3$N (2.3 ml, 16.82 mmol) in DMF (60 ml), and stirred at ambient condition for 4.5 h. The volatile component was removed in vacuo, and the residue was partitioned between 1.0 N NaOH (20 mL) and 20% MeOH/CHCl$_3$ (50 mL). The aqueous phase was washed with 20% MeOH/CHCl$_3$ (50 mL, 2×). The combined organic phase was dried (MgSO$_4$) and concentrated in vacuo. A silica gel mesh was prepared from the resultant crude material and submitted to a BIOTAGE® purification (160 g silica gel) where the column was first eluted with EtOAc until all of the higher R$^f$ spot (i.e., bis-Boc derivative 1d; 0.28 g) came out, and then the column was eluted with 5-10% MeOH/CH$_2$Cl$_2$ over 2.5 L to elute residual bis-Boc x (followed by mono-Boc V9a (0.81 g; ~containing 1.1 mol equiv of Et$_3$N). LC-MS: Anal. Calcd. for [M+H]$^+$ C$_{33}$H$_{37}$N$_6$O$_2$: 549.30. found 549.45.

Example V9

Step b

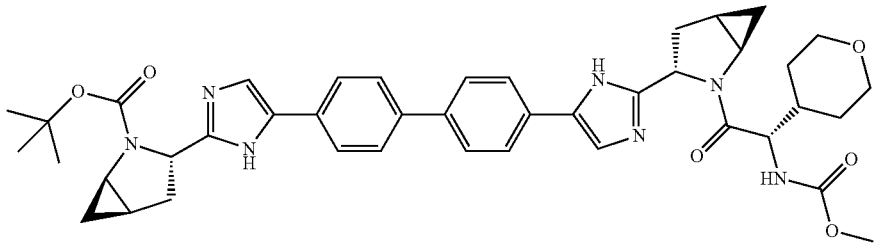 [SMILES: COC(=O)N[C@H](C(=O)N1[C@@H]2C[C@@H]2C[C@H]1c1ncc(-c2ccc(-c3ccc(-c4cnc([C@@H]5C[C@H]6C[C@H]6N5C(=O)OC(C)(C)C)[nH]4)cc3)cc2)[nH]1)C1CCOCC1]

To a solution of carbamate V9a (1 g, 1.823 mmol), (S)-2-(methoxycarbonylamino)-2-(tetrahydro-2H-pyran-4-yl)acetic acid (0.400 g, 1.841 mmol), and N,N-diisopropylethylamine (0.65 mL, 3.72 mmol) in DMF (8 mL) was added HATU (0.770 g, 2.026 mmol), and the reaction mixture was stirred at ~25° C. for 3 h. The volatile component was removed in vacuo, and the residue was taken up in 20% MeOH/CHCl$_3$ (250 mL), washed with water (3×40 mL), dried over MgSO$_4$, filtered, and concentrated in vacuo. The residue was taken up in CHCl$_3$ (4 mL) and loaded onto a Thomson's silica gel cartridge and eluted with 10% MeOH/EtOAc to afford product V9b as a tan foam (1.15 g). LC (Cond. 1a): R$_t$=1.70 min; LC-MS: Anal. Calcd. for [M+H]$^+$ C$_{42}$H$_{50}$N$_2$O$_6$: 748.38. found: 748.40.

Example V9

Step c

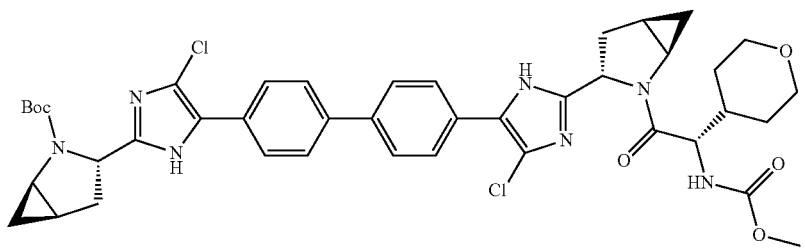 [SMILES: COC(=O)N[C@H](C(=O)N1[C@@H]2C[C@@H]2C[C@H]1c1nc(Cl)c(-c2ccc(-c3ccc(-c4[nH]c([C@@H]5C[C@H]6C[C@H]6N5C(=O)OC(C)(C)C)nc4Cl)cc3)cc2)[nH]1)C1CCOCC1]

A solution of V9b (0.9387 g, 1.255 mmol) and NCS (0.335 g, 2.51 mmol) in DMF (13 mL) was heated at 50° C. for 24.5 h. The volatile component was removed in vacuo and the residue was taken up in $CH_2Cl_2$ (200 mL), washed with water (3×50 mL), followed by brine (50 mL), dried over $MgSO_4$, filtered, and concentrated in vacuo. The residue was taken up in $CH_2Cl_2$ (6 mL) and submitted to a silica gel purification (100% ethyl acetate) to afford compound V9c as a yellow solid (720.7 mg). LC (Cond. 1a): $R_t$=3.19 min. LC-MS: Anal. Calcd. for $[M+H]^+$ $C_{42}H_{48}Cl_2N_7O_6$: 816.30. found: 816.35.

Example V9

Step d

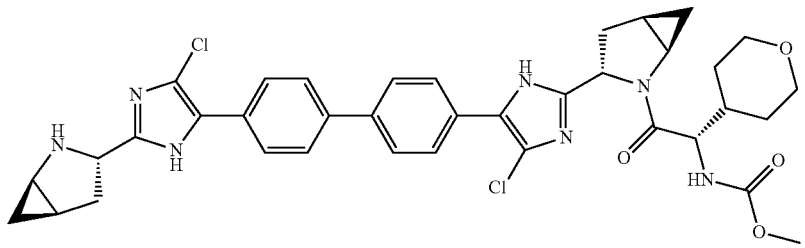 [SMILES: COC(=O)N[C@H](C(=O)N1[C@@H]2C[C@@H]2C[C@H]1c1nc(Cl)c(-c2ccc(-c3ccc(-c4[nH]c([C@@H]5C[C@H]6C[C@H]6N5)nc4Cl)cc3)cc2)[nH]1)C1CCOCC1]

Pyrroldine V9d was prepared as HCl salt from carbamate V9c according to the procedure described for the synthesis of V1b. $^1$H NMR (DMSO-$d_6$, δ=2.5 ppm, 400 MHz): 10.49-10.38 (m, 1H), 9.84-9.72 (m, 1H), 7.90-7.81 (m, 8H), 7.27 (d, J=8.6, 0.89H), 6.99 (app br s, 0.11H), 4.98-4.95 (m, 1H), 4.65-4.55 (m, 1H), 4.50-4.46 (m, 1H), 3.90-3.80 (m, 2H), 3.76-3.64 (m, 1H), 3.54 (s, 3H), 3.41-3.32 (m, 1H), 3.32-3.19 (m, 2H), 2.54-2.40 ('m' partially overlapped with solvent signal, 2H), 2.36-2.24 (m, 2H), 2.06-1.95 (m, 1H), 1.94-1.78 (m, 2H), 1.69-1.57 (m, 1H), 1.55-1.40 (m, 2H), 1.39-1.27 (m, 1H), 1.17-1.07 (m, 1H), 1.04-0.92 (m, 1H), 0.88-0.78 (m, 1H), 0.76-0.66 (m, 1H). LC (Cond. 1a): $R_t$=2.66 min; >95% homogeneity index. LC-MS: Anal. Calcd. for $[M+H]^+$ $C_{37}H_{40}Cl_2N_7O_4$: 716.25. found: 716.28.

Example V9

Example V9 (TFA salt) was prepared from the HCl salt of intermediate V9d and (S)-2-(methoxycarbonylamino)butanoic acid according to the procedure described for the synthesis of Example V1. $^1$H NMR (DMSO-$d_6$, δ=2.5 ppm, 400 MHz): 12.59 (br s, ~2H), 7.87-7.77 (m, 8H), 7.29/7.26 (two partially overlapped 'd', J=8.6/7.8, 1.82H), 6.97 (app br s, 0.18H), 4.97-4.93 (m, 2H), 4.50-4.42 (m, 2H), 3.90-3.81 (m, 2H), 3.72-3.65 (m, 1H), 3.60-3.46 (overlapping m and two s, s are at 3.54 and 3.53, 7H), 3.32-3.18 (m, 2H), 2.38-2.18 (m, 4H), 2.05-1.23 (collection of 'm', 9H), 1.09-0.85 (m, 5H), 0.76-0.59 (m, 2H). LC (Cond. 2a and 2b): >95% homogeneity index. LC (Cond. 1a): $R_t$=2.66 min. LC-MS: Anal. Calcd. for $[M+H]^+$ $C_{43}H_{49}Cl_2N_8O_2$: 859.31. found: 859.43.

Examples V10 to V16

Examples V10 to V16 (TFA salt) were prepared from the HCl salt of pyrrolidine V9d and appropriate acids according to the procedure described for the preparation of Example V1. Examples V13 to V16 required an additional reverse phase HPLC purification which employed the following condition: Column: Waters SunFire, 30×100 mm, S5; Start % B=10, Final % B=50; Gradient time=20 min; Stop time=20 min; Flow rate=30 ml/min; Wavelength=220; Solvent A=10% Acetonitrile-90% $H_2O$-0.1% TFA; Solvent B=90% Acetonitrile-10% $H_2O$-0.1% TFA.

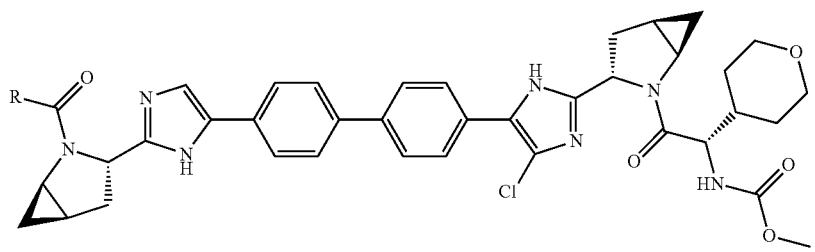

| Example | R (LC-Cond.); LC (Cond. 2a and 2b): % homogeneity index; MS data |
|---|---|
| V10 | 2.59 min (Cond. 1a); >95%; LC-MS: Anal. Calcd. for [M + H]⁺ C₄₁H₄₅Cl₂N₈O₇: 831.28; found: 831.31. |
| V11 | 2.54 min (Cond. 1a); >95%; LC-MS: Anal. Calcd. for [M + H]⁺ C₄₂H₄₇Cl₂N₈O₇: 845.29; found: 845.17. |
| V12 | 2.69 min (Cond. 1a); >95%; LC-MS: Anal. Calcd. for [M + H]⁺ C₄₄H₅₁Cl₂N₈O₇: 873.33; found: 873.27. |
| V13 | 2.73 min (Cond. 1a); >95%; LC-MS: Anal. Calcd. for [M + H]⁺ C₄₄H₄₉Cl₂N₈O₇: 871.31; found: 871.41. |
| V14 | 2.83 min (Cond. 1a); >95%; LC-MS: Anal. Calcd. for [M + H]⁺ C₄₅H₅₁Cl₂N₈O₇: 885.33; found: 885.45. |
| V15 | 2.70 min (Cond. 1a); >95%; LC-MS: Anal. Calcd. for [M + H]⁺ C₄₄H₅₁Cl₂N₈O₈: 889.32; found: 889.44. |
| V16 | 2.52 min (Cond. 1a); >95%; LC-MS: Anal. Calcd. for [M + H]⁺ C₄₂H₄₆Cl₂N₇O₆: 814.29; found: 814.18. |

Examples GW1-1 to GW1-3

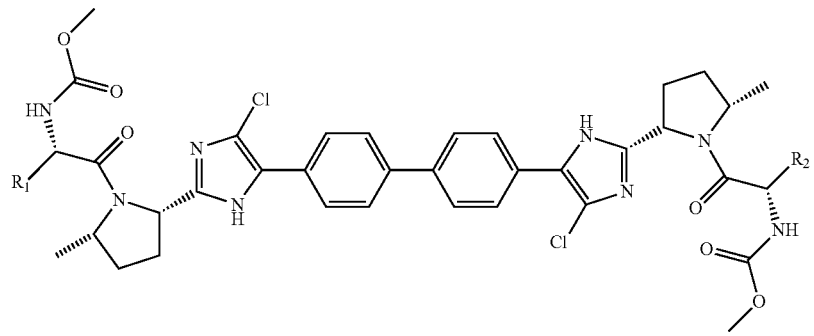

Example GW1-1

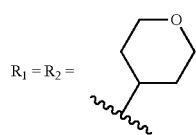

Example GW1-2

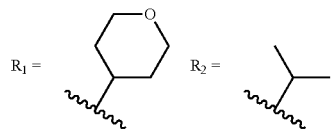

Example GW1-3

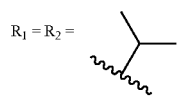

Example GW1

Step a

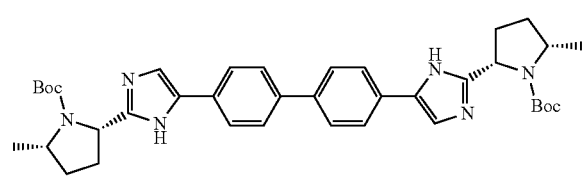

For the preparation of carbamate GW1a, see U.S. Patent Application 2009/0068140.

Example GW1

Step b

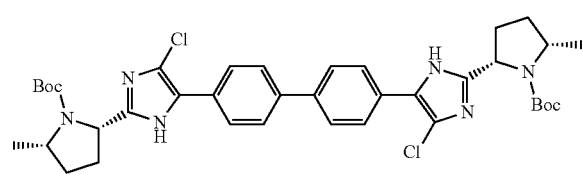

To a solution of carbamate GQ1a (0.830 g, 1.271 mmol) in DMF (9 mL) was added NCS (0.221 g, 1.653 mmol). The reaction mixture was heated at 50° C. for 16 hr. More NCS (0.1 g, 0.75 mmol) was added and heating was continued for another 4 hr. It was allowed to cool to ambient temperature and partitioned between DCM and water (20 mL each). The aqueous layer was extracted with DCM (20 mL), and the combined organic phase was dried (Na$_2$SO$_4$) and concentrated in vacuo. The resulting crude material was dissolved in MeOH and submitted to a reverse phase HPLC purification (MeOH/water/TFA; column: PHENOMENEX® Luna, 30×100 mm S10 Axia) to retrieve the TFA salts of GW1b as light yellow foam (0.25 g). $^1$H NMR (MeOD, δ=3.30 ppm, 400 MHz): 7.82 (app s, 8H), 4.95-4.85 ('m' partially overlapped with HOD signal, 2H), 4.04 (m, 2H), 2.36-2.14 (m, 6H), 1.77 (m, 2H), 1.50-1.20 (overlap of 'br s' and 'd', 24H). LC (Cond. Ia): RT=3.0 min. LC-MS: Anal. Calcd. for [M+H]$^+$ C$_{38}$H$_{47}$Cl$_2$N$_6$O$_4$: 721.30. found 721.32.

Example GW1

Step c

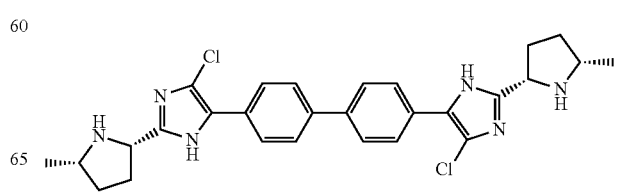

4N HCl in dioxane (10 mL) was added to carbamate GW1b (0.29 g, 0.306 mmol) and the reaction mixture was stirred at room temperature for 4 hrs. Solvent was removed and dried under vacuum overnight to give the HCl salt of product GW1c as brown solid (0.21 g). $^1$H NMR (MeOD, δ=3.30 ppm, 400 MHz): 7.85 (d, J=8.6, 4H), 7.80 (d, J=8.8, 4H), 4.95-4.85 (m, 2H), 3.89-3.80 (m, 2H), 2.58-2.31 (m, 6H), 2.01-1.91 (m, 2H), 1.50 (d, 6.5 Hz, 6H). LC (Cond. 1a): RT=3.0 min. LC-MS: Anal. Calcd. for [M+H]$^+$ $C_{28}H_{31}Cl_2N_6$: 521.20. found 521.20.

Examples GW1-1 to GW1-3

To a solution of the HCl salt of GW1c (150 mg, 0.225 mmol), (S)-2-(methoxycarbonylamino)-2-(tetrahydro-2H-pyran-4-yl)acetic acid (57.6 mg, 0.265 mmol) and (S)-2-(methoxycarbonylamino)-3-methylbutanoic acid (48.0 mg, 0.274 mmol) in DMF (10 mL) were added DIEA (0.236 mL, 1.349 mmol) and HATU (176 mg, 0.463 mmol), and the mixture was stirred at room temperature for 1 hr. Most of the volatile component was removed in vacuo and the residue was dissolved in MeOH and submitted to a reverse phase HPLC purification (MeOH/water/TFA; column: PHENOMENEX® Luna, 30×100 mm S10 Axia) to isolate the three products as TFA salts. Example GW1-1 (light yellow foam, 25 mg) was contaminated with unidentified impurity. $^1$H NMR (MeOD, δ=3.30 ppm, 400 MHz): 8.05-7.93 (m, 1.54H), 7.87-7.56 (m, 6.46H), 5.42 (br d, J=6.6, 0.68H), 4.97 (m, 1.32H), 4.76-4.69 (m, 1.2H), 4.31-4.14 (m, 2.8H), 3.98-3.84 (m, 4H), 3.68/3.67/3.63 (three 's', 6H), 3.40-3.21 ('m' partially overlapped with solvent signal, 4H), 2.72 (m, 0.7H), 2.45-1.14 (overlapped many 'm' and two 'd', 'd' at 1.51 and 1.18 with J=6.5 and 6.3, respectively; 23.3H). LC (Cond. 2a and 2b): >91.8% homogeneity index. LC (Cond. 1c): RT=6.22 min. LC-MS: Anal. Calcd. for [M+H]$^+$ $C_{46}H_{57}Cl_2N_8O_8$: 919.37. found 919.9. Example GW1-2 (light yellow foam, 39 mg); LC (Cond. 2a and 2b): >95% homogeneity index. LC (Cond. 1a): RT=2.97 min. LC-MS: Anal. Calcd. for [M+H]$^+$ $C_{44}H_{55}Cl_2N_8O_7$: 877.36. found 877.35. Example GW1-3 (light yellow foam, 22 mg), LC (Cond. 2a and 2b): >95% homogeneity index. LC (Cond. 1a): RT=3.07 min. LC-MS: Anal. Calcd. for [M+H]$^+$ $C_{42}H_{53}Cl_2N_8O_6$: 835.35. found 835.34.

Example GW2

Step a

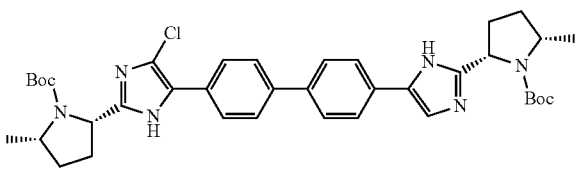

To a solution of carbamate GW1a (0.830 g, 1.271 mmol) in DMF (9 mL) was added NCS (0.221 g, 1.653 mmol). The reaction mixture was heated at 50° C. for 16 hr. Additional NCS (0.1 g, 0.75 mmol) was added and heating was continued at 50° C. for an additional 4 hr. The mixture was partitioned between DCM and water (20 mL each). The aqueous phase was extracted with DCM (20 mL), and the combined phase was dried with Na$_2$SO$_4$ and concentrated in vacuo. The resulting crude product was dissolved in MeOH and submitted to a reverse phase HPLC purification (MeOH/water/TFA; column: PHENOMENEX® Luna, 30×100 mm S10 Axia) to retrieve carbamate GW2a as light yellow foam (0.03 g). $^1$H NMR (MeOD, δ=3.30 ppm, 400 MHz): 7.76-7.64 (m, 8H), 7.34 (s, 1H), 5.10-4.65 (overlapping with HOD signal, m, 2H), 3.99 (m, 2H), 2.31-2.01 (m, 6H), 1.78-1.76 (m, 2H), 1.55-1.15 (app br m, 24H). LC (Cond. 1a): RT=2.55 min. LC-MS: Anal. Calcd. for [M+H]$^+$ $C_{38}H_{48}ClN_6O_4$: 687.34. found 687.39.

Example GW2

Step b

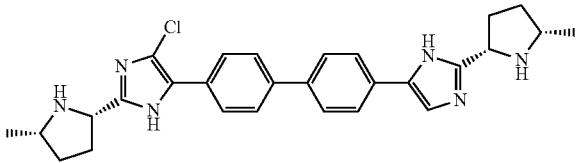

4N HCl in dioxane (10 mL) was added to carbamate GW2a (0.19 g, 0.208 mmol) and it was stirred at room temperature for 4 hr. Solvent was removed and it was dried under vacuum overnight to afford the HCl salt of pyrrolidine GW2b as Example GW2

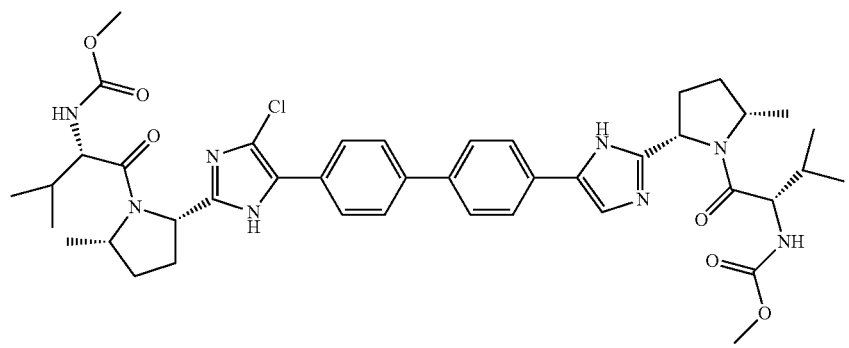

brown solid (0.16 g). ¹H NMR (MeOD, δ=3.30 ppm, 400 MHz): 8.11 (s, 1H), 7.95 (d, J=8.5, 2H), 7.87 (appears 'd', 4H), 7.82 (d, J=8.8, 2H), 5.22 (m, 1H), 4.92-4.83 (over lapping with HOD signal, m, 1H), 3.99 (m, 1H), 3.84 (m, 1H), 2.78-2.62 (m, 2H), 2.57-2.31 (m, 4H), 2.12-1.91 (m, 2H), 1.55 (d, J=6.8, 3H), 1.50 (d, J=6.8, 3H). LC (Cond. Ia): RT=1.74 min. LC-MS: Anal. Calcd. for [M+H]⁺ $C_{28}H_{32}ClN_6$: 487.24. found 487.21.

Example GW2

To a solution of the HCl salt of pyrrolidine GW2b (80 mg, 0.126 mmol) and (S)-2-(methoxycarbonylamino)-3-methylbutanoic acid (48.7 mg, 0.278 mmol) in DMF (3 mL), DIEA (0.132 mL, 0.758 mmol) and HATU (99 mg, 0.260 mmol) were added and the mixture was stirred at room temperature for 1 hr. Most of the volatile component was removed in vacuo and the residue was dissolved in MeOH and submitted to a reverse phase HPLC purification (MeOH/water/TFA; column: PHENOMENEX® Luna, 30×100 mm S10 Axia) to retrieve the TFA salts of GW2 (light yellow foam; 50 mg). ¹H NMR (MeOD, δ=3.30 ppm, 400 MHz): 8.00-7.75 (m, 9H), 5.71 (app br m, 0.2H), 5.40 (d, J=6.3, 0.45H), 5.15-5.11 (m, 0.87H), 5.00-4.96 (m, 0.92H), 4.81-4.68 (m, 1.56H), 4.26-4.03 (m, 2H), 3.71/3.70/3.64/3.63 (four 's', 6H), 2.77-1.87 (m, 9.24H), 1.65-1.48 (overlapped 'm' and 'd', 4.66H), 1.28 (d, J=0.62H), 1.17 (d, J=6.3H, 1.23H), 1.06-0.82 (m, 12.15H). LC (Cond. 2a and 2b): >95% homogeneity index. LC-MS (Cond. 1a): RT=2.46 min. LC-MS Anal. Calcd. for [M+H]⁺ $C_{42}H_{54}ClN_8O_5$: 801.39. found 801.41.

Example GW2-1

Example GW2-1 (TFA salt) was prepared from pyrrolidine GW2b and (S)-2-(methoxycarbonylamino)-2-(tetrahydro-2H-pyran-4-yl)acetic acid according to the procedure described for the preparation of Example GW2.

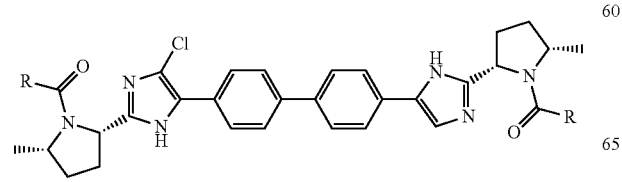

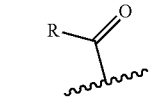

| Example | | RT (LC-Cond.); % homogeneity index; MS data |
|---|---|---|
| GW2-1 | 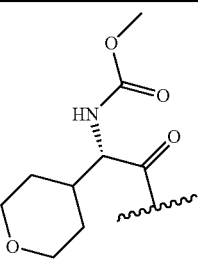 | 2.23 min (Cond. 1a); >98%; LC-MS: Anal. Calcd. for [M + H]⁺ $C_{46}H_{58}ClN_8O_8$: 885.41; found 885.37 |

Example GW3

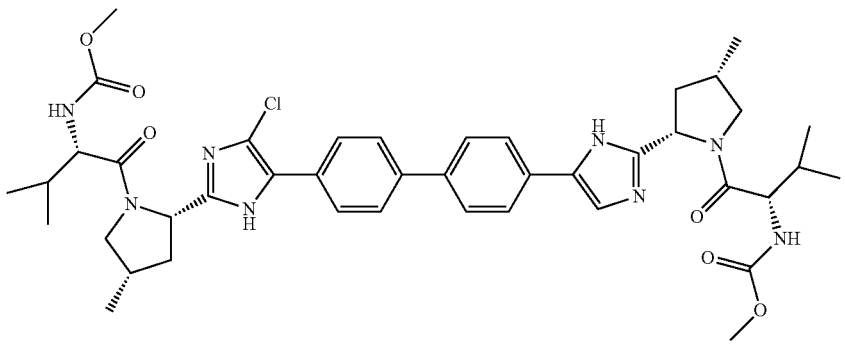 [SMILES: COC(=O)N[C@H](C(=O)N1C[C@@H](C)C[C@H]1c1ncc(-c2ccc(-c3ccc(-c4[nH]c([C@@H]5C[C@H](C)CN5C(=O)[C@@H](NC(=O)OC)C(C)C)nc4Cl)cc3)cc2)[nH]1)C(C)C]

Example GW3

Step a

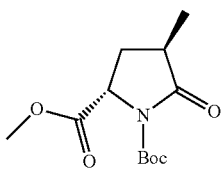

GW3a-1

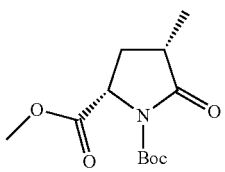

GW3a-2

GW3a-3

The above three esters were prepared from (S)-1-tert-butyl 2-methyl 5-oxopyrrolidine-1,2-dicarboxylate according to the procedure described in *Tetrahedron Letters,* 3203-3205 (2003).

Example GW3

Step b

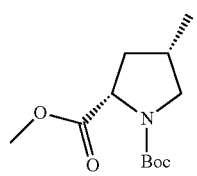

Borane-methyl sulfide complex (5.44 mL, 10.88 mmol) was added to a solution of ester GW3a-2 (1.4 g, 5.44 mmol) in THF (25 mL), and the reaction mixture was heated at 40° C. for 7 hr. The volatile component was removed in vacuo and the residue was partitioned between EtOAc and water (50 mL each). The aqueous layer was extracted with EtOAc (30 mL), and the combined organic phase was dried with $Na_2SO_4$, and concentrated in vacuo. The resultant colorless oil was purified with a flash chromatography (0-50% EtOAc/Hexane) to afford ester GW3b as a colorless oil (0.77 g). $^1$H NMR ($CDCl_3$, δ=7.24 ppm, 400 MHz): 4.29-4.18 (m, 1H), 3.78-3.66 (m, 4H), 2.99 (app t, J=10.1, 1H), 2.43-2.97 (m, 1H), 2.43-2.37 (m, 1H), 2.30-2.18 (m, 1H), 1.60-1.52 (m, 1H), 1.47/1.42 (two 's', 9H), 1.08-1.05 (m, 3H).

Example GW3

Step c

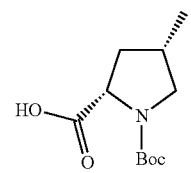

To a solution of ester GW3b (1.69 g, 6.95 mmol) in ethanol (10 mL) was added solution of LiOH (0.250 g, 10.42 mmol) in water (5.00 mL), and the reaction mixture was stirred at room temperature for 5 hr. The organic solvent was evaporated in vacuo and the residue was diluted with water (10 mL) and washed with ether (10 mL). It was chilled in ice-water bath, and acidified to a pH range of ~2 with 1N HCl. It was then extracted with EtOAc (20 mL, 3×). The organic layer was dried with $Na_2SO_4$ and concentrated in vacuo to afford acid GW3c as a colorless oil, which became a white solid upon extended exposure to high vacuum (1.38 g). $^1$H NMR ($CDCl_3$, δ=7.24 ppm, 400 MHz): 4.39-4.22 (m, 1H), 3.80-3.69 (m, 0.91H), 3.59-3.35 (m, 0.18H), 3.03-2.89 (m, 0.91H), 2.51-2.22 (m, 2H), 1.98-1.91 (m, 0.71H), 1.68-1.60 (0.29H), 1.50/1.44 (two 's', 9H), 1.09 (app m, 3H).

Example GW3

Step d

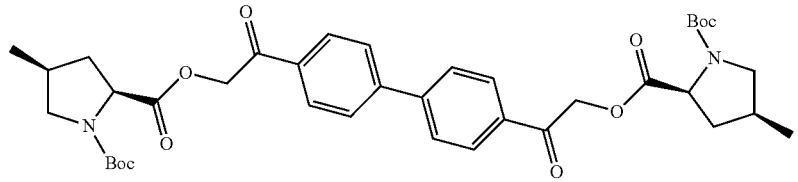

To a suspension of GW3c (1.83 g, 7.98 mmol) and 1,1'-(biphenyl-4,4'-diyl)bis(2-bromoethanone) (1.581 g, 3.99 mmol) in $CH_3CN$ (30 mL) was added DIEA (1.436 mL, 8.22 mmol), and the mixture was stirred at room temperature for 4 hr. Solvent was evaporated in vacuo and the residue was partitioned between EtOAc and water (50 mL each). The organic layer was washed with sat. $NaHCO_3$ (20 mL), dried with $Na_2SO_4$, and concentrated in vacuo to afford diester GW3d as light yellow solid (2.67 g), which was used as is for the next step.

Example GW3

Step e

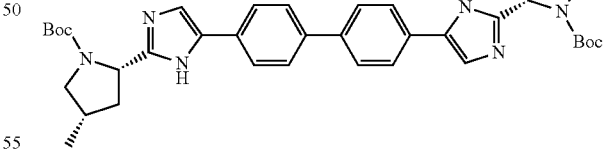

To a solution of diketoester GW3d (2.67 g, 3.85 mmol) in xylenes (30 mL) was added ammonium acetate (2.97 g, 38.5 mmol), and the mixture was heated at 140° C. for 6 hr in a sealed tube. The volatile component was removed in vacuo and the residue was partitioned between DCM (50 mL) and water (50 mL). The organic layer was washed with sat. $NaHCO_3$ (20 mL), dried with $Na_2SO_4$, and concentrated in vacuo. The resulting crude material was purified with a flash chromatography (50-100% EtOAc/Hexane, 100% EtOAc-10% MeOH/EtOAc)) to afford imidazole GW3e as orange solid (1.3 g). $^1$H NMR (DMSO-d$_6$, δ=2.5 ppm, 400 MHz): 12.21-11.87 (three br s, 2H), 7.82-7.51 (m, 9.2H), 7.30 (m, 0.6H), 6.88-6.81 (m, 0.2H), 4.9-4.67 (m, 1.81H), 3.98-3.93 (m, 0.19H), 3.77-3.54 (m, 2H), 3.07-2.76 (m, 2H), 2.43-2.04 (m, 4H), 1.80-1.56 (m, 2H), 1.41-1.33 (m, 8H), 1.10-1.04 (m, 16H). LC-MS (Cond. 1a): RT=2.09 min. LC-MS Anal. Calcd. for [M+H]$^+$ C$_{38}$H$_{49}$N$_6$O$_4$: 653.38. found 653.51.

Example GW3

Step f

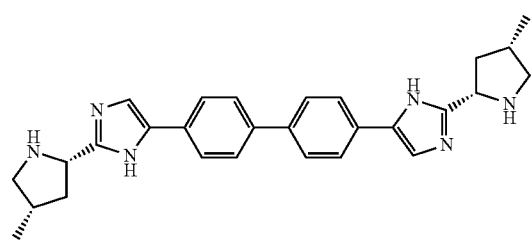

4Cl

4N HCl in dioxane (12.10 mL, 48.4 mmol) was added to carbamate GW3e (1.3 g, 1.99 mmol) and the mixture was stirred at room temperature for 5 hr. The volatile component was removed in vacuo, and the product was dried under vacuum overnight to afford HCl salt of pyrrolidine GW3f as a yellow solid (1.14 g). $^1$H NMR (DMSO-d$_6$, δ=2.5 ppm, 400 MHz): 10.32 (app br s, 2H), 9.79 (app br s, 2H), 8.13 (s, 2H), 8.02 (d, J=8.3, 4H), 7.99 (d, J=8.3, 4H), 5.01 (br m, 2H), 3.47 (br m, 2H), 3.05 (br m, 2H), 2.62 (m, 2H), 2.45 (m, 2H), 2.21 (m, 2H), 1.13 (d, J=6.3, 6H). LC-MS (Cond. 1a): RT=2.09 min. LC-MS Anal. Calcd. for [M+H]$^+$ C$_{28}$H$_{33}$N$_6$: 453.28. found 453.17.

Example GW3

Step g

To a suspension of the HCl salt of pyrrolidine GW3f (1.14 g, 1.905 mmol), (S)-2-(methoxycarbonylamino)-2-(tetrahydro-2H-pyran-4-yl)acetic acid (0.488 g, 2.248 mmol) and (S)-2-(methoxycarbonylamino)-3-methylbutanoic acid (0.407 g, 2.324 mmol) in DMF (15 mL) was added DIEA (1.996 mL, 11.43 mmol). Total dissolution was effected with the help of sonication, and then HATU (1.478 g, 3.89 mmol) was added, and the reaction mixture was stirred at room temperature for 2 hr. Most of the volatile component was removed in vacuo and the residue was dissolved in MeOH and submitted to a reverse phase HPLC purification (MeOH/water/TFA; column: PHENOMENEX® Luna, 30×100 mm S10 Axia) to afford TFA salts of three products: GW3g-1 (0.28 g), GW3g-2 (0.64 g) and GW3g-3 (0.36 g) as light yellow foam. Product GW3g-3: $^1$H NMR (DMSO, δ=2.5 ppm, 400 MHz): 14.74 (app br s, not integratable), 8.16 (s, 2H), 7.97 (d, J=8.6, 4H), 7.88 (d, J=8.3, 4H), 7.29 (d, J=8.0, <2H), 5.23 (br m, 0.1H), 5.07 (dd, J=10.6, 7, 1.9H), 4.18 (m, 2H), 4.09 (m, 2H), 3.53 (s, 6H), 3.39 (m, 2H), 2.56-2.35 ('m' partially overlapped with solvent signal, 2H), 1.95 (m, 2H), 1.82 (m, 2H), 1.13 (d, J=6.3, 6H), 0.79 (d, J=6.5, 6H), 0.76 (d, J=6.5, 6H) [Note: the last three integrations include minor rotamers with signals in the 1.1-0.85 ppm region that were not peak-picked]. LC-MS (Cond. 1a): RT=1.79 min. LC-MS Anal. Calcd. for [M+H]$^+$ C$_{42}$H$_{55}$N$_8$O$_6$: 767.42. found 767.30. Product GW3g-1, LC-MS (Cond. Ia): RT=1.62 min. LC-MS Anal. Calcd. for [M+H]$^+$ C$_{46}$H$_{59}$N$_8$O$_8$: 851.45. found 851.33. Product GW3g-2, LC-MS (Cond. 1a): RT=1.70 min. LC-MS Anal. Calcd. for [M+H]$^+$ C$_{44}$H$_{57}$N$_8$O$_7$: 809.44. found 809.30.

Example GW3

To a solution of GW3g-3/2TFA (160 mg, 0.174 mmol) in DMF (2 mL) was added NCS (30.6 mg, 0.229 mmol). The mixture was heated to 50° C. for 5.5 hr. The residue was dissolved in MeOH and submitted to a reverse phase HPLC purification (MeOH/water/TFA; column. PHENOMENEX® Luna, 30×100 mm S10 Axia) to retrieve the TFA salts of GW3 as light yellow foam (40 mg). [Note: for analogous cases the chlorination was conducted on a starting material that was in a free base form.] $^1$H NMR (MeOD, δ=3.30 ppm, 400 MHz):

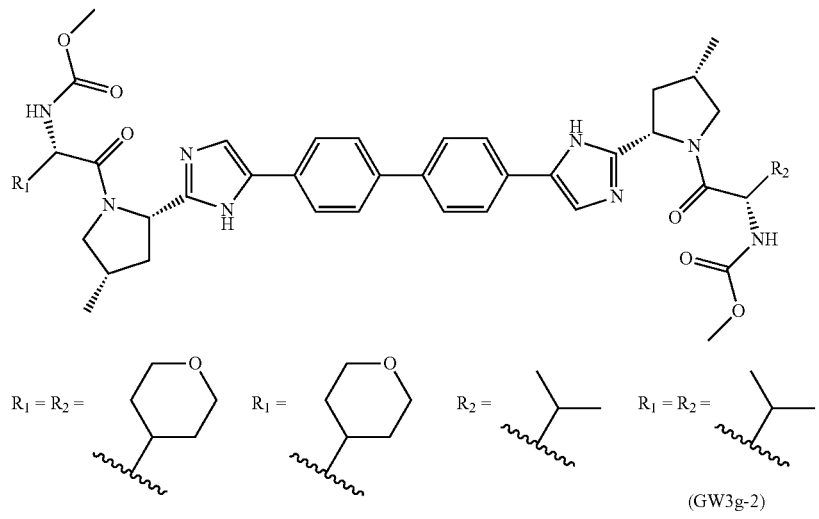

7.88 (s, 1H), 7.84-7.76 (m, 8H), 5.19 (dd, J=11.1, 7.1, 1H), 4.98 (dd, J=10.4, 7.3, 1H), 4.32 (m, 1H), 4.24-4.17 (m, 3H), 3.63 (s, 3H), 3.62 (s, 3H), 3.40-3.33 (m, 2H), 2.65 (m, 1H), 2.50 (m, 2H), 2.37 (m, 1H), 1.99 (m, 2H), 1.82 (m, 2H), 1.22 (d, J=6.3, 2.85H), 1.18 (d, J=6.3, 2.85H), 1.09 (m, 0.3H), 0.92-0.85 (m, 12H). LC (Cond. 2a and 2b): >95% homogeneity index. LC-MS (Cond. Ia): RT=2.32 min. LC-MS Anal. Calcd. for [M+H]+ $C_{42}H_{54}ClN_8O_6$: 801.39. found 801.25.

Example GW4

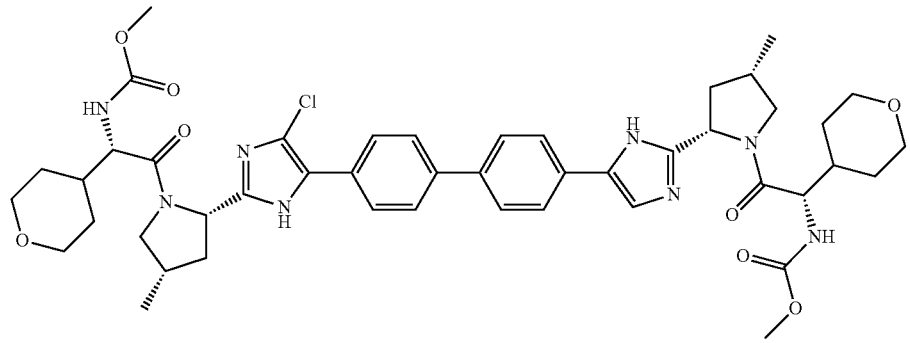 [SMILES: COC(=O)N[C@H](C(=O)N1C[C@@H](C)C[C@H]1c1ncc(-c2ccc(-c3ccc(-c4[nH]c([C@@H]5C[C@H](C)CN5C(=O)[C@@H](NC(=O)OC)C5CCOCC5)nc4Cl)cc3)cc2)[nH]1)C1CCOCC1]

Example GW4 (TFA salt) was prepared from GW3g-1 according to the procedure described for the preparation of Example GW3. LC (Cond. 2a and 2b): >95% homogeneity index. LC-MS (Cond. Ia): RT=2.17 min (Cond. 1a). LC-MS: Anal. Calcd. for [M+H]+ $C_{46}H_{58}ClN_8O_8$: 885.41. found 885.26.

Examples GW5 to GW7 and submitted to a reverse phase HPLC purification (ACN/TFA/Water, Water-SunFire 30×100 mm S5) to retrieve the TFA salts of Example GW5, GW6 and GW7. Example GW5: $^1$H NMR (MeOD, δ=3.30 ppm, 400 MHz): 7.74 (m, 8H), 5.02 (m, 2H), 4.29-4.18 (m, 4H), 3.90 (m, 2H), 3.63 (s, 6H), 3.41-3.33 (m, 4H), 2.52 (m, 2H), 2.39 (br m, 2H), 2.01-1.79 (m, 4H), 1.58-1.27 (m, 4H), 1.18 (d, J=6.5, 5.63H), 1.09 (m, 0.37H), 0.93 (d, J=6.8, 3H), 0.88 (d, J=6.5, 3H). LC (Cond. 2a and 2b): >95% homogeneity index. LC-MS (Cond. 1a): RT=2.81 min. LC-MS Anal. Calcd. for [M+H]+ $C_{44}H_{55}Cl_2N_8O_7$: 877.36. found 877.30. Example GW6: $^1$H NMR (MeOD, δ=3.30 ppm, 400 MHz): 7.86 (s, 1H), 7.82-7.73 (m, 8H), 5.19 (dd, J=11, 7, 1H), 4.98 (dd, J=10.4, 7.3, 1H), 4.33-4.19 (m, 4H), 3.90 (m, 2H), 3.67 (m, 0.35H), 3.63/3.62 (two overlapped 's', 5.65H), 3.41-3.31 (m, 4H), 2.65 (m, 1H), 2.49 (m, 2H), 2.38 (m, 1H), 2.00-1.79 (m, 4H), 1.57-1.27 (m, 4H), 1.22/1.18 (two overlapping 'd', J=6.5/6.3, respectively, 5.69H), 1.09 (m, 0.31H), 0.90/0.86 (two overlapping 'd', J=6.8/6.8, 6H). LC (Cond. 2a and 2b): >95% homogeneity index. LC-MS (Cond. Ia): RT=2.25 min. LC-MS Anal. Calcd. for [M+H]+ $C_{44}H_{56}ClN_8O_7$: 843.40. found 843.24. Example GW7: $^1$H NMR (MeOD, δ=3.30 ppm, 400 MHz): 7.87-7.75 (m, 9H), 5.19 (dd, J=11.7.0, 1H), 4.99 (dd, J=10.3, 7.3, 1H), 4.38-4.17 (m, 4H), 3.90 (m, 2H), 3.64/3.62 (two 's', 6H), 3.41-3.26 ('m' partially overlapped with solvent signal, 4H), 2.64 (m, 1H), 2.50 (m, 2H), 2.37 (m, 1H), 2.03-1.79 (m, 4H), 1.60-1.08 (m, 10H), 0.92 (d, J=6.8, 3H), 0.86 (d, J=6.8, 3H). LC (Cond. 2a and 2b): >95% homogeneity index. LC-MS (Cond. 1a): RT=2.24 min. LC-MS Anal. Calcd. for [M+H]+ $C_{44}H_{56}ClN_8O_7$: 843.40. found 843.24.

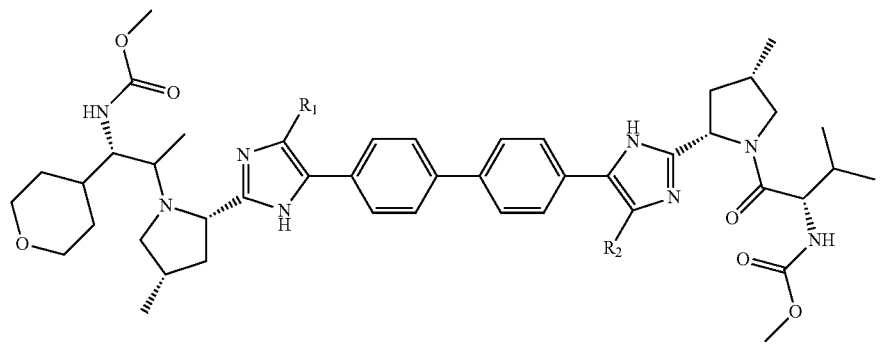

GW-5 (R$_1$ = R$_2$ = Cl)
GW-6 (R$_1$ = H, R$_2$ = Cl)
GW-7 (R$_1$ = Cl, R$_2$ = H)

To a solution of GW3g-2 (565 mg, 0.588 mmol) in DMF (2 mL) was added NCS (0.021 g, 0.161 mmol), and the reaction mixture was heated at 50° C. for 17 hr. Most of the volatile component was removed in vacuo and the residue was dissolved in MeOH and submitted to a reverse phase HPLC purification (MeOH/water/TFA; column: PHENOMENEX® Luna, 30×100 mm S10 Axia) to afford two fractions (one is GW5 and the second one is mixture of GW6 and GW7). The fractions were dried by in vacuo and retrieved as light yellow solid. Both fractions were dissolved separately in methanol

Example GW8

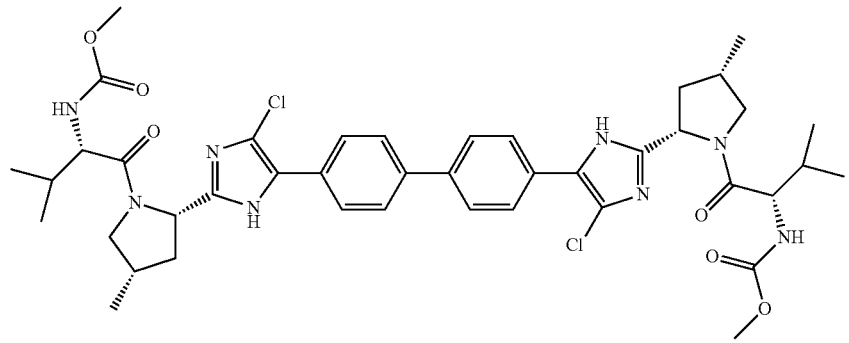 [SMILES: COC(=O)N[C@H](C(=O)N1C[C@@H](C)C[C@H]1c1nc(Cl)c(-c2ccc(-c3ccc(-c4[nH]c([C@@H]5C[C@H](C)CN5C(=O)[C@@H](NC(=O)OC)C(C)C)nc4Cl)cc3)cc2)[nH]1)C(C)C]

Example GW8

Step a

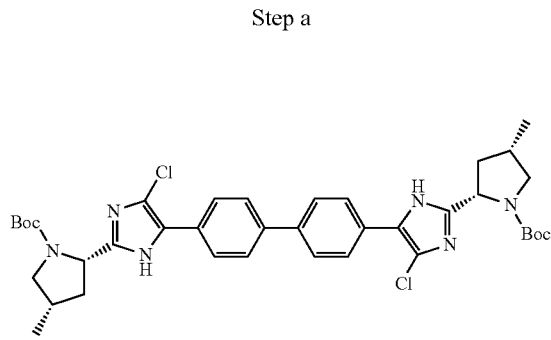

To a solution of GW3e (0.360 g, 0.551 mmol) in DMF (9 mL) was added NCS (0.096 g, 0.717 mmol), and the reaction mixture was heated at 50° C. for 15 hr. The residue was diluted with MeOH and submitted to a reverse phase HPLC purification (MeOH/water/TFA; column. PHENOMENEX® Luna, 30×100 mm S10 Axia) to retrieve the TFA salt of carbamate GW8a as light yellow foam (20 mg). TFA salts of GW3e (60 mg) and the mono-chloro analog (70 mg) were also isolated. Carbamate GW8a: $^1$H NMR (MeOD, δ=3.30 ppm, 400 MHz): 7.83 (app s, 8H), 4.95-4.79 ('m' partially overlapped with HOD signal, 2H), 3.85-3.75 (m, 2H), 3.14 (m, 2H), 2.58-2.48 (m, 2H), 2.44-2.30 (m, 2H), 1.80-1.71 (m, 2H), 1.43 (s, 6H), 1.23 (s, 12H), 1.14/1.12 (two overlapping 's', 6H). LC-MS (Cond. Ia): RT=2.98 min. LC-MS Anal. Calcd. for [M+H]$^+$ C$_{38}$H$_{47}$ClN$_6$O$_4$: 721.30. found 721.39.

Example GW8, Step b

4N HCl in dioxane (3 mL) was added to the TFA salt of GW8a (55 mg, 0.063 mmol), and the mixture was stirred at room temperature for 5 hr. Solvent was removed in vacuo and the residue was dried under vacuum overnight to afford the HCl salt of pyrrolidine GW8b as a brown solid (50 mg). LC-MS (Cond. Ia): RT=2.20 min. LC-MS Anal. Calcd. for [M+H]$^+$ C$_{28}$H$_{31}$Cl$_2$N$_6$: 521.20. found 521.20.

Example GW8

To a suspension of the HCl salt of GW8b (50 mg, 0.075 mmol) in DMF (3 mL) was added (S)-2-(methoxycarbonylamino)-3-methylbutanoic acid (28.9 mg, 0.165 mmol), DIEA (0.079 mL, 0.450 mmol), and HATU (58.7 mg, 0.154 mmol), and the mixture was stirred at room temperature for 2 hr. Most of the volatile component was removed in vacuo and the residue was dissolved in MeOH and submitted to a reverse phase HPLC purification (MeOH/water/TFA; column. PHENOMENEX® Luna, 30×100 mm S10 Axia) to retrieve the TFA salts of GW8 (light yellow foam; 40 mg). $^1$H NMR (MeOD, δ=3.30 ppm, 400 MHz): 7.80-7.75 (m, 8H), 5.01 (dd, J=10.4, 7.4, 2H), 4.26-4.17 (m, 4H), 3.63 (s, 6H), 3.38-3.33 (m, 2H), 2.52-2.49 (m, 2H), 2.45-2.33 (m, 2H), 2.03-1.95 (m, 2H), 1.87-1.79 (m, 2H), 1.19 (d, J=6.3, 6H), 0.92 (d, J=6.8, 6H), 0.87 (d, J=6.8, 6H). LC (Cond. 2a and 2b): >95% homogeneity index. LC-MS (Cond. Ia): RT=2.89 min. LC-MS Anal. Calcd. for [M+H]$^+$ C$_{42}$H$_{53}$Cl$_2$N$_8$O$_6$: 835.35. found 835.41.

Examples GW9 and GW10

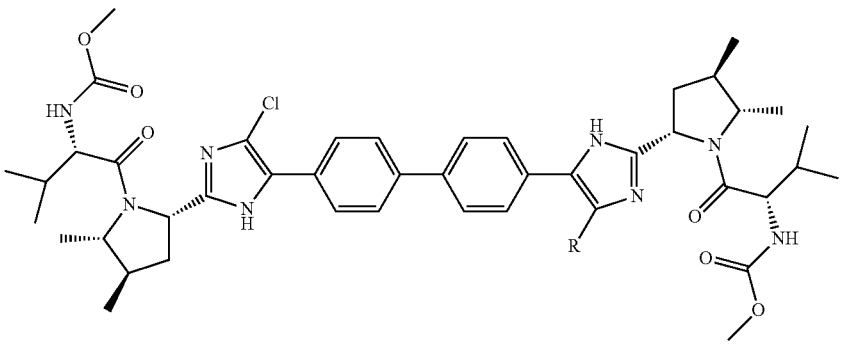

Example GW-9: R = H
Example GW-10: R = Cl

Example GW9

Step a

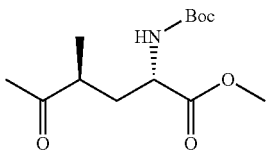 [SMILES: COC(=O)[C@H](C[C@H](C)C(C)=O)NC(=O)OC(C)(C)C]

To a solution of GW3a-2 (1.31 g, 5.09 mmol) in THF (25 mL) was added methylmagnesium bromide (2.037 mL, 6.11 mmol) dropwise at −40° C. (dry ice/acetone bath). It was stirred at the same temperature for 2 hr, and then the bath was removed and stirring was continued for an additional 1 hr. Acetic acid (1 mL), water (10 mL) and ether (50 mL) were added, the mixture was shaken and the organic layer was separated. The organic layer was washed with water, dried with $Na_2SO_4$, and concentrated in vacuo. The resultant crude material was purified with a flash chromatography (5-95% EtOAc/Hexane) to afford ester GW9a as colorless oil (0.6 g). $^1$H NMR (CDCl$_3$, δ=7.24 ppm, 400 MHz): 4.97 (br d, J=8.3, 1H), 4.29 (m, 1H), 3.74/3.73 (overlapping 's', 3H), 2.66 (m, 1H), 2.27-2.22 (m, 0.21H), 2.17 (s, 2.58H), 2.10-2.02 (m, 1.22H), 1.80-1.1.74 (m, 1H), 1.43/1.40 (overlapping 's', 9H), 1.16 (d, J=7.1, 2.6H), 1.05 (d, J=6.8, 0.4H).

Example GW9

Step b

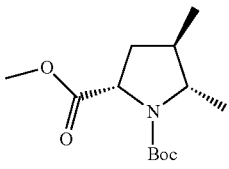
GW-9b-1

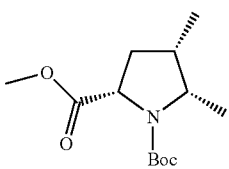
GW-9b-2

To a solution of ketone GW9a (0.6 g, 2.195 mmol) in DCM (15 mL) was added TFA (0.846 mL, 10.98 mmol), and the mixture was stirred at room temperature for 7 hr. The volatile component was removed in vacuo, and dried under vacuum overnight to afford a light yellow oil (0.63 g).

A solution of the above crude product (0.5 g, 1.8 mmol) in methanol (20 mL) was added to a 500 mL Parr shaker bottle containing Pd/C (0.025 g, 0.234 mmol). After evacuation and refilling with nitrogen was conducted (3×), the mixture was shaken under 60 psi for 24 hr. The reaction mixture was filtered through a filter paper and the volatile component was removed in vacuo to afford a light yellow oil (0.41 g).

To a solution of the above crude product (0.48 g, 1.77 mmol) in $CH_2Cl_2$ (7 mL) was added DMAP (10.81 mg, 0.088 mmol), triethylamine (0.740 mL, 5.31 mmol). Di-tert-butyl dicarbonate (0.386 g, 1.77 mmol) was added in portions over 15 min and the mixture was stirred at room temperature for 18 hr. After the volatile component was removed in vacuo, the crude material was purified with a flash chromatography (0-22% EtOAc/Hexane) to afford two major products. The first elute was GW9b-1 (0.54 g). $^1$H NMR (CDCl$_3$, δ=7.24 ppm, 400 MHz) 4.41/4.30 (br m, 1H), 3.74 (s, 3H), 3.48/3.33 (br m, 1H), 2.37-2.22 (m, 0.2H), 2.10-2.04 (m, 0.9H), 1.98-1.19 (m, 0.9H), 1.79 (m, 1H), 1.46-1.32 (m, 12H), 1.05/1.01/0.97 (three overlapping 'd', J=6.8/6.6/6.3, respectively, 3H). The second elute was GW9b-2 contaminated with unidentified impurity (0.48 g). Clean fractions of GW9b-2 was used to acquire the following spectral data: $^1$H NMR (CDCl$_3$, δ=7.24 ppm, 400 MHz) 4.23-4.12 (two overlapping 'dd', 1H), 4.00-3.85 (two overlapping 'm', 1H), 3.72/3.71 (overlapping 's', 3H), 2.34-2.20 (m, 2H), 1.69-1.55 (1H), 1.45/1.39 (overlapping 's', 9H), 1.13-1.01 (m, 3.13H), 0.97 (d, J=6.3, 2.87H).

Example GW9

Step c

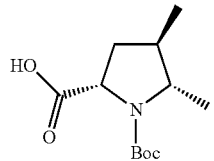

To a solution of GW9b-1 (3.73 g, 14.50 mmol) in ethanol (40 mL) was added solution of LiOH (0.417 g, 17.39 mmol) in water (20.00 mL), and the mixture was stirred at room temperature for 6 hr. More LiOH (0.1 g, 4.3 mmol) was added, and stirring was continued for an additional 2 hr. Most of the organic component was evaporated, and the remaining portion was washed with ether (20 mL). The aqueous layer was chilled with ice-water bath, acidified with 1N HCl to a pH of 2-3, extracted with EtOAc (50 mL, 4×), dried with $Na_2SO_4$, and concentrated to afford a colorless oil, which became a white solid upon exposure to high vacuum (3.43 g). The solid was dissolved in a minimum amount of EtOAc with the help of heating gun that brought it to a refluxing condition. After cooling down to room temperature, 5 drops of hexane were added and allowed to stand at ambient temperature overnight to afford acid GW9c as white needles, which was filtered and washed with hexane, dried under vacuum (2.02 g). $^1$H NMR (CDCl$_3$, δ=7.24 ppm, 400 MHz) 4.40 (app dd, J=8.3, 2.8, 1H), 3.30 (br m, 1H), 2.50 (br m, 1H), 2.01-1.93 (m, 1H), 1.68-1.59 (m, 1H), 1.52 (s, 9H), 1.29 (d, J=6.0, 3H), 1.07 (d, J=6.8, 3H).

Example GW9

Step d

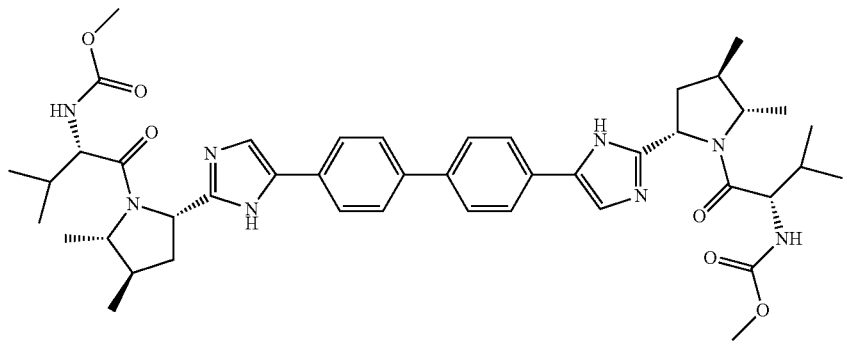 [SMILES: COC(=O)N[C@H](C(=O)N1[C@H](c2ncc(-c3ccc(-c4ccc(-c5cnc([C@@H]6C[C@@H](C)[C@H](C)N6C(=O)[C@@H](NC(=O)OC)C(C)C)[nH]5)cc4)cc3)[nH]2)C[C@@H](C)[C@@H]1C)C(C)C]

Compound GW9d (TFA salt; light yellow foam) was prepared from acid GW9c according to the procedure described for the preparation of precursors GW3g from acid GW3c with the exception that (S)-2-(methoxycarbonylamino)-3-methylbutanoic acid was employed for the final step. $^1$H NMR (MeOD, δ=3.30 ppm, 400 MHz): 7.97-7.96 (m, 2H), 7.88-7.82 (m, 8H), 5.70 (br d, J=6.7, 0.6H), 5.29 (dd, J=10.3, 1.2H), 5.19-5.14 (m, 0.2H), ~4.90 (overlapped with HOD signal, 1H), 4.38 (m, 1H), 4.12-4.06 (m, 2H), 3.71/3.67/3.64 (overlapping 's', 6H), 2.73-2.68 (m, 0.6H), 2.53-2.45 (m, 1.4H), 2.35-2.18 (m, 2.5H), 2.07-1.82 (m, 3.5H), 1.53 (d, J=6.8, 3.6H), 1.40 (d, J=7.1, 0.5H), 1.30 (d, J=7.1, 1.9H), 1.17-0.83 (collection of overlapping 'd', 18H). LC (Cond. 2a and 2b): >95% homogeneity index. LC-MS (Cond. Ia): RT=2.07 min. LC-MS Anal. Calcd. for [M+H]$^+$ $C_{44}H_{59}N_8O_6$: 795.46. found 795.44.

Examples GW9 and GW10

To a solution of GW9d (TFA salt; 310 mg, 0.328 mmol) in DMF (6 mL) was added NCS (62.5 mg, 0.468 mmol), and the mixture was heated at 50° C. for 9 hr. Most of the volatile component was removed in vacuo and the residue was dissolved in MeOH and submitted to a reverse phase HPLC purification (MeOH/water/TFA; column. PHENOMENEX® Luna, 30×100 mm S10 Axia) to separate the mono- and di-chloro products. The mono-chlorinated product was further purified with a different reverse phase HPLC condition (ACN/TFA/Water, Water-SunFire 30×100 mm S5). Example GW9 (light yellow foam; 36 mg) and Example GW10 (light yellow foam; 60 mg) were retrieved as TFA salts. Example GW9: $^1$H NMR (DMSO, δ=2.50 ppm, 400 MHz): 12.71-12.64 (br m, 1H), 8.10 (br s, 1H), 7.95-7.83 (m, 8H), 7.64-7.58 (m, 1.4H), 7.51 (d, J=8.6, 0.6H), 5.56 (m, 0.22H), 5.33 (m, 0.33H), 5.16 (m, 0.78H), 5.04 (m, 0.67H), 4.27-4.11 (m, 2H), 3.93-3.86 ('m' overlapped with H$_2$O signal, 2H), 3.56-3.53 (m, 6H), 2.62-1.64 (collection of 'm', 8H), 1.50-0.75 (collection of 'd', 24H). LC (Cond. 2a and 2b): >95% homogeneity index. LC-MS (Cond. Ia): RT=2.66 min. LC-MS Anal. Calcd. for [M+H]$^+$ $C_{44}H_{58}ClN_8O_6$: 829.42. found 829.44. Example GW10: $^1$H NMR (DMSO, δ=2.50 ppm, 400 MHz): 12.7 (br m, 2H), 8.00-7.80 (m, 8H), 7.63 (m, 0.76H), 7.51 (d, J=8.6, 1.09H), 7.08 (m, 0.09H), 6.57 (m, 0.05H), 5.33 (d, J=6.3, 0.74H), 5.05 (app t, 1.26H), 4.25-4.12 (m, 2H), 3.90-3.85 ('m' overlapped with H$_2$O signal, 2H), 3.58-3.49 (m, 6H), 2.59-2.55 (m, 0.5H), 2.33-2.13 (m, 2.7H), 1.98-1.88 (m, 4.05H), 1.71-1.63 (m, 0.75H), 1.43 (d, J=6.6, 3.7H), 1.18 (d, J=6.3, 2.05H), 1.05-0.76 (collection of 'd', 18.25H). LC (Cond. 2a and 2b): >95% homogeneity index. LC-MS (Cond. Ia): RT=3.29 min. LC-MS Anal. Calcd. for [M+H]$^+$ $C_{44}H_{52}Cl_2N_8O_6$: 863.38. found 863.38.

Examples GW11 and GW12

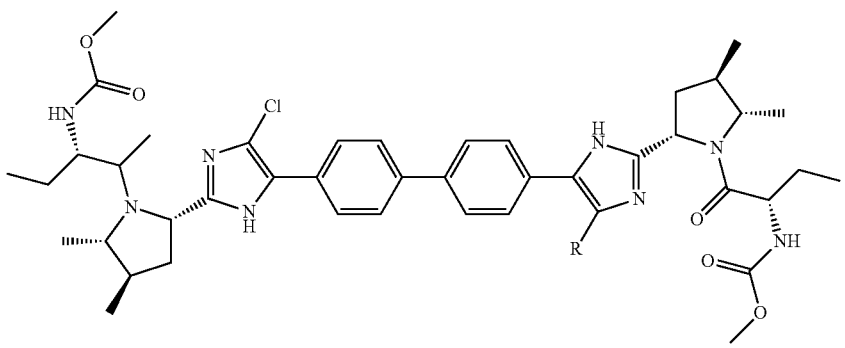

Example GW11: R = H
Example GW12: R = Cl

Examples GW11 and GW12 were prepared according to the procedure described for the preparation of Examples GW9 and GW10 with the exception that (S)-2-(methoxycarbonylamino)butanoic acid was used in place of (S)-2-(methoxycarbonylamino)-3-methylbutanoic acid. Example GW11 (TFA salt): LC-MS (Cond. Ia): RT=2.57 min. LC-MS Anal. Calcd. for [M+H]$^+$ $C_{42}H_{54}ClN_8O_6$: 801.39. found 801.38. Example GW12 (TFA salt): LC-MS (Cond. Ia): RT=3.24 min. LC-MS Anal. Calcd. for [M+H]$^+$ $C_{42}H_{53}Cl_2N_8O_6$: 835.35. found 835.31.

Examples OL1 and OL2

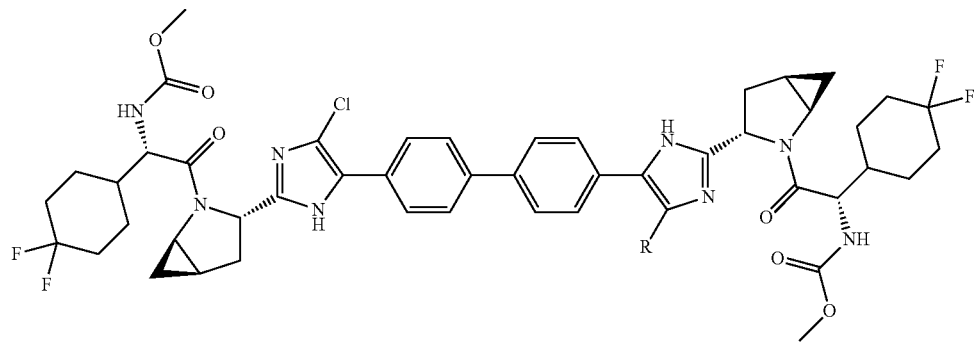

Example-1: R = H
Example-2: R = Cl

Example OL1

Step a

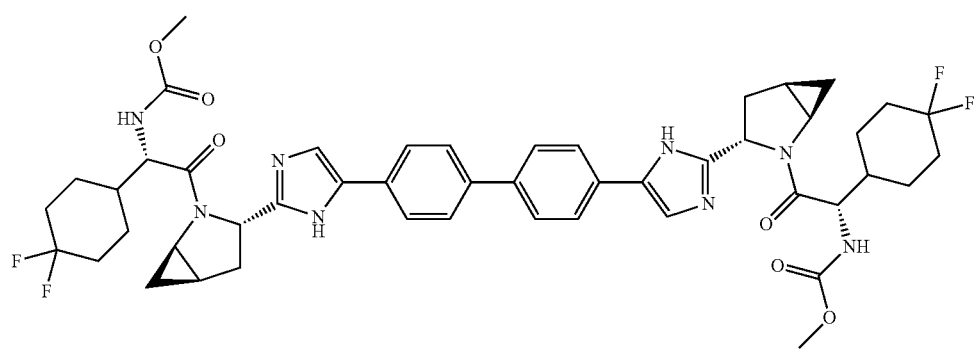 [SMILES: COC(=O)N[C@H](C(=O)N1[C@@H]2C[C@@H]2C[C@H]1c1ncc(-c2ccc(-c3ccc(-c4cnc([C@@H]5C[C@H]6C[C@H]6N5C(=O)[C@@H](NC(=O)OC)C5CCC(F)(F)CC5)[nH]4)cc3)cc2)[nH]1)C1CCC(F)(F)CC1]

Pyrrolidine 1e/4HCl (455 mg, 0.766 mmol), (S)-2-(4,4-difluorocyclohexyl)-2-(methoxycarbonylamino)acetic acid (385 mg, 1.532 mmol), HATU (612 mg, 1.609 mmol) and DIEA (0.803 mL, 4.60 mmol) were combined in DMF (30 mL) and the resulting yellow solution was stirred at ambient temperature for 3 h. Solvent was removed under reduced pressure and the residue was re-dissolved in methanol and purified by preparatory HPLC. (Solvent A: 10% Acetonitrile/ 90% water/10 mM NH$_4$OAc; Solvent B: 90% Acetonitrile/ 10% water/10 mM NH$_4$OAc; Column: SunFire Prep MS C18 30×150 mm S10; Wavelength: 220 nM; Flow rate: 40 ml/min; Gradient: 10% B to 75% B over 30 mM with a 30 min hold time). An off-white solid corresponding to product OL1a (0.37 g, 0.396 mmol) was recovered. $^1$H NMR (500 MHz, DMSO-d$_6$) δ ppm 11.67-12.26 (2H, m), 7.80 (4H, d, J=7.93 Hz), 7.67-7.76 (1 H, m), 7.65 (4H, d, J=8.24 Hz), 7.54 (2H, s), 7.23-7.35 (2H, m), 5.07 (2H, dd, J=8.24, 3.66 Hz), 4.54 (2H, t, J=7.93 Hz), 3.62 (2H, d, J=4.27 Hz), 3.55 (6H, s), 2.36 (2H, t, J=10.99 Hz), 2.20-2.30 (2H, m), 2.01 (4H, br. s.), 1.57-1.85 (9H, m), 1.19-1.53 (6H, m), 0.92-1.08 (2H, m), 0.71 (2H, br. s.). LC (Cond. OL3): R$_t$=0.79 mM. LC-MS: Anal. Calcd. for [M+H]$^+$ $C_{48}H_{55}F_4N_8O_6$: 915.42. found: 915.8. HPLC purity assessment (Cond. OL4a): R$_t$=23.12 min, homogeneity index=98.4%.

Examples OL1 and OL2

NCS (6.83 mg, 0.051 mmol) was added to a solution of amide OL1a (39 mg, 0.043 mmol) in DMF (2 mL) and the resulting mixture was heated to 50° C. for 5 h. The reaction mixture was then purified by preparatory HPLC. Solvent A: 10% MeOH/90% water/0.1% TFA; Solvent B: 90% MeOH/ 10% water/0.1% TFA; Column: SunFire Prep MS C18 30×100 mm 5u; Wavelength: 220 nM; Flow rate: 40 ml/min; Gradient: 0% B to 75% B over 30 min with a 2 min hold time. After concentration of the fractions the TFA salts of Example OL1 (15 mg) and Example OL2 (16 mg) were isolated. Example OL1: $^1$H NMR (500 MHz, DMSO-d$_6$) δ ppm 8.11 (1H, s), 7.74-8.00 (8H, m), 7.40 (1 H, d, J=8.55 Hz), 7.28 (1H, d, J=8.24 Hz), 4.91-5.05 (2H, m), 4.48-4.59 (2H, m), 3.74-3.87 (2H, m), 3.62-3.71 (1H, m), 3.55 (3H, s), 3.54 (3H, s), 2.19-2.43 (6H, m), 1.66-2.07 (19H, m), 1.56 (1H, d, J=10.38 Hz), 1.26-1.48 (5H, m), 0.89-1.02 (2 H, m), 0.81 (1H, s), 0.70 (1H, br. s.). LC (Cond. OL3): $R_f$=0.87 min. LC-MS: Anal. Calcd. For [M+H]$^+$ C$_{48}$H$_{54}$ClF$_4$N$_8$O$_6$: 949.38. found: 949.6. HPLC purity assessment (Cond. OL4a): $R_t$=9.16 min, homogeneity index=94.7%. Example OL2: $^1$H NMR (500 MHz, DMSO-d$_6$) δ ppm 7.86 (4H, d, J=8.55 Hz), 7.79 (4H, d, J=8.24 Hz), 7.29 (2 H, d, J=8.55 Hz), 4.95 (2H, dd, J=8.55, 4.88 Hz), 4.52 (2H, t, J=7.63 Hz), 3.67 (2H, t, J=4.58 Hz), 3.54 (6H, s), 2.21-2.40 (4H, m), 2.01 (4H, br. s.), 1.67-1.95 (13H, m), 1.27-1.46 (4H, m), 0.94-1.02 (2H, m), 0.70 (2H, d). LC (Cond. OL3): $R_f$=1.01 min. LC-MS: Anal. Calcd. For [M+H]$^+$ C$_{48}$H$_{53}$Cl$_2$F$_4$N$_8$O$_6$: 983.34. found: 983.7. HPLC purity assessment (Cond. OL4a): $R_t$=12.25 min, homogeneity index=94.7%.

Examples OL3 to OL5

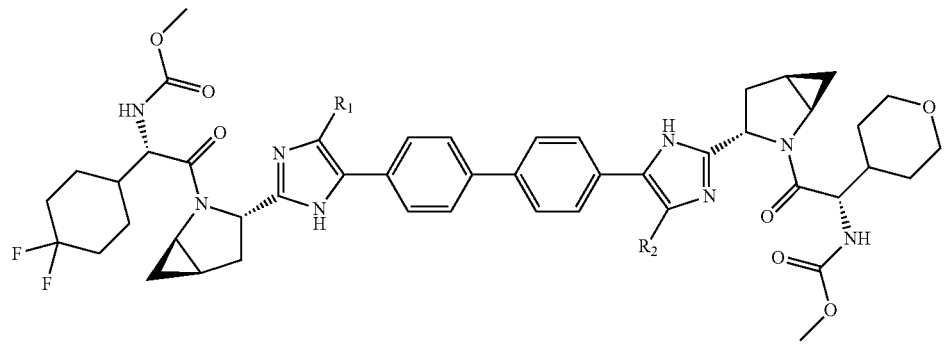

Example OL3: R$_1$ = R$_2$ = Cl
Example OL4: R$_1$/R$_2$ = Cl/H ⎤ Regiochemistry was
Example OL5: R$_1$/R$_2$ = Cl/H ⎦ not determined Example OL3

Step a

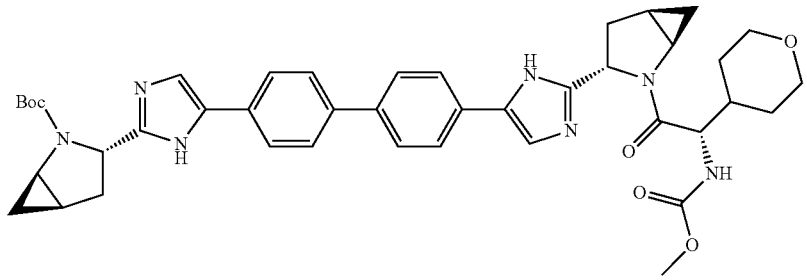

Pyrrolidine V9a (207 mg, 0.377 mmol), (S)-2-(methoxycarbonylamino)-2-(tetrahydro-2H-pyran-4-yl)acetic acid (82 mg, 0.377 mmol), HATU (158 mg, 0.415 mmol) and DIEA (0.132 mL, 0.755 mmol) were combined in DMF (5 mL) and the resulting yellow solution was stirred at ambient temperature for 3 hr. The mixture was purified by preparatory HPLC. Solvent A: 10% MeOH/90% water/0.1% TFA; Solvent B: 90% MeOH/10% water/0.1% TFA; Column: SunFire Prep MS C18 30×100 mm 5u; Wavelength: 220 nM; Flow rate: 40 mil/min; Gradient: 20% B to 80% B over 30 min. with a 2 min hold time. A white solid corresponding to the TFA salt of carbamate OL3a (0.19 g) was recovered [Note: carbamate OL3a and V9b are the same besides their form status]. $^1$H NMR (500 MHz, DMSO-d$_6$) δ ppm 8.18 (1H, br. s.), 8.12 (1H, s), 7.80-8.00 (8H, m), 7.34 (1H, d, J=8.55 Hz), 5.01 (1H, t, J=8.09 Hz), 4.79-4.90 (1H, m), 4.49 (1H, t, J=7.48 Hz), 3.74-3.87 (3H, m), 3.55 (4H, s), 3.18-3.32 (2H, m), 2.52-2.59 (2H, m), 2.37 (2H, ddd, J=19.99, 13.43, 6.26 Hz), 2.07 (1H, br. s.), 1.92 (1H, dt, J=13.20, 6.68 Hz), 1.73 (1H, ddd, J=13.20, 6.49, 6.26 Hz), 1.06-1.52 (17H, m), 0.80 (2H, br. s.), 0.74 (1H, br. s.). LC (Cond. OL1): R$_f$=1.98 min. LC-MS: Anal. Calcd. For [M+H]$^+$ C$_{42}$H$_{50}$N$_2$O$_6$: 748.38. found: 748.52.

Example OL3

Step b

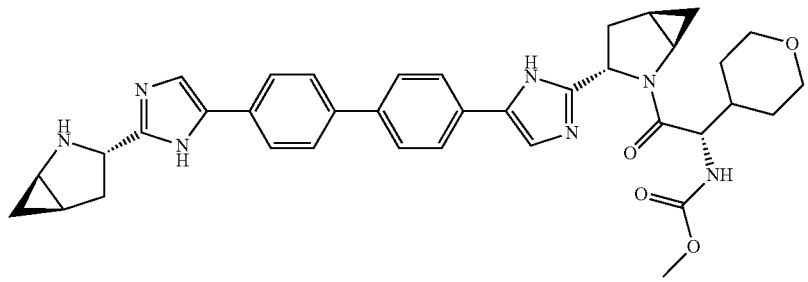 [SMILES: COC(=O)N[C@H](C(=O)N1[C@@H]2C[C@@H]2C[C@H]1c1ncc(-c2ccc(-c3ccc(-c4cnc([C@@H]5C[C@H]6C[C@H]6N5)[nH]4)cc3)cc2)[nH]1)C1CCOCC1]

Carbamate OL3a (0.19 g, 0.195 mmol) was dissolved in CH$_2$Cl$_2$ (15 mL) and charged with 4N HCl in dioxanes (3 mL, 12.00 mmol). The resulting suspension was stirred at ambient temperature for 2 h and volatiles were removed under reduced pressure. A yellowish solid corresponding to the HCl salt (3×) of pyrrolidine OL3b (0.12 g) was recovered and used without further purification. $^1$H NMR (500 MHz, DMSO-d$_6$) δ ppm 8.14 (1H, s), 7.83-8.01 (10H, m), 7.34 (1H, d, J=8.55 Hz), 5.06 (1H, t, J=7.93 Hz), 4.73 (1H, t, J=8.24 Hz), 4.50 (1H, t, J=7.48 Hz), 3.78-3.87 (3H, m), 3.64-3.74 (2H, m), 3.56 (3H, s), 3.44-3.51 (1H, m), 3.39-3.44 (1H, m), 3.20-3.35 (2H, m), 2.55-2.64 (2H, m), 2.34-2.43 (1H, m), 2.06-2.16 (1H, m), 1.87-1.97 (2H, m), 1.27-1.51 (4H, m), 1.12 (1H, d, J=4.58 Hz), 0.90-0.98 (1H, m), 0.82-0.89 (1H, m), 0.78 (1H, br. s.). LC (Cond. OL2): R$_f$=2.51 min. LC-MS: Anal. Calcd. For [M+H]$^+$ C$_{37}$H$_{42}$N$_7$O$_4$: 648.33. found: 648.4.

Example OL3

Step c

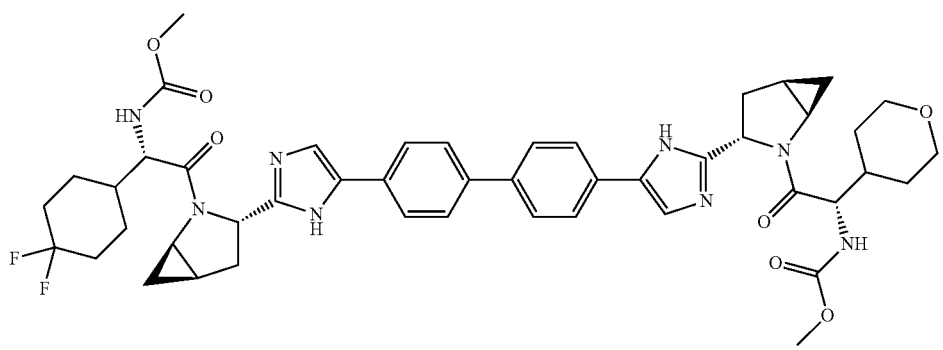 [SMILES: COC(=O)N[C@H](C(=O)N1[C@@H]2C[C@@H]2C[C@H]1c1ncc(-c2ccc(-c3ccc(-c4cnc([C@@H]5C[C@H]6C[C@H]6N5C(=O)[C@@H](NC(=O)OC)C5CCC(F)(F)CC5)[nH]4)cc3)cc2)[nH]1)C1CCOCC1]

(S)-2-(4,4-Difluorocyclohexyl)-2-(methoxycarbonylamino)acetic acid (87 mg, 0.345 mmol), the HCl salt (3×) of pyrrolidine OL3b (261 mg, 0.345 mmol), HATU (144 mg, 0.379 mmol) and DIEA (0.301 mL, 1.724 mmol) were combined in DMF (10 mL) and the resulting brownish solution was stirred at ambient temperature for 2 h. Sample was purified directly by preparatory HPLC. Solvent A: 10% MeOH/90% water/0.1% TFA; Solvent B: 90% MeOH/10% water/0.1% TFA; Column: SunFire Prep MS C18 30×100 mm 5u; Wavelength: 220 nM; Flow rate: 40 mil/min; Gradient: 30% B to 70% B over 30 min with a 2 min hold time. A white solid corresponding to the TFA salt (2×) of amide OL3c (132 mg, 0.117 mmol, 33.8% yield) was recovered. $^1$H NMR (500 MHz, DMSO-d$_6$) δ ppm 11.68-12.18 (2H, m), 7.78 (3H, t, J=8.39 Hz), 7.73 (1H, d, J=9.46 Hz), 7.66 (4H, d, J=8.55 Hz), 7.54 (2H, dd, J=4.12, 1.68 Hz), 7.28 (2H, dd, J=19.68, 8.39 Hz), 5.08 (2H, ddd, J=8.39, 4.12, 3.97 Hz), 4.46-4.58 (2H, m), 3.82-3.94 (2H, m), 3.61-3.67 (2H, m), 3.54 (6H, d, J=1.53 Hz), 3.24 (2H, t, J=11.29 Hz), 2.33-2.41 (2H, m), 2.21-2.31 (2H, m), 1.91-2.08 (4H, m), 1.75-1.89 (6H, m), 1.58 (1H, d, J=13.43 Hz), 1.40-1.52 (2H, m), 1.26-1.40 (3H, m), 0.97-1.07 (2H, m), 0.67-0.79 (2H, m). LC (Cond. OL1): R$_f$=1.94 min. LC-MS: Anal. Calcd. For [M+H]$^+$ C$_{47}$H$_{55}$N$_8$O$_7$: 881.42. found: 881.58.

Examples OL3 to OL5

NCS (22.66 mg, 0.170 mmol) was added to a solution of the TFA salt of Example OL3c (115 mg, 0.131 mmol) in DMF (3 mL) and the resulting mixture was heated to 50° C. for 5 h. The mixture was purified by preparatory HPLC. Solvent A: 05% MeCN/95% water/10 mM NH$_4$Ac; Solvent B: 95% MeCN/5% water/10 mM NH$_4$Ac; Column: SunFire Prep MS C18 30×100 mm S10; Wavelength: 220 nM; Flow rate: 35 ml/min; Gradient: 10% B to 100% B over 30 min with a 2 min hold time. Two fractions were isolated, where the first elute corresponded to a mixture of mono-chlorinated analogs (Examples OL4 and OL5) and the second one corresponded to the bis-chlorinated analog (Example OL3). After concentration of the corresponding fractions, the mixture was re-dissolved in methanol and the monochlorinated regioisomers were separated by preparatory HPLC. Solvent A: 10% Acetonitrile/90% water/0.1% TFA; Solvent B: 90% Acetonitrile/10% water/0.1% TFA; Column: PHENOMENEX® Luna 21×100 mm S10; Wavelength: 220 nM; Flow rate: 25 ml/min; Gradient: 10% B to 50% B over 60 min. with a 2 min hold time. Two fractions corresponding to Example OL4 and Example OL5 were isolated as TFA and that their relative regiochemistry was not determined.

Example OL3 (36 mg) was recovered as a white solid. $^1$H NMR (500 MHz, DMSO-d$_6$) δ ppm 12.55 (2H, d, J=1.22 Hz), 7.87 (4H, d, J=8.24 Hz), 7.78 (4H, d, J=7.02 Hz), 7.27 (2H, dd, J=18.62, 8.55 Hz), 5.76 (1H, s), 4.91-5.01 (2H, m), 4.45-4.58 (2H, m), 3.85 (2H, d, J=9.77 Hz), 3.64-3.71 (2H, m), 3.54 (6H, s), 3.20-3.31 (2H, m), 2.21-2.35 (4H, m), 2.02 (3H, d, J=3.97 Hz), 1.59-1.93 (9H, m), 1.21-1.55 (7H, m), 0.93-1.02 (2H, m), 0.71 (2H, m). LC (Cond. OL3): R$_t$=0.95 min. LC-MS: Anal. Calcd. For [M+H]$^+$ C$_{47}$H$_{53}$Cl$_2$F$_2$N$_8$O$_7$: 949.34. found: 949.8. HPLC purity assessment (Cond. OL4b): R$_t$=11.10 min, homogeneity index=100%.

Example OL4 (10 mg) was recovered as a white solid. $^1$H NMR (500 MHz, DMSO-d$_6$) δ ppm 14.62 (1H, br. s.), 12.59 (1H, br. s.), 8.12 (1H, br. s.), 7.87 (8H, dd, J=19.38, 8.09 Hz), 7.80 (2H, d, J=7.63 Hz), 7.40 (1H, d, J=8.85 Hz), 7.26 (1H, d, J=8.24 Hz), 5.00 (1H, t, J=7.93 Hz), 4.95 (1H, dd, J=8.39, 5.04 Hz), 4.54 (1H, t, J=7.48 Hz), 4.49 (1H, t, J=7.93 Hz), 3.86 (3H, dd, J=11.44, 2.59 Hz), 3.79 (1H, br. s.), 3.65-3.72 (2H, m), 3.55 (6H, d, J=5.19 Hz), 3.19-3.28 (2H, m), 2.20-2.43 (4H, m), 1.89-2.07 (5H, m), 1.30-1.89 (10H, m), 0.92-1.03 (2H, m), 0.80 (1H, br. s.), 0.72 (1 H, br. s.) LC (Cond. OL3): R$_t$=0.85 min. LC-MS: Anal. Calcd. For [M+H]$^+$ C$_{47}$H$_{54}$ClF$_2$N$_8$O$_7$: 915.38. found: 915.9. HPLC purity assessment (Cond. OL4a): R$_t$=9.03 min, homogeneity index=100%. Example OL5 (12 mg, 7.96% yield) was recovered as a white solid. $^1$H NMR (500 MHz, DMSO-d$_6$) δ ppm 14.62 (1H, br. s.), 12.59 (1H, br. s.), 8.09 (1H, br. s.), 7.87-7.98 (4H, m), 7.84 (2H, d, J=8.24 Hz), 7.80 (2H, d, J=8.24 Hz), 7.35 (1H, d, J=8.24 Hz), 7.29 (1H, d, J=8.55 Hz), 4.91-5.03 (2H, m), 4.51 (2H, ddd, J=15.64, 7.71, 7.48 Hz), 3.78-3.90 (4H, m), 3.64-3.71 (1H, m), 3.54 (6H, s), 3.16-3.31 (2H, m), 2.19-2.44 (3H, m), 2.02 (3H, br. s.), 1.64-1.95 (7H, m), 1.27-1.54 (6H, m), 0.96 (2H, dd, J=12.21, 7.32 Hz), 0.81 (1H, br. s.), 0.70 (1H, br. s.). LC (Cond. OL3): R$_t$=0.86 min. LC-MS: Anal. Calcd. For [M+H]$^+$ C$_{47}$H$_{54}$ClF$_2$N$_8$O$_7$: 915.38. found: 915.9. HPLC purity assessment (Cond. OL4a): R$_t$=8.11 min, homogeneity index=100%.

Example OL6

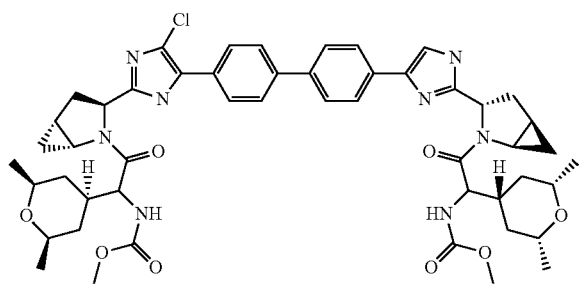

Example OL6 (TFA salt) can be prepared starting from pyrrolidine V1b/4HCl and Cap-179 (Enantiomer-1) according to the procedure described for the synthesis of Example V1. $^1$H NMR (400 MHz, DMSO-d$_6$) δ ppm 8.11 (1H, br. s.), 7.74-8.01 (8H, m), 7.22-7.35 (1H, m), 7.14 (1H, d, J=7.53 Hz), 4.87-5.15 (2H, m), 4.47 (2H, d, J=7.03 Hz), 3.80 (1H, br. s.), 3.65 (1H, br. s.), 3.55 (6H, br. s.), 3.36 (4H, br. s.), 2.20-2.37 (3H, m), 2.13 (1H, br. s.), 1.90-2.05 (2H, m), 1.85 (1H, br. s.), 1.63-1.80 (1H, m), 1.38-1.61 (2H, m), 0.62-1.14 (25H, m). LC (Cond. 2a and 2b): >95% homogeneity index. LC (Cond. OL4c): R$_t$=0.85 min. LC-MS: Anal. Calcd. for [M+H]$^+$ C$_{50}$H$_{62}$ClN$_8$O$_8$: 937.44. found: 937.5.

Example OL7

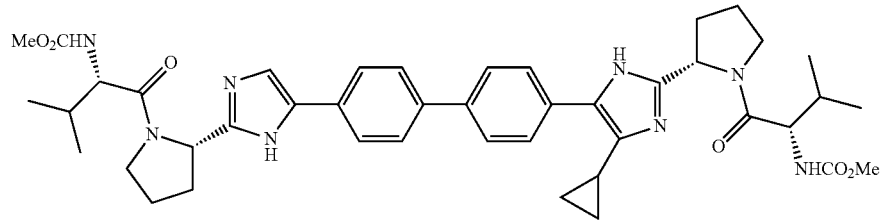

Example OL7

Step a

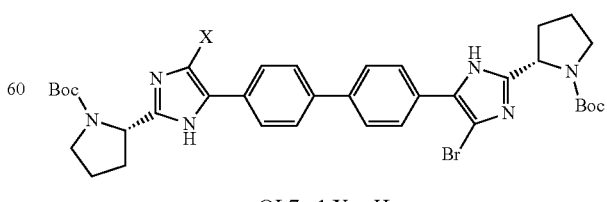

OL7a.1 X = H
OL7a.2 X = Br

To a solution of (2S,2'S)-tert-butyl 2,2'-(5,5'-(biphenyl-4,4'-diyl)bis(1H-imidazole-5,2-diyl))dipyrrolidine-1-carboxylate (500 mg, 0.800 mmol) in AcOH (30 mL) was added bromine (0.041 mL, 0.800 mmol) in AcOH (0.8 mL) dropwise over 10 min. The resulting reaction mixture was stirred at room temperature overnight, neutralized with sat. NaHCO$_3$, then extracted with CH$_2$Cl$_2$. The organic layers was dried with MgSO$_4$ and concentrated in vacuo. The resultant crude material was purified by flash chromatography (silica gel; 1:1 EtOAc/Hex then 2:1 EtOAc/Hex) to afford bromide OL7a.1 (200 mg) and dibromide OL7a.2 (140 mg) as white solids (note: the dibromide eluted first from column).

Example OL7

Step b.1

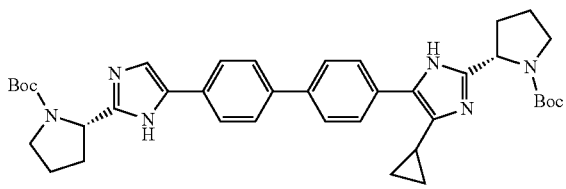 [SMILES: CC(C)(C)OC(=O)N1CCC[C@H]1c1ncc(-c2ccc(-c3ccc(-c4[nH]c([C@@H]5CCCN5C(=O)OC(C)(C)C)nc4C4CC4)cc3)cc2)[nH]1]

A mixture of cyclopropylboronic acid (13.49 mg, 0.157 mmol), potassium phosphate tribasic (90 mg, 0.423 mmol) in water (0.03 mL) was stirred at room temperature for 15 min. Bromide OL7a.1 (85 mg, 0.121 mmol), Pd(II) acetate (2.71 mg, 0.012 mmol), tricyclohexylphosphine (6.8 mg, 0.024 mmol) and toluene (1 mL) were then added, and the reaction mixture was stirred at 110° C. overnight. The volatile component was removed in vacuo and the residue was purified by preparative HPLC using the following condition. Column: Waters SunFire OBD 19×100 mm S5; Solvent A=10% ACN-90% H$_2$O-0.1% TFA; Solvent B=90% ACN-10% H$_2$O-0.1% TFA; Start % B=10; Final % B=75; Flow rate=20 ml/min; Gradient time=20 min. The TFA salt of the coupled product OL7b.1 was retrieved as a light yellow solid (79 mg).

Example OL7

Step b.2

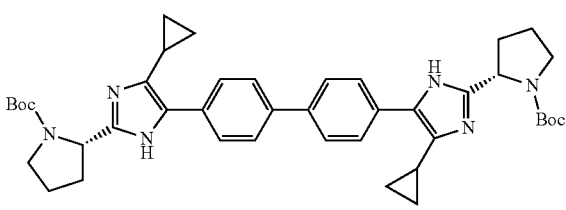 [SMILES: CC(C)(C)OC(=O)N1CCC[C@H]1c1nc(C2CC2)c(-c2ccc(-c3ccc(-c4[nH]c([C@@H]5CCCN5C(=O)OC(C)(C)C)nc4C4CC4)cc3)cc2)[nH]1]

A mixture of dibromide OL7a.2 (140 mg, 0.179 mmol), cyclopropylboronic acid (40.0 mg, 0.465 mmol), Pd(II) acetate (8.03 mg, 0.036 mmol), potassium phosphate tribasic (266 mg, 1.252 mmol), tricyclohexylphosphine (20.07 mg, 0.072 mmol) in toluene (1.5 mL) and Water (0.05 mL) was heated with a microwave at 110° C. for 1.5 hours. LCMS showed that there is no reaction. The mixture was filtered, and the filtrate was concentrated in vacuo and the resultant crude product was purified by prep. HPLC: Column=Waters SunFire OBD 19×100 mm S5; Solvent A=10% ACN-90% H$_2$O-0.1% TFA; Solvent B=90% ACN-10% H$_2$O-0.1% TFA; Start % B=10. Final % B=70; Flow rate=20 ml/min; Gradient time=20 min. The TFA salt of the coupled product OL7b.2 was obtained as a light yellow solid.

Example OL7

Step c

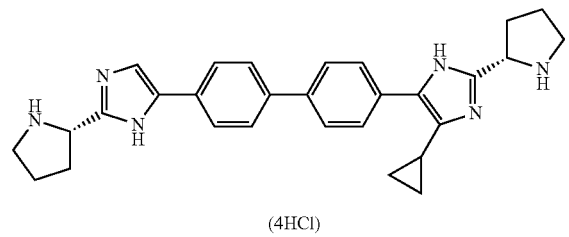 [SMILES: c1cc(-c2cnc([C@@H]3CCCN3)[nH]2)ccc1-c1ccc(-c2[nH]c([C@@H]3CCCN3)nc2C2CC2)cc1]

(4HCl)

To a solution of carbamate OL7b prepared above (79 mg) in CH$_2$Cl$_2$ (2 mL) was added HCl (2 mL, 8.00 mmol) (4 N in dioxane), and the resulting mixture was stirred at room temperature for 30 mins. The volatile component was removed in vacuo to afford the HCl salt of OL7c (69 mg), which was used in the next step without further purification.

Example OL7

To a mixture of (S)-2-(methoxycarbonylamino)-3-methylbutanoic acid (20.09 mg, 0.115 mmol), pyrrolidine OL7/4HCl (35 mg, 0.057 mmol) in DMF (1 mL) was added DiPEA (0.06 mL, 0.34 mmol) and HATU (43.6 mg, 0.115 mmol). The reaction mixture was stirred at room temperature for 1 hour, and then ammonia (2 mL, 2 M in Methanol) was added, and stirring was continued for an additional 1 hour. The volatile component was removed in vacuo, and the residue was purified by preparative HPLC: Column=Waters SunFire C18 19×100 mm 5u; Solvent A=10% MeOH-90% H$_2$O-0.1% TFA; Solvent B=90% MeOH-10% H$_2$O-0.1% TFA; Start % B=10; Final % B=75; Flow rate=25 ml/min; Gradient time=18 min. The TFA salt of Example OL7 was obtained as an off-white solid (24 mg). Rt=1.68 min (Cond. OL5a). (M+H)$^+$779.47. $^1$H NMR (500 MHz, DMSO-d$_6$) δ ppm 8.12 (1H, br. s.), 7.97 (4H, dd, J=12.97, 8.39 Hz), 7.86-7.92 (2H, m), 7.80 (2H, d, J=8.24 Hz), 7.32 (2H, t, J=8.70 Hz), 5.14 (1H, t, J=7.02 Hz), 5.05 (1H, t, J=7.48 Hz), 4.12 (2H, t, J=6.71 Hz), 3.76-3.92 (4H, m), 3.54 (6H, s), 2.39 (2H, d, J=6.10 Hz), 1.95-2.21 (9H, m), 1.08 (2H, d, J=8.24 Hz), 0.84 (7 H, t, J=7.17 Hz), 0.79 (6H, d, J=6.41 Hz), 0.67-0.74 (1H, m)

Examples OL8 to OL14

Examples OL8 to OL14 were prepared as TFA salts by employing appropriate precursors and the procedure described for the preparation of Example OL7.

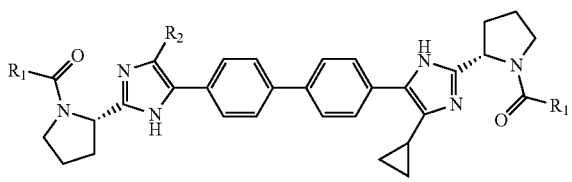

Example OL8-OL10

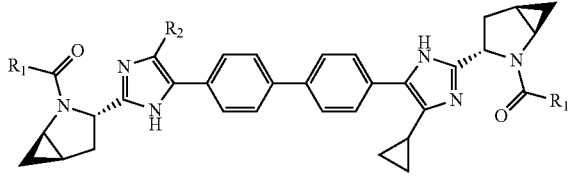

Example OL11-OL14

| Example |  | R₂ | Rt(Condition). LC-MS (M + H)⁺ observed |
|---|---|---|---|
| OL8 | 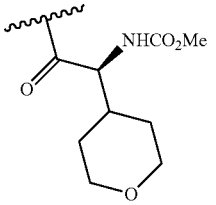 | H | Rt = 1.49 min (Cond. OL5a). (M + H)⁺ 863.48 |
| OL9 | 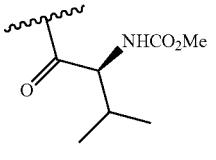 |  | Rt = 1.77 min (Cond. OL5a). (M + H)⁺ 819.55 |
| OL10 | 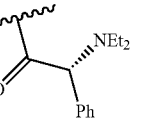 |  | Rt = 1.54 min (Cond. OL5a). (M + H)⁺ 883.51 |
| OL11 | 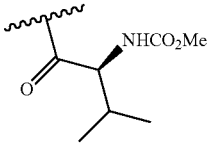 | H | Rt = 1.74 min (Cond. OL5a). (M + H)⁺ 803.41 |
| OL12 |  | H | Rt = 2.40 min (Cond. OL5b). (M + H)⁺ 887.60 |
| OL13 | 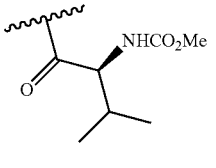 |  | Rt = 1.87 min (Cond. OL5a). (M + H)⁺ 843.39 |
| OL14 |  |  | Rt = 2.55 min (Cond. OL5b). [(M + H)/2]⁺ = 464.36 |

Example OL15

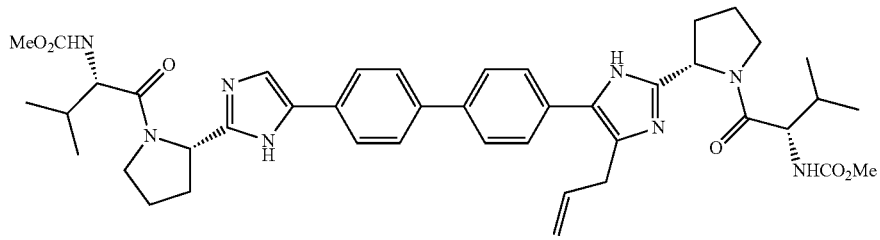

Example OL15

Step a

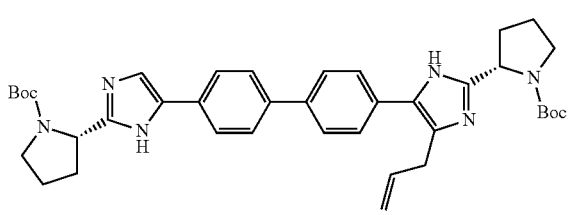 [SMILES: C=CCc1nc([C@@H]2CCCN2C(=O)OC(C)(C)C)[nH]c1-c1ccc(-c2ccc(-c3cnc([C@@H]4CCCN4C(=O)OC(C)(C)C)[nH]3)cc2)cc1]

A mixture of bromide OL7a.1 (200 mg, 0.284 mmol), CsF (0.021 mL, 0.568 mmol), Pd(Ph₃P)₄ (19.71 mg, 0.017 mmol) and 2-allyl-4,4,5,5-tetramethyl-1,3,2-dioxaborolane (0.107 mL, 0.568 mmol) in THF (3 mL) was heated at 140° C. in microwave for 1 hour. The solvent was removed in vacuo, and the residue was purified by preparative HPLC. Column, PHENOMENEX® Luna 10u (30×100 mm); Solvent A=5% CH₃CN-95% H₂O-10 mmNH₄Oac; Solvent B=95% CH₃CN-5% H₂O-10 mmNH₄OAc; Start % B=30; Final % B=100; Flow rate=25 ml/min; Gradient time=48 min. Product OL15a was obtained as a white solid (90 mg).

Example OL15

Carbamate OL15a was elaborated to the TFA salt of Example OL15 according to the procedure described for the synthesis of Example OL7. Rt=1.73 min (Cond. OL5a). (M+H)⁺779.53.

Example OL16

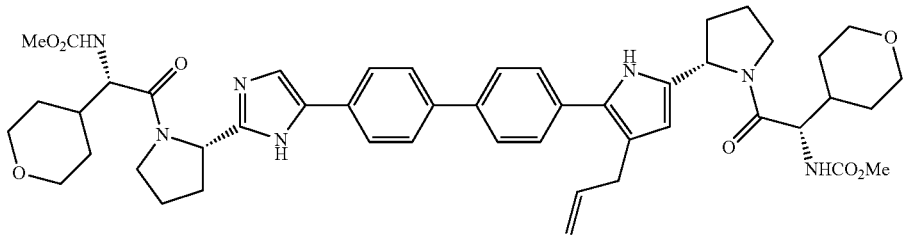

Example OL16 (TFA salt) was prepared from appropriate precursors according to the procedure described for the synthesis of Example OL15. Rt=1.73 min (Cond. OL5a). (M+H)⁺863.11.

Examples OL17 and OL18

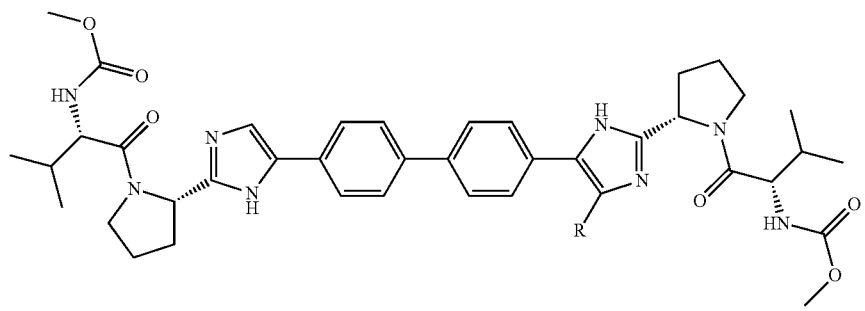

To a solution of OL15a (70 mg, 0.105 mmol), diiodomethane (0.102 mL, 1.263 mmol) in toluene (0.5 mL) at 0° C. was quickly added diethylzinc (1.263 mL, 1.263 mmol) (1 M in heptane). The resulting mixture was stirred at 0° C. for 1.5 hour then at room temperature for 4 hours. To the mixture was added a saturated aqueous NaHCO$_3$ solution and the mixture was extracted with CH$_2$Cl$_2$. The combined organic layers were dried under MgSO$_4$ and concentrated. The residue was purified by preparatory HPLC: Column, PHENOMENEX® Luna 10u (30×100 mm); Solvent A=5% CH$_3$CN-95% H$_2$O-10 mm NH$_4$Oac; Solvent B=95% CH$_3$CN-5% H$_2$O-10 mmNH$_4$OAc; Start % B=30; Final % B=100; Flow rate=25 ml/min. Gradient time=25 min. The resultant material (white solid, 40 mg) was dissolved in CH$_2$Cl$_2$ (1 mL) and treated with HCl (1 mL, 4.00 mmol) (4 N in dioxane). The mixture was stirred at room temperature for 1 hour. The volatile component was removed in vacuo to afford a product (35 mg), which was coupled with (S)-2-(methoxycarbonylamino)-3-methylbutanoic acid according to the procedure described for the synthesis of Example OL7. The obtained crude residue was purified by preparative HPLC: Column=Waters SunFire C18 19×100 mm Su; Solvent A=10% MeOH-90% H$_2$O-0.1% TFA; Solvent B=90% MeOH-10% H$_2$O-0.1% TFA; Start % B=20; Final % B=85; Flow rate=25 ml/min; Gradient time=27 min. Two fractions were isolated, where the first one to elute corresponded to the TFA salt of Example OL18 (Rt=1.74 min (Cond. OL5a). (M+H)$^+$793.54) and the second one to elute corresponded to the TFA salt of Example OL17 (Rt=1.77 min (Cond. OL5a). (M+H)$^+$793.53).

Example OL19 the residue was purified by preparative HPLC using the following condition. Column: PHENOMENEX® Luna 10u (30×100 mm); Solvent A=10% ACN-90% H$_2$O-10 mm NH$_4$OAc; Solvent B=90% ACN-10% H$_2$O-10 mmNH$_4$OAc; Start % B=10; Final % B=80; Flow rate=25 ml/min; Gradient time=15 min. The coupled product OL19a was retrieved as a light yellow solid (120 mg).

Example OL19

Step b

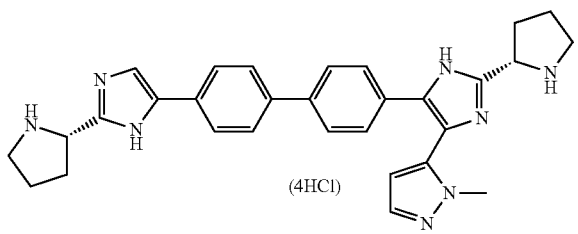

To a solution of carbamate OL19a prepared above (120 mg) in CH$_2$Cl$_2$ (1 mL) was added HCl (1 mL, 4.00 mmol) (4 N in dioxane), and the resulting mixture was stirred at room temperature for 1 h. The volatile component was removed in vacuo to afford the HCl salt of OL19b (87 mg), which was used in the next step without further purification.

Example OL19

To a mixture of (S)-2-(methoxycarbonylamino)-3-methylbutanoic acid (15.30 mg, 0.087 mmol), pyrrolidine OL19b/

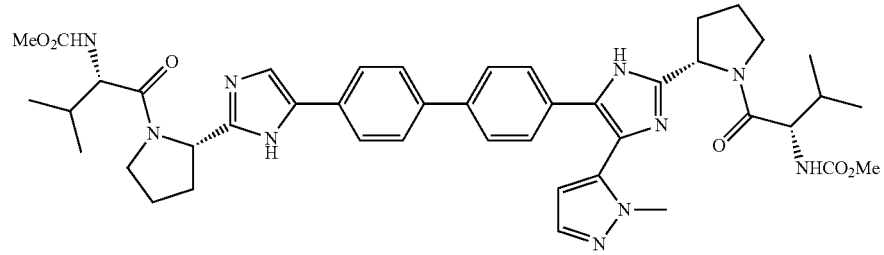

Example OL19

Step a

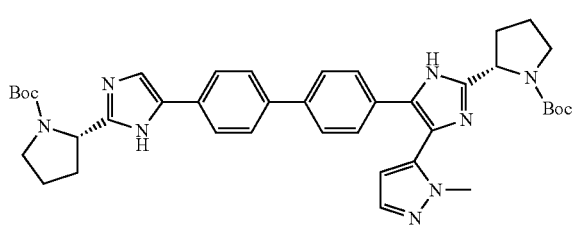 [SMILES: Cn1nccc1-c1nc([C@@H]2CCCN2C(=O)OC(C)(C)C)[nH]c1-c1ccc(-c2ccc(-c3cnc([C@@H]4CCCN4C(=O)OC(C)(C)C)[nH]3)cc2)cc1]

A mixture of 1-methyl-5-(4,4,5,5-tetramethyl-1,3,2-dioxaborolan-2-yl)-1H-pyrazole (59.1 mg, 0.284 mmol), potassium phosphate tribasic (121 mg, 0.568 mmol) in water (0.2 mL) was stirred at room temperature for 15 min. Bromide OL7a.1 (100 mg, 0.142 mmol), Pd(Ph$_3$P)$_4$ (9.85 mg, 0.008 mmol) and DMF (2 mL) were then added, and the reaction mixture was stirred for 40 min. at 130° C. under microwave radiation. The volatile component was removed in vacuo and 4HCl (30 mg, 0.044 mmol) in DMF (1 mL) was added DiPEA (0.053 mL, 0.306 mmol) and HATU (33.2 mg, 0.087 mmol). The reaction mixture was stirred at room temperature for 1 hour, the volatile component was removed in vacuo, and the residue was purified by preparative HPLC: Column=Waters Atlantis OBD 30×100 mm 5u; Solvent A=10% MeOH-90% H$_2$O-0.1% TFA; Solvent B=90% MeOH-10% H$_2$O-0.1% TFA; Start % B=20; Final % B=75; Flow rate=25 ml/min; Gradient time=25 min. The TFA salt of Example OL19 was obtained as a white solid (33 mg). Rt=1.63 min (Cond. OL5a). (M+H)$^+$819.40. $^1$H NMR (500 MHz, DMSO-d$_6$) δ ppm 8.13 (1H, s), 7.88-7.96 (2H, m), 7.78-7.88 (4H, m), 7.57 (1H, br. s.), 7.43-7.51 (2H, m), 7.33 (2H, dd, J=8.39, 3.51 Hz), 6.42 (1H, br. s.), 5.10-5.18 (2H, m), 4.11 (2H, td, J=7.93, 2.75 Hz), 3.78-3.91 (4H, m), 3.59-3.66 (3H, m), 3.54 (6H, d, J=1.53 Hz), 2.35-2.45 (1H, m), 2.30 (1H, d, J=7.32 Hz), 2.13-2.22 (2H, m), 1.93-2.13 (6H, m), 0.89 (5H, d, J=6.71 Hz), 0.83 (6H, t, J=6.87 Hz), 0.78 (3H, d, J=6.71 Hz).

Examples OL20 to OL25

Examples OL20 to OL25 were prepared as TFA salts by employing appropriate precursors and the procedure described for the preparation of Example OL19.

Example OL20-OL23

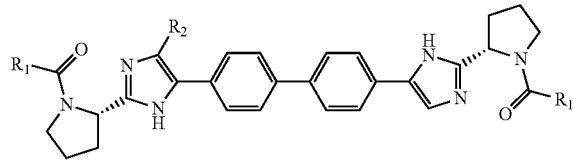

-continued

Example OL24-OL25

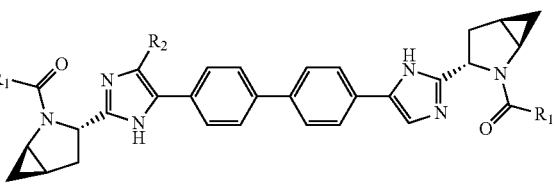

| Example | | R2 | Rt(Condition). LC-MS (M + H)+ observed |
|---|---|---|---|
| OL20 | NHCO2Me, tetrahydropyran | 1-methylpyrazol-5-yl | Rt = 2.19 min (Cond. OL5b). (M + H)+ 903.65 |
| OL21 | NHCO2Me, isopropyl | 1-methylpyrazol-4-yl | Rt = 1.56 min (Cond. OL5a). (M + H)+ 819.39 |
| OL22 | NHCO2Me, isopropyl | 1-methylimidazol-5-yl | Rt = 1.43 min (Cond. OL5a). (M + H)+ 816.66 |
| OL23 | NHCO2Me, tetrahydropyran | 1-methylimidazol-5-yl | Rt = 1.27 min (Cond. OL5a). (M + H)+ 903.61 |
| OL24 | NHCO2Me, isopropyl | isoxazol-4-yl | Rt = 1.83 min (Cond. OL5a). (M + H)+ 830.50 |
| OL25 | NHCO2Me, tetrahydropyran | isoxazol-4-yl | Rt = 1.62 min (Cond. OL5a). [(M + H)/2]+ 457.6 |

Example DSTL-1

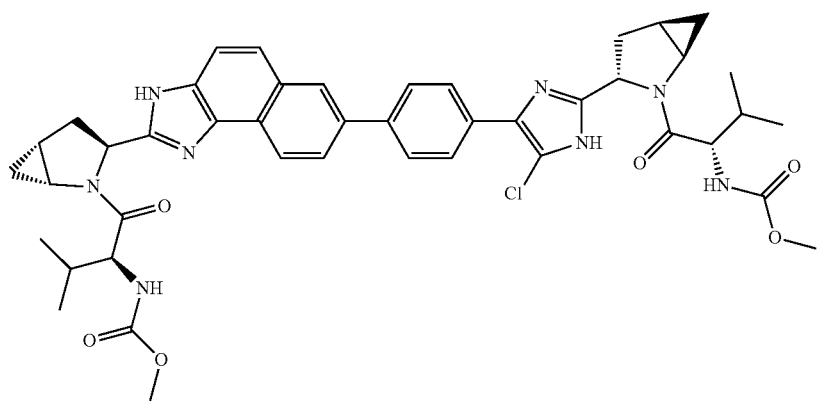 [SMILES: COC(=O)N[C@H](C(=O)N1[C@@H]2C[C@@H]2C[C@H]1c1nc(-c2ccc(-c3ccc4c(ccc5[nH]c([C@@H]6C[C@H]7C[C@H]7N6C(=O)[C@@H](NC(=O)OC)C(C)C)nc54)c3)cc2)c(Cl)[nH]1)C(C)C]

Example DSTL-1

Step a

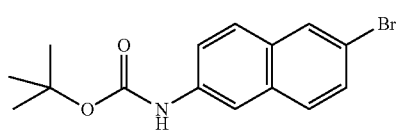 [SMILES: CC(C)(C)OC(=O)Nc1ccc2cc(Br)ccc2c1]

Diphenylphosphoryl azide (17.09 mL, 79 mmol) was added to a solution of 6-bromo-2-naphthoic acid (16.5 g, 65.7 mmol), triethylamine (18.32 mL, 131 mmol), and tert-butylalcohol (7.54 mL, 79 mmol) in toluene (225 mL) and stirred for 4 h at 100° C. The volatiles were removed by rotary evaporation and the residue taken up in EtOAc (500 mL) and washed with water and brine. A precipitate formed upon concentration which was isolated by filtration and washed with 1:1 Et$_2$O/Hex to give Example DSTL-1, Step a (10.5 g). A second crop of less pure product was isolated upon concentration of the mother liquor (9.8 g); combined yield (93%). LC-MS (Cond.-J4): RT=3.44 min. LC-MS Anal. Calcd. for [M+Na]$^+$ C$_{15}$H$_{16}$BrNO$_2$: 345.02. found 345.03.

Example DSTL-1

Step b

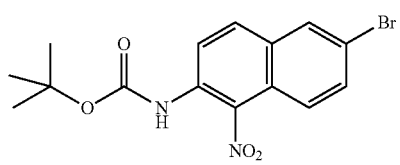 [SMILES: CC(C)(C)OC(=O)Nc1ccc2cc(Br)ccc2c1[N+](=O)[O-]]

Example DSTL-1, Step a (5 g, 15.52 mmol) was diluted in acetic acid (50 mL) and fuming nitric acid (2.3 mL) was added dropwise over 20 min. The reaction was stirred for 2 h and the product, isolated by filtration, was partitioned between DCM and sat'd NaHCO$_3$ soln. The organic layer was concentrated and Example DSTL-1, Step b was obtained 5.7 g (quant). LC-MS (Cond.-J4): RT=3.52 min. LC-MS Anal. Calcd. for [M+Na]$^+$ C$_{15}$H$_{15}$BrN$_2$O$_4$: 390.02. found 390.99.

Example DSTL-1

Step c

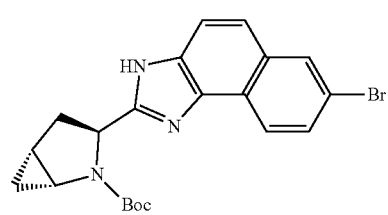 [SMILES: CC(C)(C)OC(=O)N1[C@@H]2C[C@@H]2C[C@H]1c1nc2c(ccc3cc(Br)ccc32)[nH]1]

HCl salt

Tin(II)chloride dehydrate (3 g, 16.34 mmol) was added to a solution of Example DSTL-1, Step b (2 g, 5.47 mmol) in MeOH (100 mL) and the solution was stirred for 18 h at 70° C. The solvent was removed by rotary evaporation and Example DSTL-1, Step c (assume theoretical 1.25 g) was dried under high vacuum. LC-MS (Cond.-J4): RT=1.49 min. LC-MS Anal. Calcd. for [M+H]$^+$ C$_{10}$H$_9$BrN$_2$: 237.00. found 236.96.

Example DSTL-1

Step d

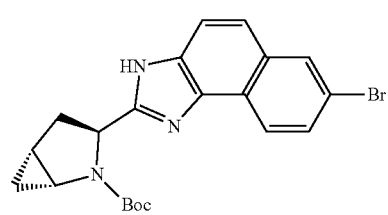 [SMILES: CC(C)(C)OC(=O)N1[C@@H]2C[C@@H]2C[C@H]1c1nc2c(ccc3cc(Br)ccc32)[nH]1]

HATU (2.085 g, 5.48 mmol) was added to a solution of Example DSTL-1, Step c (1.25 g, 5.48 mmol), Example 1, Step b (1.246 g, 5.48 mmol), and Hunig's base (7.09 g, 54.8 mmol) in DMF (70 mL) and the reaction mixture was stirred for 6 h before being partitioned between EtOAc (500 mL) and sat'd NaHCO$_3$ (150 mL). The tin salts that precipitated were removed by filtration through CELITE®, and the organic phase was concentrated to yield a residue which was taken up in AcOH (100 mL) and heated at 60° C. for 18 h. The solvent was removed by rotary evaporation under high vacuum, and residue taken up in CH$_2$Cl$_2$ and washed with sat'd NaHCO$_3$ soln. After concentration, the crude product was charged (DCM) to a Thompson silica gel cartridge (110 g) and subject to gradient elution; 15-100% B over 1 L to give Example DSTL-1, Step d (420 mg, 44%). LC-MS (Cond.-J4): RT=2.51 min. LC-MS Anal. Calcd. for [M+H]$^+$ C$_{21}$H$_{22}$BrN$_3$O$_2$: 430.10. found 430.06.

Example DSTL-1

Step d.1

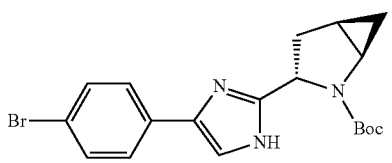 [SMILES: CC(C)(C)OC(=O)N1[C@@H]2C[C@@H]2C[C@H]1c1nc(-c2ccc(Br)cc2)c[nH]1]

Example DSTL-1, Step d.1 was prepared from Example 1, Step b according to the procedure described for the synthesis of its desmethano analog in patent application WO 2008/021927.

Example DSTL-1

Step e

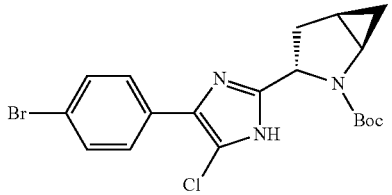 [SMILES: CC(C)(C)OC(=O)N1[C@@H]2C[C@@H]2C[C@H]1c1nc(-c2ccc(Br)cc2)c(Cl)[nH]1]

To a solution of Example DSTL-1, Step d.1 (560 mg, 1.39 mmol) in DMF (15 mL) was added NCS (203 mg, 1.52 mmol). The reaction mixture was heated at 50° C. for 16 h. The solution was purged with nitrogen to evaporate DMF, and the crude residue was charged (DCM) to a Thompson SiO$_2$ column (80 g) and gradient elution performed (BIOTAGE®). Segment 1: 10-100% B over 1.5 L. Segment 2: Hold 100% B 300 mL. (A/B Hexanes/EtOAc). There was isolated Example DSTL-1, Step e (589.1 mg, 92% yield). LC-MS (Cond.-D4): RT=2.61 min. LC-MS Anal. Calcd. for [M+Na]$^+$ C$_{19}$H$_{22}$ClN$_3$O$_2$: 462.04. found 462.07.

Example DSTL-1

Step f

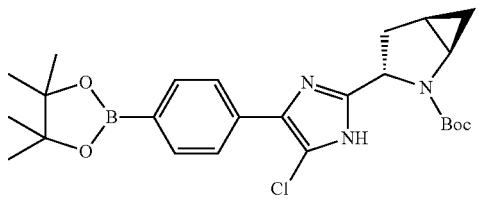 [SMILES: CC(C)(C)OC(=O)N1[C@@H]2C[C@@H]2C[C@H]1c1nc(-c2ccc(B3OC(C)(C)C(C)(C)O3)cc2)c(Cl)[nH]1]

Tetrakis(triphenylphosphine) palladium (76 mg, 0.066 mmol) was added in one portion to a stirred suspension of Example DSTL-1, Step e (580 mg, 1.32 mmol), bis(pinacolato)diboron (671 mg, 2.64 mmol) and potassium acetate (324 mg, 3.30 mmol) in a solution of dioxane (12 mL) in a screw-capped pressure vessel. The reaction mixture was evacuated and flushed with argon (3×) and placed into a pre-heated oil bath (80° C.) and stirred for 16 h. Upon cooling, the reaction mixture was diluted with EtOAc, washed with sat'd NaHCO$_3$ soln, brine and dried over Na$_2$SO$_4$. The crude residue was charged (DCM) to a Thompson SiO$_2$ column (80 g) and gradient elution performed (BIOTAGE®). Segment 1: 5-100% B over 1.5 L. Segment 2: Hold 100% B 300 mL. (A/B CH$_2$Cl$_2$/EtOAc). There was isolated Example DTSL-1, Step f (714.7 mg, 95%) as yellow foam. LC-MS (Cond.-D4): RT=2.69 min. LC-MS Anal. Calcd. for [M+H]$^+$ C$_{25}$H$_{34}$BClN$_3$O$_4$: 486.24. found 486.26.

Example DSTL-1

Step g

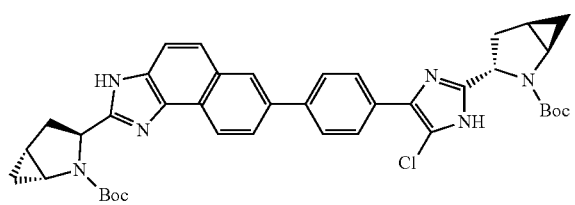 [SMILES: CC(C)(C)OC(=O)N1[C@@H]2C[C@@H]2C[C@H]1c1nc(-c2ccc(-c3ccc4c(ccc5[nH]c([C@@H]6C[C@H]7C[C@H]7N6C(=O)OC(C)(C)C)nc54)c3)cc2)c(Cl)[nH]1]

Tetrakis(triphenylphosphine) palladium (27.0 mg, 0.023 mmol) was added in one portion to a stirred suspension of Example DSTL-1, Step d (200 mg, 0.467 mmol), Example DSTL-1, Step f (250 mg, 0.514 mmol) and NaHCO$_3$ (196 mg, 2.335 mmol) in a degassed solution of DME (4 mL) and water (1 mL) under argon in a screw-capped pressure vessel. The solution was evacuated and charged with argon (3×) and placed into a pre-heated oil bath (80° C.) and stirred for 14 h. The mixture was diluted with EtOAc (10 mL), THF (2 mL) and MeOH (1 mL), washed with brine and dried over Na$_2$SO$_4$. After concentration to remove solvent, the residue was charged to a Thompson SiO$_2$ column (80 g) and eluted (BIOTAGE®) by gradient. Segment 1: 20-100% B over 1.5 L, Segment 2: hold 100% B for 300 mL; A/B Hexanes/EtOAc. There was isolated DSTL-1, Step g (195.0 mg, 52.6%) as a tan solid. LC-MS (Cond.-D4): RT=2.40 min. LC-MS Anal. Calcd. for [M+H]$^+$ C$_{40}$H$_{44}$ClN$_6$O$_4$: 707.31. found 707.43.

Example DSTL-1

Step h

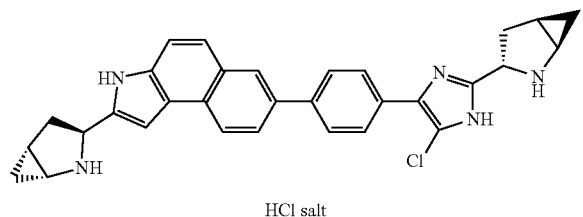 [SMILES: Clc1[nH]c([C@@H]2C[C@H]3C[C@H]3N2)nc1-c1ccc(-c2ccc3c(ccc4[nH]c([C@@H]5C[C@H]6C[C@H]6N5)cc43)c2)cc1]

HCl salt

Cold (0° C.) 4N HCl in dioxane (4 mL) was added to a stirred solution of Example DSTL-1, Step g (65 mg, 0.092 mmol) in MeOH (1 mL). The mixture was stirred at rt for 3 h, concentrated, and placed under high vacuum to provide DSTL-1, Step h as an orange-tan solid and as a tetra HCl salt. LC-MS (Cond.-D4): RT=1.63 min. LC-MS Anal. Calcd. for [M+H]+ $C_{30}H_{28}ClN_6$: 507.21. found 507.26.

Example DSTL-1

Example DSTL-1 was prepared from Example DSTL-1, Step h according to the procedure described for the preparation of Example GW2. Purification was accomplished by preparative HPLC (0-50% B) over a 25 min gradient (at 40 ml/min) using a Waters SunFire column (30×100 mm, S5) where Solvent B=90% $CH_3CN$-10% $H_2O$-0.1% TFA and A=5% $CH_3CN$-95% $H_2O$-0.1% TFA. %). There was isolated Example DSTL-1 (70.4 mg, 67.7%) as a white solid. $^1H$ NMR (MeOD, 500 MHz, δ): 8.47 (d, J=8.6 Hz, 1H), 8.44 (s, 1H), 8.15 (s, 1H), 8.13 (s, 1H), 7.91 (d, J=8.6 Hz, 2H), 7.85 (d, J=8.6 Hz, 2H), 7.80 (d, J=8.6 Hz, 1H), 5.34-5.31 (m, 1H), 5.07 (t, J=7.32 Hz, 1H), 4.61-4.58 (m, 2H), 3.39-3.31 (m, 1H), 3.75-3.72 (m, 1H), 3.69 (s, 3H), 3.68 (s, 3H), 2.83-2.81 (m, 1H), 2.64-2.59 (m, 1H), 2.49-2.48 (m, 2H), 2.23-2.14 (m, 3H), 2.05-2.03 (m, 1H), 1.18-1.12 (m, 2H), 1.05-0.92 (m, 13H), 0.83-0.81 (m, 1H). LC-MS (Cond.-D4): RT=2.24 min. LC-MS Anal. Calcd. for [M+H]+ $C_{44}H_{50}ClN_8O_6$: 821.36. found 821.54.

Example DSTL-2

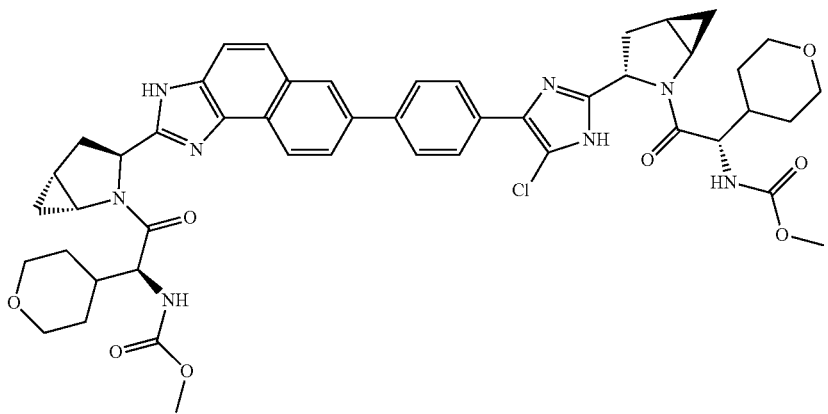 [SMILES: COC(=O)N[C@H](C(=O)N1[C@@H]2C[C@@H]2C[C@H]1c1nc(-c2ccc(-c3ccc4c(ccc5[nH]c([C@@H]6C[C@H]7C[C@H]7N6C(=O)[C@@H](NC(=O)OC)C6CCOCC6)nc54)c3)cc2)c(Cl)[nH]1)C1CCOCC1]

Example DSTL-2 was prepared from Example DSTL-1, Step h according to the procedure described for the preparation of Example GW2 except using (S)-2-(methoxycarbonylamino)-2-(tetrahydro-2H-pyran-4-yl)acetic acid instead of Cap-51. Purification was accomplished by preparative HPLC (0-50% B) over a 25 min gradient (at 40 ml/min) using a Waters SunFire column (30×100 mm, S5) where Solvent B=90% $CH_3CN$-10% $H_2O$-0.1% TFA and A=5% $CH_3CN$-95% $H_2O$-0.1% TFA. There was isolated Example DSTL-2 (18.0 mg) as a white solid. LC-MS (Cond.-D4): RT=2.04 min. LC-MS Anal. Calcd. for [M+H]+ $C_{48}H_{54}ClN_8O_6$: 905.38. found 905.60.

Examples DSTL-3 and DSTL-4

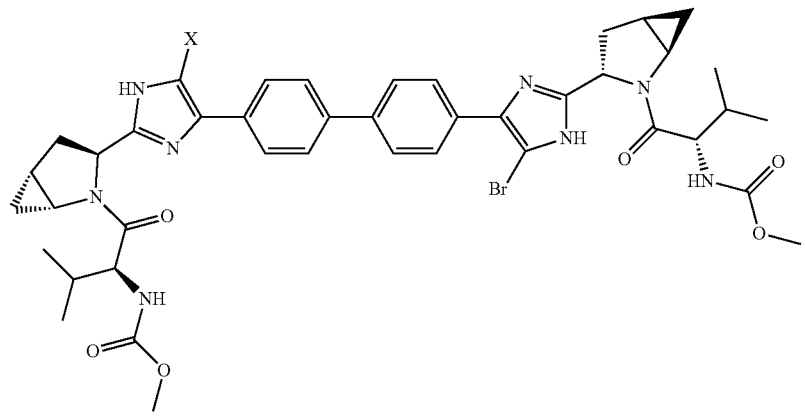

Example DSTL-3, X = H
Example DSTL-4, X = Br

Examples DSTL-3, Step a and DSTL-4, Step a

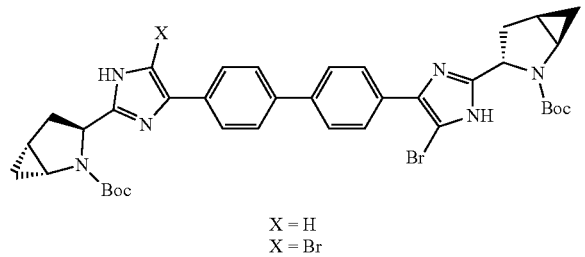

X = H
X = Br

A solution of bromine (0.079 mL, 1.54 mmol) in AcOH (1 mL) was added portionwise to a stirred solution of Example 1, Step d (1.0 g, 1.541 mmol) in AcOH (40 mL), and the mixture was stirred at rt for 3 h. The solvent was removed in vacuo and the residue was taken up in DCM and washed with sat'd NaHCO$_3$ soln. The aqueous layer was extracted twice more with DCM and the combined organic extracts were washed with brine and dried (Na$_2$SO$_4$). The residue was charged (DCM) to a Thompson silica gel cartridge (160 g) and eluted with 30-100% B over 2 L. Segment 2: hold 100% B for 800 mL. A/B Hexanes/EtOAc. There was isolated 3 components; Starting material (303.6 mg); Example DSTL-3, Step a (X=H, 382.1 mg); yellow solid. LC-MS (Cond.-D4): RT=2.21 min. LC-MS Anal. Calcd. for [M+H]$^+$ C$_{38}$H$_{44}$BrN$_6$O$_4$: 729.26. found; 729.28; Example DTSL-4, Step a (X=Br; 287.2 mg); light, yellow solid. LC-MS (Cond.-D4) RT=2.62 min. LC-MS Anal. Calcd. for [M+H]$^+$ C$_{38}$H$_{43}$Br$_2$N$_6$O$_4$: 807.17. found: 807.33.

Examples DSTL-3

Step b and DSTL-4, Step b

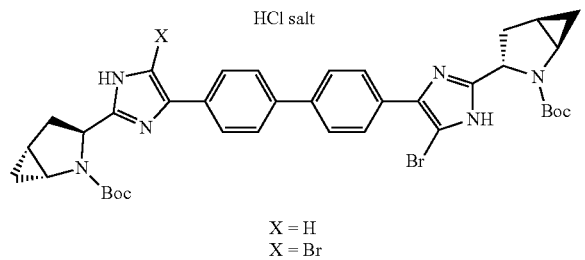

HCl salt

X = H
X = Br

The products of Example DSTL-3, Step b and DSTL-4, Step b were brought forward separately. Removal of the protecting groups was performed as described in the procedure from Example DSTL-1, Step h. X=H; Example DTSL-3, Step b: Yellow solid, 33.1 mg (97% pure); LC-MS (Cond.-D4): RT=1.49 min. LC-MS Anal. Calcd. for [M+H]$^+$ C$_{28}$H$_{28}$BrN$_6$: 529.16. found 529.24. X=Br; Example DTSL-4, Step b: Yellow solid, 33 mg (96% pure); LC-MS (Cond.-D4): RT=1.82 min. LC-MS Anal. Calcd. for [M+H]$^+$ C$_{28}$H$_{27}$Br$_2$N$_6$: 607.07. found 607.16.

Example DSTL-3

Example DSTL-3 was prepared from Example DSTL-3, Step b according to the procedure described for the preparation of Example GW2. Purification was accomplished by preparative HPLC; 0%-50% B over a 30 min gradient (at 40 ml/min) using a Waters SunFire column (30×100 mm, S5) B=90% CH$_3$CN-10% H$_2$O-0.1% TFA and A=5% CH$_3$CN-95% H$_2$O-0.1% TFA. There was isolated Example DSTL-3 (29.0 mg) as a white solid. LC-MS (Cond.-D4): RT=2.07 min. LC-MS Anal. Calcd. for [M+H]$^+$ C$_{42}$H$_{50}$BrN$_8$O$_6$: 843.30. found 843.39.

Example DSTL-4

Example DSTL-4 was prepared from Example DSTL-4, Step b according to the procedure described for the preparation of Example GW2. Purification was accomplished by preparative HPLC; 0%-50% B over a 30 min gradient at 40 ml/min using a Waters SunFire column (30×100 mm, S5) B=90% CH$_3$CN-10% H$_2$O-0.1% TFA and A=5% CH$_3$CN-95% H$_2$O-0.1% TFA. There was isolated Example DSTL-4 (30.2 mg) as a white solid. $^1$H NMR (MeOD, 500 MHz, δ): 7.82 (s, 8H), 5.08-5.05 (m, 2H), 4.58 (app d, J=6.7 Hz, 2H), 3.76-3.74 (m. 2H), 3.67 (s, 6H), 2.57-2.52 (m, 2H), 2.50-2.44 (m, 2H), 2.22-2.17 (m, 2H), 2.06-2.01 (m, 2H), 1.12-1.08 (m, 2H), 1.04 (d, J=6.7 Hz, 6H), 0.95 (d, J=6.7 Hz, 6H), 0.84-0.82 (m, 2H). LC-MS (Cond.-D4): RT=2.56 min. LC-MS Anal. Calcd. for [M+H]$^+$ C$_{42}$H$_{49}$BrN$_8$O$_6$: 921.31. found 921.30.

Example DSTL-5

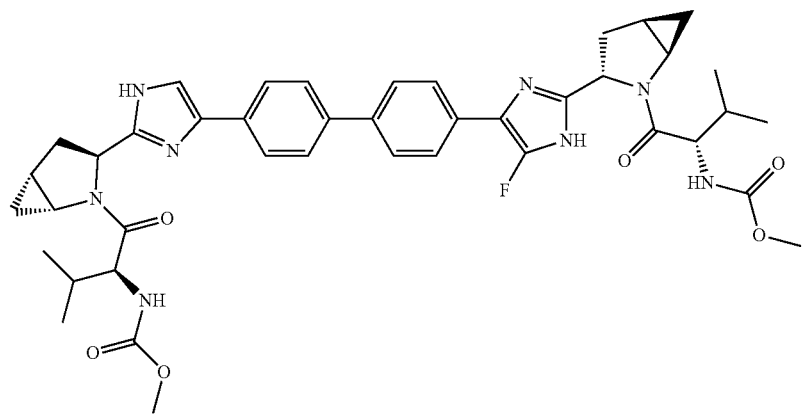 [SMILES: COC(=O)N[C@H](C(=O)N1[C@@H]2C[C@@H]2C[C@H]1c1nc(-c2ccc(-c3ccc(-c4nc([C@@H]5C[C@H]6C[C@H]6N5C(=O)[C@@H](NC(=O)OC)C(C)C)[nH]c4F)cc3)cc2)c[nH]1)C(C)C]

Example DSTL-5

Step a

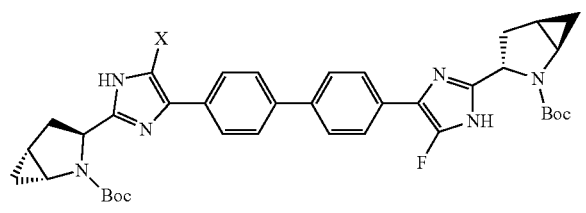

X = H
X = F

Accufluor (45-50% on alumina) (345 mg, 1.2 mmol) was added in one portion to a stirred suspension of Example 1, Step d, (1R,1'R,3S,3'S,5R,5'R)-tert-butyl 3,3'-(5,5'-(biphenyl-4,4'-diyl)bis(1H-imidazole-5,2-diyl))bis(2-azabicyclo[3.1.0]hexane-2-carboxylate) (500 mg, 0.77 mmol) in dry DMF (5 mL) at rt. The mixture was placed into a preheated oil bath at 60° C. and stirred 4 h before the solvent was removed by rotary evaporation under high vacuum. The crude product was charged to a Thompson 90 g silica gel cartridge and eluted 10-100% B over 2 L, and hold 100% B for 1 L (Solvent B=EtOAc; Solvent A=hexanes). A second gradient was applied eluting 0-100% B over 2 L (Solvent B=methanol; Solvent A=EtOAc). Three fractions were collected: Example DSTL-5, Step a (X=F), (1R,1'R,3S,3'S,5R,5'R)-tert-butyl 3,3'-(5,5'-(biphenyl-4,4'-diyl)bis(4-fluoro-1H-imidazole-5,2-diyl))bis(2-azabicyclo[3.1.0]hexane-2-carboxylate) (45.0 mg, 7%) as a yellow solid; Example DSTL-5, Step a (X=H) ((1R,3S,5R)-tert-butyl 3-(5-(4'-(2-((1R,3S,5R)-2-(tert-butoxycarbonyl)-2-azabicyclo[3.1.0]hexan-3-yl)-1H-imidazol-5-yl)biphenyl-4-yl)-4-fluoro-1H-imidazol-2-yl)-2-azabicyclo[3.1.0]hexane-2-carboxylate (193 mg, 32%) as a yellow solid, and recovered starting material (153 mg, 24%).

Example DSTL-5, Step a X=F: A sample (~10 mg) of the first eluting compound was further purified by preparative HPLC (0-100% B) over a 30 min gradient (at 40 ml/min) using a PHENOMENEX® Luna column (30×100 mm, 10u) where Solvent B=90% $CH_3CN$-10% $H_2O$-0.1% TFA and A=5% $CH_3CN$-95% $H_2O$-0.1% TFA. There was isolated (4.6 mg) as a light yellow solid. LC-MS (Cond.-D4): RT=4.43 min. LC-MS Anal. Calcd. for $[M+H]^+$ $C_{38}H_{43}F_2N_6O_4$: 685.33. found 685.38.

Example DSTL-5, Step a X=H: A sample (~15 mg) of the second eluting compound was further purified by preparative HPLC (0-100% B) over a 30 min gradient (at 40 ml/min) using a PHENOMENEX® Luna column (30×100 mm, 10u) where Solvent B=90% $CH_3CN$-10% $H_2O$-0.1% TFA and A=5% $CH_3CN$-95% $H_2O$-0.1% TFA. There was isolated (11.2 mg) as an off-white solid. LC-MS (Cond.-D4): RT=4.43 min. LC-MS Anal. Calcd. for $[M+H]^+$ $C_{38}H_{44}FN_6O_4$: 667.34. found 667.40.

Example DSTL-5

Step b

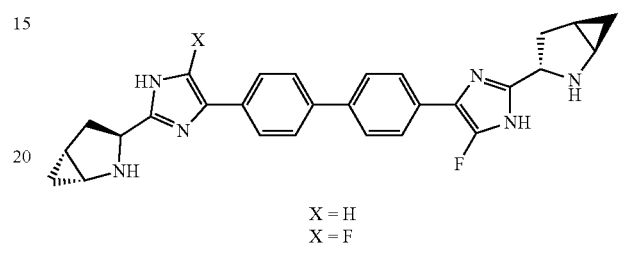

X = H
X = F

The products of Example DSTL-5, Step a, (X=F) and (X=H), were brought forward separately. Removal of the protecting groups was performed as described in the procedure from Example DSTL-1, Step h.

Example DTSL-5, Step b (X=F): Yellow solid, 23.4 mg; LC-MS (Cond.-D4): RT=2.89 min. LC-MS Anal. Calcd. for $[M+H]^+$ $C_{28}H_{27}F_2N_6$: 485.22. found 485.25.

Example DTSL-5, Step b (X=H): 18 mg (95% pure); LC-MS (Cond.-D4): RT=2.55 min. LC-MS Anal. Calcd. for $[M+H]^+$ $C_{28}H_{28}FN_6$: 467.25. found 467.27.

Example DSTL-5

Example DSTL-5 was prepared from Example DSTL-5, Step b (X=H) according to the procedure described for the preparation of Example GW2. Purification was accomplished by preparative HPLC; 0%-50% B over a 30 min gradient at 40 ml/min using a Waters SunFire column (30×100 mm, S5) B=90% $CH_3CN$-10% $H_2O$-0.1% TFA and A=5% $CH_3CN$-95% $H_2O$-0.1% TFA. There was isolated Example DSTL-5 (37.3 mg, 39%) as a pale yellow solid. $^1$H NMR (MeOD, 500 MHz, δ): 7.88 (s, 1H), 7.84 (d, J=8.5 Hz, 2H), 7.80 (d, J=8.5 Hz, 2H), 7.77 (d, J=8.5 Hz, 2H), 7.68 (d, J=8.5 Hz, 2H), 5.13 (t, J=7.0 Hz, 1H), 5.04 (t, J=6.1 Hz, 1H), 4.56 (d, J=6.7 Hz, 2H) 3.82 (br. s, 1H), 3.68-3.67 (m, 7H), 2.72-2.68 (m, 1H), 2.51-2.43 (m, 3H), 2.21-2.14 (m, 2H), 2.09 (br. s, 1H), 2.03 (br. s, 1H), 1.15-1.09 (m, 2H), 1.02 (d, J=6.7 Hz, 6H), 0.94 (t, J=7.0 Hz, 6H), 0.90 (br. s, 1H), 0.81 (br. s, 1H). LC-MS (Cond.-D4): RT=3.45 min. LC-MS Anal. Calcd. for $[M+H]^+$ $C_{42}H_{50}FN_8O_6$: 781.39. found 781.54.

Example DSTL-6

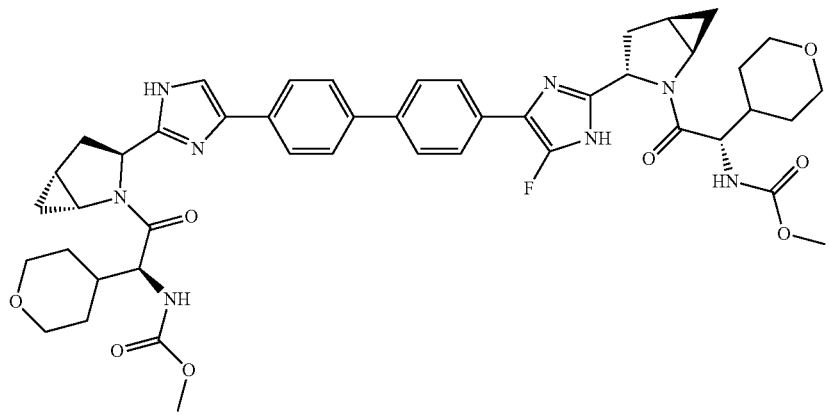 [SMILES: COC(=O)N[C@H](C(=O)N1[C@@H]2C[C@@H]2C[C@H]1c1nc(-c2ccc(-c3ccc(-c4nc([C@@H]5C[C@H]6C[C@H]6N5C(=O)[C@@H](NC(=O)OC)C5CCOCC5)[nH]c4F)cc3)cc2)c[nH]1)C1CCOCC1]

Example DSTL-6 was prepared from Example DSTL-5, Step b (X=H) according to the procedure described for the preparation of Example GW2 except using (S)-2-(methoxycarbonylamino)-2-(tetrahydro-2H-pyran-4-yl)acetic acid instead of Cap-51. Purification was accomplished by preparative HPLC (0-50% B) over a 25 min gradient (at 40 ml/min) using a Waters SunFire column (30×100 mm, S5) where Solvent B=90% $CH_3CN$-10% $H_2O$-0.1% TFA and A=5% $CH_3CN$-95% $H_2O$-0.1% TFA. There was isolated Example DSTL-6 (37.1 mg, 36%) as a white solid. LC-MS (Cond.-D4): RT=3.17 min. LC-MS Anal. Calcd. for $[M+H]^+$ $C_{48}H_{54}FN_8O_6$: 865.41. found 865.55.

Example DSTL-7

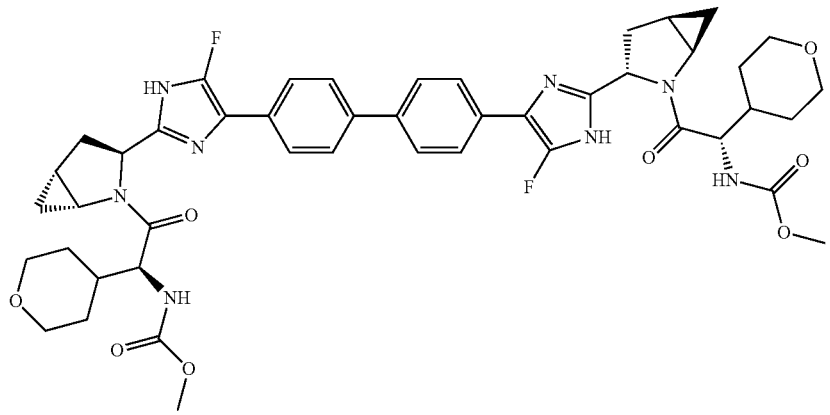 [SMILES: COC(=O)N[C@H](C(=O)N1[C@@H]2C[C@@H]2C[C@H]1c1nc(-c2ccc(-c3ccc(-c4nc([C@@H]5C[C@H]6C[C@H]6N5C(=O)[C@@H](NC(=O)OC)C5CCOCC5)[nH]c4F)cc3)cc2)c(F)[nH]1)C1CCOCC1]

Example DSTL-7 was prepared from Example DSTL-5, Step b (X=F) according to the procedure described for the preparation of Example GW2 except using (S)-2-(methoxycarbonylamino)-2-(tetrahydro-2H-pyran-4-yl)acetic acid instead of Cap-51. Purification was accomplished by preparative HPLC (0-50% B) over a 25 min gradient (at 40 ml/min) using a Waters SunFire column (30×100 mm, S5) where Solvent B=90% $CH_3CN$-10% $H_2O$-0.1% TFA and A=5% $CH_3CN$-95% $H_2O$-0.1% TFA. There was isolated Example DSTL-7 (14 mg, 25%) as a white solid. $^1H$ NMR (MeOD, 500 MHz, δ) 7.72 (d, J=8.5 Hz, 4H), 7.64 (d, J=8.5 Hz, 4H), 5.03 (t, J=6.7 Hz, 2H), 4.63 (d, J=7.6 Hz, 2H), 3.97-3.93 (m, 4H), 3.72 (br. s, 2H). 3.67 (s, 6H), 3.42-3.37 (m, 4H), 2.44-2.42 (m, 4H), 2.02 (br. s, 4H), 1.63-1.57 (m, 6H), 1.46-1.43 (m, 2H), 1.14-1.19 (m, 2H), 0.80 (br. s, 2H): LC-MS (Cond.-D4): RT=3.17 min. LC-MS Anal. Calcd. for $[M+H]^+$ $C_{46}H_{53}F_2N_8O_6$: 883.40. found 883.57.

Example DSTL-8

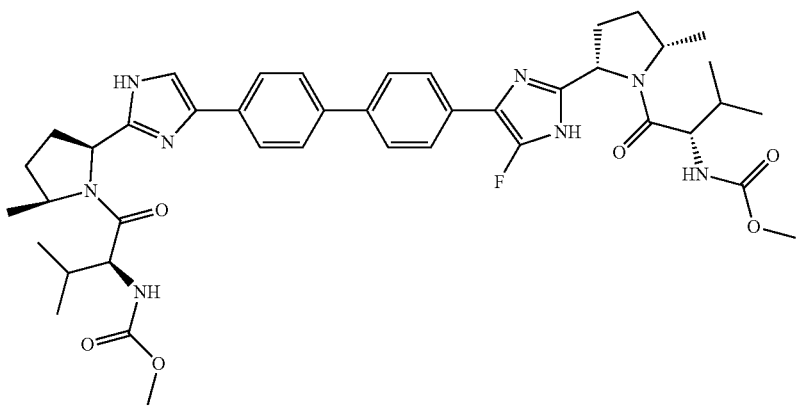

Example DSTL-8

Step a

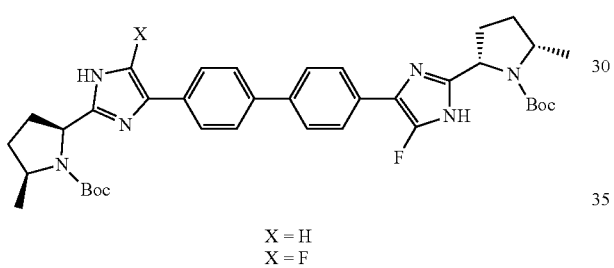

X = H
X = F

Accufluor (45-50% on alumina) (274 mg, 0.92 mmol) was added in one portion to a stirred suspension of Example GW1, Step a, (2S,2'S,5S,5'S)-tert-butyl 5,5'-(5,5'-(biphenyl-4,4'-diyl)bis(1H-imidazole-5,2-diyl))bis(2-methylpyrrolidine-1-carboxylate) (400 mg, 0.6 mmol) in dry DMF (4 mL) at rt. The mixture was placed into a preheated oil bath at 60° C. and stirred 4 h before an additional 135 mg of Accufluor was added and stirring was continued at 60° C. for 16 h. The solvent was removed by rotary evaporation under high vacuum, and the crude product was charged to a Thompson 90 g silica gel cartridge and eluted 10-100% B over 2 L, and hold 100% B for 1 L (Solvent B=EtOAc; Solvent A=hexanes). A second gradient was applied eluting 0-100% B over 2 L (Solvent B=methanol; Solvent A=EtOAc). Three fractions were collected: Example DSTL-8, Step a (X=F), (2S,2'S,5S,5'S)-tert-butyl 5,5'-(5,5'-(biphenyl-4,4'-diyl)bis(4-fluoro-1H-imidazole-5,2-diyl))bis(2-methylpyrrolidine-1-carboxylate) (33 mg, 5.1%) as a yellow-orange solid LC-MS (Cond.-D4): RT=4.64 min. LC-MS Anal. Calcd. for [M+H]$^+$ $C_{38}H_{47}F_2N_6O_4$: 689.36. found 689.50. Example DSTL-8, Step a (X=H) (2S,5S)-tert-butyl 2-(5-(4'-(2-((2S,5S)-1-(tert-butoxycarbonyl)-5-methylpyrrolidin-2-yl)-1H-imidazol-5-yl)biphenyl-4-yl)-4-fluoro-1H-imidazol-2-yl)-5-methylpyrrolidine-1-carboxylate (108.6 mg, 17%) as a yellow-orange solid. LC-MS (Cond.-D4): RT=3.83 min. LC-MS Anal. Calcd. for [M+H]$^+$ $C_{38}H_{48}FN_6O_4$: 671.37. found 671.48 and recovered starting material (321.2 mg, 80%) as a reddish-orange solid.

Example DSTL-8

Step b

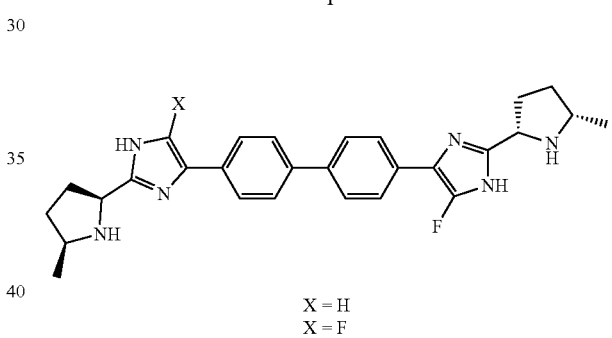

X = H
X = F

The products of Example DSTL-8, Step a, (X=F) and (X=H), were brought forward separately. Removal of the protecting groups was performed as described in the procedure from Example DSTL-1, Step h.

Example DTSL-8, Step b (X=F): Yellow solid, 22.7 mg; LC-MS (Cond.-D4): RT=3.03 min. LC-MS Anal. Calcd. for [M+H]$^+$ $C_{28}H_{30}F_2N_6$: 489.26. found 489.35.

Example DTSL-8, Step b (X=H): 35 mg (95% pure); LC-MS (Cond.-D4): RT=2.63 min. LC-MS Anal. Calcd. for [M+H]$^+$ $C_{28}H_{31}FN_6$: 471.27. found 471.33.

Example DSTL-8

Example DSTL-5 was prepared from Example DSTL-8, Step b (X=H) according to the procedure described for the preparation of Example GW2. Purification was accomplished by preparative HPLC; 0%-50% B over a 30 min gradient at 40 ml/min using a Waters SunFire column (30×100 mm, S5) B=90% $CH_3CN$-10% $H_2O$-0.1% TFA and A=5% $CH_3CN$-95% $H_2O$-0.1% TFA. There was isolated Example DSTL-8 (31.9 mg, 41%) as a light peach-colored solid. LC-MS (Cond.-D4): RT=3.66 min. LC-MS Anal. Calcd. for [M+H]$^+$ $C_{42}H_{54}FN_8O_6$: 785.42. found 785.48.

Example DSTL-9

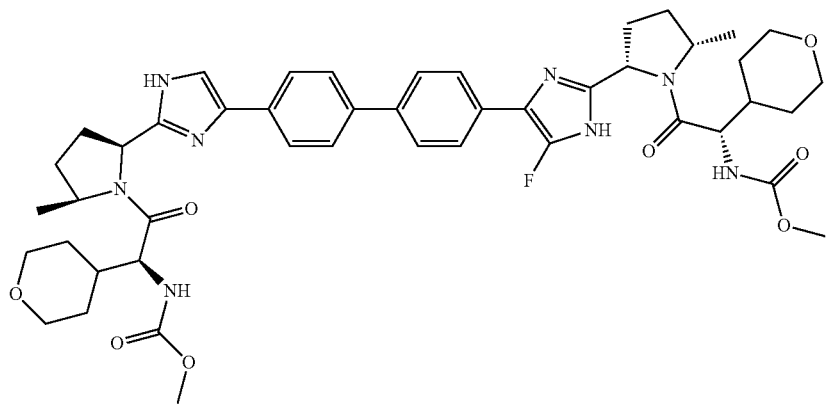 [SMILES: COC(=O)N[C@H](C(=O)N1[C@@H](C)CC[C@H]1c1nc(-c2ccc(-c3ccc(-c4nc([C@@H]5CC[C@H](C)N5C(=O)[C@@H](NC(=O)OC)C5CCOCC5)[nH]c4F)cc3)cc2)c[nH]1)C1CCOCC1]

Example DSTL-9 was prepared from Example DSTL-8, Step b (X=H) according to the procedure described for the preparation of Example GW2 except using (S)-2-(methoxycarbonylamino)-2-(tetrahydro-2H-pyran-4-yl)acetic acid instead of Cap-51. Purification was accomplished by preparative HPLC (0-50% B) over a 25 min gradient (at 40 ml/min) using a Waters SunFire column (30×100 mm, S5) where Solvent B=90% CH$_3$CN-10% H$_2$O-0.1% TFA and A=5% CH$_3$CN-95% H$_2$O-0.1% TFA. There was isolated Example DSTL-9 (27.2 mg, 32%) as a pale yellow solid. LC-MS (Cond.-D4): RT=3.37 min. LC-MS Anal. Calcd. for [M+H]$^+$ C$_{46}$H$_{58}$FN$_8$O$_8$: 869.44. found 869.54.

Example DSTL-10

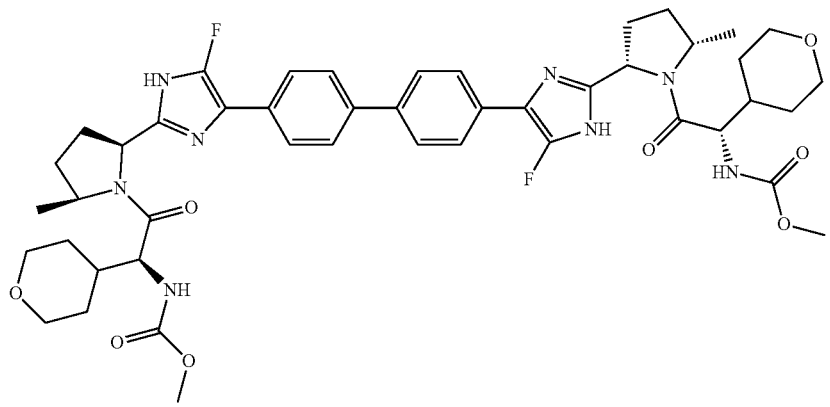 [SMILES: COC(=O)N[C@H](C(=O)N1[C@@H](C)CC[C@H]1c1nc(-c2ccc(-c3ccc(-c4nc([C@@H]5CC[C@H](C)N5C(=O)[C@@H](NC(=O)OC)C5CCOCC5)[nH]c4F)cc3)cc2)c(F)[nH]1)C1CCOCC1]

Example DSTL-10 was prepared from Example DSTL-8, Step b (X=F) according to the procedure described for the preparation of Example GW2 except using (S)-2-(methoxycarbonylamino)-2-(tetrahydro-2H-pyran-4-yl)acetic acid instead of Cap-51. Purification was accomplished by preparative HPLC (0-50% B) over a 25 min gradient (at 40 ml/min) using a Waters SunFire column (30×100 mm, S5) where Solvent B=90% CH$_3$CN-10% H$_2$O-0.1% TFA and A=5% CH$_3$CN-95% H$_2$O-0.1% TFA. There was isolated Example DSTL-10 (13.8 mg, 25%) as a pale yellow solid. LC-MS (Cond.-D4): RT=4.28 min. LC-MS Anal. Calcd. for [M+H]$^+$ C$_{46}$H$_{57}$F$_2$N$_8$O$_8$: 887.43. found 887.50.

Example DSTL-11

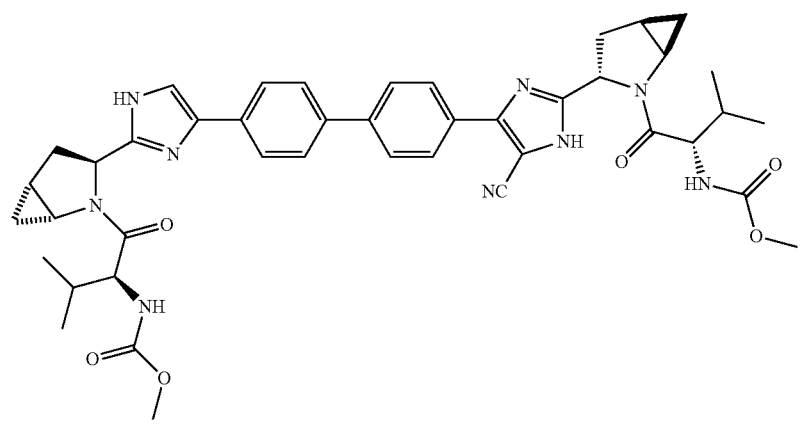

Example DSTL-11

Step a

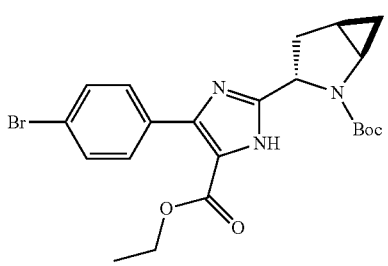

The preparation of DSTL-11, Step a, was conducted in analogous fashion to compound J5 in patent application 20080213 US 10889A USCIP. LC-MS (Cond.-D4): RT=2.22 min. LC-MS Anal. Calcd. for [M+H]+ $C_{22}H_{27}BrN_3O_4$: 476.12. found 478.17.

Example DSTL-11

Step b

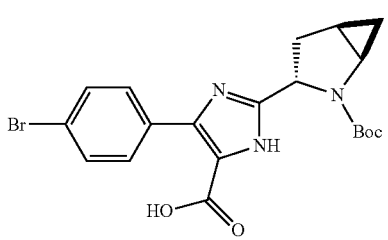

5N sodium hydroxide (1.469 mL, 7.4 mmol) was added to a solution of DSTL-11, Step a (1R,3S,5R)-tert-butyl 3-(4-(4-bromophenyl)-5-(ethoxycarbonyl)-1H-imidazol-2-yl)-2-azabicyclo[3.1.0]hexane-2-carboxylate (1.75 g, 3.7 mmol) in ethanol (40 mL). The mixture was stirred at 50° C. for 16 h and additional 5N NaOH (1.5 mL) was added. The mixture was stirred at 60° C. for 6 h and additional 5N NaOH (0.75 mL) and stirring was continued at 60° C. for 16 h. The ethanol was removed by rotary evaporation and the residue was taken up in ethyl acetate and neutralized to pH=5 (1N HCl approx 20 mL until close to pH=7, then with pH=5 phosphate buffer). The organic layer was separated, washed with brine, dried and concentrated. There was isolated Example DSTL-11, Step b (1.6 g, 92%) as a white solid. LC-MS (Cond.-D4): RT=1.78 min. LC-MS Anal. Calcd. for [M+H]+ $C_{20}H_{22}BrN_3O_4$: 448.09. found 447.97.

Example DSTL-11

Step c

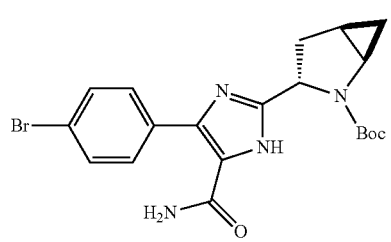

CDI (0.58 g, 3.57 mmol) was added in one portion to a stirred soln of DSTL-11, Step b, 4-(4-bromophenyl)-2-((1R,3S,5R)-2-(tert-butoxycarbonyl)-2-azabicyclo[3.1.0]hexan-3-yl)-1H-imidazole-5-carboxylic acid (1.6 g, 3.57 mmol) in dry THF (30 mL). The mixture was stirred at 50° C. for 4 h before being cooled to rt and NH4OH (conc) (4.96 mL, 35.7 mmol) was added. The mixture was stirred for 16 h before, diluted with EtOAc, washed with sat'd NaHCO3 soln, brine, and dried. The crude product was charged to a Thompson 160 g silica gel cartridge and eluted 40-100% B over 3 L, followed by a hold at 100% B for 1 L. (Solvent B=EtOAc; Solvent A=hexanes). There was isolated Example DSTL-11, Step c, (1.76 g 99%). LC-MS (Cond.-D4): RT=1.75 min. LC-MS Anal. Calcd. for [M+H]+ $C_{20}H_{24}BrN_4O_3$ 449.10. found: 449.06.

Example DSTL-11

Step d

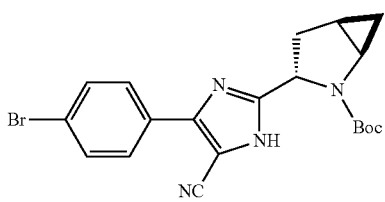

2,4,6-Trichloro-1,3,5-triazine (cyanuric chloride) (168 mg, 0.91 mmol) was added in one portion to a stirred solution of Example DSTL-11, Step c, (1R,3S,5R)-tert-butyl 3-(4-(4-bromophenyl)-5-carbamoyl-1H-imidazol-2-yl)-2-azabicyclo[3.1.0]hexane-2-carboxylate (903 mg, 1.82 mmol) in dry DMF (4 mL). The mixture was stirred at for 2 h and then warmed to 50° C. for 16 h. Additional cyanuric chloride (20 mg) was added and the mixture was stirred further at 50° C. for 24 h, diluted with EtOAc and water, and the organic layer was washed with sat'd $NaHCO_3$ soln, brine, and dried $(Na_2SO_4)$. The crude product was charged to a Thompson 90 g silica gel cartridge and eluted 25-100% B over 1.5 L, followed by a hold at 100% B 500 mL. (Solvent B=EtOAc; Solvent A=hexanes). There was isolated Example DSTL-11, Step d, (346 g 60%) as a yellowish-tan foam. LC-MS (Cond.-D4): RT=3.93 min. LC-MS Anal. Calcd. for $[M+H]^+$ $C_{20}H_{22}BrN_4O_2$ 431.09. found: 431.01.

Example DSTL-11

Step e

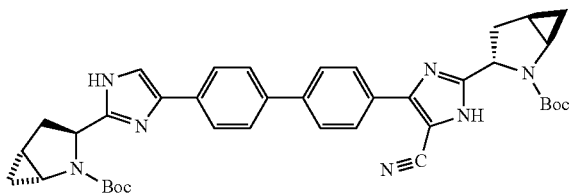

Tetrakis(triphenyl)palladium (45.8 mg, 0.04 mmol) was added to a argon purged suspension of Example DSTL-11, Step d, (1R,3S,5R)-tert-butyl 3-(5-(4-bromophenyl)-4-cyano-1H-imidazol-2-yl)-2-azabicyclo[3.1.0]hexane-2-carboxylate (340 mg, 0.79 mmol). (1R,3S,5R)-tert-butyl 3-(4-(4-(4,4,5,5-tetramethyl-1,3,2-dioxaborolan-2-yl)phenyl)-1H-imidazol-2-yl)-2-azabicyclo[3.1.0]hexane-2-carboxylate (393 mg, 0.871 mmol), and $NaHCO_3$ (333 mg, 3.96 mmol) in DME (6 mL) and Water (1.5 mL) in a thick-walled, screw-topped tube. The reaction mixture was flushed with argon, sealed, and immersed in a pre-heated oil bath (80° C.) and stirred 14 h. The mixture was diluted with EtOAc, washed with sat'd $NaHCO_3$ soln, brine, dried over $(Na_2SO_4)$. The crude product was charged to a Thompson 90 g silica gel cartridge and eluted with 35-100% B over 1.5 L, followed by hold at 100% B for 0.5 L. (Solvent B=EtOAc; Solvent A=hexanes). There was isolated Example DSTL-11, Step e, (200 mg, 36%) as a light yellow foam.

A small sample (~20 mg) was subject to further purification by prep. HPLC (0% B to 100% B over a 25 min gradient at 40 ml/min) using a PHENOMENEX® Gemini column (30×100 mm, 10u) where Solvent B=95% $CH_3CN$-5% $H_2O$-10 mM $NH_4OAc$ and A=5% $CH_3CN$-95% $H_2O$-10 mM $NH_4OAc$. (12.9 mg) LC-MS (Cond.-D4): RT=3.51 min. LC-MS Anal. Calcd. for $[M+H]^+$ $C_{39}H_{44}N_7O_4$ 674.35. found: 674.29.

Example DSTL-11

Step f

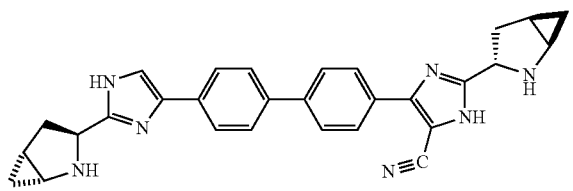

The product of Example DSTL-11, Step f was obtained upon removal of the protecting groups as described in the procedure from Example DSTL-1, Step h. LC-MS (Cond.-D4): RT=2.36 min. LC-MS Anal. Calcd. for $[M+H]^+$ $C_{29}H_{28}N_7$: 474.24. found 474.13.

Example DSTL-11

Example DSTL-11 was prepared from Example DSTL-11, Step f according to the procedure described for the preparation of Example GW2. Purification was accomplished by preparative HPLC; 0%-50% B over a 30 min gradient at 40 ml/min using a Waters SunFire column (30×100 mm, S5) B=90% $CH_3CN$-10% $H_2O$-0.1% TFA and A=5% $CH_3CN$-95% $H_2O$-0.1% TFA. There was isolated Example DSTL-11 (21.5 mg, 31%) as an off white solid. $^1H$ NMR (MeOD, 500 MHz, δ): 7.93-7.82 (m, 9 H), 5.15-5.08 (m, 2H), 4.58-4.56 (m, 2H), 3.82 (br. s, 1H), 3.72 (br. s, 1H) 3.67 (s, 6H), 2.73-2.67 (m, 1H), 2.50-2.46 (m, 3H), 2.21-2.14 (m, 2H), 2.09 (br. s, 1H), 2.03 (br. s, 1H), 1.14-1.10 (m, 2H), 1.05-1.02 (m, 6H), 0.97-0.93 (m, 6H), 0.90 (br. s, 1H), 0.83 (br. s, 1H). LC-MS (Cond.-D4): RT=3.25 min. LC-MS Anal. Calcd. for $[M+H]^+$ $C_{43}H_{50}N_9O_6$: 780.39. found 788.31.

Example DSTL-12

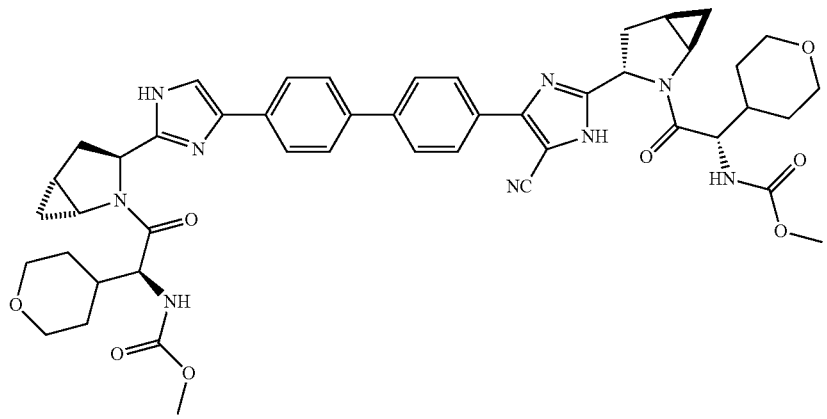

Example DSTL-12 was prepared from Example DSTL-11, Step f according to the procedure described for the preparation of Example GW2 except using (S)-2-(methoxycarbonylamino)-2-(tetrahydro-2H-pyran-4-yl)acetic acid instead of Cap-51. Purification was accomplished by preparative HPLC (0-50% B) over a 25 min gradient (at 40 ml/min) using a Waters SunFire column (30×100 mm, S5) where Solvent B=90% CH$_3$CN-10% H$_2$O-0.1% TFA and A=5% CH$_3$CN-95% H$_2$O-0.1% TFA. There was isolated Example DSTL-12 (26.7 mg, 35%) as an off white solid. LC-MS (Cond.-D4): RT=2.98 min. LC-MS Anal. Calcd. for [M+H]$^+$ C$_{42}$H$_{54}$N$_9$O$_8$: 872.41. found 872.35.

Example JLR-1

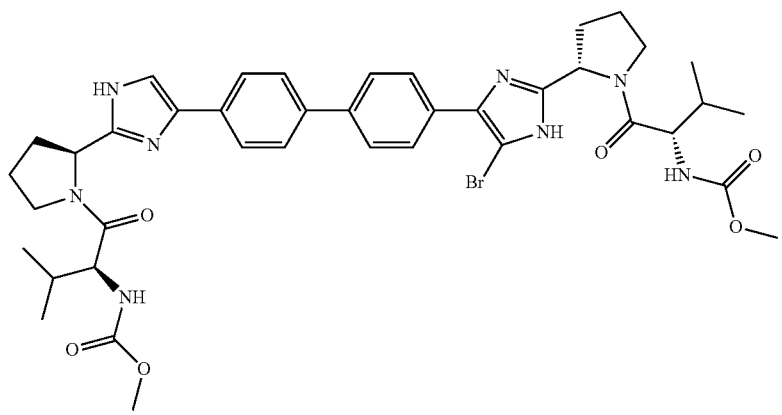 [SMILES: COC(=O)N[C@H](C(=O)N1CCC[C@H]1c1nc(-c2ccc(-c3ccc(-c4nc([C@@H]5CCCN5C(=O)[C@@H](NC(=O)OC)C(C)C)[nH]c4Br)cc3)cc2)c[nH]1)C(C)C]

Example JLR-1
Step a

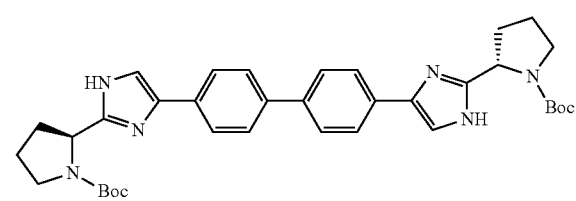 [SMILES: CC(C)(C)OC(=O)N1CCC[C@H]1c1nc(-c2ccc(-c3ccc(-c4c[nH]c([C@@H]5CCCN5C(=O)OC(C)(C)C)n4)cc3)cc2)c[nH]1]

Example JLR-1
Step b

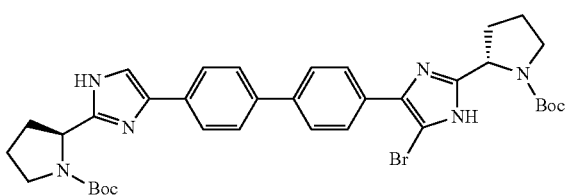 [SMILES: CC(C)(C)OC(=O)N1CCC[C@H]1c1nc(-c2ccc(-c3ccc(-c4nc([C@@H]5CCCN5C(=O)OC(C)(C)C)[nH]c4Br)cc3)cc2)c[nH]1]

For the synthesis of Example JLR-1, Step a, see the process patent application WO 2009/020825.

A solution of a 1 M bromine in AcOH (0.4 mL) was added to a solution of Example JLR-1, Step a (250 mg, 0.40 mmol)

in acetic acid (15 mL) and stirred for 3 h. The reaction mixture was poured onto DCM (100 mL) and treated with sat'd NaHCO$_3$ soln and solid NaHCO$_3$, until pH=neutral. The organic phase was concentrated and dried under vacuum. The reaction gave a 1:1:1 mixture of starting material:mono bromide: dibromide which were separated upon application (DCM) to a Thompson SiO$_2$ column (25 g). Elution (BIOTAGE®) by gradient 15-100% B over 500 mL gave Example JLR-1, Step b (180 mg). LC-MS (Cond.-J4): RT=2.75 min. LC-MS Anal. Calcd. for [M+H]$^+$ C$_{36}$H$_{44}$BrN$_6$O$_4$: 705.26. found 705.22.

Example JLR-1

Step c

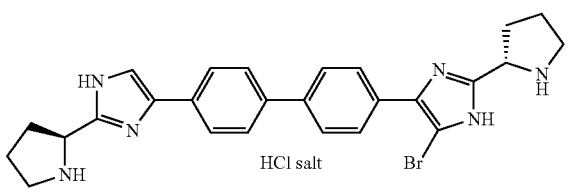 [SMILES: Brc1[nH]c([C@@H]2CCCN2)nc1-c1ccc(-c2ccc(-c3c[nH]c([C@@H]4CCCN4)n3)cc2)cc1]

A solution of 4N HCl in dioxane (4 mL) was added to Example JLR-1, Step b (38 mg, 0.054 mmol) in MeOH (4 mL) and stirred for 4 h. The solvent was removed under vacuum and the tetra HCl salt was dried under high vacuum. LC-MS (Cond.-J4): RT=1.75 min. LC-MS Anal. Calcd. for [M+H]$^+$ C$_{26}$H$_{28}$BrN$_6$: 503.16. found 503.26.

Example JLR-1

Example JLR-1 was prepared from Example JLR-1, Step c according to the procedure described for the preparation of Example GW2. Purification by preparative HPLC PHENOMENEX® Luna column (30×100 mm S10) running 25 min gradient from 15-100% B (at 40 ml/min) where Solvent B=90% MeOH-10% H$_2$O-0.1% TFA and A=5% MeOH-95% H$_2$O-0.1% TFA. LC-MS (Cond.-J4): RT=2.61 min. LC-MS Anal. Calcd. for [M+H]$^+$ C$_{40}$H$_{50}$BrN$_8$O$_6$: 819.31. found 819.23.

Example JLR-2

Step a

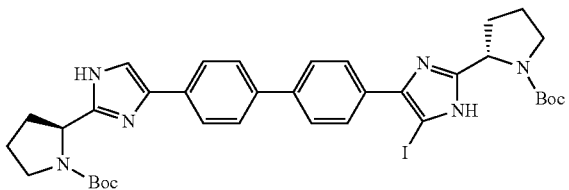 [SMILES: CC(C)(C)OC(=O)N1CCC[C@H]1c1nc(-c2ccc(-c3ccc(-c4nc([C@@H]5CCCN5C(=O)OC(C)(C)C)[nH]c4I)cc3)cc2)c[nH]1]

Iodine (162 mg, 0.640 mmol) was added to a solution of Example JLR-1, Step a (400 mg, 0.640 mmol) and NaHCO$_3$ (161 mg, 1.921 mmol) in dioxane (15 mL) and water (15 mL) and the reaction stirred for 6 h, quenched with 10% Na$_2$S$_2$O$_3$ solution (40 mL) and diluted with EtOAc/THF (2:1). The organic phase was concentrated and the crude product was applied (DCM) to a Thompson silica gel column (40 g) and eluted with 35-100% B over 1 L (A/B DCM/EtOAc) to give a mixture of starting material, diiodide (255 mg), and Example JLR-2, Step a (46 mg, 9%). LC-MS (Cond.-J4): RT=2.45 min. LC-MS Anal. Calcd. for [M+H]$^+$ C$_{36}$H$_{44}$IN$_6$O$_4$: 751.24. found 751.18.

Example JLR-2

Step b

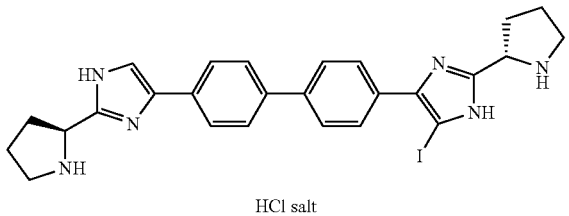 [SMILES: Ic1[nH]c([C@@H]2CCCN2)nc1-c1ccc(-c2ccc(-c3c[nH]c([C@@H]4CCCN4)n3)cc2)cc1]

A solution of 4N HCl in dioxane (5 mL) was added to MR-2, Step a (46 mg, 0.061 mmol) in MeOH (5 mL) and stirred for 4 h. The solvent was removed under vacuum and the tetra HCl salt was dried under high vacuum. LC-MS (Cond.-J4): RT=1.70 min. LC-MS Anal. Calcd. for [M+H]$^+$ C$_{26}$H$_{28}$IN$_6$: 551.13. found 551.09.

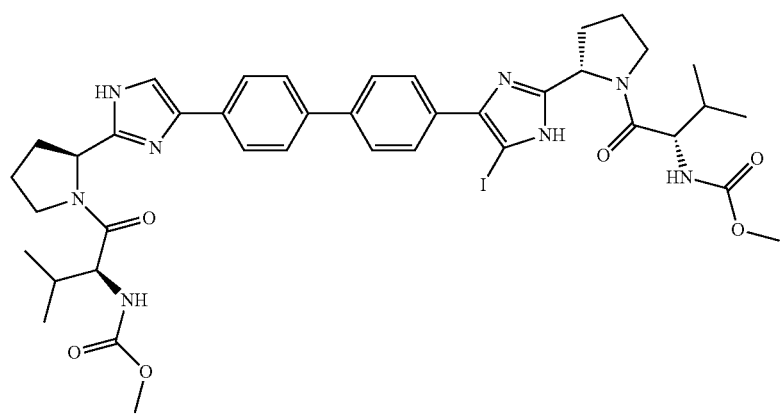

Example JLR-2

Example JLR-2 was prepared from Example JLR-2, Step b according to the procedure described for the preparation of Example GW2. Purification by semi-prep HPLC; Dynamax 6A semi-prep C8 column; 5%-95% B over 30 min (at 20 ml/min) where Solvent B=90% CH$_3$CN-10% H$_2$O-1% NH$_4$OAc and A=5% CH$_3$CN-95% H$_2$O-1% NH$_4$OAc. LC-MS (Cond.-J4): RT=2.35 min. LC-MS Anal. Calcd. for [M+H]$^+$ C$_{40}$H$_{50}$IN$_8$O$_6$: 865.29. found 865.31.

Example JLR-3

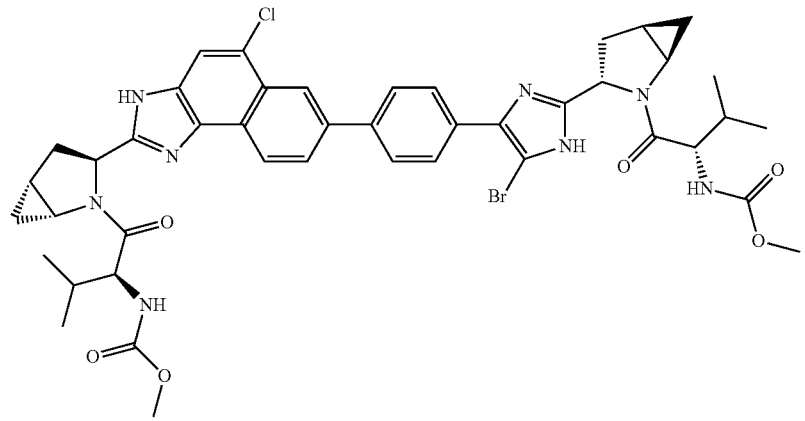 [SMILES: COC(=O)N[C@H](C(=O)N1[C@@H]2C[C@@H]2C[C@H]1c1nc(-c2ccc(-c3ccc4c(c3)c(Cl)cc3[nH]c([C@@H]5C[C@H]6C[C@H]6N5C(=O)[C@@H](NC(=O)OC)C(C)C)nc34)cc2)c(Br)[nH]1)C(C)C]

Example JLR-3

Step a

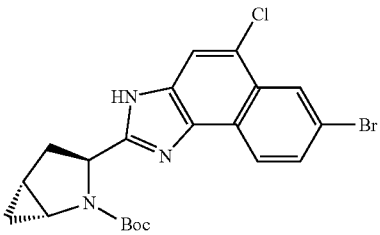 [SMILES: CC(C)(C)OC(=O)N1[C@@H]2C[C@@H]2C[C@H]1c1nc2c(cc(Cl)c3cc(Br)ccc32)[nH]1]

NCS (175 mg, 1.310 mmol) was added to a solution of Example DSTL-1, Step d (510 mg, 1.191 mmol) in DMF (10 mL) and stirred for 18 h at 50° C. The solvent was removed by rotary evaporation under high vacuum, and the residue charged (DCM) to a Thomson silica gel cartridge (80 g). Gradient elution was performed from 25-100% B over 750 mL (A/B Hex/EtOAc) to give Example JLR-3, Step a (250 mg, 46%). $^1$H NMR (MeOD, 500 MHz, δ): 8.58 (s, 1H), 8.39 (d, J=8.6 Hz, 1H), 7.97 (s. 1H), 7.93 (d, J=7.6 Hz, 1H), 4.98 (s, 1H), 3.70 (s, 1H), 2.76-2.71 (m, 1H), 2.50-2.45 (m, 1H), 1.86 (s, 1H), 1.48/1.12 (s, 9H), 0.96-0.92 (m, 1H), 0.79-0.77 (m, 1H). LC-MS (Cond.-J4): RT=3.13 min. LC-MS Anal. Calcd. for [M+H]$^+$ C$_{21}$H$_{22}$BrClN$_3$O$_2$: 464.06. found 464.05.

Example JLR-3

Step a.1

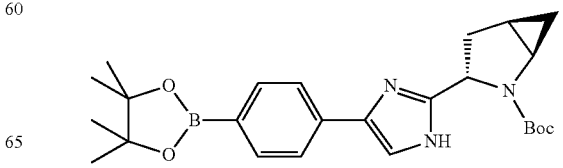

Example JLR-3, Step a.1 was prepared from Example DSTL-1, Step d.1 according to a procedure described in patent application WO 2008/021927 for the preparation of its desmethano analog.

Example JLR-3

Step b

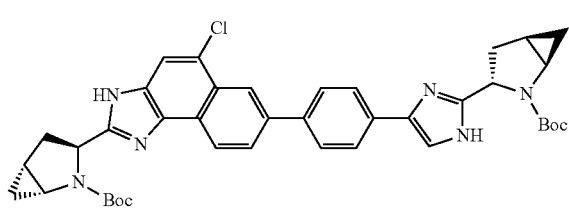 [SMILES: CC(C)(C)OC(=O)N1[C@@H]2C[C@@H]2C[C@H]1c1nc(-c2ccc(-c3ccc4c(c3)c(Cl)cc3[nH]c([C@@H]5C[C@H]6C[C@H]6N5C(=O)OC(C)(C)C)nc34)cc2)c[nH]1]

Example JLR-3, Step b was prepared from Example JLR-3, Step a and Example JLR-3, Step a.1 according to the procedure described for the preparation Example DSTL-1, Step g to give Example JLR-3, Step b. LC-MS (Cond.-J4): RT=2.72 min. LC-MS Anal. Calcd. for [M+H]$^+$ C$_{40}$H$_{44}$ClN$_6$O$_4$: 707.31. found 707.44.

Example JLR-3

Step c

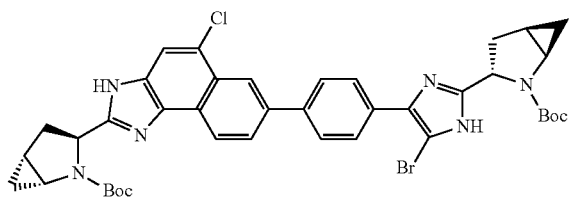 [SMILES: CC(C)(C)OC(=O)N1[C@@H]2C[C@@H]2C[C@H]1c1nc(-c2ccc(-c3ccc4c(c3)c(Cl)cc3[nH]c([C@@H]5C[C@H]6C[C@H]6N5C(=O)OC(C)(C)C)nc34)cc2)c(Br)[nH]1]

Example JLR-3, Step c was prepared from Example JLR-3, Step b according to the procedure described for the preparation DSTL-3, Step a to give Example JLR-3, Step c. LC-MS (Cond.-J4): RT=3.30 min. LC-MS Anal. Calcd. for [M+H]$^+$ C$_{40}$H$_{43}$BrClN$_6$O$_4$: 787.21. found 787.34.

Example JLR-3

Step d

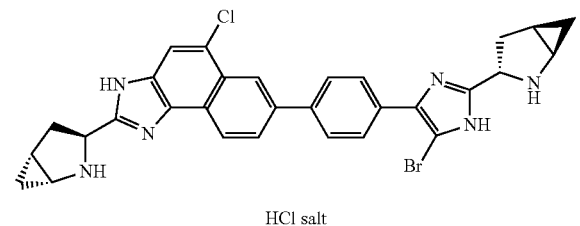 [SMILES: Clc1cc2[nH]c([C@@H]3C[C@H]4C[C@H]4N3)nc2c2ccc(-c3ccc(-c4nc([C@@H]5C[C@H]6C[C@H]6N5)[nH]c4Br)cc3)cc12]

HCl salt

Example JLR-3, Step d was prepared from Example JLR-3, Step c according to the procedure described in the procedure from Example JLR-1, Step b. LC-MS (Cond.-J4): RT=2.37 min. LC-MS Anal. Calcd. for [M+H]$^+$ C$_{30}$H$_{27}$BrClN$_6$: 587.12. found 587.14.

Example JLR-3

Example JLR-3 was prepared from Example JLR-3, Step d according to the procedure described for the preparation of Example GW2. Purification by preparative HPLC PHE-NOMENEX® Luna column (30×100 mm S10) running 18 min gradient from 15-100% B (at 40 ml/min) where Solvent B=90% MeOH-10% H$_2$O-0.1% TFA and A=5% MeOH-95% H$_2$O-0.1% TFA. $^1$H NMR (MeOD, 500 MHz, δ): 8.69-8.68 (m, 1H), 8.52-8.50 (m, 1H), 8.18-8.16 (m, 1H), 7.98-7.96 (m, 1H), 7.91-7.90 (m, 4H), 5.34-5.34 (m, 1H), 5.09-5.06 (m, 1H), 4.62-4.58 (m, 2H), 3.91 (br s, 1H), 3.76 (br s, 1H) 3.69 (s, 6H), 2.77-2.73 (m, 1H), 2.64-2.59 (m, 1H), 2.51-2.48 (m, 2H), 2.23-2.16 (m, 3H), 2.06 (br s, 1H), 1.17-1.12 (m, 2H), 1.06-0.92 (m, 13H), 0.83 (m, 1H). LC-MS (Cond.-J4): RT=3.14 min. LC-MS Anal. Calcd. for [M+H]$^+$ C$_{44}$H$_4$BrClN$_8$O$_6$: 901.27. found 901.45.

Example JLR-4

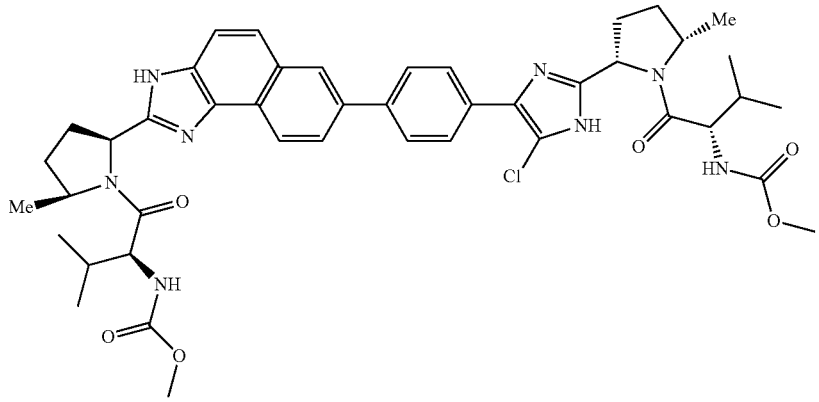 [SMILES: COC(=O)N[C@H](C(=O)N1[C@@H](C)CC[C@H]1c1nc(-c2ccc(-c3ccc4c(ccc5[nH]c([C@@H]6CC[C@H](C)N6C(=O)[C@@H](NC(=O)OC)C(C)C)nc54)c3)cc2)c(Cl)[nH]1)C(C)C]

Example JLR-4

Step a

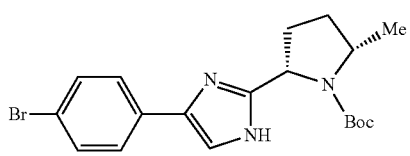 [SMILES: C[C@H]1CC[C@@H](c2nc(-c3ccc(Br)cc3)c[nH]2)N1C(=O)OC(C)(C)C]

Hunig's base (1.2 g, 9 mmol) was added to a solution of 2-bromo-1-(4-bromophenyl)ethanone (2.5 g, 8.99 mmol) and (2S,5S)-1-(tert-butoxycarbonyl)-5-methylpyrrolidine-2-carboxylic acid (1.9 g, 8.29 mmol) in acetonitrile (75 mL) and stirred for 6 h at 24° C. The reaction mixture was concentrated and the residue taken up in EtOAc and washed with water. Concentration gave a white solid which was taken up in xylene (90 mL). Ammonium acetate (4.23 g, 70.4 mmol) was added, and the solution was stirred in a screw-capped pressure vessel at 135° C. for 3.5 h. The reaction mixture was diluted with EtOAc (400 mL) and washed with sat'd NaHCO$_3$ soln and concentrated. The crude product was charged (DCM) to a 80 g Thompson silica gel cartridge and gradient elution was performed from 15% to 100% B over 1 L (A/B Hex/EtOAc) gave Example JLR-4, Step a (yield not determined). LC-MS (Cond.-J4): RT=2.21 min. LC-MS Anal. Calcd. for [M+H]$^+$ C$_{19}$H$_{25}$BrN$_3$O$_2$: 406.12. found 406.10. [Note: for the synthesis of the starting carboxylic acid, see U.S. Patent Application 2009/0068140).

Example JLR-4

Step b

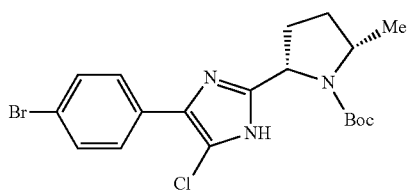 [SMILES: C[C@H]1CC[C@@H](c2nc(-c3ccc(Br)cc3)c(Cl)[nH]2)N1C(=O)OC(C)(C)C]

NCS (161 mg, 1.21 mmol) was added to a solution of Example JLR-4, Step a (700 mg, 1.7 mmol) in DMF (10 mL) and stirred for 18 h at 50° C. Additional NCS (50 mg) and the reaction continued for 6 h before removing the solvent by nitrogen purge. The crude product was charged (DCM) to a 40 g Thompson silica gel cartridge, and gradient elution was performed from 15% to 100% B over 750 mL (A/B Hex/EtOAc) to give Example JLR-4, Step b (580 mg, 70%). $^1$H NMR (MeOD, 500 MHz, δ): 7.62 (appr s, 4H), 4.77 (br. s, 1H), 4.03 (br. s, 1H), 2.24 (br s, 2H), 2.16-2.11 (m, 1H) 1.79 (br. s, 1H), 1.47-1.25 (m, 12H). LC-MS (Cond.-J4): RT=3.33 min. LC-MS Anal. Calcd. for [M+H]$^+$ C$_{19}$H$_{24}$BrClN$_3$O$_2$: 440.08. found 440.0.

Example JLR-4

Step c

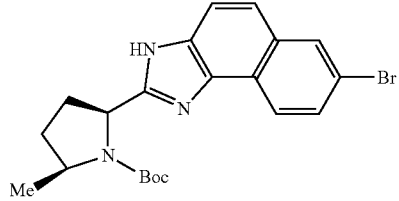 [SMILES: C[C@H]1CC[C@@H](c2nc3c(ccc4cc(Br)ccc43)[nH]2)N1C(=O)OC(C)(C)C]

EEDQ (1.67 g, 6.75 mmol) was added to a solution of Example DSTL-1, Step c (1.6 g, 6.75 mmol) and (2S,5S)-1-(tert-butoxycarbonyl)-5-methylpyrrolidine-2-carboxylic acid (1.55 g, 6.75 mmol) in DCM (100 mL) and stirred for 6 h. (Note: The dianiline was not completely soluble). The reaction mixture was diluted with DCM (1 vol) and washed with half sat'd NaHCO$_3$ soln. Concentration gave a solid (2.5 g). LC-MS (Cond.-J4): RT=3.07 min. LC-MS Anal. Calcd. for [M+H]$^+$ C$_{21}$H$_{27}$BrN$_3$O$_3$: 448.13. found 448.11.

The crude solid (2.5 g, 5.58 mmol) was taken up in AcOH (200 mL) and stirred for 18 h at 60° C. Concentration under high vacuum removed the solvent. The residue was taken up in DCM, washed with sat'd NaHCO$_3$ soln, and concentrated. The residue was charged (DCM) to a 80 g Thompson silica gel cartridge and gradient elution was performed from 15% to 100% B over 750 mL. (A/B Hex/EtOAc) to give Example JLR-4, Step c (2.6 g). $^1$H NMR (MeOD, 500 MHz, δ): 8.36-8.35 (m, 2H), 8.0 (d, J=9 Hz, 1H), 7.91 (dd, J=9, 2 Hz, 1H), 7.87 (d, J=9 Hz, 1H), 5.31-5.28 (m, 1H), 4.17 (br. s, 1H), 2.59-2.56 (m, 1H), 2.39-2.31 (m, 2H) 1.86-1.83 (m, 1H), 1.52-1.19 (m, 12H). LC-MS (Cond.-J4): RT=2.57 min. LC-MS Anal. Calcd. for [M+H]$^+$ C$_{21}$H$_{25}$BrN$_3$O$_2$: 430.12. found 430.09.

Example JLR-4

Step d

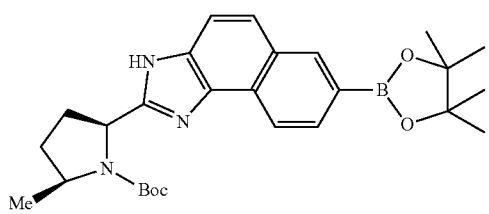 [SMILES: C[C@H]1CC[C@@H](c2nc3c(ccc4cc(B5OC(C)(C)C(C)(C)O5)ccc43)[nH]2)N1C(=O)OC(C)(C)C]

Example JLR-4, Step d was prepared from Example JLR-4, Step c according to the procedure described for the preparation of Example DSTL-1 Step f. LC-MS (Cond.-J4): RT=2.86 min. LC-MS Anal. Calcd. for [M+H]$^+$ C$_{27}$H$_{37}$BN$_3$O$_4$: 478.29. found 478.25.

Example JLR-4

Step e

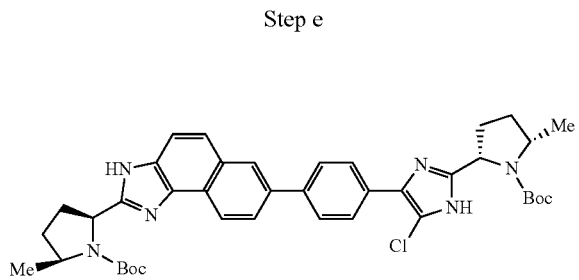

Example JLR-4, Step e was prepared from Example JLR-4, Step d and Example JLR-4, Step b according to the procedure described for the preparation DSTL-1, Step g to give Example JLR-4, Step e. $^1$H NMR (MeOD, 500 MHz, δ): 8.53 (d, J=8.6 Hz, 1H), 8.49 (s, 1H), 8.20 (dd, J=8.6, 2 Hz, 2H), 7.97 (d, J=8.6 Hz, 2H), 7.92 (d, J=8.6 Hz, 2H), 7.88 (d, J=8.9 Hz, 1H). 5.32 (t, J=6.4 Hz, 1H), 4.85 (br. s, 1H), 4.20 (br. s, 1H), 4.06 (br. s, 1H). 2.59-2.58 (m, 1H), 2.44-2.28 (m, 4H), 2.19-2.15 (m, 1H). 1.89-1.84 (m, 1H), 1.83-1.79 (m, 1H), 1.54-1.20 (m, 24H). LC-MS (Cond.-J4): RT=3.18 min. LC-MS Anal. Calcd. for [M+H]$^+$ C$_{40}$H$_{48}$ClN$_6$O$_4$: 711.34. found 711.31.

Example JLR-4

Step f

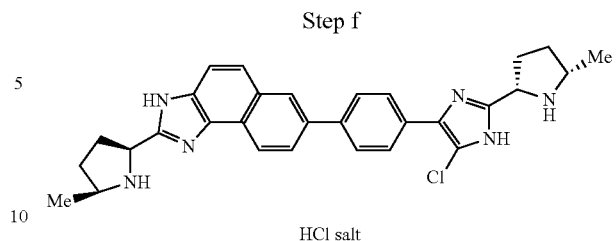

HCl salt

Example JLR-4, Step f was prepared from Example JLR-4, Step e according to the procedure described for the preparation Example JLR-1, Step b to give Example JLR-4, Step f. LC-MS (Cond.-J4): RT=2.19 min. LC-MS Anal. Calcd. for [M+H]$^+$ C$_{30}$H$_{32}$ClN$_6$: 511.24. found 711.23.

Example JLR-4

Example JLR-4 was prepared from Example JLR-4, Step f according to the procedure described for the preparation of Example GW2. Purification by preparative HPLC Luna Axia column (30×100 mm C18) running 25 min gradient from 15-100% B (at 40 ml/min) where Solvent B=90% MeOH-10% H$_2$O-0.1% TFA and A=5% MeOH-95% H$_2$O-0.1% TFA. LC-MS (Cond.-J4): RT=3.12 min. LC-MS Anal. Calcd. for [M+H]$^+$ C$_{44}$H$_{54}$ClN$_8$O$_6$: 825.39. found 825.31.

Example JLR-5

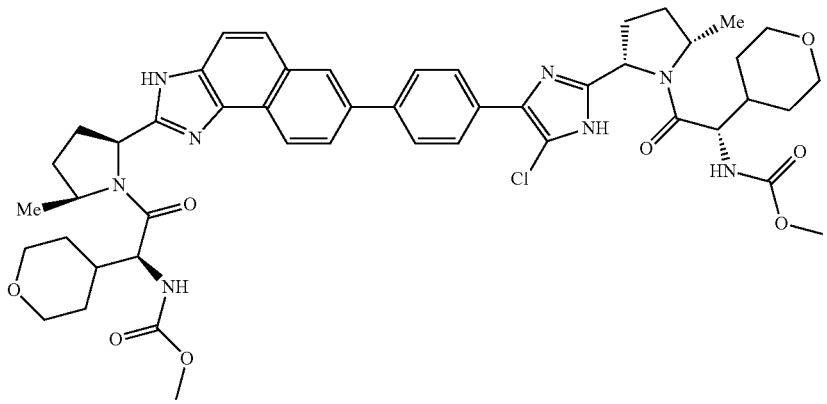 [SMILES: COC(=O)N[C@H](C(=O)N1[C@@H](C)CC[C@H]1c1nc(-c2ccc(-c3ccc4c(ccc5[nH]c([C@@H]6CC[C@H](C)N6C(=O)[C@@H](NC(=O)OC)C6CCOCC6)nc54)c3)cc2)c(Cl)[nH]1)C1CCOCC1]

Example JLR-5 was prepared from Example JLR-4, Step f according to the procedure described for the preparation of Example GW2 except using and (S)-2-(methoxycarbonylamino)-2-(tetrahydro-2H-pyran-4-yl)acetic acid. Purification by preparative HPLC Luna Axia column (30×100 mm C18) running 25 min gradient from 15-100% B (at 40 ml/min) where Solvent B=90% MeOH-10% H$_2$O-0.1% TFA and A=5% MeOH-95% H$_2$O-0.1% TFA. LC-MS (Cond.-J4): RT=2.85 min. LC-MS Anal. Calcd. for [M+H]$^+$ C$_{48}$H$_{58}$ClN$_8$O$_6$: 909.41. found 909.39.

Example ZY1

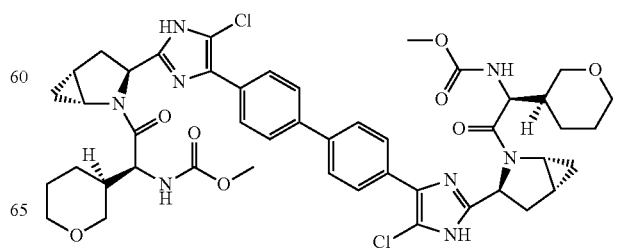

Example ZY1

Step a

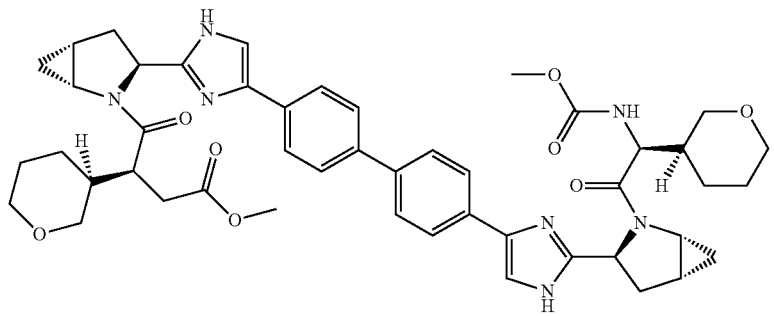 [SMILES: COC(=O)C[C@H](C(=O)N1[C@@H]2C[C@@H]2C[C@H]1c1nc(-c2ccc(-c3ccc(-c4c[nH]c([C@@H]5C[C@H]6C[C@H]6N5C(=O)[C@@H](NC(=O)OC)[C@@H]5CCCOC5)n4)cc3)cc2)c[nH]1)[C@@H]1CCCOC1]

HATU (151 mg, 0.40 mmol) was added to a solution of an HCl salt of 4,4'-bis(2-((1R,3S,5R)-2-azabicyclo[3.1.0]hexan-3-yl)-1H-imidazol-4-yl)biphenyl (Example 1e) (107 mg, 0.18 mmol) and (S)-2-(methoxycarbonylamino)-2-((S)-tetrahydro-2H-pyran-3-yl)acetic acid (cap-177a) (86 mg, 0.40 mmol) in DMF (1.5 mL) and DIPEA (0.25 mL, 1.4 mmol) and the mixture was stirred at rt for 2 h. The reaction mixture was diluted with MeOH and purified by prep HPLC ($H_2O$-MeOH with 0.1% TFA buffer) to yield a TFA salt of dimethyl(S,1S,1'S)-2,2'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(2-oxo-1-((S)-tetrahydro-2H-pyran-3-yl)ethane-2,1-diyl)dicarbamate (148.5 mg) as light yellow solid. LC-MS retention time=1.61 min; m/z=847 [M+H]$^+$. (Column: PHENOMENEX® Luna 3.0×50 mm S10. Solvent A=90% Water: 10% Methanol: 0.1% TFA. Solvent B=10% Water: 90% Methanol: 0.1% TFA. Flow Rate=4 mL/min. Start % B=0. Final % B=100. Gradient Time=3 min. Wavelength=220). $^1$H NMR (400 MHz, MeOD) δ ppm 7.80-7.91 (m, 10H), 5.13 (dd, J=9.3, 7.0 Hz, 2H), 4.79 (d, J=8.3 Hz, 2H), 3.84-3.97 (m, 2H), 3.70-3.80 (m, 4H), 3.68 (s, 6H), 3.52-3.63 (m, 2H), 3.34-3.42 (m, 2H), 2.61-2.75 (m, 2H), 2.43-2.54 (m, 2H), 1.98-2.15 (m, 4H), 1.67-1.84 (m, 4H), 1.48-1.65 (m, 4H), 0.98-1.16 (m, 2H), 0.77-0.93 (m, 2H).

Example ZY1

NCS (8.2 mg, 0.061 mmol) was added to a solution of a TFA salt of dimethyl (S,1S,1'S)-2,2'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(2-oxo-1-((S)-tetrahydro-2H-pyran-3-yl)ethane-2,1-diyl)dicarbamate (Example ZY1, Step a) (33 mg, 0.031 mmol) in DMF (1 mL) and the mixture was stirred at 50° C. for 16 h. The reaction mixture was diluted with MeOH, filtered and purified by prep HPLC ($H_2O$-MeOH with 0.1% TFA buffer) to yield a TFA salt of dimethyl(S,1S,1'S)-2,2'-((1R,1'R,3S,3'S,5R,5'R)-3,3'-(4,4'-(biphenyl-4,4'-diyl)bis(5-chloro-1H-imidazole-4,2-diyl))bis(2-azabicyclo[3.1.0]hexane-3,2-diyl))bis(2-oxo-1-((S)-tetrahydro-2H-pyran-3-yl)ethane-2,1-diyl)dicarbamate, (Example ZY1) (25 mg) as white solid. LC-MS retention time=1.92 min; m/z=458 [M/2+H]$^+$. (Column: PHENOMENEX® Luna 3.0×50 mm S10. Solvent A=95% Water/5% Methanol/10 mM Ammonium Acetate. Solvent B=5% Water/95% Methanol/10 mM Ammonium Acetate. Flow Rate=4 mL/min. Start % B=0. Final % B=100. Gradient Time=2 min. Wavelength=220). $^1$H NMR (400 MHz, MeOD) δ ppm 7.77-7.85 (m, 8H), 5.03 (dd, J=8.8, 6.0 Hz, 2H), 4.75-4.86 (m, 2H), 3.71-3.89 (m, 6H), 3.67 (s, 6H), 3.36-3.62 (m, 4H), 2.38-2.57 (m, 4H), 1.94-2.12 (m, 4H), 1.69-1.87 (m, 4H), 1.46-1.65 (m, 4H), 1.03-1.17 (m, 2H), 0.77-0.85 (m, 2H).

Example ZY2

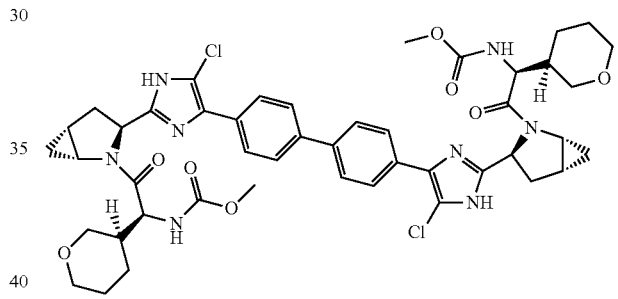

Example ZY2

Step a

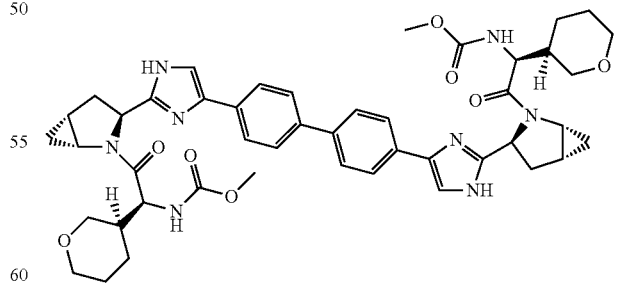

HATU (140 mg, 0.37 mmol) was added to a solution of an HCl salt of 4,4'-bis(2-((1R,3S,5R)-2-azabicyclo[3.1.0]hexan-3-yl)-1H-imidazol-4-yl)biphenyl, (Example 1e) (100 mg, 0.17 mmol) and (S)-2-(methoxycarbonylamino)-2-((R)-tetrahydro-2H-pyran-3-yl)acetic acid (cap117b) (80 mg, 0.37 mmol) in DMF (1.5 mL) and DIPEA (0.23 mL, 1.3 mmol) and the mixture was stirred at rt for 3 h. Then the reaction mixture was diluted with MeOH and purified by prep HPLC (H₂O-MeOH with 0.1% TFA buffer) to yield a TFA salt of dimethyl(R,1S,1'S)-2,2'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(2-oxo-1-((R)-tetrahydro-2H-pyran-3-yl)ethane-2,1-diyl)dicarbamate (Example ZY2, Step a) (76.2 mg) as white solid. LC-MS retention time=1.53 min; m/z=847 [M+H]⁺. (Column: PHENOMENEX® Luna 3.0×50 mm S10. Solvent A=90% Water: 10% Methanol: 0.1% TFA. Solvent B=10% Water: 90% Methanol: 0.1% TFA. Flow Rate=4 mL/min. Start % B=0. Final % B=100. Gradient Time=3 min. Wavelength=220). ¹H NMR (400 MHz, MeOD) δ ppm 7.75-7.96 (m, 10H), 5.13 (dd, J=9.3, 7.0 Hz, 2H), 4.60 (d, J=8.3 Hz, 2H), 3.77-3.95 (m, 6H), 3.67 (s, 6H), 3.24-3.47 (m, 4H), 2.62-2.76 (m, 2H), 2.40-2.57 (m, 2H), 1.97-2.19 (m, 4H), 1.54-1.82 (m, 6H), 1.36-1.54 (m, 2 H), 1.00-1.17 (m, 2H), 0.79-0.93 (m, 2H).

Example ZY2

NCS (5.2 mg, 0.039 mmol) was added to a solution of a TFA salt of dimethyl (R,1S,1'S)-2,2'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(2-oxo-1-((R)-tetrahydro-2H-pyran-3-yl)ethane-2,1-diyl)dicarbamate (Example ZY2, Step a) (21 mg, 0.020 mmol) in DMF (1 mL) and the mixture was stirred at 50° C. for 16 h. Then the reaction mixture was diluted with MeOH, filtered and purified by prep HPLC (H₂O-MeOH with 0.1% TFA buffer) to yield a TFA salt of dimethyl(R,1S,1'S)-2,2'-((1R,1'R,3S,3'S,5R,5'R)-3,3'-(4,4'-(biphenyl-4,4'-diyl)bis(5-chloro-1H-imidazole-4,2-diyl))bis(2-azabicyclo[3.1.0]hexane-3,2-diyl))bis(2-oxo-1-((R)-tetrahydro-2H-pyran-3-yl)ethane-2,1-diyl)dicarbamate (Example ZY2) (10.8 mg) as white solid. LC-MS retention time=1.92 min; m/z=458 [M/2+H]⁺. (Column: PHENOMENEX® Luna 3.0×50 mm S10. Solvent A=95% Water/5% Methanol/10 mM Ammonium Acetate. Solvent B=5% Water/95% Methanol/10 mM Ammonium Acetate. Flow Rate=4 mL/min. Start % B=0. Final % B=100. Gradient Time=2 min. Wavelength=220). ¹H NMR (400 MHz, MeOD) δ ppm 7.76-7.87 (m, 8H), 5.04 (dd, J=8.8, 6.0 Hz, 2H), 4.61 (d, J=8.3 Hz, 2H), 3.75-3.95 (m, 6H), 3.66 (s, 6H), 3.35-3.48 (m, 4H), 2.39-2.58 (m, 4H), 1.97-2.16 (m, 4H), 1.73-1.87 (m, 2H), 1.40-1.73 (m, 6H), 1.01-1.16 (m, 2H), 0.81 (d, J=1.8 Hz, 2H).

Example ZY3

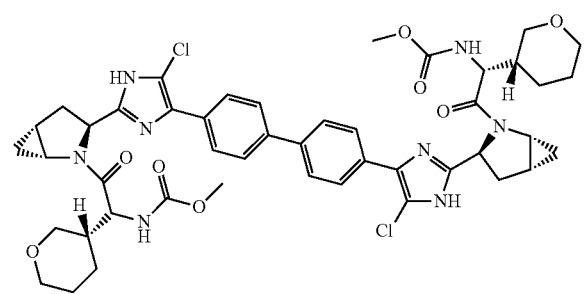 [SMILES: COC(=O)NC(C(=O)N1[C@@H]2C[C@@H]2C[C@H]1c1nc(-c2ccc(-c3ccc(-c4nc([C@@H]5C[C@H]6C[C@H]6N5C(=O)[C@H](NC(=O)OC)[C@H]5CCCOC5)[nH]c4Cl)cc3)cc2)c(Cl)[nH]1)[C@@H]1CCCOC1]

Example ZY3

Step a

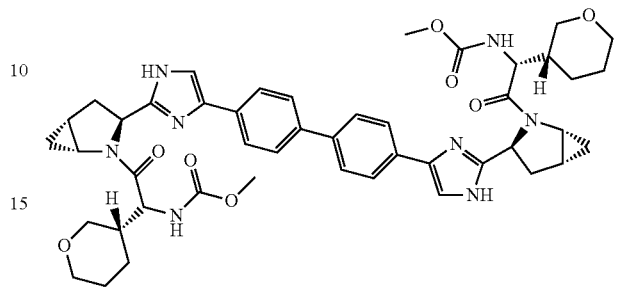

HATU (82 mg, 0.22 mmol) was added to a solution of an HCl salt of 4,4'-bis(2-((1R,3S,5R)-2-azabicyclo[3.1.0]hexan-3-yl)-1H-imidazol-4-yl)biphenyl (Example 1e) (58.3 mg, 0.098 mmol) and (R)-2-(methoxycarbonylamino)-2-((R)-tetrahydro-2H-pyran-3-yl)acetic acid (cap 117c) (49 mg, 0.23 mmol) in DMF (1 mL) and DIPEA (0.14 mL, 0.79 mmol) and the mixture was stirred at rt for 3 h. Then the reaction mixture was diluted with MeOH, filtered and purified by prep HPLC (H₂O-MeOH with 0.1% TFA buffer) to yield a TFA salt of dimethyl(R,1R,1'R)-2,2'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(2-oxo-1-((R)-tetrahydro-2H-pyran-3-yl)ethane-2,1-diyl)dicarbamate (Example ZY3, Step a) (79.8 mg) as white solid. LC-MS retention time=1.63 min; m/z=847 [M+H]⁺. (Column: PHENOMENEX® Luna 3.0×50 mm S10. Solvent A=90% Water: 10% Methanol: 0.1% TFA. Solvent B=10% Water: 90% Methanol: 0.1% TFA. Flow Rate=4 mL/min. Start % B=0. Final % B=100. Gradient Time=3 min. Wavelength=220).

Example ZY3

NCS (6.7 mg, 0.050 mmol) was added to a solution of a TFA salt of dimethyl (R,1R,1'R)-2,2'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(2-oxo-1-((R)-tetrahydro-2H-pyran-3-yl)ethane-2,1-diyl)dicarbamate (Example ZY3, Step a) (27 mg, 0.025 mmol) in DMF (1 mL) and the mixture was stirred at 50° C. for 16 h. Then the reaction mixture was diluted with MeOH, filtered and purified by prep HPLC (H₂O-MeOH with 0.1% TFA buffer) to yield a TFA salt of dimethyl(R,1R,1'R)-2,2'-((1R,1'R,3S,3'S,5R,5'R)-3,3'-(4,4'-(biphenyl-4,4'-diyl)bis(5-chloro-1H-imidazole-4,2-diyl))bis(2-azabicyclo[3.1.0]hexane-3,2-diyl))bis(2-oxo-1-((R)-tetrahydro-2H-pyran-3-yl)ethane-2,1-diyl)dicarbamate (Example ZY3) (15.8 mg) as white solid. LC-MS retention time=1.93 min; m/z=458 [M/2+H]⁺. (Column: PHENOMENEX® Luna 3.0×50 mm S10. Solvent A=95% Water/5% Methanol/10 mM Ammonium Acetate. Solvent B=5% Water/95% Methanol/10 mM Ammonium Acetate. Flow Rate=4 mL/min. Start % B=0. Final % B=100. Gradient Time=2 min. Wavelength=220).

Example ZY4

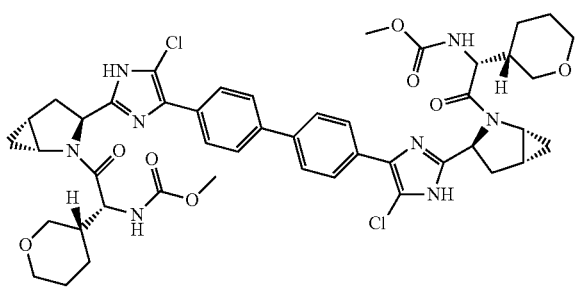 [SMILES: COC(=O)N[C@@H](C(=O)N1[C@@H]2C[C@@H]2C[C@H]1c1nc(-c2ccc(-c3ccc(-c4nc([C@@H]5C[C@H]6C[C@H]6N5C(=O)[C@H](NC(=O)OC)[C@@H]5CCCOC5)[nH]c4Cl)cc3)cc2)c(Cl)[nH]1)[C@@H]1CCCOC1]

Example ZY4

Step a

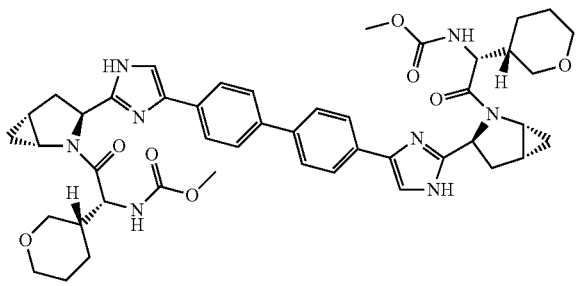 [SMILES: COC(=O)N[C@@H](C(=O)N1[C@@H]2C[C@@H]2C[C@H]1c1nc(-c2ccc(-c3ccc(-c4c[nH]c([C@@H]5C[C@H]6C[C@H]6N5C(=O)[C@H](NC(=O)OC)[C@@H]5CCCOC5)n4)cc3)cc2)c[nH]1)[C@@H]1CCCOC1]

HATU (75 mg, 0.20 mmol) was added to a solution of an HCl salt of 4,4'-bis(2-((1R,3S,5R)-2-azabicyclo[3.1.0]hexan-3-yl)-1H-imidazol-4-yl)biphenyl (Example 1e) (53.5 mg, 0.090 mmol) and (R)-2-(methoxycarbonylamino)-2-((S)-tetrahydro-2H-pyran-3-yl)acetic acid (cap117d) (45 mg, 0.21 mmol) in DMF (1 mL) and DIPEA (0.13 mL, 0.72 mmol) and the mixture was stirred at rt for 3 h. Then the reaction mixture was diluted with MeOH, filtered and purified by prep HPLC (H$_2$O-MeOH with 0.1% TFA buffer) to yield a TFA salt of dimethyl(S,1R,1'R)-2,2'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(2-oxo-1-((S)-tetrahydro-2H-pyran-3-yl)ethane-2,1-diyl)dicarbamate (Example ZY4, Step a) (78.5 mg) as white solid. LC-MS retention time=1.57 min; m/z=847 [M+H]$^+$. (Column: PHENOMENEX® Luna 3.0×50 mm S10. Solvent A=90% Water: 10% Methanol: 0.1% TFA. Solvent B=10% Water: 90% Methanol: 0.1% TFA. Flow Rate=4 mL/min. Start % B=0. Final % B=100. Gradient Time=3 min. Wavelength=220).

Example ZY4

NCS (9.2 mg, 0.069 mmol) was added to a solution of a TFA salt of dimethyl (S,1R,1'R)-2,2'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(2-oxo-1-((S)-tetrahydro-2H-pyran-3-yl)ethane-2,1-diyl)dicarbamate (Example ZY4, Step a) (37 mg, 0.034 mmol) in DMF (1 mL) and the mixture was stirred at 50° C. for 16 h. Then the reaction mixture was diluted with MeOH, filtered and purified by prep HPLC (H$_2$O-MeOH with 0.1% TFA buffer) to yield a TFA salt of dimethyl(S,1R,1'R)-2,2'-((1R,1'R,3S,3'S,5R,5'R)-3,3'-(4,4'-(biphenyl-4,4'-diyl)bis(5-chloro-1H-imidazole-4,2-diyl))bis(2-azabicyclo[3.1.0]hexane-3,2-diyl))bis(2-oxo-1-((S)-tetrahydro-2H-pyran-3-yl)ethane-2,1-diyl)dicarbamate (Example ZY4) (25 mg) as white solid. LC-MS retention time=1.93 min; m/z=458 [M/2+H]$^+$. (Column: PHENOMENEX® Luna 3.0×50 mm S10. Solvent A=95% Water/5% Methanol/10 mM Ammonium Acetate. Solvent B=5% Water/95% Methanol/10 mM Ammonium Acetate. Flow Rate=4 mL/min. Start % B=0. Final % B=100. Gradient Time=2 min. Wavelength=220).

Example ZY5

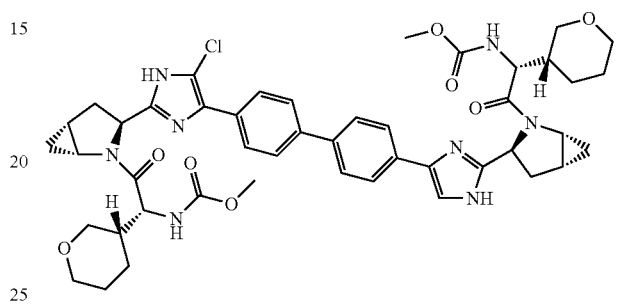

NCS (5.3 mg, 0.039 mmol) was added to a solution of a TFA salt of dimethyl (S,1S,1'S)-2,2'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(2-oxo-1-((S)-tetrahydro-2H-pyran-3-yl)ethane-2,1-diyl)dicarbamate (Example ZY1, Step a) (42.4 mg, 0.039 mmol) in DMF (1 mL) and the mixture was stirred at 50° C. for 16 h. Then the reaction mixture was diluted with MeOH, filtered and purified by prep HPLC (H$_2$O-MeOH with 0.1% TFA buffer) to yield Example ZY5 as a TFA salt (11.7 mg, white solid). LC-MS retention time=2.04 min; m/z=881 [M+H]$^+$. (Column: PHENOMENEX® Luna 3.0×50 mm S10. Solvent A=90% Water: 10% Methanol: 0.1% TFA. Solvent B=10% Water: 90% Methanol: 0.1% TFA. Flow Rate=4 mL/min. Start % B=0. Final % B=100. Gradient Time=3 min. Wavelength=220). $^1$H NMR (400 MHz, MeOD) δ ppm 7.76-7.92 (m, 9H), 5.13 (dd, J=9.2, 6.9 Hz, 1H), 5.04 (dd, J=8.0, 6.5 Hz, 1H), 4.74-4.80 (m, 2H), 3.71-3.94 (m, 6H), 3.68 (s, 3H), 3.67 (s, 3H), 3.36-3.63 (m, 4H), 2.63-2.75 (m, 1H), 2.40-2.55 (m, 3H), 1.95-2.15 (m, 4H), 1.67-1.86 (m, 4H), 1.45-1.65 (m, 4H), 1.03-1.18 (m, 2H), 0.84-0.91 (m, 1H), 0.75-0.83 (m, 1H).

Example ZY6

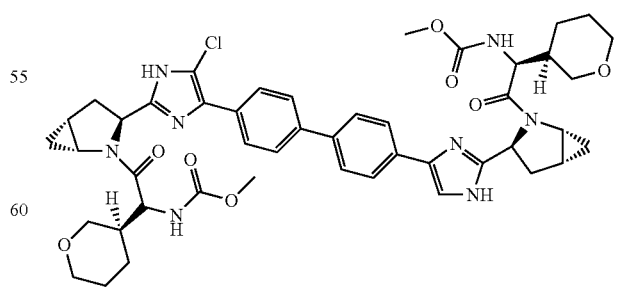

NCS (1.1 mg, 8.4 µmol) was added to a solution of a TFA salt of dimethyl (R,1S,1'S)-2,2'-((1R,1'R,3S,3'S,5R,5'R)-3,3'-(4,4'-(biphenyl-4,4'-diyl)bis(1H-imidazole-4,2-diyl))bis (2-azabicyclo[3.1.0]hexane-3,2-diyl))bis(2-oxo-1-((R)-tetrahydro-2H-pyran-3-yl)ethane-2,1-diyl)dicarbamate (Example ZY2, Step a) (8.1 mg, 8.4 µmol) in DMF (1 mL) and the mixture was stirred at 50° C. for 16 h. Then the reaction was diluted with MeOH, filtered and purified by prep HPLC (H₂O-MeOH with 0.1% TFA buffer) to yield a TFA salt of Example ZY6 (2.2 mg) as white solid. LC-MS retention time=2.01 min; m/z=881 [M+H]⁺. (Column: PHENOMENEX® Luna 3.0×50 mm S10. Solvent A=90% Water: 10% Methanol: 0.1% TFA. Solvent B=10% Water: 90% Methanol: 0.1% TFA. Flow Rate=4 mL/min. Start % B=0. Final % B=100. Gradient Time=3 min. Wavelength=220). ¹H NMR (400 MHz, MeOD) δ ppm 7.77-7.90 (m, 9H), 5.12 (dd, J=9.2, 6.9 Hz, 1H), 5.05 (dd, J=7.9, 6.1 Hz, 1H), 4.58-4.96 (m, 2H), 3.71-3.94 (m, 6H), 3.68 (s, 3H), 3.66 (br. s., 3H), 3.34-3.46 (m, 4H), 2.64-2.75 (m, 1H), 2.40-2.54 (m, 3H), 1.96-2.16 (m, 4H), 1.40-1.85 (m, 8H), 1.04-1.18 (m, 2H), 0.84-0.92 (m, 1H), 0.79 (m, 1H).

Example ZY7

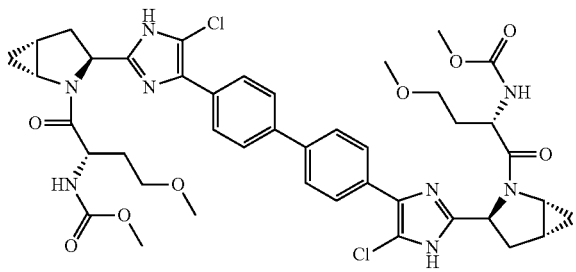 [SMILES: COCC[C@H](NC(=O)OC)C(=O)N1[C@@H]2C[C@@H]2C[C@H]1c1nc(-c2ccc(-c3ccc(-c4nc([C@@H]5C[C@H]6C[C@H]6N5C(=O)[C@H](CCOC)NC(=O)OC)[nH]c4Cl)cc3)cc2)c(Cl)[nH]1]

Example ZY7

Step a

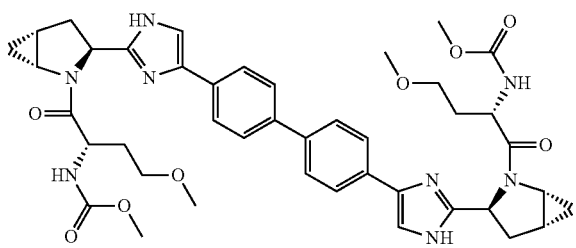 [SMILES: COCC[C@H](NC(=O)OC)C(=O)N1[C@@H]2C[C@@H]2C[C@H]1c1nc(-c2ccc(-c3ccc(-c4c[nH]c([C@@H]5C[C@H]6C[C@H]6N5C(=O)[C@H](CCOC)NC(=O)OC)n4)cc3)cc2)c[nH]1]

HATU (95 mg, 0.25 mmol) was added to a solution of an HCl salt of 4,4'-bis(2-(((1R,3S,5R)-2-azabicyclo[3.1.0]hexan-3-yl)-1H-imidazol-4-yl)biphenyl (Example 1e) (67.6 mg, 0.114 mmol) and (S)-4-methoxy-2-(methoxycarbonylamino)butanoic acid (Example ZY7, Step a) (50 mg, 0.26 mmol) in DMF (1 mL) and DIPEA (0.16 mL, 0.91 mmol) and the mixture was stirred at rt for 3 h. The reaction mixture was diluted with MeOH, filtered and purified by prep HPLC (H₂O-MeOH with 0.1% TFA buffer) to yield a TFA salt of dimethyl (2S,2'S)-1,1'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(4-methoxy-1-oxobutane-2,1-diyl)dicarbamate (Example ZY7, Step a) (96.4 mg) as white solid. LC-MS retention time=1.53 min; m/z 795 [M+H]⁺. (Column: PHENOMENEX® Luna 3.0×50 mm S10. Solvent A=90% Water: 10% Methanol: 0.1% TFA. Solvent B=10% Water: 90% Methanol: 0.1% TFA. Flow Rate=4 mL/min. Start % B=0. Final % B=100. Gradient Time=3 min. Wavelength=220). ¹H NMR (400 MHz, MeOD) δ ppm 7.78-7.97 (m, 10H), 5.16 (dd, J=9.2, 6.7 Hz, 2H), 4.76-4.83 (m, 2H), 3.75-3.84 (m, 2H), 3.66 (s, 6H), 3.45-3.56 (m, 4H), 3.32 (s, 6H), 2.68 (dd, J=13.4, 9.4 Hz, 2H), 2.42-2.53 (m, 2H), 2.01-2.23 (m, 4H), 1.80-1.95 (m, 2H), 1.05-1.18 (m, 2H), 0.78-0.98 (m, 2H).

Example ZY7

NCS (9.7 mg, 0.073 mmol) was added to a solution of a TFA salt of dimethyl (2S,2'S)-1,1'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(4-methoxy-1-oxobutane-2,1-diyl)dicarbamate (Example ZY7, Step a) (29 mg, 0.036 mmol) in DMF (1 mL) and the mixture was stirred at 50° C. for 16 h. The reaction mixture was diluted with MeOH, filtered and purified by prep HPLC (H₂O-MeOH with 0.1% TFA buffer) to yield a TFA salt of dimethyl (2S,2'S)-1,1'-((1R,1'R,3S,3'S,5R,5'R)-3,3'-(4,4'-(biphenyl-4,4'-diyl)bis(5-chloro-1H-imidazole-4,2-diyl))bis(2-azabicyclo[3.1.0]hexane-3,2-diyl))bis(4-methoxy-1-oxobutane-2,1-diyl)dicarbamate (Example ZY7) (7.9 mg) as white solid. LC-MS retention time=2.51 min; m/z=863 [M+H]⁺. (Column: PHENOMENEX® Luna 3.0×50 mm S10. Solvent A=90% Water: 10% Methanol: 0.1% TFA. Solvent B=10% Water: 90% Methanol: 0.1% TFA. Flow Rate=4 mL/min. Start % B=0. Final % B=100. Gradient Time=3 min. Wavelength=220). ¹H NMR (400 MHz, MeOD) δ ppm 7.82 (s, 8H), 5.07 (dd, J=8.5, 5.8 Hz, 2H), 4.75-4.83 (m, 2H), 3.70-3.76 (m, 2H), 3.66 (s, 6H), 3.44-3.54 (m, 4H), 3.32 (s, 6H), 2.39-2.57 (m, 4H), 1.98-2.21 (m, 4H), 1.82-1.94 (m, 2H), 1.05-1.19 (m, 2H), 0.78-0.92 (m, 2H).

Example ZY8

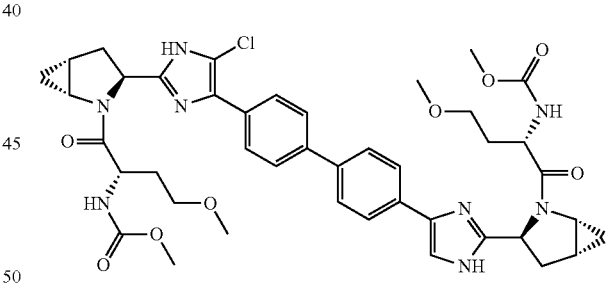

NCS (5.6 mg, 0.042 mmol) was added to a solution of a TFA salt of dimethyl (2S,2'S)-1,1'-((1R,1'R,3S,3'S,5R,5'R)-3,3'-(4,4'-(biphenyl-4,4'-diyl)bis(1H-imidazole-4,2-diyl))bis(2-azabicyclo[3.1.0]hexane-3,2-diyl))bis(4-methoxy-1-oxobutane-2,1-diyl)dicarbamate (Example ZY7, Step b) (33.3 mg, 0.042 mmol) in DMF (1 mL) and the mixture was stirred at 50° C. for 16 h. The reaction mixture was diluted with MeOH, filtered and purified by prep HPLC (H₂O-MeOH with 0.1% TFA buffer) to yield a TFA salt of Example ZY8 (9.4 mg) as a white solid. LC-MS retention time=1.99 min; m/z=829 [M+H]⁺. (Column: PHENOMENEX® Luna 3.0× 50 mm S10. Solvent A=90% Water: 10% Methanol: 0.1% TFA. Solvent B=10% Water: 90% Methanol: 0.1% TFA. Flow Rate=4 mL/min. Start % B=0. Final % B=100. Gradient Time=3 min. Wavelength=220). ¹H NMR (400 MHz, MeOD) δ ppm 7.77-7.91 (m, 9H), 5.15 (dd, J=9.2, 6.7 Hz, 1H), 5.07

(t, J=7.0 Hz, 1H), 4.77-4.83 (m, 2H), 3.76-3.83 (m, 1H), 3.68-3.75 (m, 1H), 3.66 (s, 6H), 3.44-3.56 (m, 4H), 3.33 (s, 6H), 2.63-2.75 (m, 1H), 2.41-2.56 (m, 3H), 1.97-2.23 (m, 4H), 1.80-1.95 (m, 2H), 1.06-1.19 (m, 2H), 0.87-0.96 (m, 1H), 0.84 (m, 1H).

Biological Activity

An HCV Replicon assay was utilized in the present disclosure, and was prepared, conducted and validated as described in commonly owned PCT/US2006/022197 and in O'Boyle et al., *Antimicrob. Agents Chemother.*, 49(4):1346-1353 (April 2005). Assay methods incorporating luciferase reporters have also been used as described (Apath.com).

HCV-neo replicon cells and replicon cells containing resistance substitutions in the NS5A region were used to test the currently described family of compounds. The compounds were determined to have differing degrees of reduced inhibitory activity on cells containing mutations vs. the corresponding inhibitory potency against wild-type cells. Thus, the compounds of the present disclosure can be effective in inhibiting the function of the HCV NS5A protein and are understood to be as effective in combinations as previously described in application PCT/US2006/022197 and commonly owned WO 04/014852. It should be understood that the compounds of the present disclosure can inhibit multiple genotypes of HCV. Table 2 shows the $EC_{50}$ (Effective 50% inhibitory concentration) values of representative compounds of the present disclosure against the HCV 1b genotype. In one embodiment, compounds of the present disclosure are inhibitory versus 1a, 1b, 2a, 2b, 3a, 4a, and 5a genotypes. $EC_{50}$ values against HCV 1b are as follows. $EC_{50}$ values against HCV 1b are as follows: A=0.2 pM-<1 pM; B=1 pM-<10 pM; and C=10 pM-<100 pM; and D=100 pM-0.15 μM.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A.

TABLE 2

| Example | $EC_{50}$ (μM) | $EC_{50}$-Range |
|---|---|---|
| M1 | | B |
| M2 | | B |
| M4 | | B |
| M5 | | B |
| M6 | 4.08E−06 | B |
| M7 | 2.13E−06 | B |
| V1 | | B |
| V2 | 8.88E−05 | C |
| V3 | | B |
| V4 | 3.22E−05 | C |
| V5 | 6.58E−07 | A |
| V5.1 | 3.90E−06 | B |
| V5.2 | 3.06E−05 | C |
| V5.3 | 1.33E−04 | D |
| V6 | | A |
| V7 | | B |
| V8 | | B |
| V9 | 2.70E−06 | B |
| V10 | | B |
| V11 | | B |
| V12 | | B |
| V13 | | B |
| V14 | | B |
| V15 | | C |
| V16 | 9.66E−07 | A |
| GW1-1 | | B |
| GW1-2 | | B |
| GW1-3 | | B |
| GW2 | | B |
| GW2-1 | 1.27E−05 | C |
| GW3 | | B |
| GW4 | | C |
| GW5 | | B |
| GW6 | | B |
| GW7 | | B |
| GW8 | | B |
| GW9 | | A |
| GW10 | | B |
| GW11 | | A |
| GW12 | | A |
| OL1 | 3.06E−06 | B |
| OL2 | | B |
| OL3 | | B |
| OL4 | | B |
| OL5 | | B |
| OL6 | | B |
| OL7 | | B |
| OL8 | 2.09E−04 | D |
| OL9 | 6.08E−06 | B |
| OL10 | | D |
| OL11 | | B |
| OL12 | | C |
| OL13 | | B |
| OL14 | | C |
| OL15 | | B |
| OL16 | | C |
| OL17 | | B |
| OL18 | | B |
| OL19 | | C |
| OL20 | | D |
| OL21 | | C |
| OL22 | 4.08E−04 | D |
| OL23 | | D |
| OL24 | | B |
| OL25 | | D |
| DSTL-1 | | A |
| DSTL-2 | | C |
| DSTL-3 | 1.25E−06 | B |
| DSTL-4 | | A |
| DSTL-5 | 5.59E−07 | A |
| DSTL-6 | | B |
| DSTL-7 | | B |
| DSTL-8 | | A |
| DSTL-9 | | B |
| DSTL-10 | | B |
| DSTL-11 | | A |
| DSTL-12 | | C |
| JLR-1 | | B |
| JLR-2 | | B |
| JLR-3 | | A |
| JLR-4 | 7.69E−07 | A |
| JLR-5 | | B |
| ZY1 | | B |
| ZY2 | | B |
| ZY3 | | B |
| ZY4 | | B |
| ZY5 | | B |
| ZY6 | 1.08E−05 | C |
| ZY7 | | B |
| ZY8 | | B |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula (I)

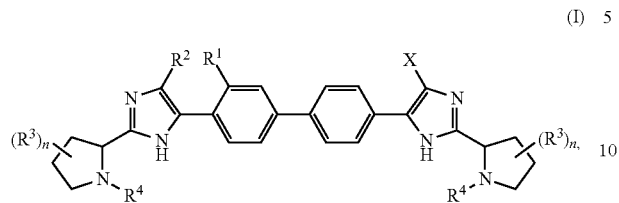

or a pharmaceutically acceptable salt thereof, wherein:
n is 0, 1, or 2;
X is selected from hydrogen, alkenyl, cyano, cycloalkyl, (cycloalkyl)alkyl, halo, and heterocyclyl;
$R^1$ is selected from hydrogen and halo;
$R^2$ is selected from hydrogen, alkenyl, cyano, cycloalkyl, (cycloalkyl)alkyl, halo, and heterocyclyl; or
$R^1$ and $R^2$, together with the carbon atoms to which they are attached, form a six-membered aromatic ring optionally substituted with one halo group;
provided that at least one of X and $R^2$ is selected from alkenyl, cyano, cycloalkyl, (cycloalkyl)alkyl, halo, and heterocyclyl;

each $R^3$ is alkyl, wherein the alkyl can optionally form a fused three- or four-membered ring with an adjacent carbon atom or a spirocyclic three- or four-membered ring with the carbon atom to which it is attached; wherein the fused and spirocyclic rings are optionally substituted with one or two alkyl groups;
each $R^4$ is independently selected from hydrogen and —C(O)$R^5$; and
each $R^5$ is independently selected from alkoxy, alkyl, arylalkoxy, arylalkyl, cycloalkyl, heterocyclyl, heterocyclylalkyl, (NR$^c$R$^d$)alkenyl, and (NR$^c$R$^d$)alkyl.

2. A compound of claim 1, or a pharmaceutically acceptable salt thereof, wherein each $R^5$ is independently selected from alkoxy, heterocyclyl, and (NR$^c$R$^d$)alkyl.

3. A compound of claim 1, or a pharmaceutically acceptable salt thereof, wherein X is halo.

4. A compound of claim 3, or a pharmaceutically acceptable salt thereof, wherein $R^2$ is halo.

5. A compound of claim 1, or a pharmaceutically acceptable salt thereof, wherein $R^1$ and $R^2$, together with the carbon atoms to which they are attached, form a six-membered aromatic ring optionally substituted with one halo group.

6. A compound of claim 1, or a pharmaceutically acceptable salt thereof, wherein X is hydrogen.

7. A compound selected from:

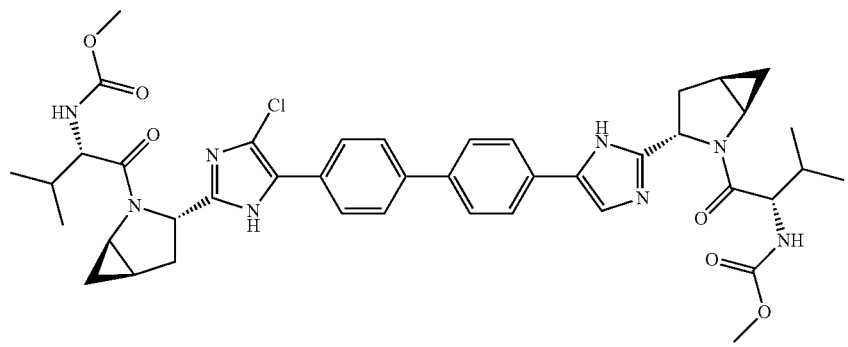

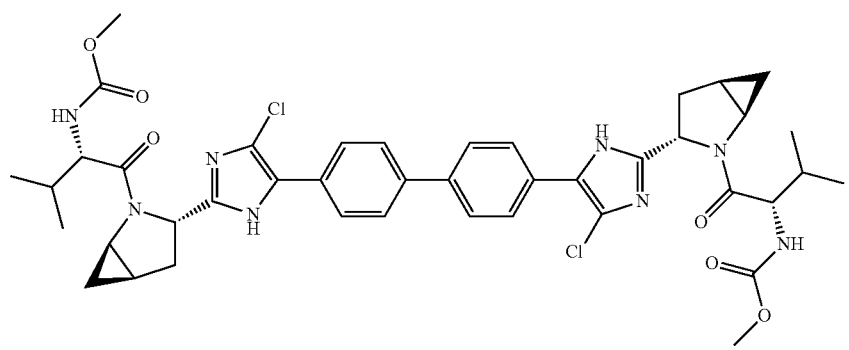

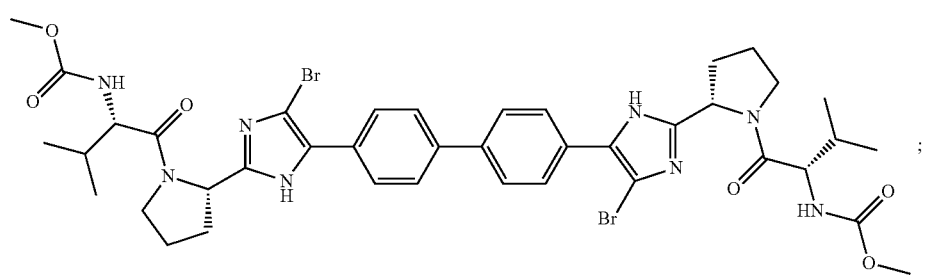

-continued
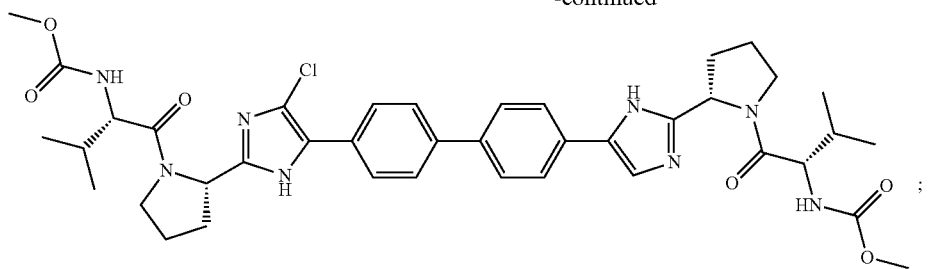
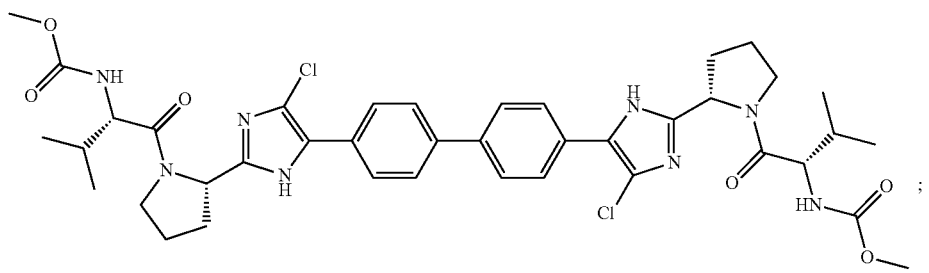
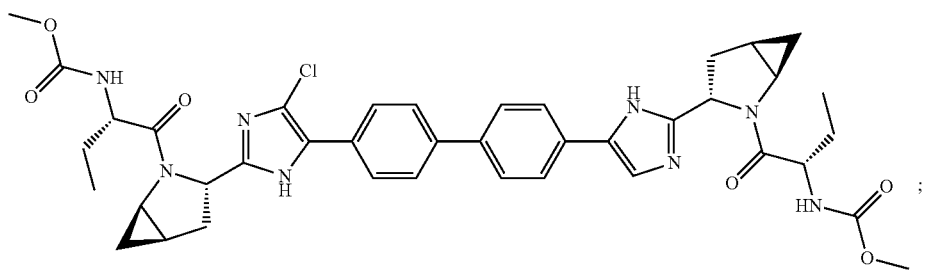
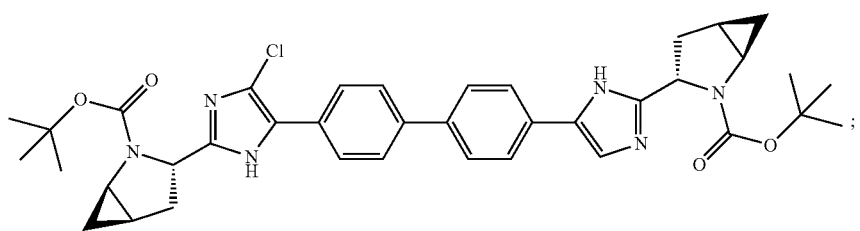
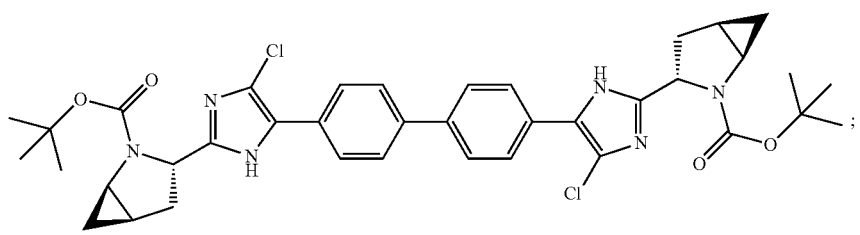
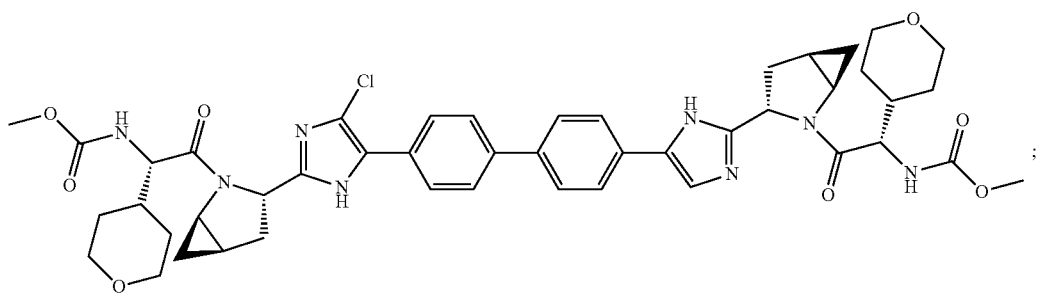

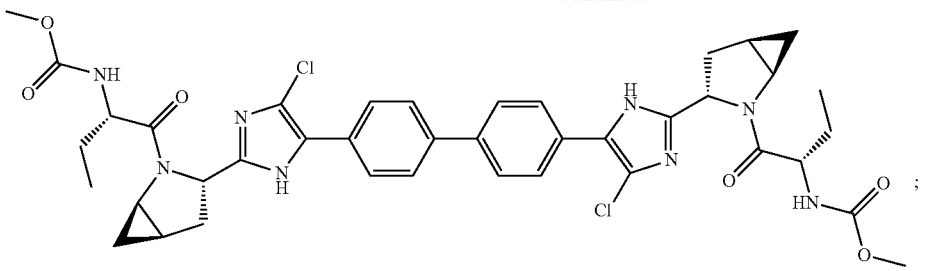
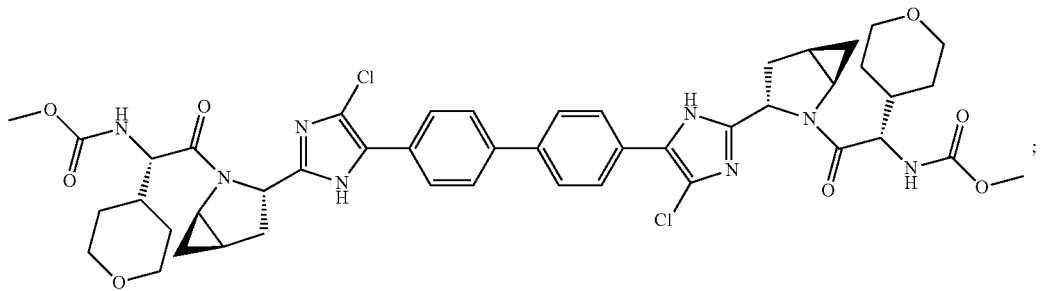
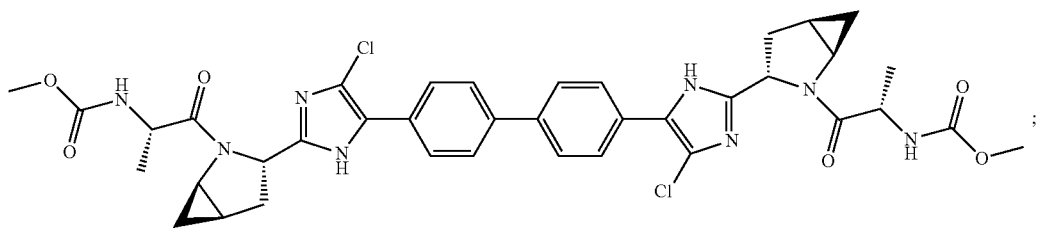
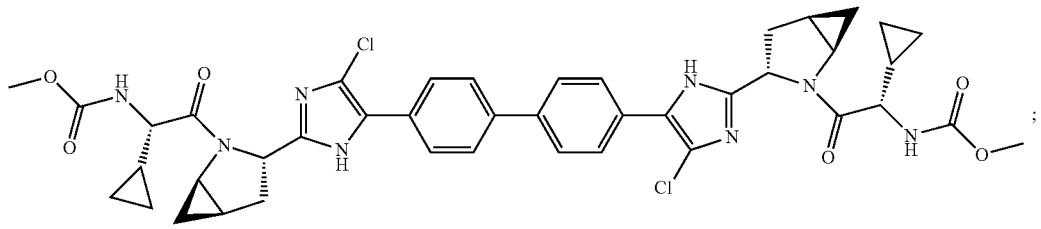
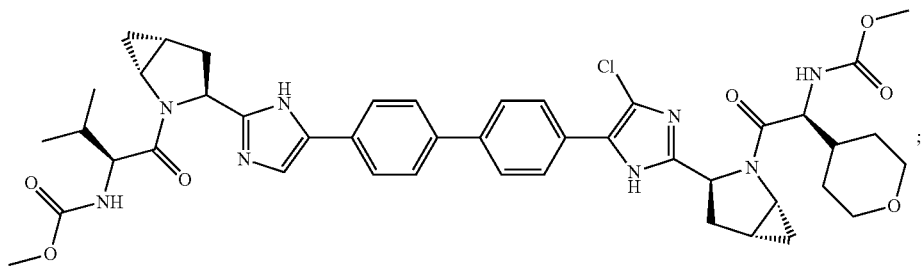
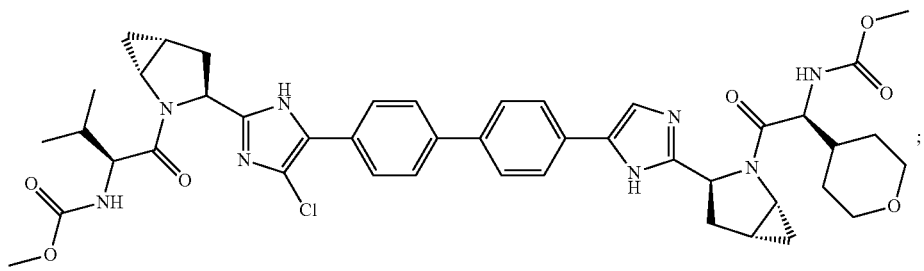

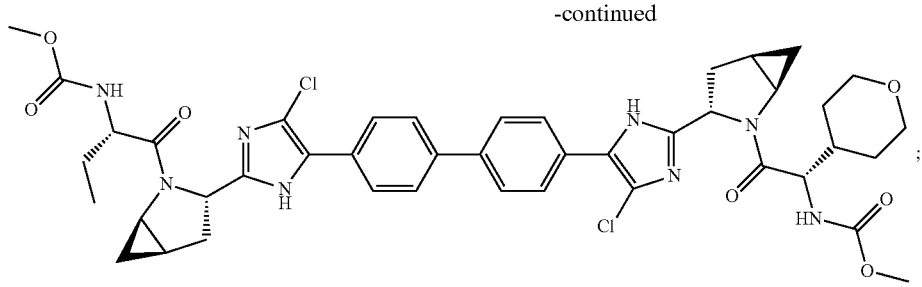
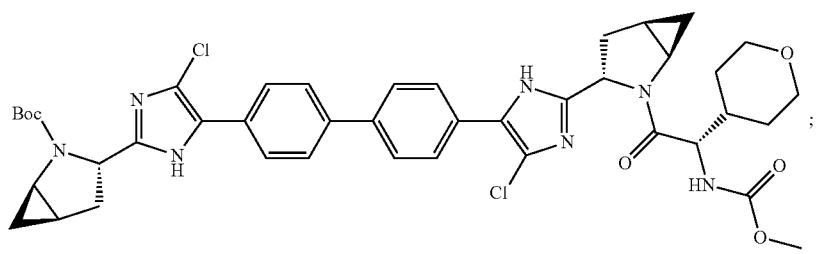
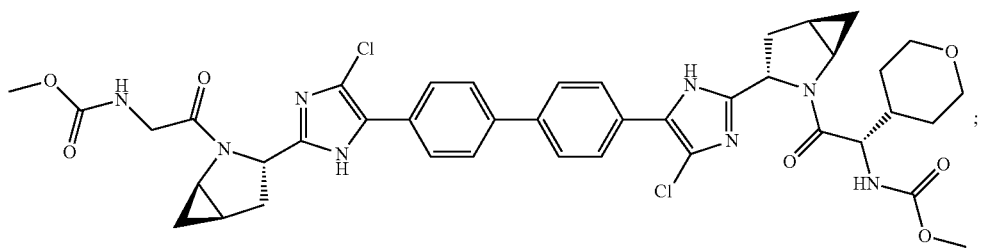
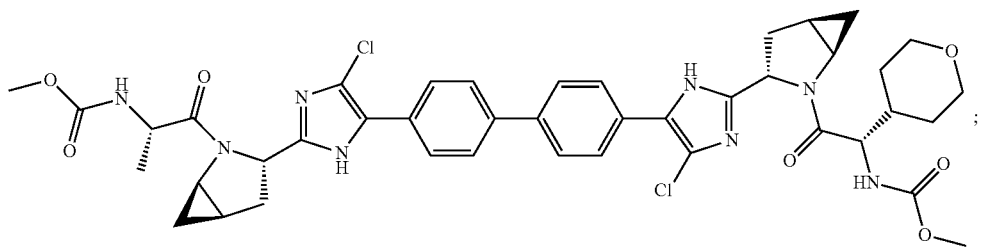
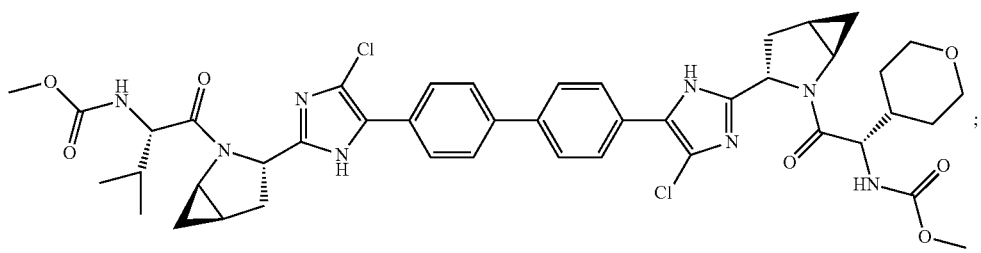
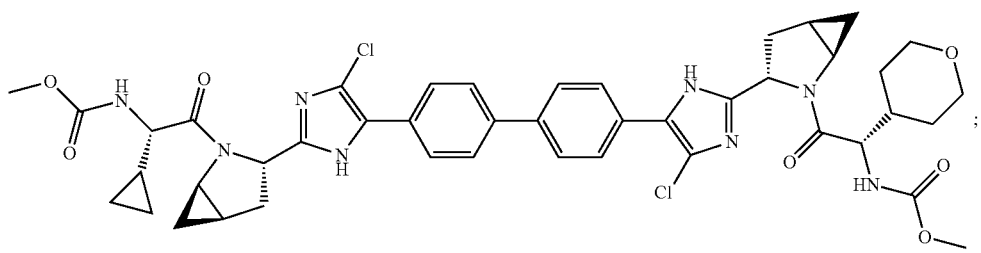

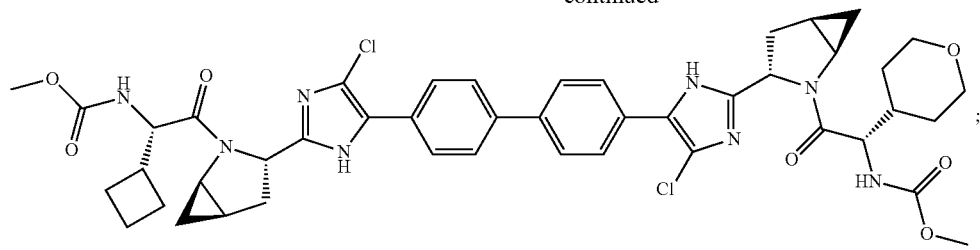
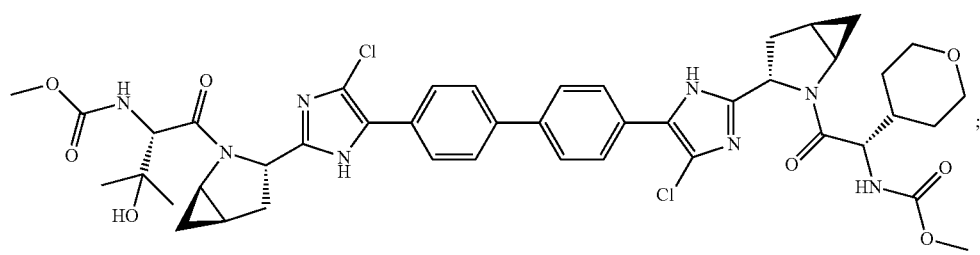
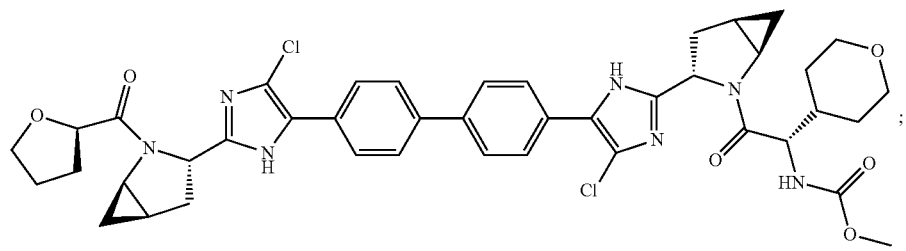
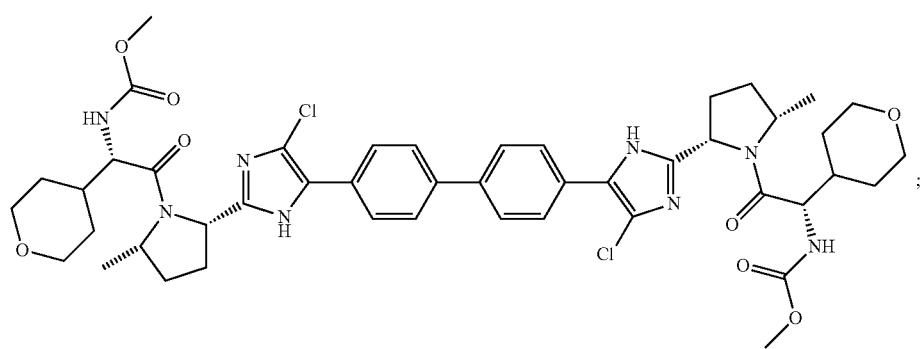
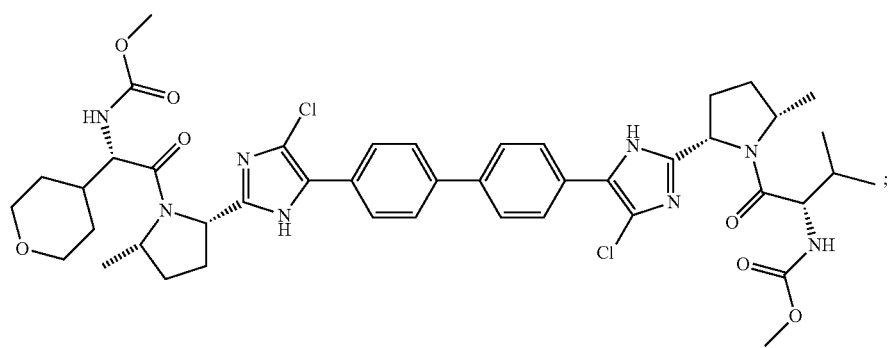

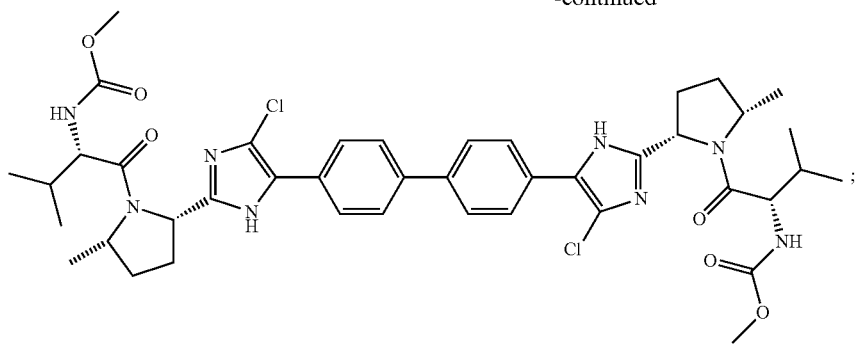
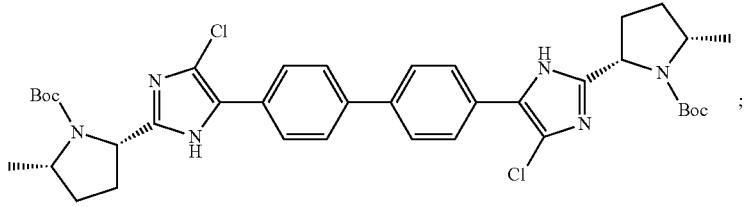
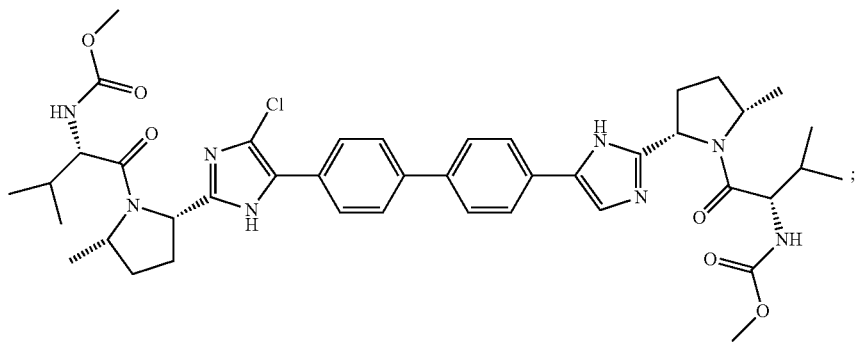
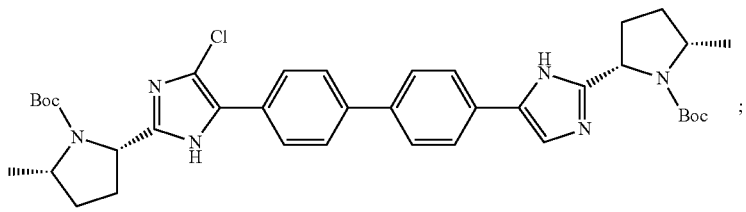
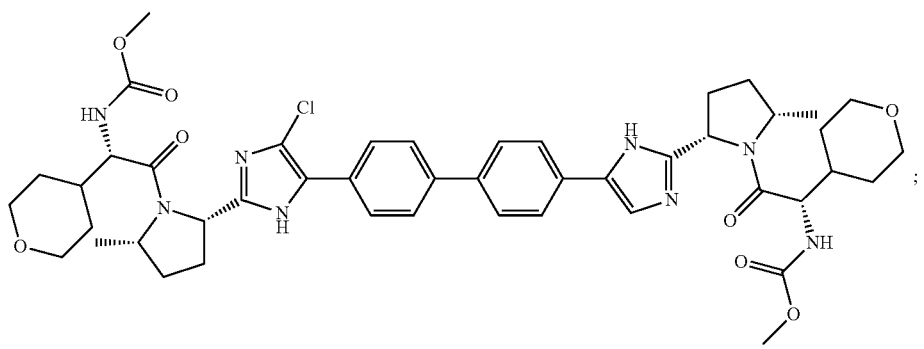

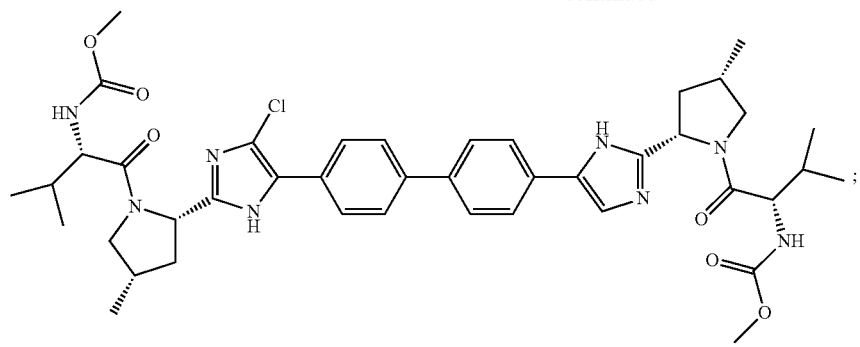
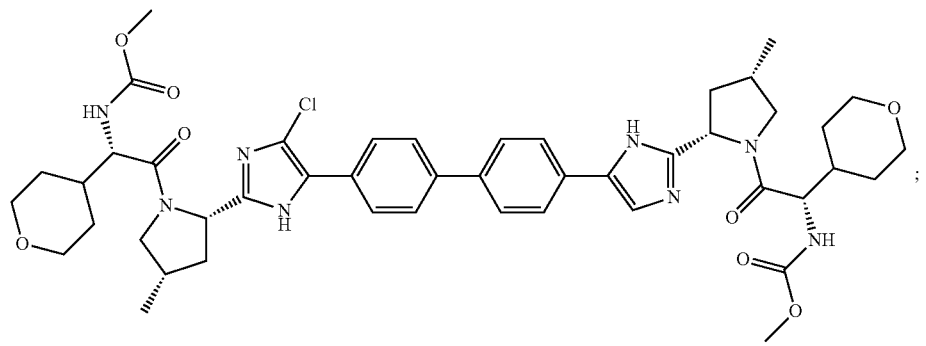
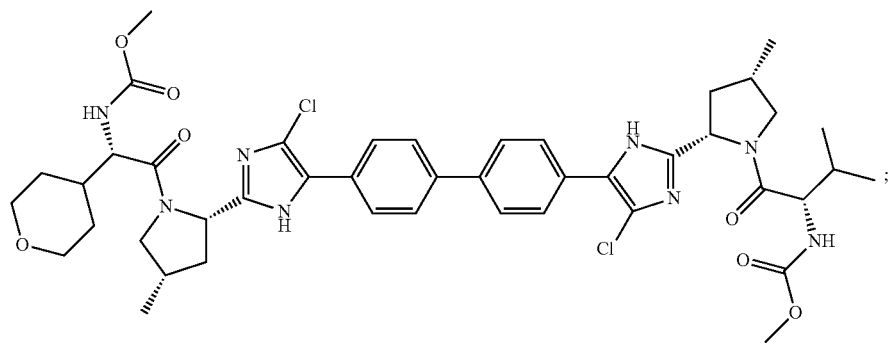
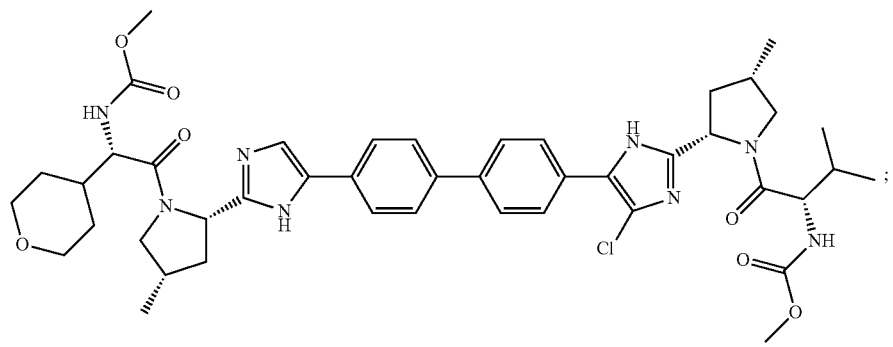
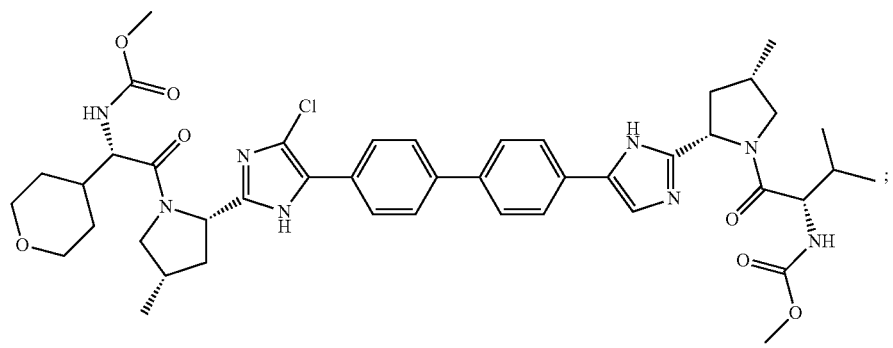

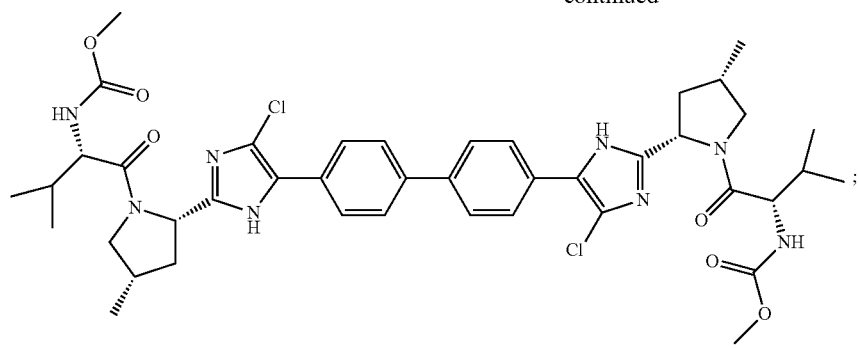
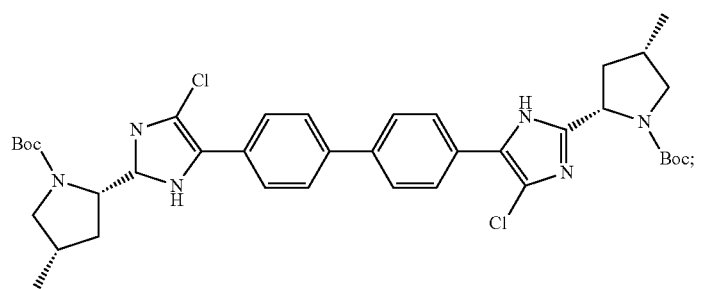
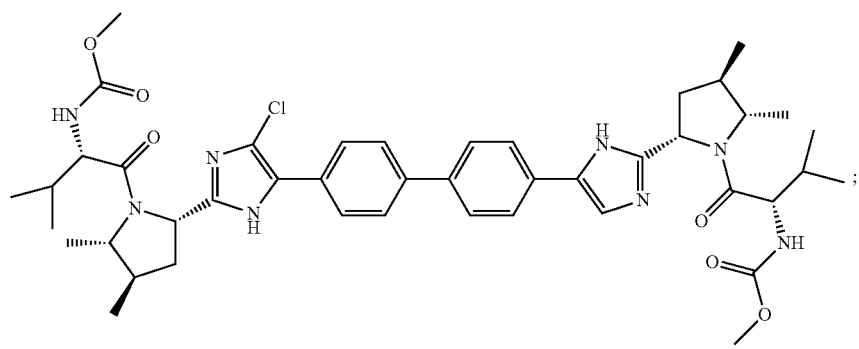
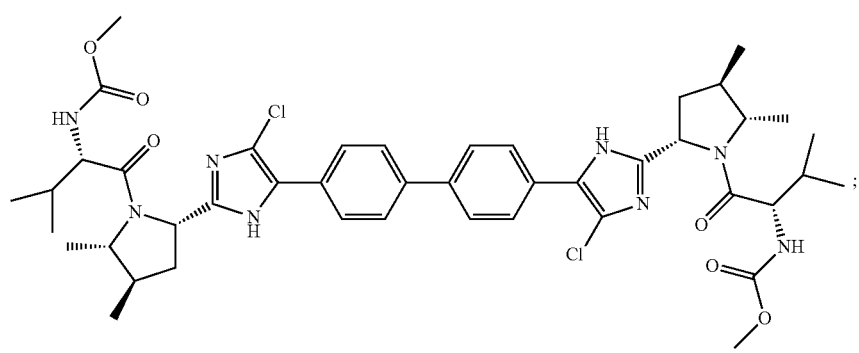
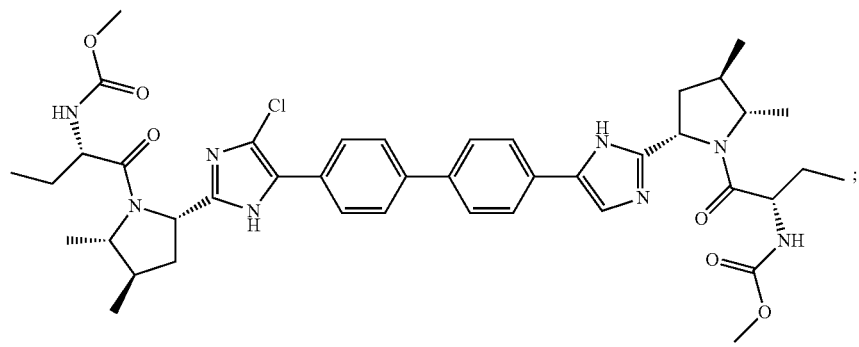

-continued
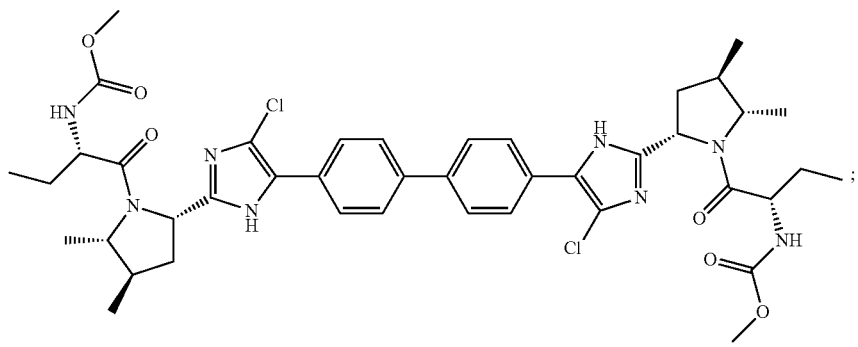
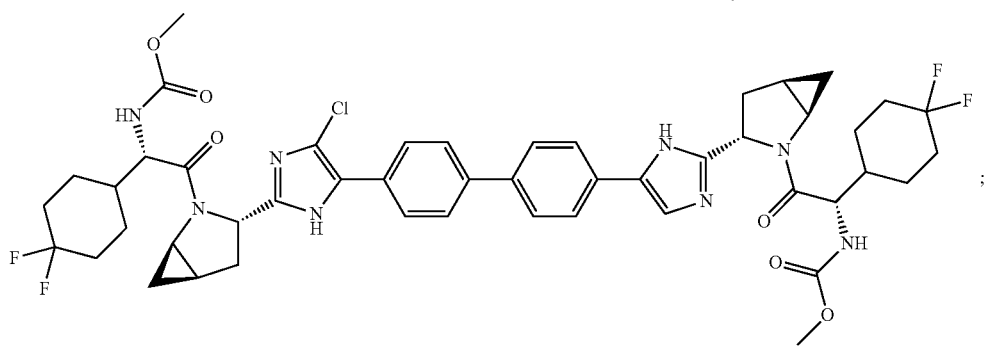
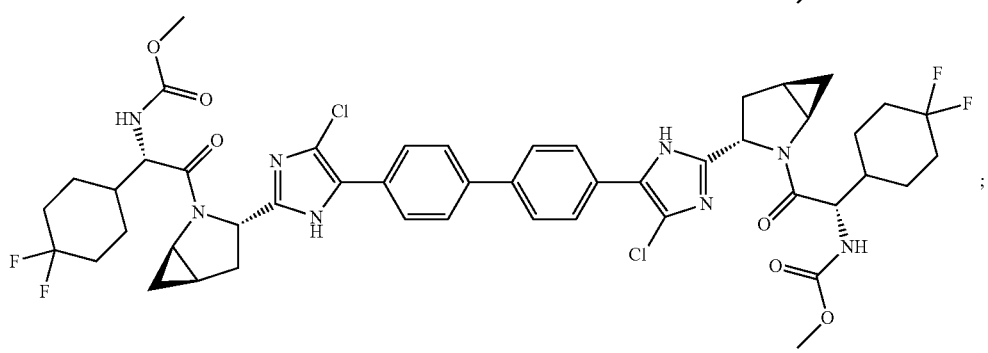
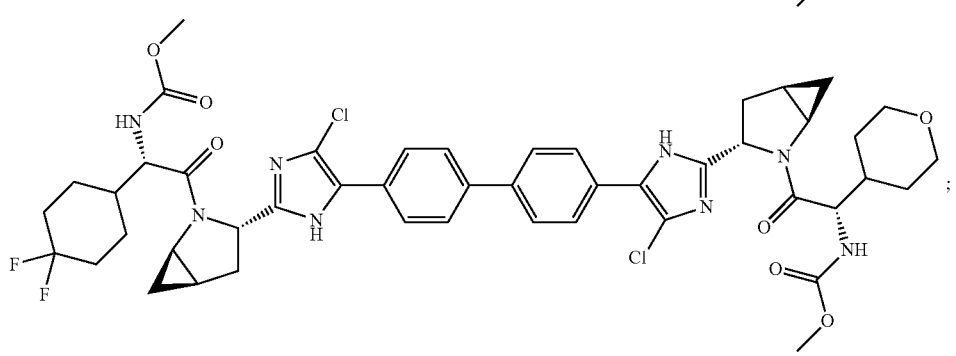
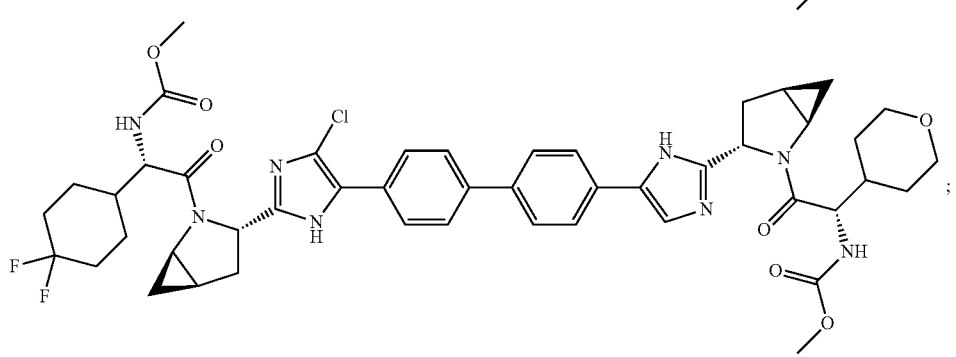

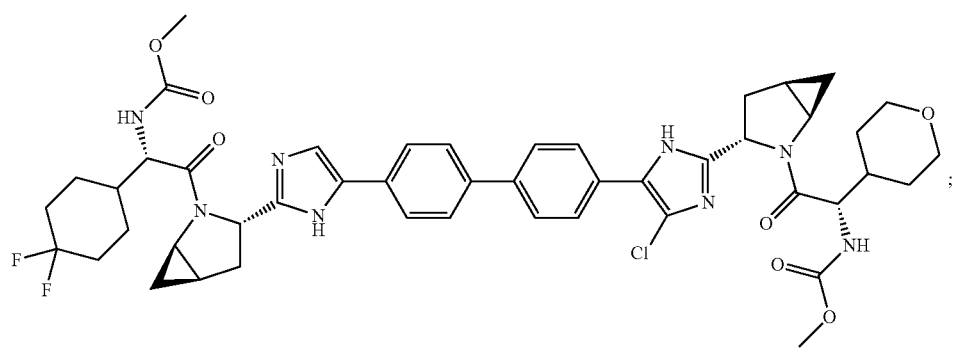
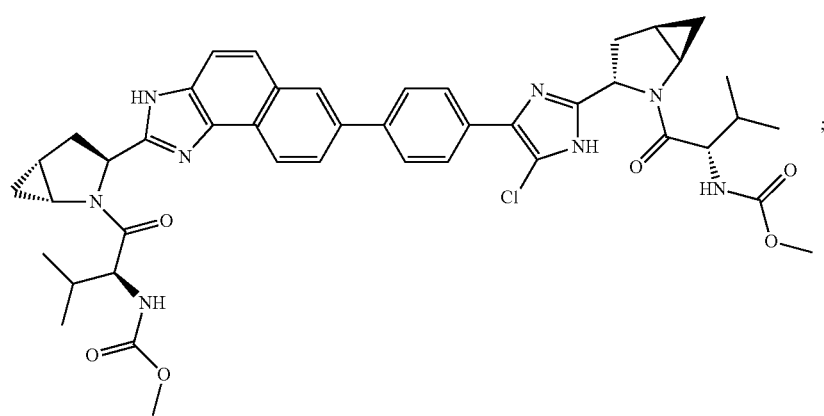
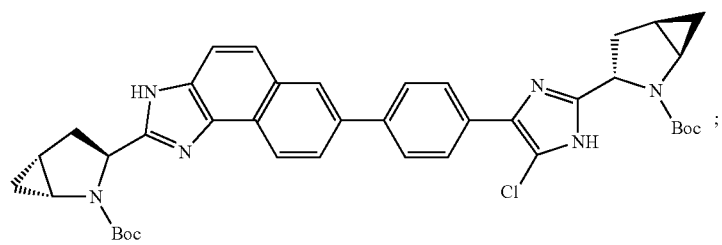
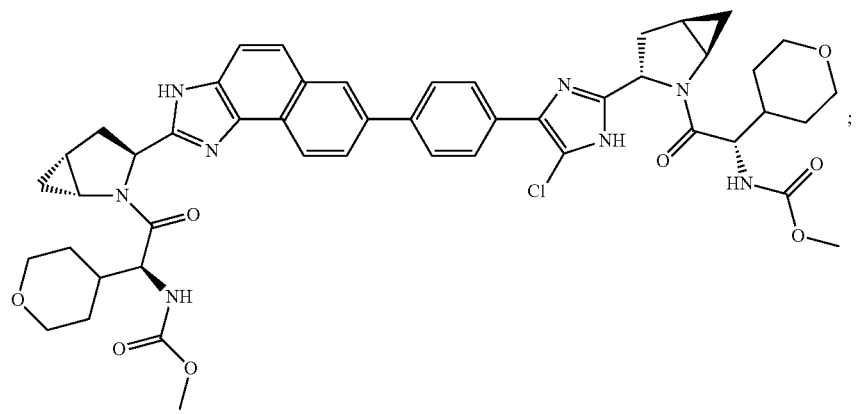

-continued
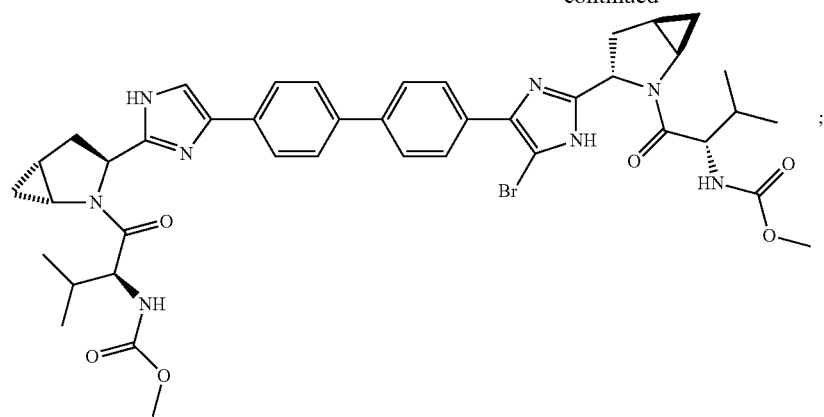
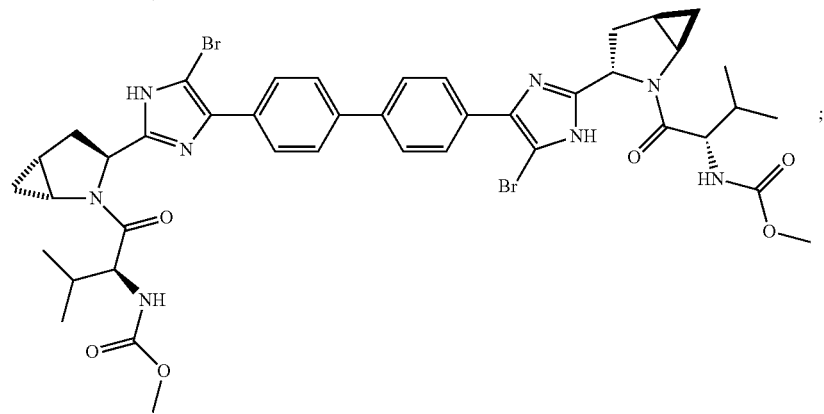
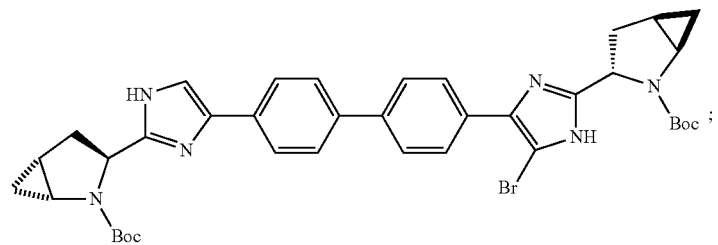
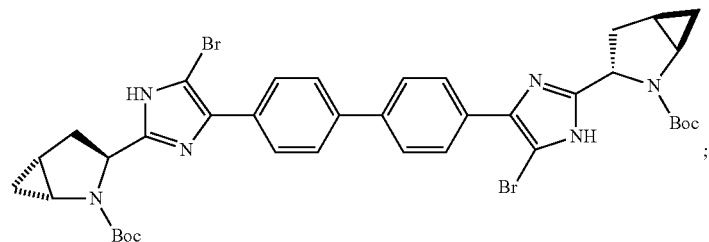
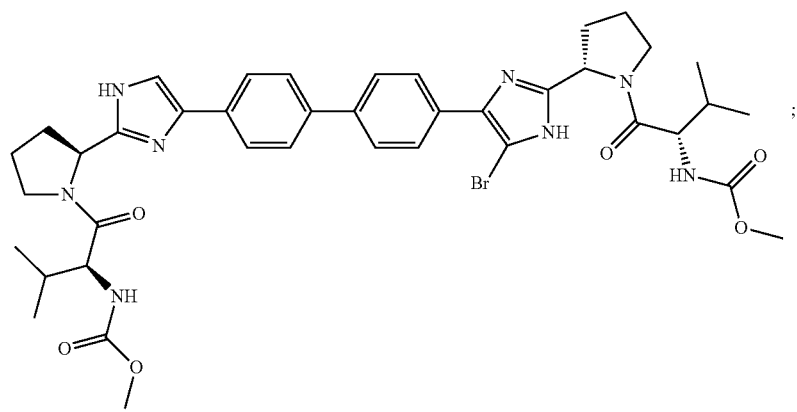

-continued
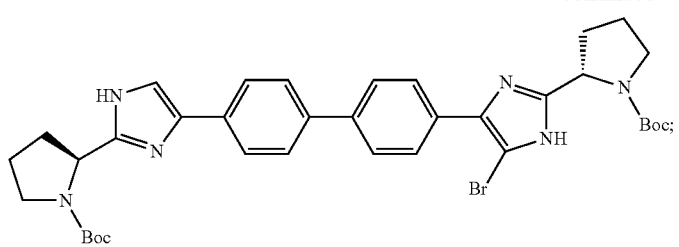
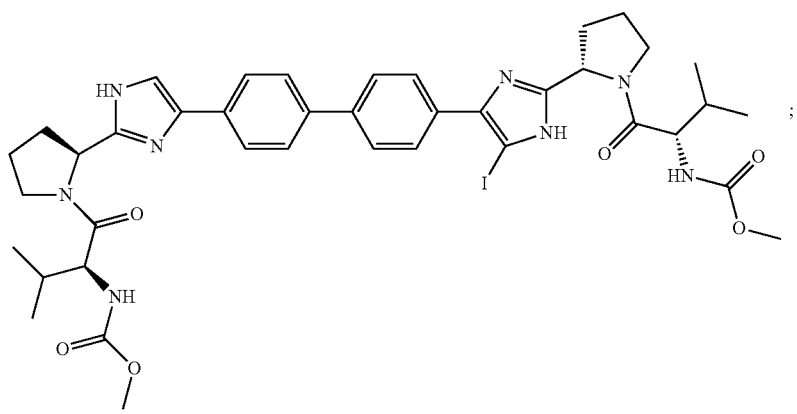
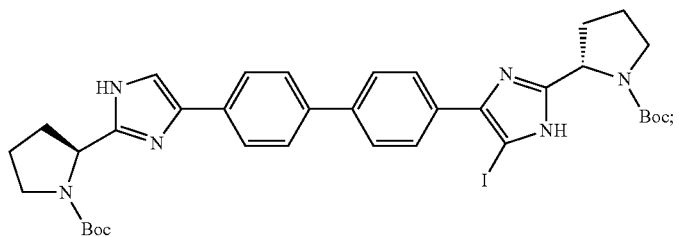
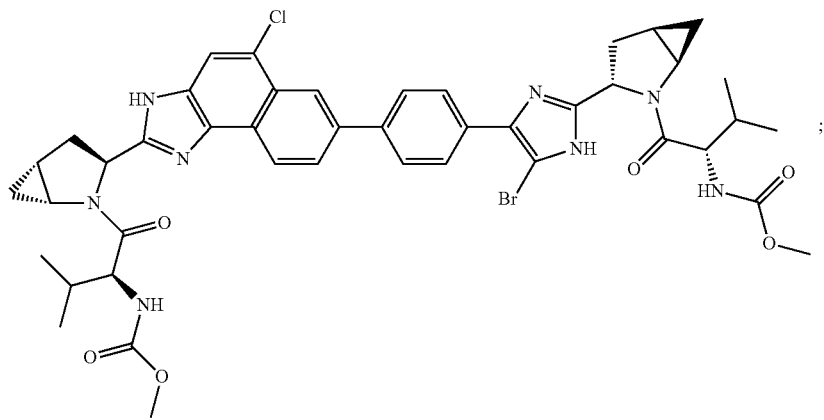
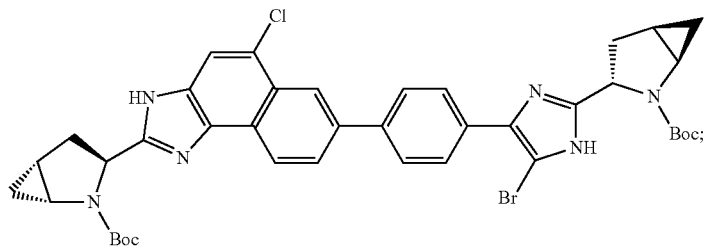

-continued
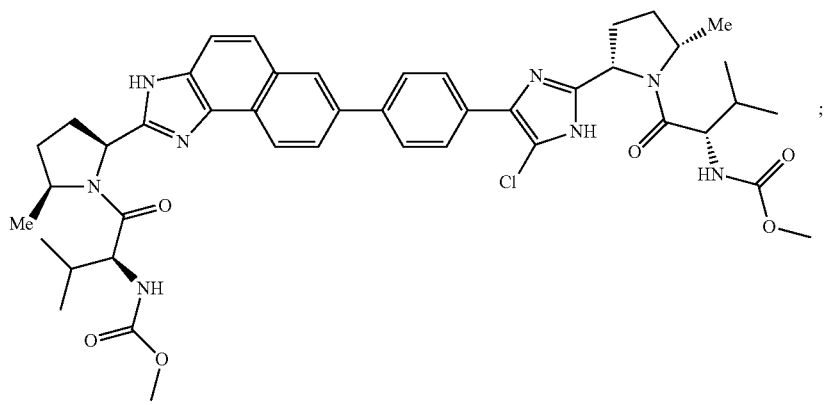
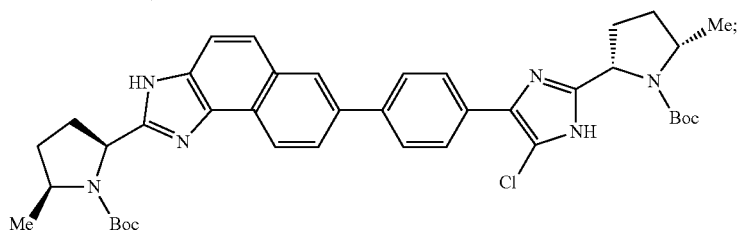
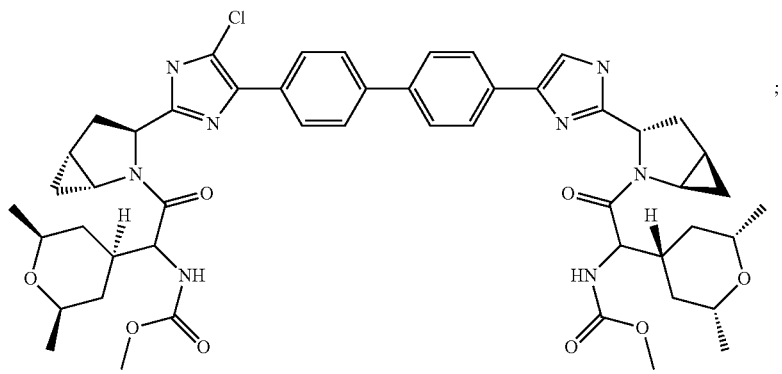
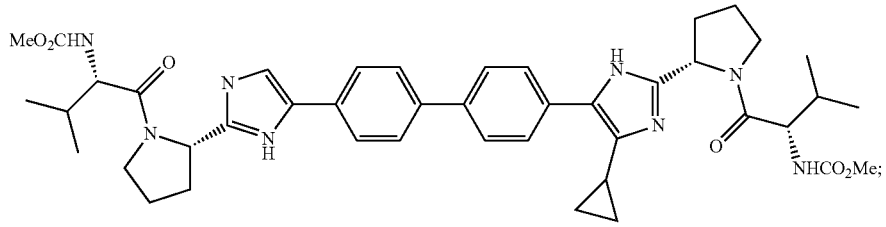
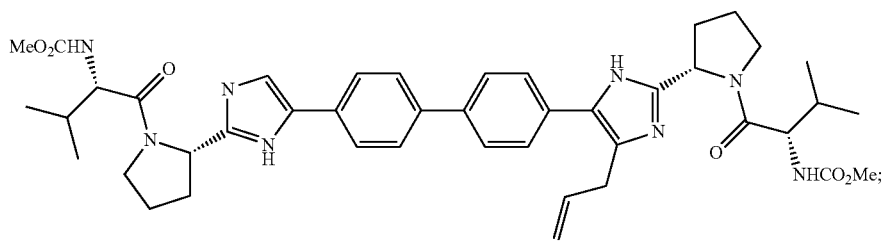
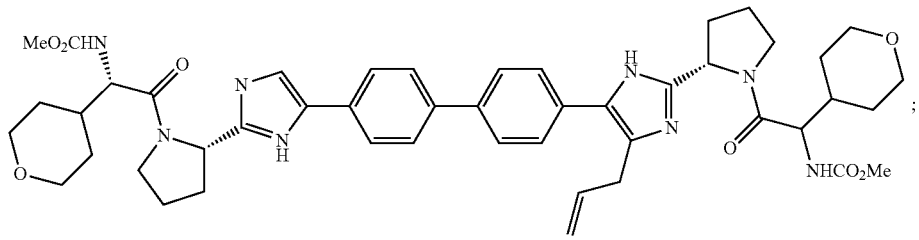

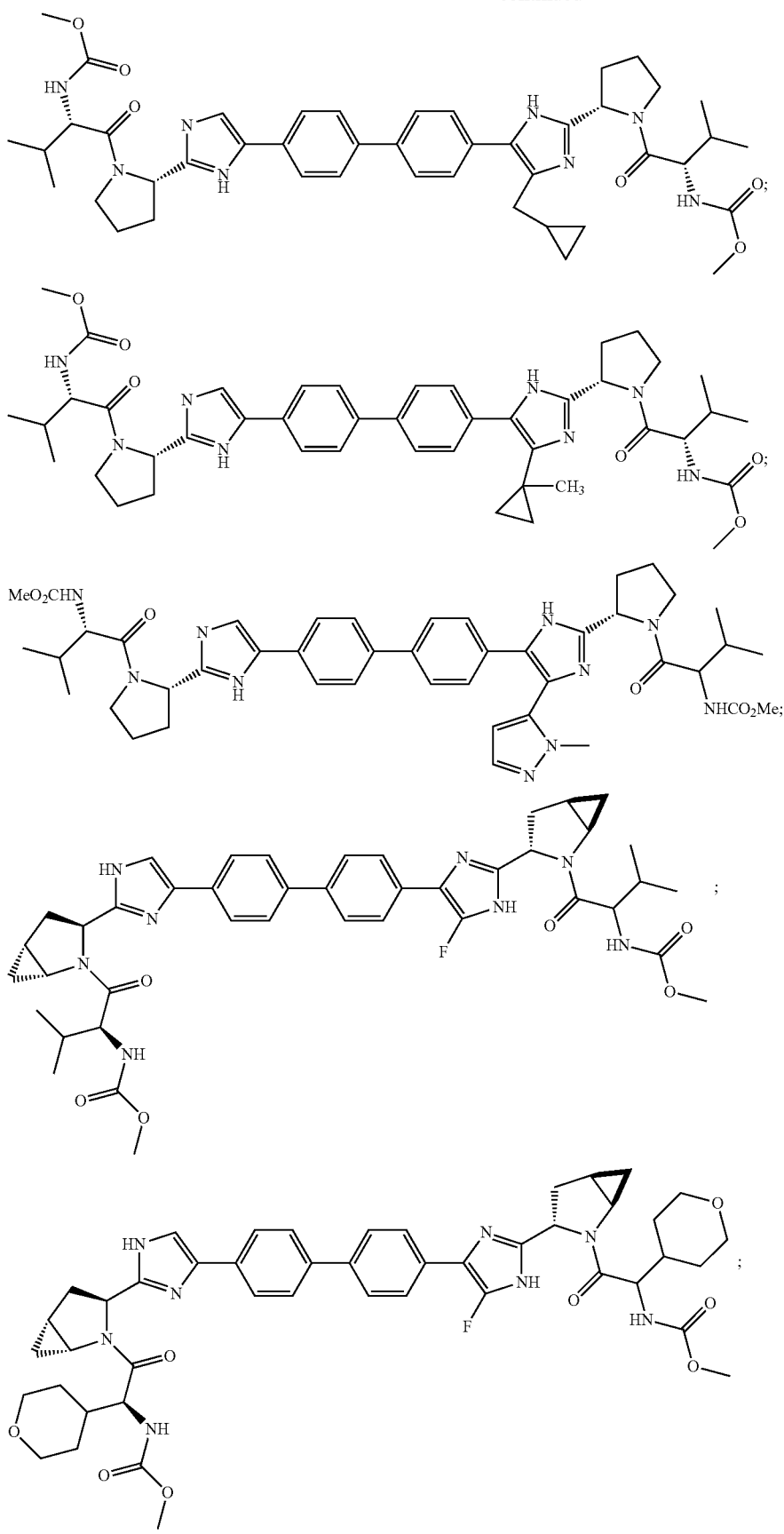

-continued
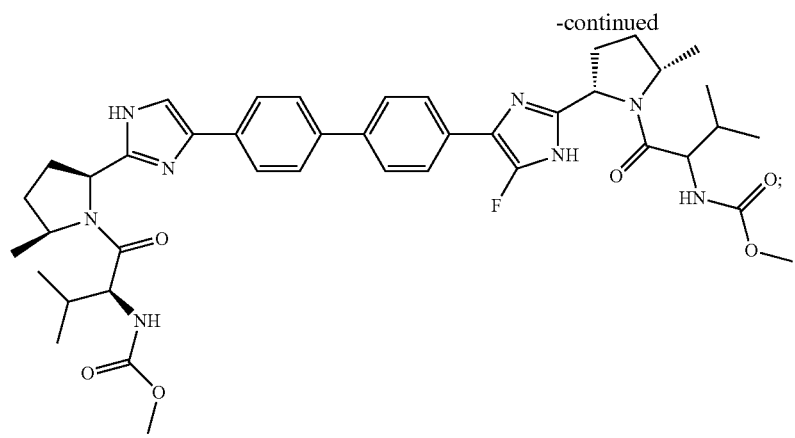
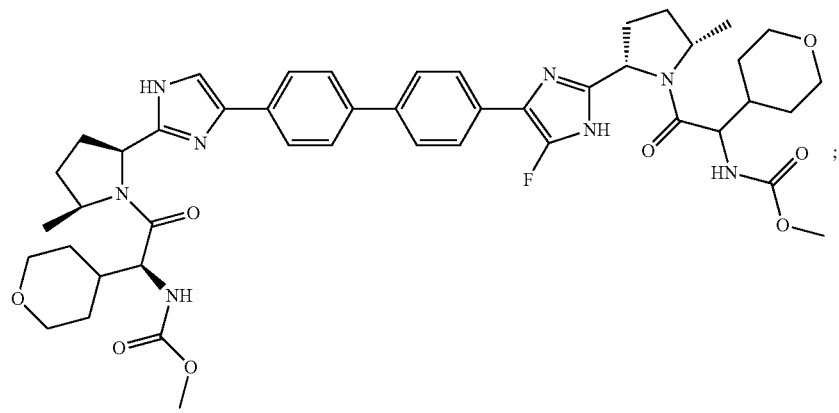
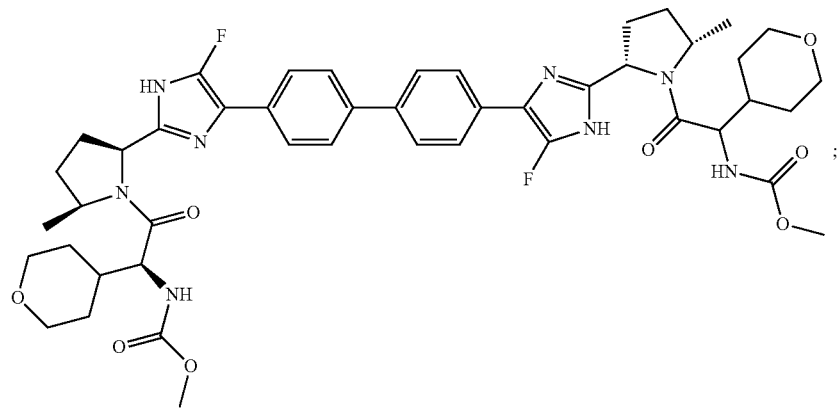
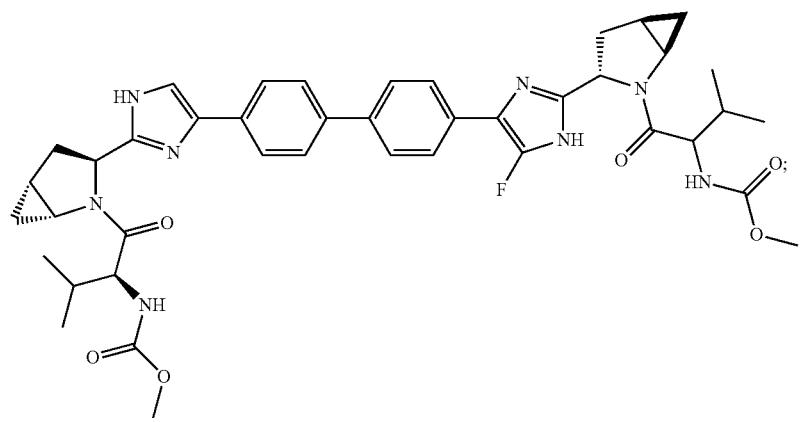

-continued
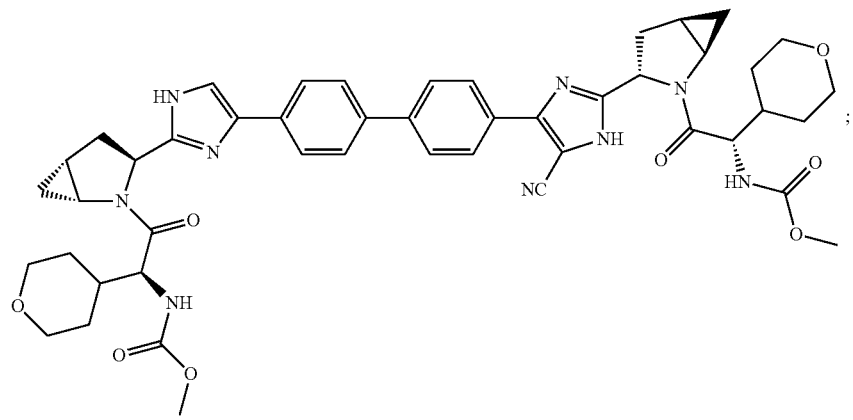
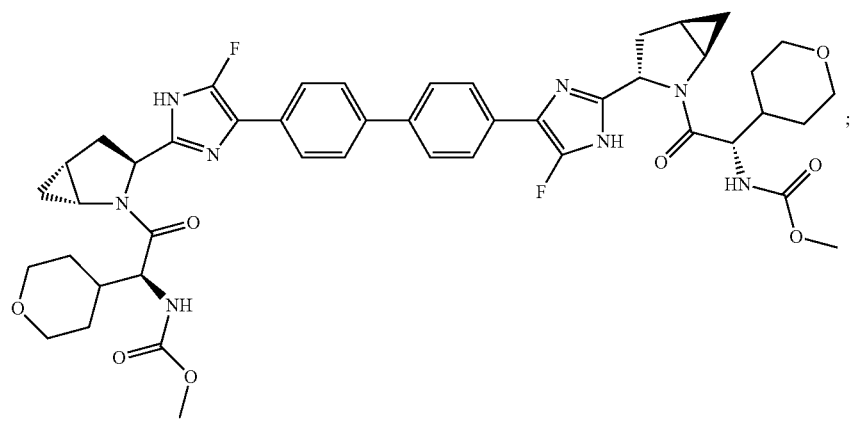
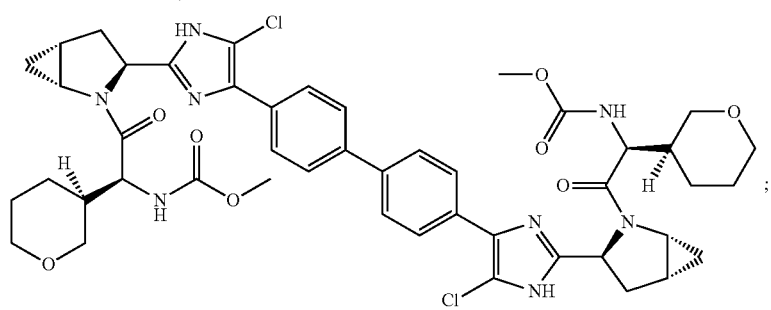
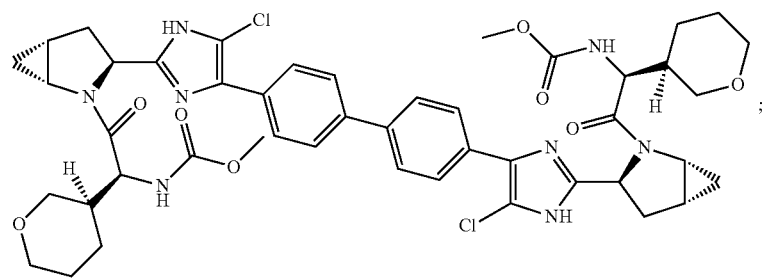
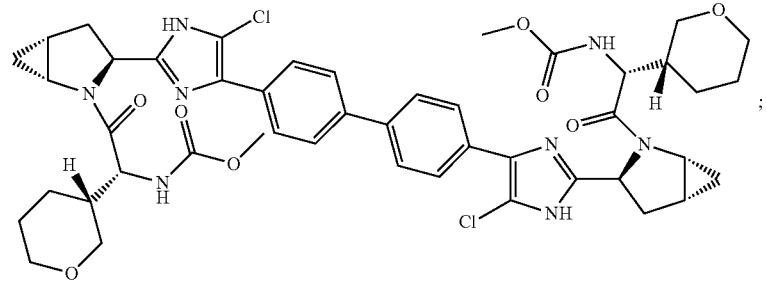

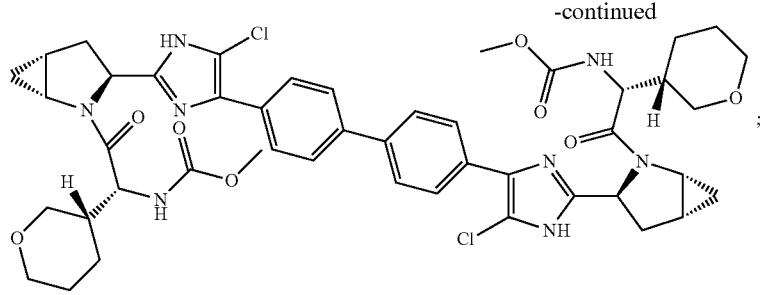
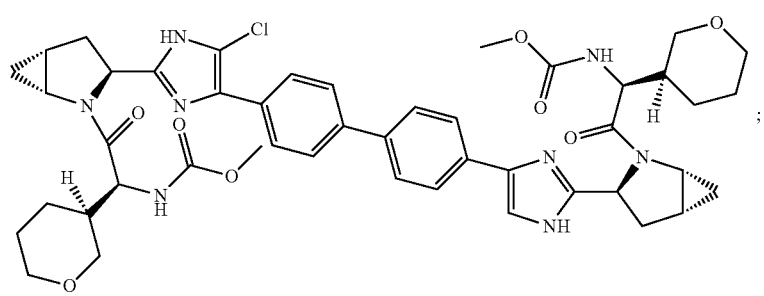
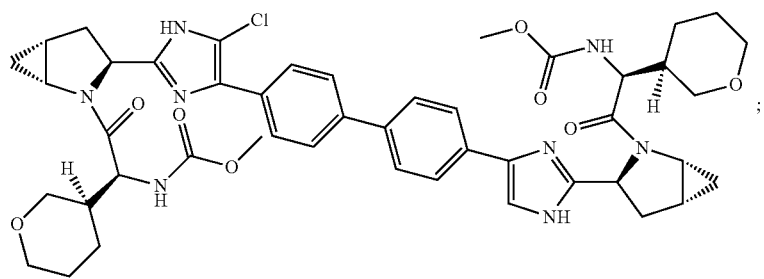
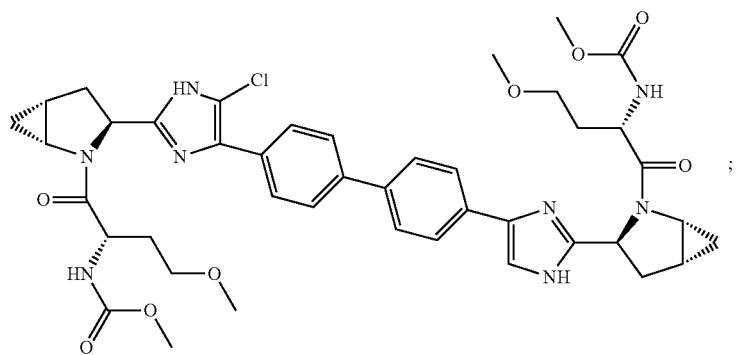
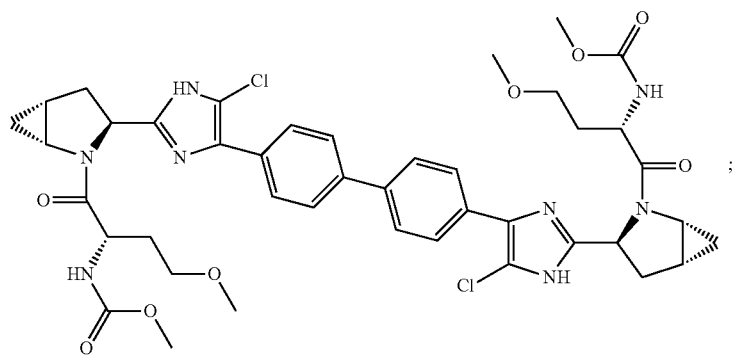

-continued
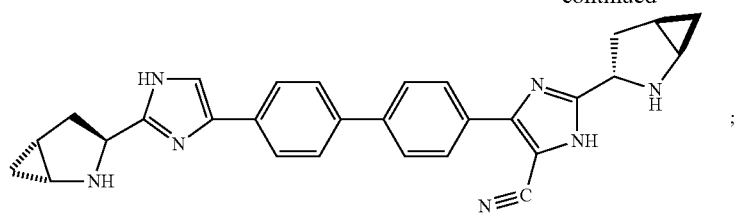
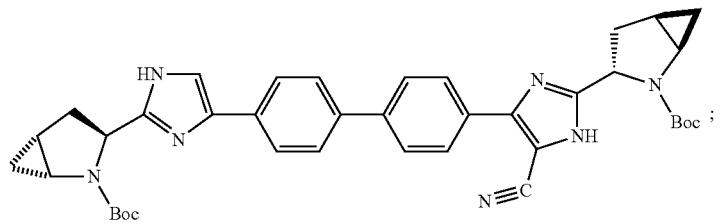
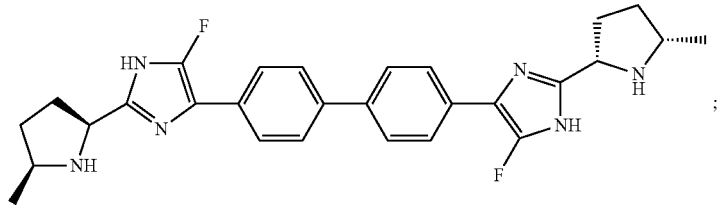
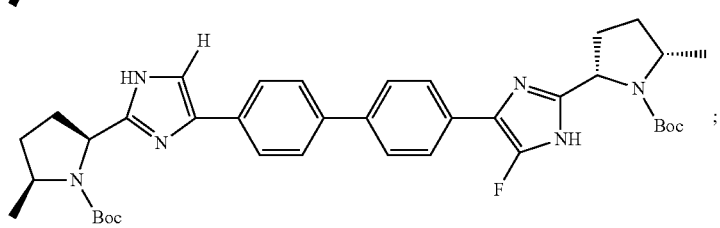
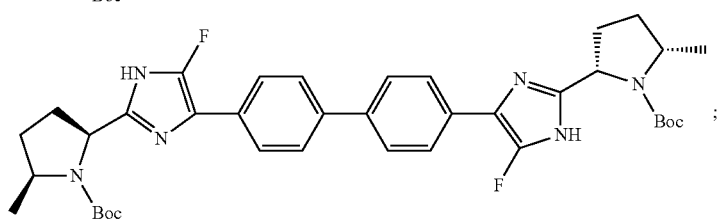
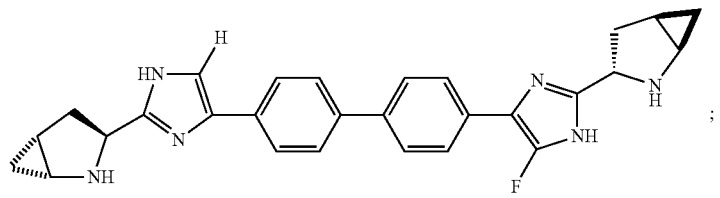
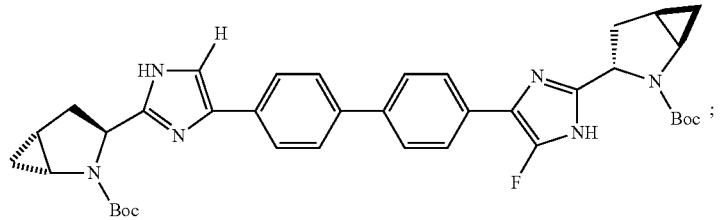
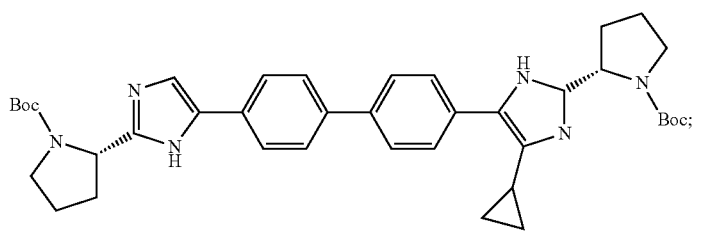

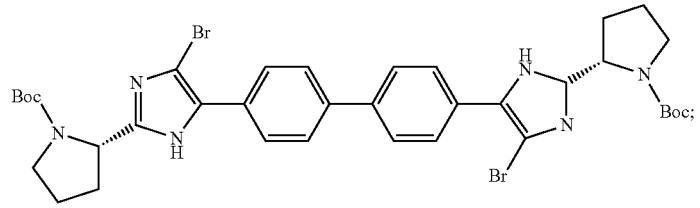
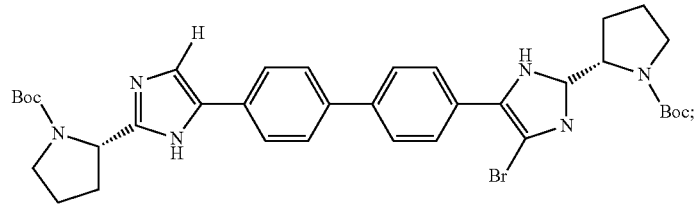
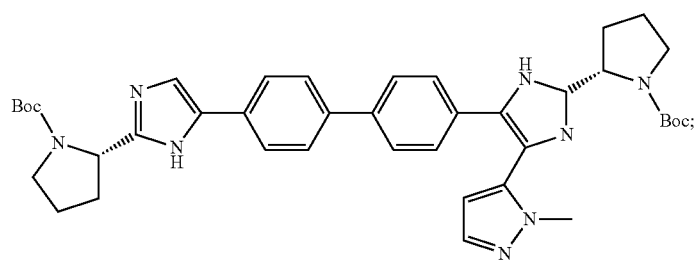
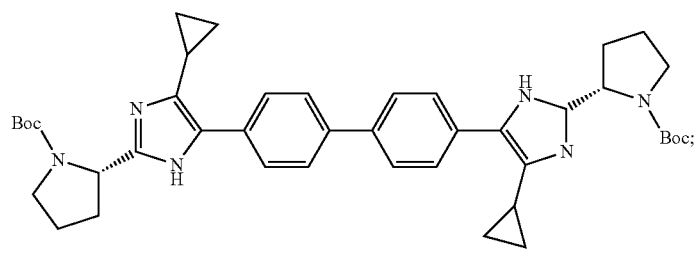
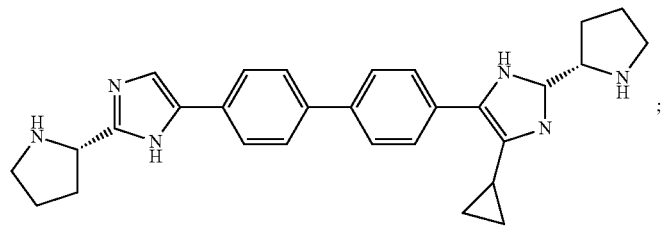
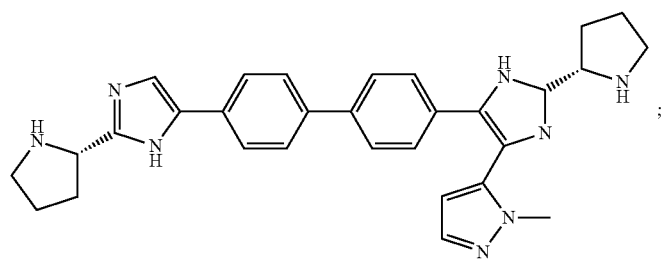
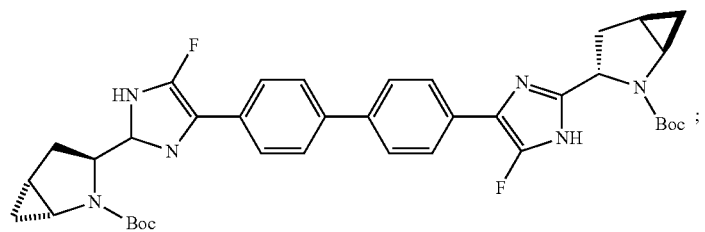

-continued
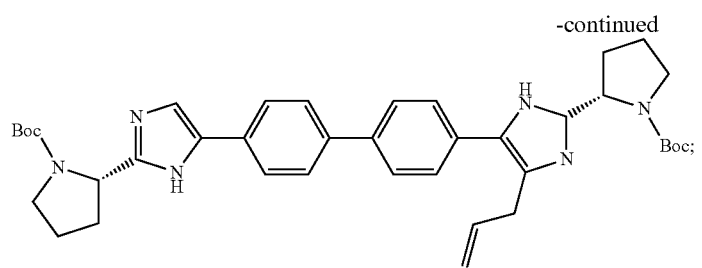
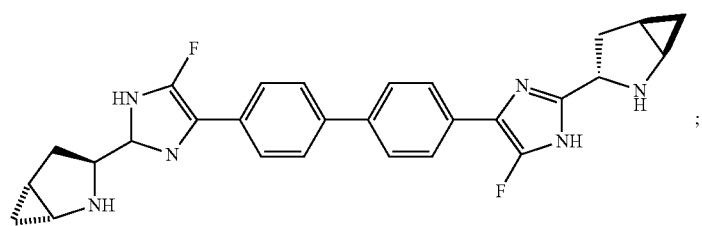
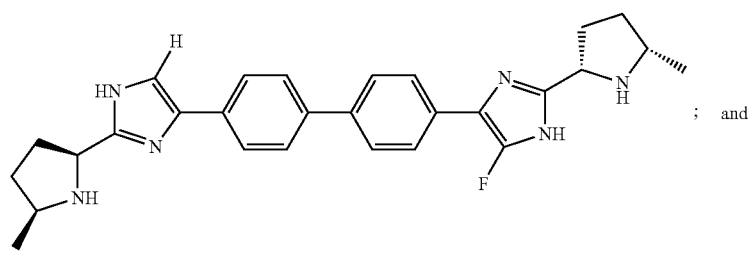
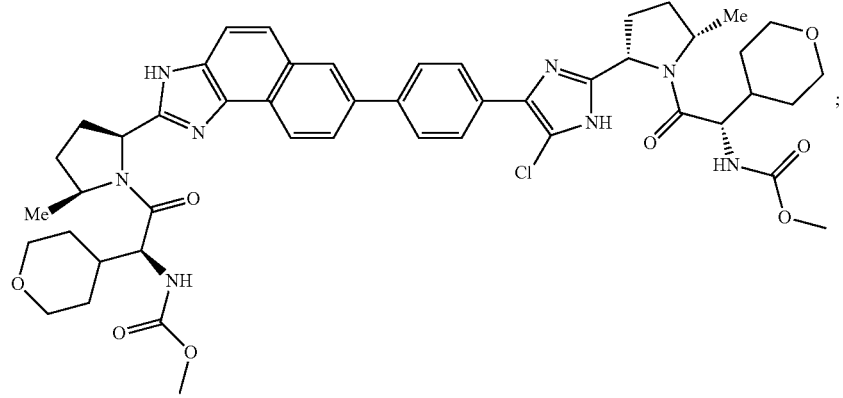
or a pharmaceutically acceptable salt thereof.
8. A compound selected from
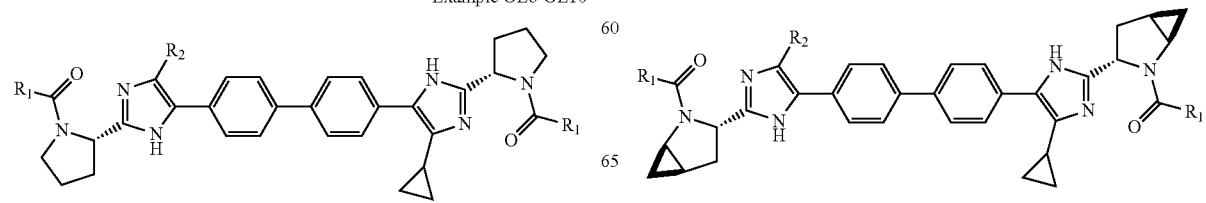

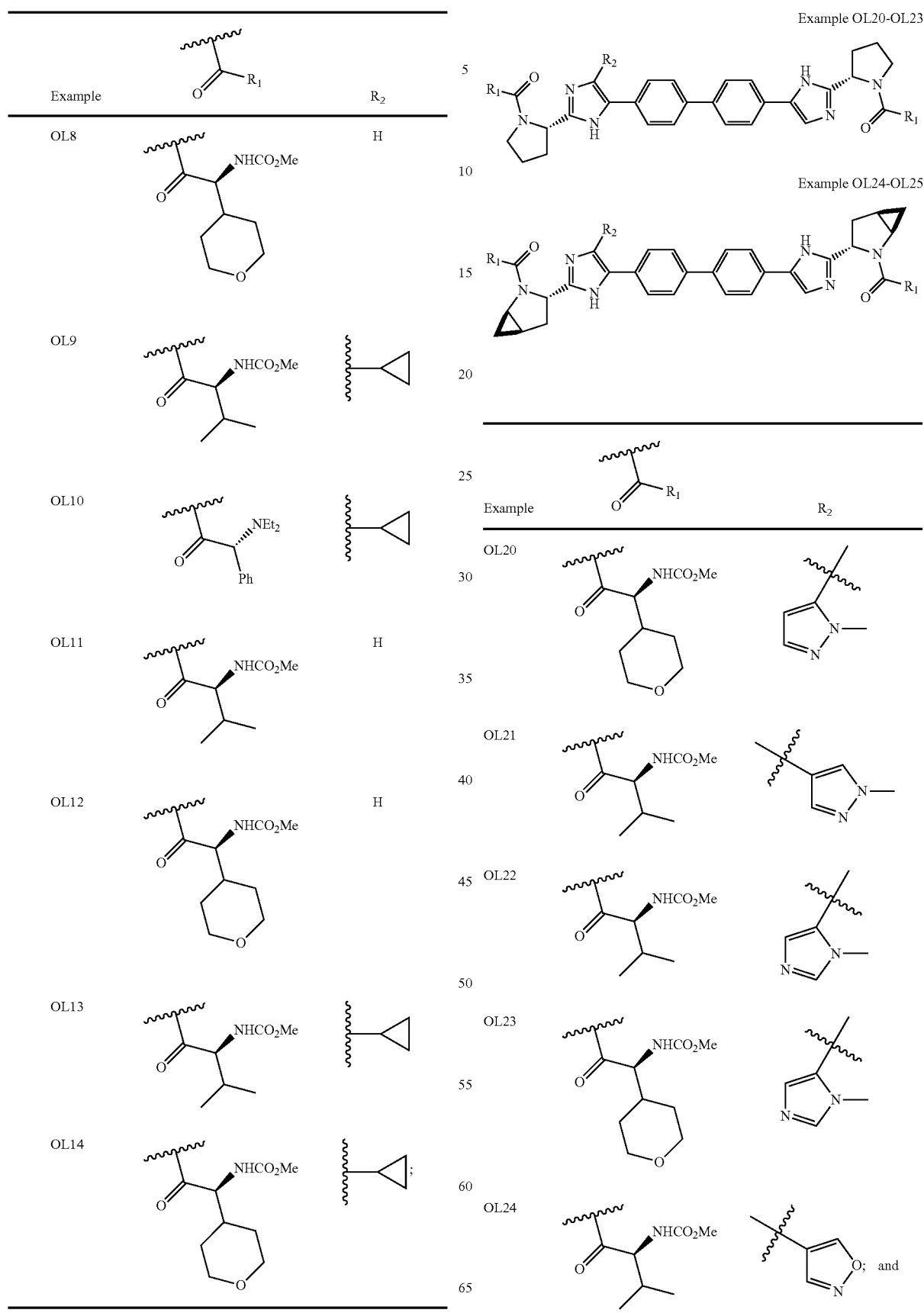

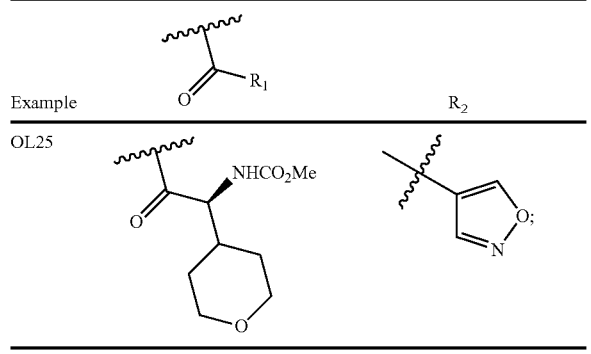

or a pharmaceutically acceptable salt thereof.

9. A composition comprising a compound of claim 1, or a pharmaceutically acceptable salt thereof, and a pharmaceutically acceptable carrier.

10. The composition of claim 9 wherein at least one of the additional compounds is an interferon or a ribavirin.

11. The composition of claim 10 wherein the interferon is selected from interferon alpha 2B, pegylated interferon alpha, consensus interferon, interferon alpha 2A, and lymphoblastoid interferon tau.

12. The composition of claim 9 wherein the composition further comprises at least one additional compound having anti-HCV activity, where at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

13. A method of treating an HCV infection in a patient, comprising administering to the patient a therapeutically effective amount of a compound of claim 1, or a pharmaceutically acceptable salt thereof.

14. The method of claim 13, further comprising administering at least one additional compound having anti-HCV activity prior to, after or simultaneously with the compound of claim 1, or a pharmaceutically acceptable salt thereof, wherein at least one of the additional compounds is an interferon or a ribavirin.

15. The method of claim 14 wherein the interferon is selected from interferon alpha 2B, pegylated interferon alpha, consensus interferon, interferon alpha 2A, and lymphoblastoid interferon tau.

16. The method of claim 13, further comprising administering at least one additional compound having anti-HCV activity prior to, after or simultaneously with the compound of claim 1, or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiquimod, ribavirin, an inosine 5'-monophosphate dehydrogenase inhibitor, amantadine, and rimantadine.

* * * * *

UNITED STATES PATENT AND TRADEMARK OFFICE
CERTIFICATE OF CORRECTION

| | | |
|---|---|---|
| PATENT NO. | : 8,377,980 B2 | Page 1 of 1 |
| APPLICATION NO. | : 12/957512 | |
| DATED | : February 19, 2013 | |
| INVENTOR(S) | : Belema et al. | |

It is certified that error appears in the above-identified patent and that said Letters Patent is hereby corrected as shown below:

In the Specification:

Column 3, line 23, change "Imiqimod," to -- Imiquimod, --.

Column 3, line 24, change "5'-monophospate" to -- 5'-monophosphate --.

Column 3, line 62, change "Imiqimod," to -- Imiquimod, --.

Column 3, line 63, change "5'-monophospate" to -- 5'-monophosphate --.

In the Claims:

Claim 10:

Column 295, line 21, after "claim 9", insert -- wherein the composition further comprises at least one additional compound having anti-HCV activity, --.

Claim 12:

Column 295, line 29, change "where" to -- wherein --.

Column 296, line 3, change "Imiqimod," to -- Imiquimod, --.

Column 296, line 3, change "5'-monophospate" to -- 5'-monophosphate --.

Signed and Sealed this
Twenty-ninth Day of April, 2014

Michelle K. Lee
*Deputy Director of the United States Patent and Trademark Office*